United States Patent
Shen et al.

(10) Patent No.: US 9,988,381 B2
(45) Date of Patent: Jun. 5, 2018

(54) FIVE-MEMBER-HETEROCYCLE FUSED PYRIDINE COMPOUNDS, METHOD OF PRODUCING THE SAME, AND USE THEREOF

(71) Applicants: SHANGHAI INSTITUTE OF MATERIA MEDICA, CHINESE ACADEMY OF SCIENCES, Shanghai (CN); SHANGHAI GREEN VALLEY PHARMACEUTICAL CO., LTD., Shanghai (CN)

(72) Inventors: Jingkang Shen, Shanghai (CN); Meiyu Geng, Shanghai (CN); Jian Ding, Shanghai (CN); Bing Xiong, Shanghai (CN); Jing Ai, Shanghai (CN); Yuchi Ma, Shanghai (CN); Xin Wang, Shanghai (CN); Xia Peng, Shanghai (CN); Yuelei Chen, Shanghai (CN); Danqi Chen, Shanghai (CN); Tao Meng, Shanghai (CN); Lanping Ma, Shanghai (CN); Yinchun Ji, Shanghai (CN)

(73) Assignees: Shanghai Institute of Materia Medica, Chinese Academy of Sciences, Shanghai (CN); Shanghai Haihe Pharmaceutical Co., Ltd., Shanghai (CN)

( * ) Notice: Subject to any disclaimer, the term of this patent is extended or adjusted under 35 U.S.C. 154(b) by 0 days. days.

(21) Appl. No.: 14/895,832

(22) PCT Filed: Jun. 18, 2014

(86) PCT No.: PCT/CN2014/000600
§ 371 (c)(1),
(2) Date: Dec. 3, 2015

(87) PCT Pub. No.: WO2014/201857
PCT Pub. Date: Dec. 24, 2014

(65) Prior Publication Data
US 2016/0137640 A1 May 19, 2016

(30) Foreign Application Priority Data
Jun. 19, 2013 (CN) .......................... 2013 1 0245354

(51) Int. Cl.
*C07D 471/04* (2006.01)
*C07D 519/00* (2006.01)
*C07D 487/04* (2006.01)
*C07D 495/04* (2006.01)

(52) U.S. Cl.
CPC ......... *C07D 471/04* (2013.01); *C07D 487/04* (2013.01); *C07D 495/04* (2013.01); *C07D 519/00* (2013.01)

(58) Field of Classification Search
None
See application file for complete search history.

(56) References Cited

U.S. PATENT DOCUMENTS

| | | | | |
|---|---|---|---|---|
| 7,259,165 B2* | 8/2007 | Bernotas | .............. | C07D 471/04 514/253.04 |
| 7,576,087 B2* | 8/2009 | Bernotas | .............. | C07D 471/04 514/252.19 |
| 7,696,229 B2* | 4/2010 | Dunn | .................... | C07D 401/04 514/254.09 |
| 2014/0303121 A1* | 10/2014 | Zhang | .................. | C07D 471/04 514/81 |

FOREIGN PATENT DOCUMENTS

| | | |
|---|---|---|
| WO | 2004/074286 A1 | 9/2004 |
| WO | 2009/033084 A1 | 3/2009 |
| WO | 2013169704 A2 | 11/2013 |
| WO | 2014/145051 A1 | 9/2014 |
| WO | 2015/108861 A1 | 7/2015 |

OTHER PUBLICATIONS

McCoull, W. et al., MedChemComm (2014), 5(10), 1533-1539.*
Porter, et al., Discovery of 4-azaindoles as Novel Inhibitors of c-Met Kinase, Bioorganic & Medicinal Chemistry Letters, 2009, 19:2780-2784.
Tai, et al., Pharmacophore Modeling and Virtual Screening Studies to Identify New c-Met Inhibitors, J. Mol. Model, 2012, 18:3087-3100.
PCT International Search Report, PCT/CN2014/000600, Sep. 9, 2014, 6 pages.
Yuan, et al., Novel Strategy for Three-Dimensional Fragment-Based Lead Discovery, Journal of Chemical Information and Modeling 2011, ACS Publications, American Chemical Society, pp. 959-974.
Supplementary European Search Report issued in corresponding European Patent Application No. 14 81 3825, dated Nov. 8, 2016, 2 pages.

* cited by examiner

*Primary Examiner* — Heidi Reese
(74) *Attorney, Agent, or Firm* — Quarles & Brady LLP

(57) ABSTRACT

This invention provides a class of five-member-heterocycle fused pyridine compounds as shown below in Formula (X), pharmaceutically acceptable salts or pharmaceutically acceptable solvates thereof, a method of producing the same, pharmaceutical compositions containing the compound, and use of the compounds in preparing medicament for preventing and/or treating diseases and tumors associated with abnormal protein tyrosine kinase.

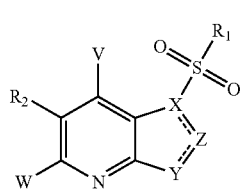

21 Claims, 1 Drawing Sheet

US 9,988,381 B2

FIVE-MEMBER-HETEROCYCLE FUSED PYRIDINE COMPOUNDS, METHOD OF PRODUCING THE SAME, AND USE THEREOF

CROSS-REFERENCE TO RELATED APPLICATIONS

This application represents the national stage entry of PCT International Application No. PCT/CN2014/000600 filed Jun. 18, 2014, which claims priority of Chinese Patent Application No. 201310245354.8 filed Jun. 19, 2013, the disclosures of which are incorporated by reference here in their entirety for all purposes.

TECHNICAL FIELD

This invention relates to a class of five-member-heterocycle fused pyridine compounds having inhibitory activity against protein tyrosine kinase, particularly c-Met, as well as pharmaceutically acceptable salts or pharmaceutically acceptable solvates of said compounds, process for producing the same, pharmaceutical compositions containing said compounds, and use of said compounds as inhibitors against protein tyrosine kinase, particularly as inhibitors against c-Met, as well as use of the same in preparation of medicament for preventing and/or treating protein diseases and tumors associated with abnormal protein tyrosine kinase.

BACKGROUND ART

Based on data published by Ministry of Health on major causes for death among Chinese urban and rural residents during 2007-2012, the top three causes for death among urban residents are malignant cancer, cerebrovascular disease and heart disease, while the top three causes for death among rural residents are malignant tumors, cerebrovascular disease and respiratory diseases, wherein mortality due to malignant cancer is steadily rising. Accordingly, malignant cancer has become the leading cause for death of Chinese residents, and its development is accelerating.

In recent years, along with deepening life science research and the rapid progress, receptor tyrosine kinases, which exhibit aberrant activation in cancer, has become an important target in the anticancer drug research and development because of the critical roles they play in tumorigenesis, invasion and metastasis, drug resistance, etc.

Protein tyrosine kinases (PTKs) are closely related to tumor development and progression. Protein tyrosine kinase hyperactivity may cause activation of downstream signaling pathways, in turn, lead to cell differentiation, proliferation, migration, and inhibition of apoptosis, and eventually, result in tumor formation and metastasis [Top Med Chem, 2007 (1): 83-132]. Accordingly, protein tyrosine kinase inhibitor has become one of the fastest growing class of anticancer drugs, having a number of small molecule protein tyrosine kinase inhibitors including lapatinib, sunitinib, crizotinib and the like marketed by the end of 2012. Compared with conventional cytotoxic anticancer drugs, these drugs exhibit improved selectivity, higher efficacy, less side effects, and have become the hotspot in anticancer drug research.

Hepatocyte Growth Factor (HGF) receptor c-Met is an important member of the receptor tyrosine kinase family. HGF is overexpressed and abnormally activated in most cancers and some sarcomas, closely associated with poor prognosis in patients having cancer, such as lung cancer, stomach cancer, liver cancer, breast cancer, colon cancer, prostate cancer, pancreatic cancer, esophageal cancer, ovarian cancer, kidney cancer, glioma, thyroid cancer, melanoma, etc. Upon activation through interaction with HGF or otherwise, c-Met induces tumor cell proliferation and resistance to apoptosis, promote tumor cell migration, invasion, and angiogenesis (*Nature Reviews Drug Discovery* 2008, 7, 504-516; Nat Rev Cancer. 2012; 12 (2): 89-103). Unlike other kinases, c-Met, a critical node in tumor signaling pathways, may interact with other tumor-associated molecules on cell surface to activate and magnify tumor-related effects through crosslinking, and promote tumor development and metastasis (*Nature Reviews Drug Discovery* 2008, 7, 504-516.). In addition, abnormal activation of HGF/c-Met is closely associated with resistance to inhibitors against EGFR, HER2, and B-Raf as well as some chemotherapeutic drugs (Science 2007, 316, 1039-1043; Clinical Cancer Research 2011, 17, 2260-2269; Nature 2012 Jul. 26; 487 (7408): 500-4; British Journal of Cancer 2012, 107, 793-799). Accordingly, investigation targeting c-Met inhibitors has become one hot frontier in anticancer drug researches.

Therefore, there is an pressing need for development of novel protein tyrosine kinase inhibitor having new structure, high activity, and low toxic side effects. As a receptor-type protein tyrosine kinase, c-Met is expressed in both normal cells and tumor cells. Normal HGF/c-Met signal transduction plays an important role in embryonic development, tissue repair, whereas abnormal HGF/c-Met signal transduction is closely associated with tumorigenesis, especially, with invasion and metastasis (Gao G F, Vande Woude G F. HGF/SR-Met signaling in tumor progression, Cell Res, 2005, 15(1): 49-51). Overexpression of c-Met is found in human hepatocellular carcinoma, cholangiocarcinoma, pancreatic cancer, lung cancer, thyroid cancer, pleural mesothelioma, etc., especially in metastatic tumors. Its role may include impacting adhesion of tumor cells, promoting degradation of extracellular matrix, inducing angiogenesis and promoting cell proliferation. All these indicate that c-Met is an important target for cancer therapeutics. Currently, blocking HGF/c-Met signal transduction is an important strategy for antitumor therapy. Since c-Met inhibitors, especially small molecule inhibitors as anticancer drugs are mostly in clinical studies and yet to be marketed, and antibody drugs are often more expensive, a broad space is available for development of these inhibitors. Accordingly, c-Met kinase is a promising target for anticancer drug researches. Although many inhibitors are developed against this signaling pathway, their structures are rather confined. This application designs a new class of 5-member-heterocycle fused pyridine compounds and discover that they possess desirable c-Met inhibitory activity.

SUMMARY OF THE INVENTION

One object of this application is to provide a class of 5-member-heterocycle fused pyridine compounds, or pharmaceutically acceptable salts or pharmaceutically acceptable solvates thereof. Having structures shown in the formulae below, said compounds are protein tyrosine kinase inhibitors, particularly effective in inhibiting c-Met.

Another object of this application is to provide a process for producing compounds having structures shown in the formulae below, or pharmaceutically acceptable salts or pharmaceutically acceptable solvates thereof.

Still another object of this application is to provide a use of compounds having structures shown in the formulae below, pharmaceutically acceptable salts or pharmaceutically acceptable solvates thereof, in preparation of medicaments serving as protein tyrosine inhibitors, particularly, c-Met inhibitors.

Yet another object of this application is to provide a use of compounds having structures shown in the formulae below, pharmaceutically acceptable salts or pharmaceutically acceptable solvates thereof, in preparation of medicaments for preventing or treating diseases associated with abnormal cell proliferation, morphological change and hyperkinesis related to abnormal protein tyrosine kinase in vivo, or diseases associated with angiogenesis or cancer metastasis, particularly, in preparation of medicaments for treating or preventing tumor growth and metastasis.

Yet another object of this application is to provide a pharmaceutical composition comprising a compound having structures shown in formula I, pharmaceutically acceptable salts or pharmaceutically acceptable solvates thereof, as the active ingredient, said pharmaceutical composition may further comprise a pharmaceutically acceptable carrier.

Yet another object of this application is to provide a use of above pharmaceutical composition in preparation of medicaments for preventing or treating diseases associated with abnormal cell proliferation, morphological change and hyperkinesis related to abnormal protein tyrosine kinase in vivo, or diseases associated with angiogenesis or cancer metastasis, particularly, in preparation of medicaments for treating or preventing tumor growth and metastasis.

Yet another object of this application is to provide a method of preventing or treating diseases associated with abnormal cell proliferation, morphological change and hyperkinesis related to abnormal protein tyrosine kinase in vivo, and diseases related to angiogenesis or cancer metastasis, in a subject in need thereof. Said method comprises administering therapeutic effective amount of a compound having a structure shown in the formulae below, a pharmaceutically acceptable salt or pharmaceutically acceptable solvate of the same, or a pharmaceutical composition comprising a compound having a structure shown in the formulae below, a pharmaceutically acceptable salt or pharmaceutically acceptable solvate of the same, or a mixture thereof, as the active ingredient.

DETAILED DESCRIPTION OF PREFERRED EMBODIMENTS

Figure 1:
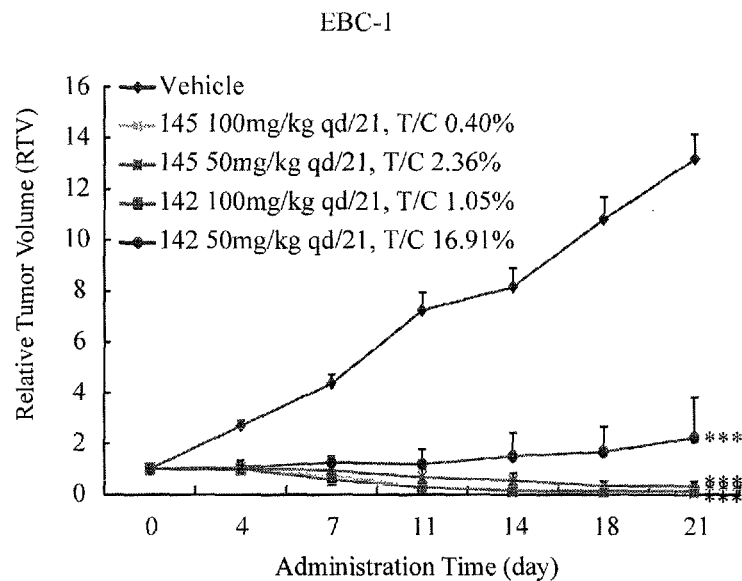
FIG. 1 shows the effect of the compound according to this invention on growth of human lung cancer EBC-1 xenograft in nude mice.

In first aspect, this application provides a 5-member-heterocycle fused pyridine compound having structure shown below in Formula (X), a pharmaceutically acceptable salt or pharmaceutically acceptable solvate of the same,

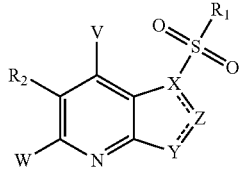

(X)

wherein,
X, Y and Z are each independently N or C, and at least one of X, Y and Z is N, provided that Z is N when X is N;

W and V are each independently selected from H, halogen, unsubstituted or halogen substituted $C_1$-$C_4$ alkyl, unsubstituted or halogen substituted $C_1$-$C_4$ alkoxy, nitro, or cyano;

$R_1$ is substituted or unsubstituted $C_6$-$C_{20}$ aryl; substituted or unsubstituted 5 to 10-membered heteroaryl comprising 1 to 5 heteroatom(s) selected from N, O, and S; or substituted or unsubstituted 4 to 10-membered heterocyclyl comprising 1 to 5 heteroatom(s) selected from N, O, and S; wherein substituent(s) in the substituted group(s) is halogen, nitro, cyano, hydroxyl, unsubstituted or halogen- or morpholinyl-substituted $C_1$-$C_6$ alkyl, $C_1$-$C_6$ alkoxy, $C_1$-$C_6$ alkylcarbonyl, $C_1$-$C_6$ alkoxycarbonyl, —$NR_aR_b$, —$C(O)(NR_aR_b)$, —$OC(O)$—$R_f$, unsubstituted phenyl or phenyl substituted by 1 to 4 of $R_3$, or unsubstituted 4- to 7-membered heteroaryl comprising 1 to 5 heteroatom(s) selected from N, O, and S or 4- to 7-membered heteroaryl comprising 1 to 5 heteroatom(s) selected from N, O, and S substituted by 1 to 4 of $R_4$;

$R_2$ is cyano; $C_1$-$C_4$ alkoxycarbonyl; —$NR_cR_d$; —NHC(O)—$R_e$; substituted or unsubstituted $C_6$-$C_{20}$ aryl; substituted or unsubstituted 5- to 10-membered heteroaryl comprising 1 to 5 heteroatom(s) selected from N, O, and S; or substituted or unsubstituted 4- to 10-membered heterocyclyl comprising 1 to 5 heteroatom(s) selected from N, O, and S; wherein substituent(s) in the substituted group(s) is halogen, nitro, cyano, $C_1$-$C_4$ alkylenedioxy, unsubstituted or halogen- or —$NR_cR_d$-substituted $C_1$-$C_6$ alkyl or $C_3$-$C_6$ cycloalkyl, $C_1$-$C_6$ alkoxy, $C_1$-$C_6$ sulfamido, —$NR_aR_b$, —C(O)R', morpholinyl, morpholinyl methyl, or unsubstituted or R"-substituted piperidinyl;

wherein $R_3$ is halogen, nitro, cyano, $C_1$-$C_4$ alkylenedioxy, unsubstituted or halogen- or morpholinyl-substituted $C_1$-$C_6$ alkyl, $C_1$-$C_6$ alkoxy, —$NR_aR_b$, —C(O)R', or morpholinyl;

$R_4$ is halogen, nitro, cyano, unsubstituted or halogen-substituted $C_1$-$C_6$ alkyl, $C_1$-$C_6$ alkoxy, —$NR_aR_b$, —C(O)R', or unsubstituted or $C_1$-$C_6$ alkoxycarbonyl-substituted piperidinyl;

R' is $C_1$-$C_6$ alkyl, $C_1$-$C_6$ alkoxy, —$NR_aR_b$, or unsubstituted or halogen- or $C_1$-$C_6$ alkyl-substituted 4- to 7-membered heterocyclyl;

R" is $C_1$-$C_6$ alkyl, $C_3$-$C_6$ cycloalkyl, $C_1$-$C_6$ alkylcarbonyl, $C_1$-$C_6$ alkoxycarbonyl, $C_3$-$C_6$ cycloalkylcarbonyl, or unsubstituted or substituted benzoyl where substituent is selected from halogen, $C_1$-$C_6$ alkyl, and halogen-substituted $C_1$-$C_6$ alkyl;

$R_a$ and $R_b$ are each independently H, $C_1$-$C_6$ alkyl or $C_1$-$C_6$ alkylcarbonyl;

$R_c$ and $R_d$ are each independently H or $C_1$-$C_6$ alkyl; alternatively, $R_c$ and $R_d$, together with the N atom to which they are attached, form 3- to 7-membered heterocyclyl;

$R_e$ is unsubstituted or $C_1$-$C_6$ alkyl- or halogen- or $C_1$-$C_6$ alkoxy-substituted $C_6$-$C_{20}$ aryl, unsubstituted or halogen-substituted $C_1$-$C_6$ alkyl;

$R_f$ is $C_1$-$C_6$ alkyl or unsubstituted or halogen- or $C_1$-$C_6$ alkyl-substituted 4- to 7-membered heteroaryl.

For the purpose of this invention, the term "alkyl" used herein refers to unsubstituted or substituted, saturated hydrocarbon group containing from 1 to 10 carbon atoms, preferably from 1 to 6 carbon atoms, more preferably 1 to 4 carbon atoms, unless otherwise stated. Preferably, alkyl includes, but not limited to, substituted or unsubstituted methyl, ethyl, propyl, isopropyl and butyl. The term "aryl" used herein refers to aromatic carbon cyclic group. Preferably, aryl includes, but not limited to, phenyl, tolyl, xylyl, cumenyl, naphthyl, biphenyl and fluorenyl. These groups can be substituted or unsubstituted. The term "heteroaryl" used herein refers to aromatic heterocyclyl, which may be a monocyclic or bicyclic group. Preferably, heteroaryl includes, but not limited to, thienyl, furanyl, pyrrolyl, pyridinyl, pyrazinyl, thiazolyl, pyrazolyl, pyrimidinyl, quinolinyl, isoquinolinyl, tetrazolyl, benzothiazolyl, benzofuranyl, indole indolyl, isoindolyl, and the likes. The term "heterocyclyl" refers to saturated or unsaturated cyclic group containing carbon atom(s) and 1 to 5 heteroatom(s). Preferably, heterocyclyl in this invention includes, but not limited to, piperazinyl, morpholinyl, tetrahydrofuranyl, tetrahydropyranyl and piperidinyl. The term "halogen" refers to F, Cl, Br, or I. Preferably, the halogen is F, Cl and Br, and more preferably, Cl and F. The term "substituted" means replacing one or more, such as 2 or 3, hydrogen atoms of a group with substituent(s), for instance, single substitution, double substitution, or triple substitution. A person skilled in the art will appreciate that, when this term is used herein, it means any specific means of substitutions are explicitly and specifically disclosed, unless otherwise stated. ==== represents single bond or double bond, and X, Y and Z abide by valence-bond theory. In this specification, substituents expressed with the same notation share the same definition, unless otherwise stated.

In one embodiment of this invention, W and V are each independently selected from H, halogen, unsubstituted or halogen-substituted $C_1$-$C_4$ alkyl. More preferably, W is H, V is independently selected from H, halogen, unsubstituted or halogen-substituted $C_1$-$C_4$ alkyl.

In any of the above embodiments, X and Z are N, Y is C. In another preferred embodiment, X and Z are C, Y is N. In another preferred embodiment, X is C, Y and Z are N.

In any of the above embodiments, $R_1$ is preferably substituted or unsubstituted $C_6$-$C_{10}$ aryl; substituted or unsubstituted 5- to 10-membered heteroaryl comprising 1 to 5 heteroatom(s) selected from N, O, and S; or substituted or unsubstituted 5- to 10-membered heterocyclyl comprising 1 to 5 heteroatom(s) selected from N, O, and S. More preferably, $R_1$ is selected from substituted or unsubstituted phenyl, naphthyl, isoxazolyl, 8- to 10-membered bicyclic heteroaryl comprising 2 to 3 heteroatoms selected from N, O, and S (such as imidazo[2,1-b]thiazolyl, imidazo[1,2-a]pyridinyl, benzo[1,2,5]oxadiazolyl, imidazo[1,2-b]pyridazinyl, pyrazolo[1,5-a]imidazolyl, imidazo[1,2-a]pyrimidinyl, and the likes). Substituent(s) in $R_1$ is halogen, nitro, cyano, unsubstituted or- or morpholinyl-substituted $C_1$-$C_5$ alkyl, hydroxyl, $C_1$-$C_5$ alkoxy, $C_1$-$C_5$ alkylcarbonyl, $C_1$-$C_5$ alkoxycarbonyl, —$NR_aR_b$, —C(O)(N$R_aR_b$), —OC(O)—$R_f$, unsubstituted phenyl or phenyl substituted by 1 to 3 of $R_3$, or unsubstituted 5- to 7-membered heteroaryl comprising 1-3 heteroatom(s) selected from N, O, and S or 5- to 7-membered heteroaryl comprising 1-3 heteroatom(s) selected from N, O, and S substituted by 1 to 3 of $R_4$; wherein the heteroaryl is preferably furanyl, thienyl, pyrrolyl, pyrazolyl, imidazolyl, oxazolyl, isoxazolyl, pyranyl, pyridinyl, morpholinyl, oxazinyl, pyrazinyl (wherein $R_a$, $R_b$, $R_f$, $R_3$, $R_4$ are defined as any of the above embodiments or the preferred embodiments). Said substituent(s) can replace any hydrogen in $R_1$ group.

In any of the above embodiments, $R_2$ is preferably cyano; $C_1$-$C_4$ alkoxycarbonyl; —$NR_cR_d$; —NHC(O)—$R_e$; substituted or unsubstituted $C_6$-$C_{10}$ aryl; substituted or unsubstituted 5- to 10-membered heteroaryl comprising 1-5 heteroatom(s) selected from N, O, and S; or substituted or unsubstituted 5- to 10-membered heterocyclyl comprising 1-5 heteroatom(s) selected from N, O, and S. Specifically, $R_2$ is selected from substituted or unsubstituted phenyl, naphthyl, pyrrolyl, pyrazolyl, 2H-imidazolyl, 1,2,3-triazolyl, 1,2,4-triazolyl, isoxazolyl, oxazolyl, 1,2,4-oxadiazolyl, 2H-pyranyl, 4H-pyranyl, pyridinyl, pyridazinyl, pyrimidinyl, pyrazinyl, piperazinyl, cis(s)-triazinyl, 4H-1,2-oxazinyl, 2H-1,3-oxazinyl, 1,4-oxazinyl, morpholinyl, azepinyl, oxapinanyl, 4H-1,2-diazepinyl, indenyl, 2H-indenyl, benzofuranyl, isobenzofuranyl, indolyl, 3H-indolyl, 1H-indolyl, benzooxazolyl, 2H-1-benzopyranyl, quinolinyl, isoquinolinyl, quinazolinyl, 2H-1,4-benzooxazinyl, pyrrolidinyl, pyrrolinyl, quinoxalinyl, furanyl, thienyl, benzoimidazolyl. More preferably, $R_2$ is selected from substituted or unsubstituted phenyl, naphthyl, pyrazolyl, pyrrolyl, thienyl, pyridinyl, furanyl, tetrahydropyridine, 1,4-benzodioxanyl, isoquinolinyl. The substituent within the substituted group is halogen, nitro, cyano, $C_1$-$C_4$ alkylenedioxy, unsubstituted $C_1$-$C_5$ alkyl or $C_1$-$C_5$ alkyl substituted by halogen or —$NR_cR_d$, $C_1$-$C_5$ alkoxy, $C_1$-$C_5$ sulfamido, —$NR_aR_b$, —C(O)R', morpholinyl, or unsubstituted or R"-substituted piperidinyl (wherein $R_c$, $R_d$, $R_e$, R', R" are as defined above in any of the above embodiments or preferred embodiments). Said substituent may substitute any hydrogen of $R_2$ group.

In any of the above embodiments, $R_3$ is preferably halogen, nitro, cyano, $C_1$-$C_4$ alkylenedioxy, unsubstituted $C_1$-$C_5$ alkyl or $C_1$-$C_5$ alkyl substituted by halogen or morpholinyl, $C_1$-$C_5$ alkoxy, —$NR_aR_b$, —C(O)R', or morpholinyl. $R_4$ is halogen, nitro, cyano, unsubstituted or halogen-substituted $C_1$-$C_5$ alkyl, $C_1$-$C_5$ alkoxy, —$NR_aR_b$, —C(O)R', or unsubstituted or $C_1$-$C_5$ alkoxycarbonyl-substituted piperidinyl. R' is $C_1$-$C_5$ alkyl, $C_1$-$C_5$ alkoxy, —$NR_aR_b$, or unsubstituted 5- to 6-membered heterocyclyl or 5- to 6-membered heterocyclyl substituted by halogen or $C_1$-$C_5$ alkyl. R" is $C_1$-$C_5$ alkyl, $C_3$-$C_6$ cycloalkyl, $C_1$-$C_5$ alkylcarbonyl, $C_1$-$C_5$ alkoxycarbonyl, $C_3$-$C_6$ cycloalkylcarbonyl, or unsubstituted benzoyl or benzoyl substituted by substituent(s) selected from halogen, $C_1$-$C_5$ alkyl, and halogen-substituted $C_1$-$C_5$ alkyl. $R_a$ and $R_b$ are each independently H or $C_1$-$C_5$ alkyl; $R_c$ and $R_d$ are each independently H or $C_1$-$C_5$ alkyl; alternatively, $R_c$ and $R_d$, together with the N atom to which they are attached, form 3-7 membered heterocyclyl; $R_e$ is unsubstituted $C_6$-$C_{20}$ aryl or $C_6$-$C_{20}$ aryl substituted by $C_1$-$C_6$ alkyl or halogen or $C_1$-$C_6$ alkoxy, unsubstituted or halogen-substituted $C_1$-$C_6$ alkyl, $R_f$ is $C_1$-$C_6$ alkyl, or unsubstituted or halogen- or $C_1$-$C_6$ alkyl-substituted 4-7 membered heteroaryl (for example, preferably furanyl, pyrrolyl, thienyl).

In a preferred embodiment of this invention, W and V are each independently selected from H, $C_1$-$C_4$ alkyl, $C_1$-$C_4$ alkoxy; X and Z are N, Y is C;

$R_1$ is

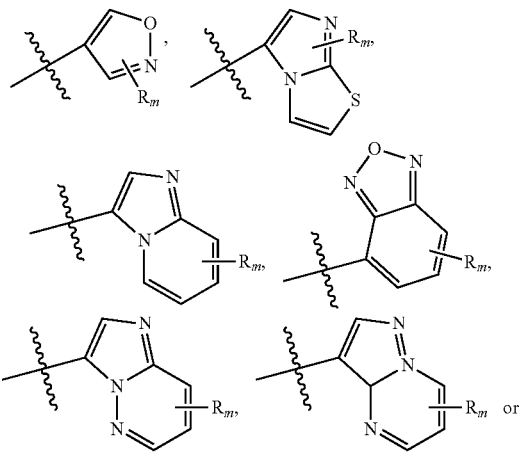

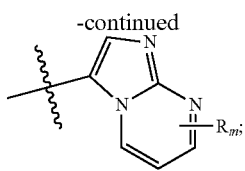

Wherein, $R_m$ is H, halogen, nitro, cyano, unsubstituted or halogen- or morpholinyl-substituted $C_1$-$C_4$ alkyl, $C_1$-$C_4$ alkoxy, $C_1$-$C_4$ alkylcarbonyl, $C_1$-$C_4$ alkoxycarbonyl, —$NR_aR_b$, —$C(O)(NR_aR_b)$, —$OC(O)$—$R_f$, unsubstituted phenyl or phenyl substituted by 1-3 of $R_3$, or unsubstituted 5-7 membered heteroaryl comprising 1-3 heteroatoms selected from N, O, and S or 5-7 membered heteroaryl comprising 1-3 heteroatoms selected from N, O, and S which is substituted by 1-3 of $R_4$; wherein said heteroaryl is selected from furanyl, thienyl, pyrrolyl, pyrazolyl, imidazolyl, oxazolyl, isoxazolyl, pyranyl, pyridinyl, morpholinyl, oxazinyl, pyrazinyl;

$R_2$ is cyano; $C_1$-$C_4$ alkoxycarbonyl; —$NR_cR_d$; —NHC(O)—$R_e$; substituted or unsubstituted $C_6$-$C_{20}$ aryl; substituted or unsubstituted 5-10 membered heteroaryl comprising 1-5 heteroatoms selected from N, O, and S; or substituted or unsubstituted 4-10 membered heterocylyl comprising 1-5 heteroatoms selected from N, O, and S; wherein the substituent(s) in said substituted group is halogen, nitro, cyano, $C_1$-$C_4$ alkylenedioxy, unsubstituted $C_1$-$C_6$ alkyl or $C_3$-$C_6$ cycloalkyl or $C_1$-$C_6$ alkyl or $C_3$-$C_6$ cycloalkyl substituted by halogen or —$NR_cR_d$, $C_1$-$C_6$ alkoxy, $C_1$-$C_6$ sulfamido, —$NR_aR_b$, —$C(O)R'$, morpholinyl, morpholinylmethyl, or unsubstituted or R''-substituted piperidinyl;

$R_3$ is halogen, nitro, cyano, $C_1$-$C_2$ alkylenedioxy; unsubstituted or halogen- or morpholinyl-substituted $C_1$-$C_4$ alkyl, $C_1$-$C_4$ alkoxy, —$NR_aR_b$, —$C(O)R'$, or 4-morpholinyl;

$R_4$ is halogen, nitro, cyano, unsubstituted or halogen-substituted $C_1$-$C_4$ alkyl, $C_1$-$C_4$ alkoxy, —$NR_aR_b$, —$C(O)R'$, 4-piperidinyl, or 1-t-butoxycarbonyl-4-piperidinyl;

$R'$ is $C_1$-$C_4$ alkyl, $C_1$-$C_4$ alkoxy, —$NR_aR_b$, or 4-methylpiperazinyl;

$R''$ is $C_1$-$C_4$ alkyl, $C_3$-$C_6$ cycloalkyl, $C_1$-$C_4$ alkylcarbonyl, $C_1$-$C_4$ alkoxycarbonyl, $C_3$-$C_6$ cycloalkylcarbonyl, or p-trifluoromethylbenzoyl;

$R_a$ and $R_b$ are each independently H, $C_1$-$C_4$ alkyl or $C_1$-$C_4$ alkylcarbonyl;

$R_e$ is unsubstituted $C_6$-$C_{20}$ aryl or $C_6$-$C_{20}$ aryl substituted by $C_1$-$C_6$ alkyl or halogen or $C_1$-$C_6$ alkoxy, unsubstituted or halogen-substituted $C_1$-$C_6$ alkyl;

$R_f$ is $C_1$-$C_6$ alkyl or 4-7 membered heteroaryl or 4-7 membered heteroaryl substituted by halogen or $C_1$-$C_6$ alkyl, said 4-7 membered heteroaryl is selected from furanyl, pyrrolyl, thienyl.

In another embodiment of this invention, the 5-membered-heterocyle fused pyridine compound has a structure as shown below in formula I:

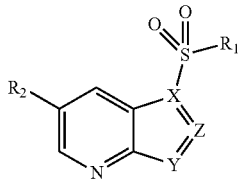

wherein, $R_1$ is substituted or unsubstituted $C_6$-$C_{20}$ aryl; substituted or unsubstituted 5-10 membered heteroaryl comprising 1-5 heteroatoms selected from N, O, and S; or substituted or unsubstituted 4-10 membered heterocyclyl comprising 1-5 heteroatoms selected from N, O, and S; wherein the substituent(s) in the substituted group is halogen, nitro, cyano, unsubstituted or halogen- or morpholinyl-substituted $C_1$-$C_6$ alkyl, $C_1$-$C_6$ alkoxy, $C_1$-$C_6$ alkylcarbonyl, $C_1$-$C_6$ alkoxycarbonyl, —$NR_aR_b$, —$C(O)(NR_aR_b)$, unsubstituted phenyl or phenyl substituted by 1-4 of $R_3$, or unsubstituted 4-7 membered heteroaryl comprising 1-5 heteroatoms selected from N, O, and S or 4-7 membered heteroaryl comprising 1-5 heteroatoms selected from N, O, and S, which is substituted by 1-4 of $R_4$;

$R_2$ is substituted or unsubstituted $C_6$-$C_{20}$ aryl; substituted or unsubstituted 5-10 membered heteroaryl comprising 1-5 heteroatoms selected from N, O, and S; or substituted or unsubstituted 4-10 membered heterocyclyl comprising 1-5 heteroatoms selected from N, O, and S; wherein substituent in the substituted group is halogen, nitro, cyano, $C_1$-$C_4$ alkylenedioxy, unsubstituted $C_1$-$C_6$ alkyl or $C_1$-$C_6$ alkyl substituted by halogen or —$NR_cR_d$, $C_1$-$C_6$ alkoxy, $C_1$-$C_6$ sulfamido, —$NR_aR_b$, —$C(O)R'$, morpholinyl, or unsubstituted or R''-substituted piperidinyl;

wherein $R_3$ is halogen, nitro, cyano, $C_1$-$C_4$ alkylenedioxy, unsubstituted or halogen- or morpholinyl-substituted $C_1$-$C_6$ alkyl, $C_1$-$C_6$ alkoxy, —$NR_aR_b$, —$C(O)R'$, or morpholinyl;

$R_4$ is halogen, nitro, cyano, unsubstituted or halogen-substituted $C_1$-$C_6$ alkyl, $C_1$-$C_6$ alkoxy, —$NR_aR_b$, —$C(O)R'$, or unsubstituted or $C_1$-$C_6$ alkoxycarbonyl-substituted piperidinyl;

$R'$ is $C_1$-$C_6$ alkyl; $C_1$-$C_6$ alkoxy; —$NR_aR_b$; or unsubstituted or halogen- or $C_1$-$C_6$ alkyl-substituted 4-7 membered heterocyclyl;

$R''$ is $C_1$-$C_6$ alkyl; $C_3$-$C_6$ cycloalkyl; $C_1$-$C_6$ alkylcarbonyl; $C_1$-$C_6$ alkoxycarbonyl; $C_3$-$C_6$ cycloalkylcarbonyl; or unsubstituted benzoyl or benzoyl substituted by substituent(s) selected from halogen, $C_1$-$C_6$ alkyl, or halogen-substituted $C_1$-$C_6$ alkyl;

$R_a$ and $R_b$ are independently H or $C_1$-$C_6$ alkyl;

$R_c$ and $R_d$ are independently H or $C_1$-$C_6$ alkyl; alternatively, $R_c$ and $R_d$, together with the N atom to which they are attached, form 3-7 membered heterocyclyl;

X, Y and Z are independently N or C, and at least one of X, Y and Z is N;

═══ represents single bond or double bond, while X, Y and Z abide by the valence bond theory.

In embodiments described above, preferably, in the compound of Formula I, $R_1$ is substituted or unsubstituted $C_6$-$C_{10}$ aryl; substituted or unsubstituted 5-10 membered heteroaryl comprising 1-5 heteroatoms selected from N, O, and S; or substituted or unsubstituted 5-10 membered heterocyclyl comprising 1-5 heteroatoms selected from N, O, and S; wherein, substituent(s) in the substituted group is halogen, nitro, cyano, unsubstituted or halogen- or morpholinyl-substituted $C_1$-$C_5$ alkyl, $C_1$-$C_5$ alkoxy, $C_1$-$C_5$ alkylcarbonyl, $C_1$-$C_5$ alkoxycarbonyl, —$NR_aR_b$; —$C(O)(NR_aR_b)$, unsubstituted phenyl or phenyl substituted by 1-3 of $R_3$, or unsubstituted 5-7 membered heteroaryl comprising 1-3 heteroatoms selected from N, O, and S or 5-7 membered heteroaryl comprising 1-3 heteroatoms selected from N, O, and S substituted by 1-3 of $R_4$.

Preferably, in the compound of Formula I, $R_2$ is substituted or unsubstituted $C_6$-$C_{10}$ aryl; substituted or unsubstituted 5-10 membered heteroaryl comprising 1-5 heteroatoms selected from N, O, and S; or substituted or unsubstituted 5-10 membered heterocyclyl comprising 1-5 heteroatoms selected from N, O, and S; wherein, substituent in the substituted group is halogen, nitro, cyano, $C_1$-$C_4$ alkylenedioxy, unsubstituted $C_1$-$C_5$ alkyl or $C_1$-$C_5$ alkyl substituted by halogen or —NR$_c$R$_d$, C$_1$-C$_5$ alkoxy, C$_1$-C$_5$ sulfamido, —NR$_a$R$_b$, —C(O)R', morpholinyl, or unsubstituted or R"-substituted piperidinyl.

Preferably, R$_3$ is halogen, nitro, cyano, C$_1$-C$_4$ alkylenedioxy, unsubstituted or halogen- or morpholinyl-substituted C$_1$-C$_5$ alkyl, C$_1$-C$_5$ alkoxy, —NR$_a$R$_b$, —C(O)R', or morpholinyl.

Preferably, R$_4$ is halogen, nitro, cyano, unsubstituted or halogen-substituted C$_1$-C$_5$ alkyl, C$_1$-C$_5$ alkoxy, —NR$_a$R$_b$, —C(O)R', or unsubstituted or C$_1$-C$_5$ alkoxycarbonyl-substituted piperidinyl.

Preferably, R' is C$_1$-C$_5$ alkyl, C$_1$-C$_5$ alkoxy, —NR$_a$R$_b$, or unsubstituted or halogen- or C$_1$-C$_5$ alkyl-substituted 5-6 membered heterocyclyl.

Preferably, R" is C$_1$-C$_5$ alkyl, C$_3$-C$_6$ cycloalkyl, C$_1$-C$_5$ alkylcarbonyl, C$_1$-C$_5$ alkoxycarbonyl, C$_3$-C$_6$ cycloalkylcarbonyl, or unsubstituted benzoyl or benzoyl substituted by substituent(s) selected from halogen, C$_1$-C$_5$ alkyl and halogen-substituted C$_1$-C$_5$ alkyl.

Preferably, R$_a$ and R$_b$ are independently H or C$_1$-C$_5$ alkyl;

Preferably, R$_c$ and R$_d$ are independently H or C$_1$-C$_5$ alkyl; or, R$_c$ and R$_d$, together with the N atom to which they are attached, form 3-7 membered heterocyclyl;

Preferably, X, Y and Z are independently N or C, and at least one of X, Y and Z is N, and X, Y and Z abide by valence bond theory. More preferably, said X and Z are N, said Y is C. In another preferred embodiment, said X and Z are C, said Y is N. In another preferred embodiment, said X is C, said Y and Z are N.

More preferably, in the compound of Formula I, R$_1$ is substituted or unsubstituted C$_6$-C$_{10}$ aryl, or substituted or unsubstituted 5-10 membered heteroaryl comprising 1-3 heteroatoms selected from N, O, and S; wherein, the substituent in the substituted group is halogen, nitro, cyano, unsubstituted or halogen- or morpholinyl-substituted C$_1$-C$_4$ alkyl, C$_1$-C$_4$ alkoxy, C$_1$-C$_4$ alkylcarbonyl, C$_1$-C$_4$ alkoxycarbonyl, —NR$_a$R$_b$, —C(O)(NR$_a$R$_b$), unsubstituted phenyl or phenyl substituted by 1-3 of R$_3$; or unsubstituted 5-7 membered heteroaryl comprising 1-3 heteroatoms selected from N, O, and S or 5-7 membered heteroaryl comprising 1-3 heteroatoms selected from N, O, and S substituted by 1-3 of R$_4$.

More preferably, in the compound of Formula I, R$_2$ is substituted or unsubstituted C$_6$-C$_{10}$ aryl, substituted or unsubstituted 5-10 membered heteroaryl comprising 1-3 heteroatoms selected from N, O, and S; or substituted or unsubstituted 5-10 membered heterocyclyl comprising 1-3 heteroatoms selected from N, O, and S; wherein, substituent in the substituted group is halogen, nitro, cyano, C$_1$-C$_2$ alkylenedioxy, unsubstituted or halogen or —NR$_c$R$_d$ substituted C$_1$-C$_4$ alkyl, C$_1$-C$_4$ alkoxy, C$_1$-C$_4$ sulfamido, —NR$_a$R$_b$, —C(O)R', morpholinyl, or unsubstituted or R"-substituted piperidinyl.

More preferably, R$_3$ is halogen, nitro, cyano, C$_1$-C$_2$ alkylenedioxy, unsubstituted or halogen- or morpholinyl-substituted C$_1$-C$_4$ alkyl, C$_1$-C$_4$ alkoxy, —NR$_a$R$_b$, —C(O)R', or morpholinyl.

More preferably, R$_4$ is halogen, nitro, cyano, unsubstituted or halogen-substituted C$_1$-C$_4$ alkyl; C$_1$-C$_4$ alkoxy; —NR$_a$R$_b$; —C(O)R'; or unsubstituted or C$_1$-C$_4$ alkoxycarbonyl-substituted piperidinyl.

More preferably, the above R' is C$_1$-C$_4$ alkyl; C$_1$-C$_4$ alkoxy; —NR$_a$R$_b$; or 4-methylpiperazinyl.

More preferably, the above R" is C$_1$-C$_4$ alkyl; C$_3$-C$_6$ cycloalkyl; C$_1$-C$_4$ alkylcarbonyl; C$_1$-C$_4$ alkoxycarbonyl; C$_3$-C$_6$ cycloalkylcarbonyl; or p-trifluoromethylbenzoyl.

More preferably, the above R$_a$ and R$_b$ are independently H or C$_1$-C$_4$ alkyl;

Preferably, R$_c$ and R$_d$ are independently H or C$_1$-C$_4$ alkyl; or, R$_c$ and R$_d$, together with the N atom to which they are attached, form 3-7 membered heterocyclyl;

More preferably, one or two of the above X, Y and Z are N, while the remaining is C, and X, Y and Z abidy by valence bond theory.

Further preferably, in the compound of Formula I, R$_1$ is

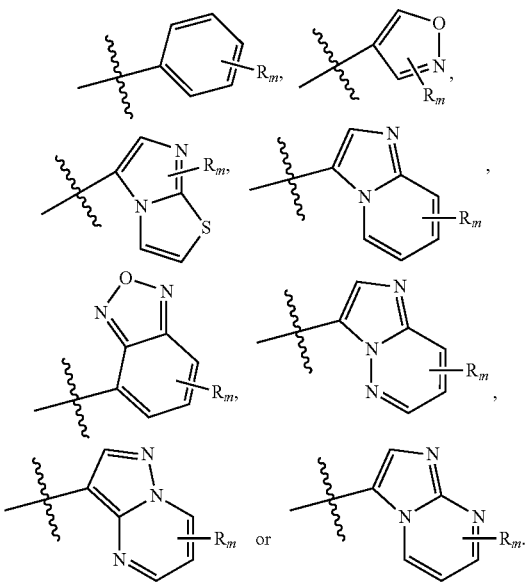

Further preferably, in the compound of Formula I, R$_2$ is

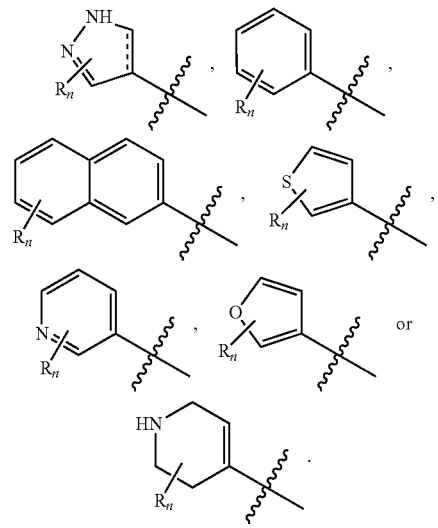

wherein, the above R$_m$ is halogen, nitro, cyano, unsubstituted or halogen- or morpholinyl-substituted C$_1$-C$_4$ alkyl, C$_1$-C$_4$ alkoxy, C$_1$-C$_4$ alkylcarbonyl, C$_1$-C$_4$ alkoxycarbonyl, —NR$_a$R$_b$, —C(O)(NR$_a$R$_b$), unsubstituted phenyl or phenyl substituted by 1-3 of R$_3$, or unsubstituted 5-7 membered heteroaryl comprising 1-3 heteroatoms selected from N, O, and S or 5-7 membered heteroaryl comprising 1-3 heteroatoms selected from N, O, and S substituted by 1-3 of R$_4$.

The above $R_n$ is halogen; nitro; cyano; $C_1$-$C_2$ alkylenedioxy; unsubstituted or halogen-, dimethylamino-, 4-morpholinyl-, 1-aziridinyl-, 1-azetidinyl-, 1-tetrahydropyrrolyl-, 1-piperidinyl- or 1-homopiperidinyl-substituted $C_1$-$C_4$ alkyl; $C_1$-$C_4$ alkoxy; $C_1$-$C_4$ sulfamido; —$NR_aR_b$; —C(O)R'; 4-morpholinyl; or unsubstituted or R"-substituted piperidinyl;

wherein, the above $R_3$ is halogen, nitro, cyano, $C_1$-$C_2$ alkylenedioxy, unsubstituted or halogen- or morpholinyl-substituted $C_1$-$C_4$ alkyl, $C_1$-$C_4$ alkoxy, —$NR_aR_b$, —C(O)R', or 4-morpholinyl;

the above $R_4$ is halogen, nitro, cyano, unsubstituted or halogen-substituted $C_1$-$C_4$ alkyl; $C_1$-$C_4$ alkoxy; —$NR_aR_b$; —C(O)R'; 4-piperidinyl; or 1-t-butoxy-4-piperidinyl;

the above R' is $C_1$-$C_4$ alkyl, $C_1$-$C_4$ alkoxy, —$NR_aR_b$, or 4-methylpiperazinyl;

the above R" is $C_1$-$C_4$ alkyl, $C_3$-$C_6$ cycloalkyl, $C_1$-$C_4$ alkylcarbonyl, $C_1$-$C_4$ alkoxycarbonyl, $C_3$-$C_6$ cycloalkylcarbonyl, or p-trifluoromethylbenzoyl;

the above $R_a$ and $R_b$ are independently H or $C_1$-$C_4$ alkyl.

In this specification, $R_m$ refers to the corresponding substituent in $R_1$ group, $R_n$ refers to the corresponding substituent in $R_2$ group. In $R_1$ group, there may be 1, 2, 3 or more identical or various $R_m$ substituents. In $R_2$ group, there may be 1, 2, 3 or more identical or various $R_n$ substituents. In one preferred embodiment, when $R_1$ is $C_6$-$C_{20}$ aryl, 5-10 membered heteroaryl comprising 1-5 heteroatoms selected from N, O, and S, or 4-10 membered heterocyclyl comprising 1-5 heteroatoms selected from N, O, and S, it is desirable to have substituent $R_m$ therein in the 2-, 3-, 4-, 5-, 6-, 7-, 8-, 9-, or 10-position of said aryl, heteroaryl, heterocyclyl (with the provision that there is hydrogen atom available for substitution in said position). When $R_2$ is $C_6$-$C_{20}$ aryl, 5-10 membered heteroaryl comprising 1-5 heteroatoms selected from N, O, and S, or 4-10 membered heterocyclyl comprising 1-5 heteroatoms selected from N, O, and S, it is desirable to have substituent $R_n$ therein in the 2-, 3-, 4-, 5-, 6-, 7-, 8-, 9-, or 10-position of said aryl, heteroaryl, heterocyclyl (with the provision that there is hydrogen atom available for substitution in said position). In a further preferred embodiment, $R_1$ and/or $R_2$ have polycyclic structure, $R_m$ and/or $R_n$ substituent attached to positions in the cyclic structure different from where the sulfonyl is attached.

Preferably, the 5-member-heterocycle fused pyridine compound of Formula I is following 5-member-heterocycle fused pyridine compounds as shown in Formulae (II), (III), and (IV),

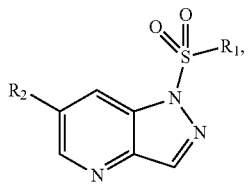

(II)

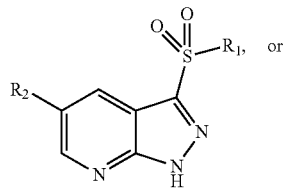

(III)

(IV)

wherein, $R_1$ and $R_2$ are as defined above.

Therefore, in any of the above embodiments, preferably, said 5-member-heterocycle fused pyridine compound has a structure as shown above in Formula II, wherein:

$R_1$ is selected from phenyl, naphthyl, isoxazolyl, 8-10 membered bicyclic heteroaryl comprising 2-3 heteroatoms selected from N, O, and S (such as imidazo[2,1-b]thiazolyl, imidazo[1,2-a]pyridinyl, benzo[1,2,5]oxadiazolyl, imidazo[1,2-b]pyridazinyl, pyrazolo[1,5-a]imidazolyl, imidazo[1,2-a]pyrimidinyl, etc.). Substituent in the substituted group is halogen; nitro; hydroxyl; cyano; unsubstituted or halogen- or morpholinyl-substituted $C_1$-$C_5$ alkyl; $C_1$-$C_5$ alkoxy; $C_1$-$C_5$ alkylcarbonyl; $C_1$-$C_5$ alkoxycarbonyl; —$NR_aR_b$; —C(O)($NR_aR_b$); —OC(O)—$R_f$; unsubstituted phenyl or phenyl substituted by 1-3 of $R_3$; or unsubstituted 5-7 membered heteroaryl comprising 1-3 heteroatoms selected from N, O, and S or 5-7 membered heteroaryl comprising 1-3 heteroatoms selected from N, O, and S substituted by 1-3 of $R_4$, wherein said heteroaryl is preferably furanyl, thienyl, pyrrolyl, pyrazolyl, imidazolyl, oxazolyl, isoxazolyl, pyranyl, pyridinyl, morpholinyl, oxazinyl, pyrazinyl;

$R_2$ is cyano; $C_1$-$C_4$ alkoxycarbonyl; —$NR_cR_d$; —NHC(O)—$R_e$; substituted or unsubstituted $C_6$-$C_{10}$ aryl; substituted or unsubstituted 5-10 membered heteroaryl comprising 1-5 heteroatoms selected from N, O, and S; or substituted or unsubstituted 5-10 membered heterocyclyl comprising 1-5 heteroatoms selected from N, O, and S; wherein, substituent in the substituted group is halogen, nitro, cyano, $C_1$-$C_4$ alkylenedioxy; unsubstituted $C_1$-$C_5$ alkyl or $C_1$-$C_5$ alkyl substituted by halogen or —$NR_cR_d$; $C_1$-$C_5$ alkoxy; $C_1$-$C_5$ sulfamido; —$NR_aR_b$; —C(O)R'; morpholinyl; or unsubstituted or R"-substituted piperidinyl;

$R_3$ is halogen; nitro; cyano; $C_1$-$C_4$ alkylenedioxy; unsubstituted or halogen- or morpholinyl-substituted $C_1$-$C_5$ alkyl; $C_1$-$C_5$ alkoxy; —$NR_aR_b$; —C(O)R'; or morpholinyl;

$R_4$ is halogen, nitro, cyano, unsubstituted or halogen-substituted $C_1$-$C_5$ alkyl; $C_1$-$C_5$ alkoxy; —$NR_aR_b$; —C(O)R'; or unsubstituted or $C_1$-$C_5$ alkoxycarbonyl-substituted piperidinyl;

R' is $C_1$-$C_5$ alkyl; $C_1$-$C_5$ alkoxy; —$NR_aR_b$; or unsubstituted or halogen- or $C_1$-$C_5$ alkyl-substituted 5-6 membered heterocyclyl;

R" is $C_1$-$C_5$ alkyl; $C_3$-$C_6$ cycloalkyl; $C_1$-$C_5$ alkylcarbonyl; $C_1$-$C_5$ alkoxycarbonyl; $C_3$-$C_6$ cycloalkylcarbonyl; or unsubstituted benzoyl or benzoyl substituted by substituent(s) selected from halogen, $C_1$-$C_5$ alkyl, halogen-substituted $C_1$-$C_5$ alkyl;

$R_a$ and $R_b$ are independently H or $C_1$-$C_5$ alkyl;

$R_c$ and $R_d$ are independently H or $C_1$-$C_5$ alkyl; or, $R_c$ and $R_d$, together with the N atom to which they are attached, form 3-7 membered heterocyclyl.

$R_e$ is unsubstituted or $C_1$-$C_6$ alkyl- or halogen- or $C_1$-$C_6$ alkoxy-substituted $C_6$-$C_{20}$ aryl, unsubstituted or halogen-substituted $C_1$-$C_6$ alkyl;

$R_f$ is $C_1$-$C_6$ alkyl, or unsubstituted or halogen- or $C_1$-$C_6$ alkyl-substituted 4-7 membered heteroaryl.

In another embodiment of this invention, said 5-member-heterocycle fused pyridine compound has a structure as shown below in Formula (X),

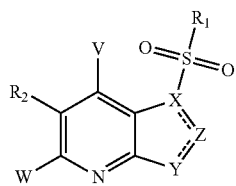

wherein, W and V are independently selected from hydrogen, $C_1$-$C_4$ alkyl, $C_1$-$C_4$ alkoxy;

X and Z are N, Y is C;

$R_1$ is

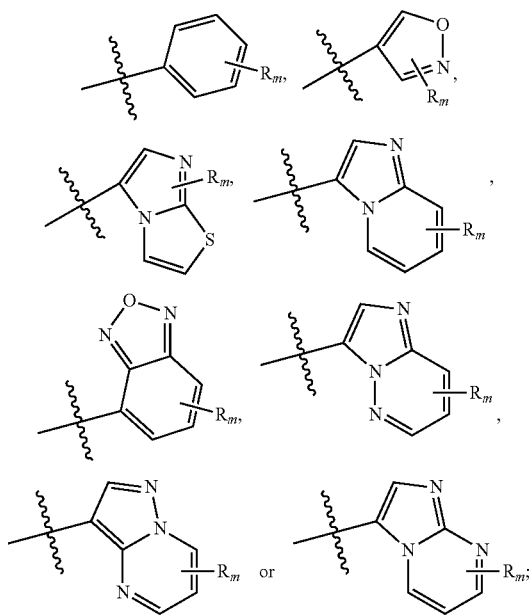

$R_2$ is

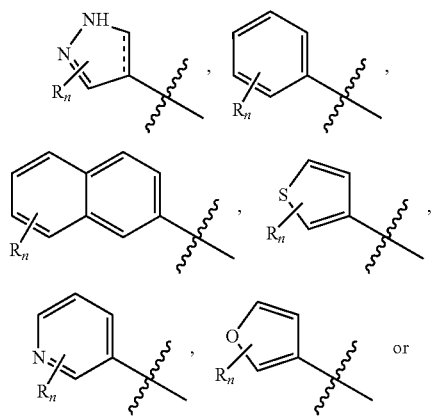

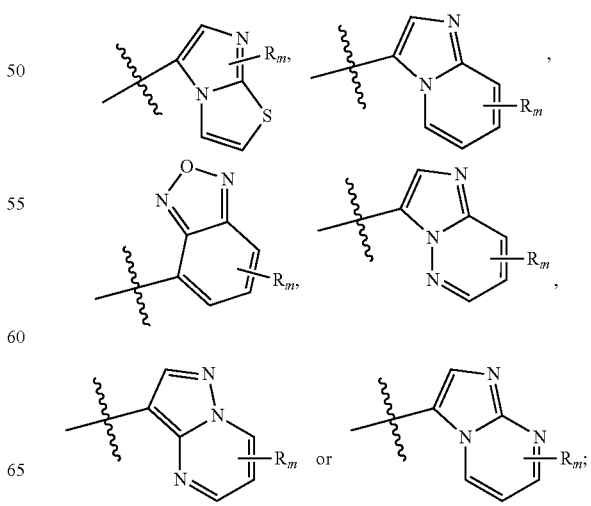

wherein, $R_m$ is H, halogen, nitro, cyano, unsubstituted or halogen- or morpholinyl-substituted $C_1$-$C_4$ alkyl; $C_1$-$C_4$ alkoxy; $C_1$-$C_4$ alkylcarbonyl; $C_1$-$C_4$ alkoxycarbonyl; —$NR_aR_b$; —C(O)($NR_aR_b$); —OC(O)—$R_f$; unsubstituted phenyl or phenyl substituted by 1-3 of $R_3$; or unsubstituted 5-7 membered heteroaryl comprising 1-3 heteroatoms selected from N, O, and S or 5-7 membered heteroaryl comprising 1-3 heteroatoms selected from N, O, and S substituted by 1-3 of $R_4$, wherein said heteroaryl is selected from furanyl, thienyl, pyrrolyl, pyrazolyl, imidazolyl, oxazolyl, isoxazolyl, pyranyl, pyridinyl, morpholinyl, oxazinyl, pyrazinyl;

$R_n$ is H, halogen, nitro, cyano, $C_1$-$C_2$ alkylenedioxy; unsubstituted or halogen-, dimethylamino-, 4-morpholinyl-, 1-aziridinyl-, 1-azetidinyl-, 1-tetrahydropyrrolyl-, 1-piperidinyl- or 1-homopiperidinyl-substituted $C_1$-$C_4$ alkyl; $C_1$-$C_4$ alkoxy; $C_1$-$C_4$ sulfamido; —$NR_aR_b$; —C(O)R'; 4-morpholinyl; or unsubstituted or R"-substituted piperidinyl;

$R_3$ is halogen, nitro, cyano, $C_1$-$C_2$ alkylenedioxy; unsubstituted or halogen- or morpholinyl-substituted $C_1$-$C_4$ alkyl; $C_1$-$C_4$ alkoxy; —$NR_aR_b$; —C(O)R'; or 4-morpholinyl;

$R_4$ is halogen, nitro, cyano, unsubstituted or halogen-substituted $C_1$-$C_4$ alkyl; $C_1$-$C_4$ alkoxy; —$NR_aR_b$; —C(O)R'; 4-piperidinyl; or 1-t-butoxycarbonyl-4-piperidinyl;

R' is $C_1$-$C_4$ alkyl; $C_1$-$C_4$ alkoxy; —$NR_aR_b$; or 4-methylpiperazinyl;

R" is $C_1$-$C_4$ alkyl; $C_3$-$C_6$ cycloalkyl; $C_1$-$C_4$ alkylcarbonyl; $C_1$-$C_4$ alkoxycarbonyl; $C_3$-$C_6$ cycloalkylcarbonyl; or p-trifluoromethylbenzoyl;

$R_a$ and $R_b$ are independently hydrogen, $C_1$-$C_4$ alkyl or $C_1$-$C_4$ alkylcarbonyl;

$R_f$ is $C_1$-$C_6$ alkyl or unsubstituted or halogen- or $C_1$-$C_6$ alkyl-substituted 4-7 membered heteroaryl, said 4-7 membered heteroaryl is selected from furanyl, pyrrolyl, thienyl.

In another embodiment of this invention, said 5-member-heterocycle fused pyridine compound has a structure as shown in Formula II, wherein:

$R_1$ is $R_2$ is

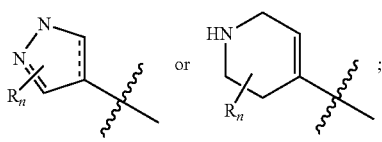

wherein, $R_m$ is H, halogen, nitro, cyano, $C_1$-$C_4$ alkyl, $C_1$-$C_4$ alkoxy, $C_1$-$C_4$ alkylcarbonyl, $C_1$-$C_4$ alkoxycarbonyl;

$R_n$ is H, halogen; nitro; cyano; $C_1$-$C_2$ alkylenedioxy; unsubstituted or halogen-, dimethylamino-, 4-morpholinyl-, 1-aziridinyl-, 1-azetidinyl-, 1-tetrahydropyrrolyl-, 1-piperidinyl- or 1-homopiperidinyl-substituted $C_1$-$C_4$ alkyl; $C_1$-$C_4$ alkoxy; $C_1$-$C_4$ sulfamido; —$NR_aR_b$; —C(O)R'; 4-morpholinyl; or unsubstituted or R''-substituted piperidinyl;

R' is $C_1$-$C_4$ alkyl; $C_1$-$C_4$ alkoxy; —$NR_aR_b$; or 4-methylpiperazinyl;

R'' is $C_1$-$C_4$ alkyl; $C_3$-$C_6$ cycloalkyl; $C_1$-$C_4$ alkylcarbonyl; $C_1$-$C_4$ alkoxycarbonyl; $C_3$-$C_6$ cycloalkylcarbonyl; or p-trifluoromethylbenzoyl;

$R_a$ and $R_b$ are independently H, $C_1$-$C_4$ alkyl or $C_1$-$C_4$ alkylcarbonyl;

$R_f$ is $C_1$-$C_6$ alkyl, or unsubstituted or halogen- or $C_1$-$C_6$ alkyl-substituted 4-7 membered heteroaryl.

In another embodiment of this invention, said 5-member-heterocycle fused pyridine compound has a structure as shown in Formula II, wherein:

$R_1$ is

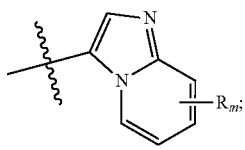

$R_2$ is

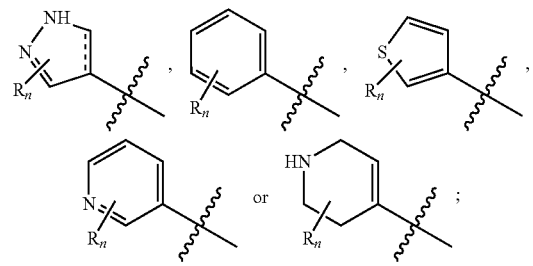

wherein, $R_m$ is H, halogen; nitro; hydroxyl; $C_1$-$C_4$ alkoxy; unsubstituted phenyl or phenyl substituted by 1-3 of $R_3$; or unsubstituted 5-7 membered heteroaryl comprising 1-3 heteroatoms selected from N, O, and S or 5-7 membered heteroaryl comprising 1-3 heteroatoms selected from N, O, and S substituted by 1-3 of $R_4$, wherein said heteroaryl is selected from furanyl, thienyl, pyrrolyl, pyrazolyl, imidazolyl, oxazolyl, isoxazolyl, pyranyl, pyridinyl, morpholinyl, oxazinyl, pyrazinyl;

$R_n$ is H, halogen, nitro, cyano unsubstituted or halogen-, dimethylamino-, 4-morpholinyl-, 1-aziridinyl-, 1-azetidinyl-, 1-tetrahydropyrrolyl-, 1-piperidinyl- or 1-homopiperidinyl-substituted $C_1$-$C_4$ alkyl; $C_1$-$C_4$ alkoxy; $C_1$-$C_4$ sulfamido; —$NR_aR_b$; —C(O)R'; 4-morpholinyl; or unsubstituted or R''-substituted piperidinyl;

R' is $C_1$-$C_4$ alkyl; $C_1$-$C_4$ alkoxy; —$NR_aR_b$; or 4-methylpiperazinyl;

R'' is $C_1$-$C_4$ alkyl; $C_3$-$C_6$ cycloalkyl; $C_1$-$C_4$ alkylcarbonyl; $C_1$-$C_4$ alkoxycarbonyl; $C_3$-$C_6$ cycloalkylcarbonyl; or p-trifluoromethylbenzoyl;

$R_a$ and $R_b$ are independently H, $C_1$-$C_4$ alkyl or $C_1$-$C_4$ alkylcarbonyl.

In another embodiment of this invention, said 5-member-heterocycle fused pyridine compound has a structure as shown in Formula II, wherein:

$R_1$ is

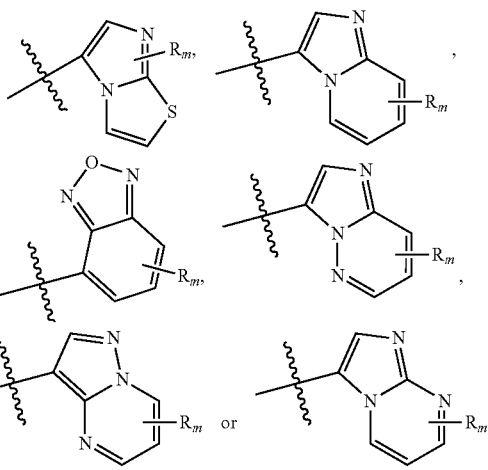

$R_2$ is

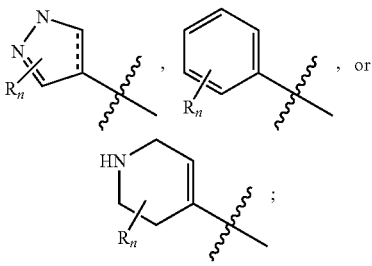

wherein, $R_m$ is H, halogen; nitro; cyano; unsubstituted or halogen- or morpholinyl-substituted $C_1$-$C_4$ alkyl; $C_1$-$C_4$ alkoxy; $C_1$-$C_4$ alkylcarbonyl; $C_1$-$C_4$ alkoxycarbonyl; —$NR_aR_b$; —C(O)($NR_aR_b$); —OC(O)—$R_f$; unsubstituted phenyl or phenyl substituted by 1-3 of $R_3$; or unsubstituted 5-7 membered heteroaryl comprising 1-3 heteroatoms selected from N, O, and S or 5-7 membered heteroaryl comprising 1-3 heteroatoms selected from N, O, and S substituted by 1-3 of $R_4$, wherein said heteroaryl is selected from furanyl, thienyl, pyrrolyl, pyrazolyl, imidazolyl, oxazolyl, isoxazolyl, pyranyl, pyridinyl, morpholinyl, oxazinyl, pyrazinyl;

$R_n$ is H, halogen; unsubstituted or halogen-, dimethylamino-, 4-morpholinyl-, 1-aziridinyl-, 1-azetidinyl-, 1-tetrahydropyrrolyl-, 1-piperidinyl- or 1-homopiperidinyl-substituted $C_1$-$C_4$ alkyl; $C_1$-$C_4$ alkoxy; $C_1$-$C_4$ sulfamido; —C(O)R'; 4-morpholinyl; or unsubstituted or R''-substituted piperidinyl;

R₃ is halogen, nitro, cyano, $C_1$-$C_2$ alkylenedioxy; unsubstituted or halogen- or morpholinyl-substituted $C_1$-$C_4$ alkyl; $C_1$-$C_4$ alkoxy; —$NR_aR_b$; —C(O)R'; or 4-morpholinyl;

R₄ is halogen, nitro, cyano, unsubstituted or halogen-substituted $C_1$-$C_4$ alkyl; $C_1$-$C_4$ alkoxy; —$NR_aR_b$; —C(O)R'; 4-piperidinyl; or 1-t-butoxycarbonyl-4-piperidinyl;

R' is $C_1$-$C_4$ alkyl; $C_1$-$C_4$ alkoxy; —$NR_aR_b$; or 4-methylpiperazinyl;

R" is $C_1$-$C_4$ alkyl; $C_3$-$C_6$ cycloalkyl; $C_1$-$C_4$ alkylcarbonyl; $C_1$-$C_4$ alkoxycarbonyl; $C_3$-$C_6$ cycloalkylcarbonyl; or p-trifluoromethylbenzoyl;

$R_a$ and $R_b$ are independently H, $C_1$-$C_4$ alkyl or $C_1$-$C_4$ alkylcarbonyl;

$R_f$ is $C_1$-$C_6$ alkyl, or unsubstituted or halogen- or $C_1$-$C_6$ alkyl-substituted 4-7 membered heteroaryl, said 4-7 membered heteroaryl is selected from furanyl, pyrrolyl, thienyl.

A person skilled in the art will appreciate that, any of the embodiments described above, including any preferred embodiments or more preferred embodiment, may combine with each other in any way to form new technical solutions, such technical solutions shall be considered as within the scope of explicit description provided herein.

In preferred embodiment of this invention, said 5-member-heterocycle fused pyridine compound is a compound selected from the following compound:

| No. | Compound | Structure |
|---|---|---|
| 01 | 1-(2-nitrobenzenesulfonyl)-6-[(1-methyl)-4-pyrazolyl]-1-H-pyrrolo[3,2-b]pyridine | 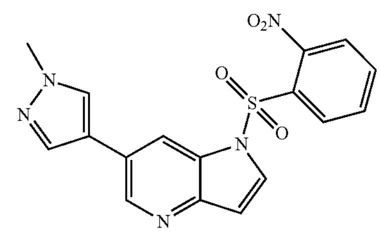 [SMILES: Cn1cc(-c2cnc3ccn(S(=O)(=O)c4ccccc4[N+](=O)[O-])c3c2)cn1] |
| 02 | 3-(2-nitrobenzenesulfonyl)-5-[(1-methyl)-4-pyrazolyl]-1-H-pyrazolo[3,4-b]pyridine | 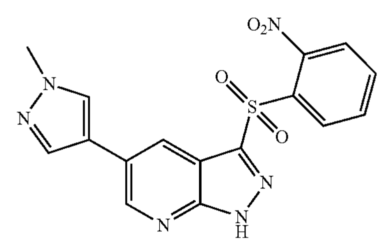 [SMILES: Cn1cc(-c2cnc3[nH]nc(S(=O)(=O)c4ccccc4[N+](=O)[O-])c3c2)cn1] |
| 03 | 1-(2-nitrobenzenesulfonyl)-6-[(1-methyl)-4-pyrazolyl]-1-H-pyrazolo[4,3-b]pyridine | 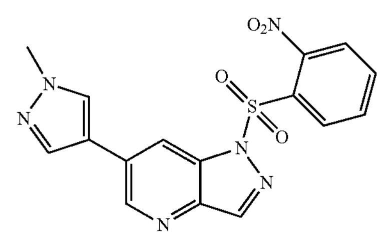 [SMILES: Cn1cc(-c2cnc3cnn(S(=O)(=O)c4ccccc4[N+](=O)[O-])c3c2)cn1] |
| 04 | 1-benzenesulfonyl-6-[(1-methyl)-4-pyrazolyl]-1-H-pyrazolo[4,3-b]pyridine | 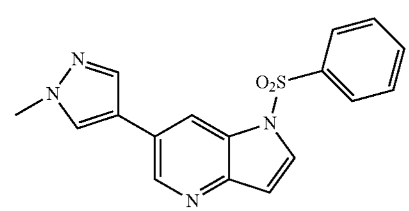 [SMILES: Cn1cc(-c2cnc3ccn(S(=O)(=O)c4ccccc4)c3c2)cn1] |
| 05 | 1-(3-fluorobenzenesulfonyl)-6-[(1-methyl)-4-pyrazolyl]-1-H-pyrazolo[4,3-b]pyridine | 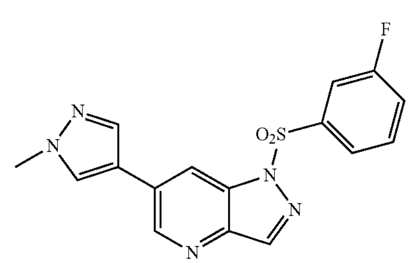 [SMILES: Cn1cc(-c2cnc3cnn(S(=O)(=O)c4cccc(F)c4)c3c2)cn1] |

-continued

| No. | Compound | Structure |
|---|---|---|
| 06 | 1-(2-fluorobenzenesulfonyl)-6-[(1-methyl)-4-pyrazolyl]-1-H-pyrazolo[4,3-b]pyridine | 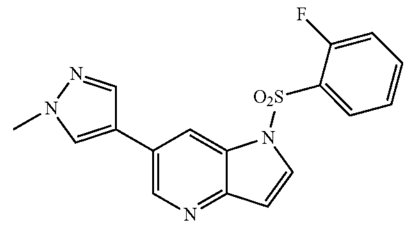 [SMILES: Cn1cc(-c2cnc3ccn(S(=O)(=O)c4ccccc4F)c3c2)cn1] |
| 07 | 1-(4-fluorobenzenesulfonyl)-6-[(1-methyl)-4-pyrazolyl]1-H-pyrazolo[4,3-b]pyridine | 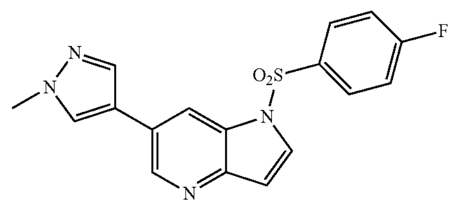 [SMILES: Cn1cc(-c2cnc3ccn(S(=O)(=O)c4ccc(F)cc4)c3c2)cn1] |
| 08 | 1-(2-cyanobenzenesulfonyl)-6-[(1-methyl)-4-pyrazolyl]-1-H-pyrazolo[4,3-b]pyridine | 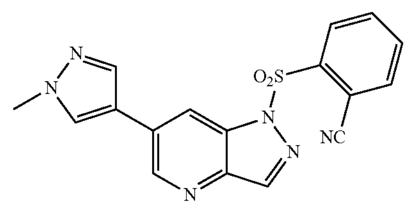 [SMILES: Cn1cc(-c2cnc3cnn(S(=O)(=O)c4ccccc4C#N)c3c2)cn1] |
| 09 | 1-(4-nitrobenzenesulfonyl)-6-[(1-methyl)-4-pyrazolyl]-1-H-pyrazolo[4,3-b]pyridine | 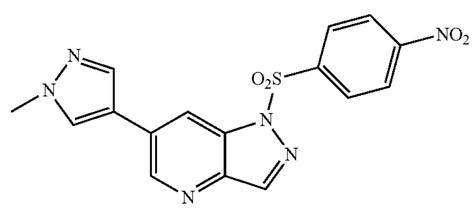 [SMILES: Cn1cc(-c2cnc3cnn(S(=O)(=O)c4ccc([N+](=O)[O-])cc4)c3c2)cn1] |
| 10 | 1-(3,4-dimethoxybenzenesulfonyl)-6-[(1-methyl)-4-pyrazolyl]-1-H-pyrazolo[4,3-b]pyridine | 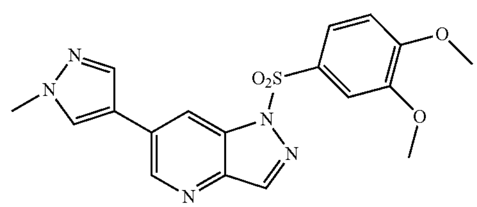 |
| 11 | 1-(3,5-dimethylisoxazolsulfonyl)-6-[(1-methyl)-4-pyrazolyl]-1-H-pyrazolo[4,3-b]pyridine | 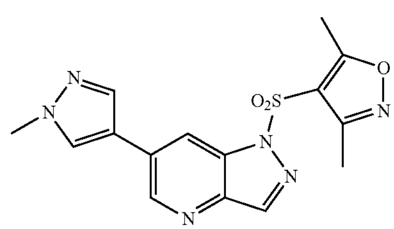 [SMILES: Cc1noc(C)c1S(=O)(=O)n1ncc2ncc(-c3cnn(C)c3)cc21] |
| 12 | 1-(2,4-difluorobenzenesulfonyl)-6-[(1-methyl)-4-pyrazolyl]-1-H-pyrazolo[4,3-b]pyridine | 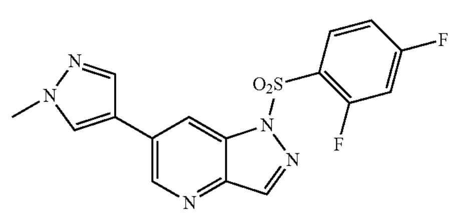 [SMILES: Cn1cc(-c2cnc3cnn(S(=O)(=O)c4ccc(F)cc4F)c3c2)cn1] |

-continued

| No. | Compound | Structure |
|-----|----------|-----------|
| 13 | 1-(4-acetylbenzenesulfonyl)-6-[(1-methyl)-4-pyrazolyl]-1-H-pyrazolo[4,3-b]pyridine | 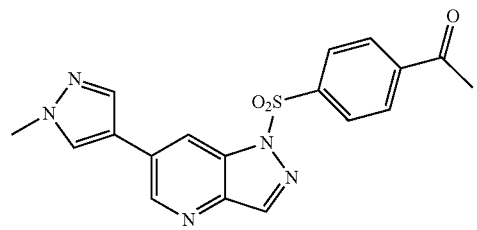 [SMILES: CC(=O)c1ccc(S(=O)(=O)n2ncc3ncc(-c4cnn(C)c4)cc32)cc1] |
| 14 | 1-(2-trifluoromethylbenzenesulfonyl)-6-[(1-methyl)-4-pyrazolyl]-1-H-pyrazolo[4,3-b]pyridine | 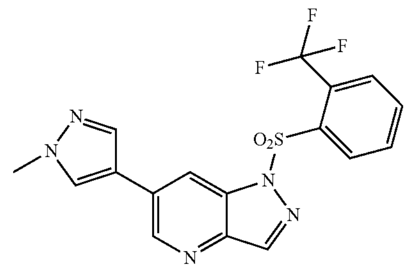 [SMILES: Cn1cc(-c2cnc3cnn(S(=O)(=O)c4ccccc4C(F)(F)F)c3c2)cn1] |
| 15 | 1-(4-trifluoromethylbenzenesulfonyl)-6-[(1-methyl)-4-pyrazolyl]-1-H-pyrazolo[4,3-b]pyridine | 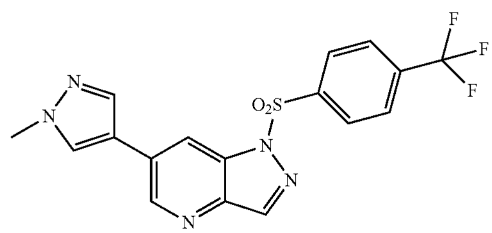 [SMILES: Cn1cc(-c2cnc3cnn(S(=O)(=O)c4ccc(C(F)(F)F)cc4)c3c2)cn1] |
| 16 | 1-(3-trifluoromethylbenzenesulfonyl)-6-[(1-methyl)-4-pyrazolyl]-1-H-pyrazolo[4,3-b]pyridine | 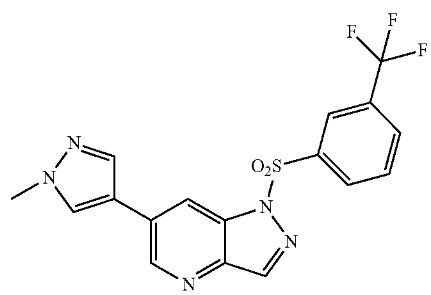 [SMILES: Cn1cc(-c2cnc3cnn(S(=O)(=O)c4cccc(C(F)(F)F)c4)c3c2)cn1] |
| 17 | 1-(4-methoxybenzenesulfonyl)-6-[(1-methyl)-4-pyrazolyl]-1-H-pyrazolo[4,3-b]pyridine | 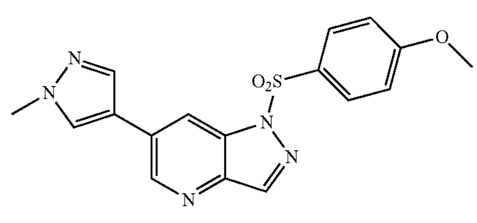 |
| 18 | 1-[(6-chloro-imidazo[2,1-b]thiazole)-5-sulfonyl)]-6-[(1-methyl)-4-pyrazolyl]-1-H-pyrazolo[4,3-b]pyridine | 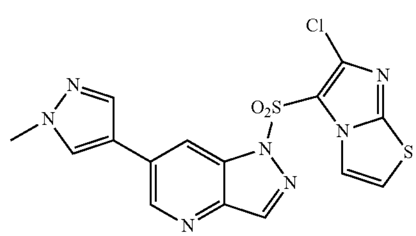 [SMILES: Cn1cc(-c2cnc3cnn(S(=O)(=O)c4c(Cl)nc5sccn45)c3c2)cn1] |

-continued

| No. | Compound | Structure |
|---|---|---|
| 19 | 1-(imidazo[1,2-a]pyridine-3-sulfonyl)-6-[(1-methyl)-4-pyrazolyl]-1-H-pyrazolo[4,3-b]pyridine | 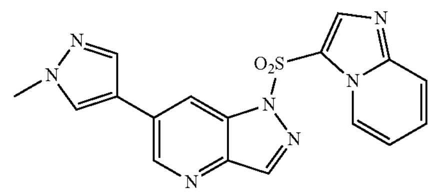 [SMILES: Cn1cc(-c2cnc3cnn(S(=O)(=O)c4cnc5ccccn45)c3c2)cn1] |
| 20 | 1-(benzo[1,2,5]oxadiazole-4-sulfonyl)-6-[(1-methyl)-4-pyrazolyl]-1-H-pyrazolo[4,3-b]pyridine | 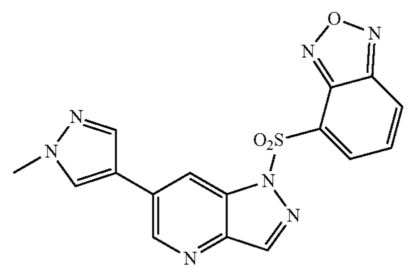 [SMILES: Cn1cc(-c2cnc3cnn(S(=O)(=O)c4cccc5nonc45)c3c2)cn1] |
| 21 | 1-(imidazo[1,2-b]pyridazine-3-sulfonyl)-6-[(1-methyl)-4-pyrazolyl]-1-H-pyrazolo[4,3-b]pyridine | 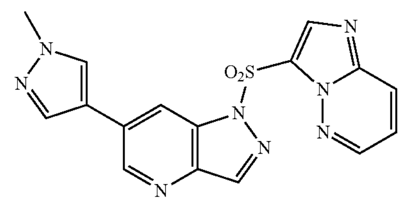 [SMILES: Cn1cc(-c2cnc3cnn(S(=O)(=O)c4cnc5cccnn45)c3c2)cn1] |
| 22 | 1-(pyrazolo[1,5-a]pyrimidine-3-sulfonyl)-6-[(1-methyl)-4-pyrazolyl]-1-H-pyrazolo[4,3-b]pyridine | 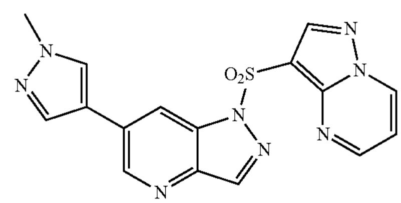 [SMILES: Cn1cc(-c2cnc3cnn(S(=O)(=O)c4cnn5cccnc45)c3c2)cn1] |
| 23 | 1-(imidazo[1,2-a]pyrimidine-3-sulfonyl)-6-[(1-methyl)-4-pyrazolyl]-1-H-pyrazolo[4,3-b]pyridine | 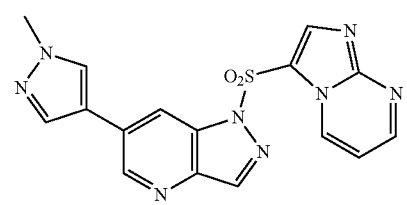 [SMILES: Cn1cc(-c2cnc3cnn(S(=O)(=O)c4cnc5ncccn45)c3c2)cn1] |
| 24 | 1-[(6-chloro-imidazo[1,2-a]pyridine)-3-sulfonyl]-6-[(1-methyl)-4-pyrazolyl]-1-H-pyrazolo[4,3-b]pyridine | 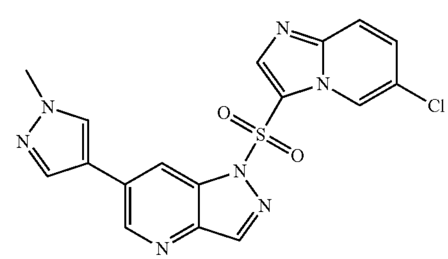 [SMILES: Cn1cc(-c2cnc3cnn(S(=O)(=O)c4cnc5ccc(Cl)cn45)c3c2)cn1] |

-continued

| No. | Compound | Structure |
|-----|----------|-----------|
| 25 | 1-[(6-chloro-imidazo[1,2-b]pyridazine)-3-sulfonyl)]-6-[(1-methyl)-4-pyrazolyl]-1-H-pyrazolo[4,3-b]pyridine | 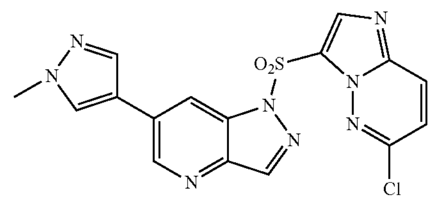 [SMILES: Cn1cc(-c2cnc3cnn(S(=O)(=O)c4cnc5ccc(Cl)nn45)c3c2)cn1] |
| 26 | 1-[(6-trifluoromethyl-imidazo[1,2-a]pyridine)-3-sulfonyl)]-6-[(1-methyl)-4-pyrazolyl]-1-H-pyrazolo[4,3-b]pyridine | 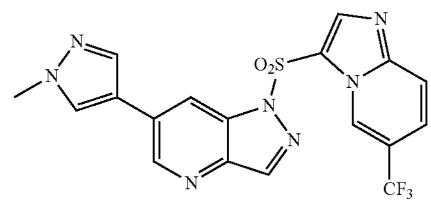 [SMILES: Cn1cc(-c2cnc3cnn(S(=O)(=O)c4cnc5ccc(C(F)(F)F)cn45)c3c2)cn1] |
| 27 | 1-{(6-[(1-methyl)-4-pyrazolyl]-imidazo[1,2-a]pyridine)-3-sulfonyl}-6-[(1-methyl)-4-pyrazolyl]-1-H-pyrazolo[4,3-b]pyridine | 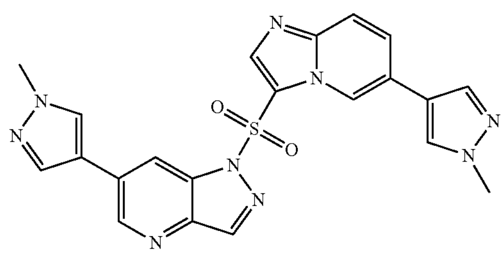 [SMILES: Cn1cc(-c2cnc3cnn(S(=O)(=O)c4cnc5ccc(-c6cnn(C)c6)cn45)c3c2)cn1] |
| 28 | 1-(imidazo[1,2-a]pyridine-3-sulfonyl)-6-phenyl-1-H-pyrazolo[4,3-b]pyridine | 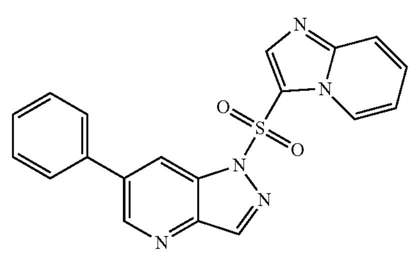 [SMILES: O=S(=O)(c1cnc2ccccn12)n1ncc2ncc(-c3ccccc3)cc21] |
| 29 | 1-(imidazo[1,2-a]pyridine-3-sulfonyl)-6-(3-thienyl)-1-H-pyrazolo[4,3-b]pyridine | 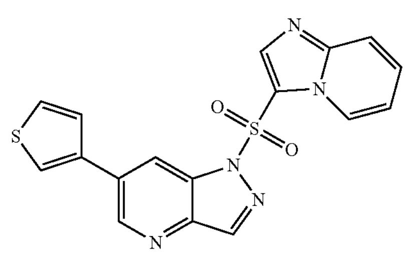 [SMILES: O=S(=O)(c1cnc2ccccn12)n1ncc2ncc(-c3ccsc3)cc21] |
| 30 | 1-(imidazo[1,2-a]pyridine-3-sulfonyl)-6-(3-pyridinyl)-1-H-pyrazolo[4,3-b]pyridine | 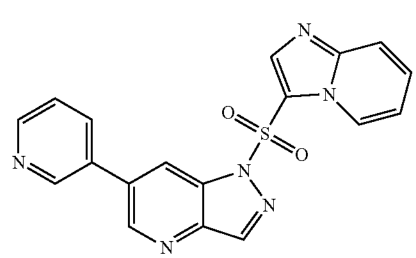 [SMILES: O=S(=O)(c1cnc2ccccn12)n1ncc2ncc(-c3cccnc3)cc21] |

| No. | Compound | Structure |
|---|---|---|
| 31 | 1-(imidazo[1,2-a]pyridine-3-sulfonyl)-6-(3-furanyl)-1-H-pyrazolo[4,3-b]pyridine | 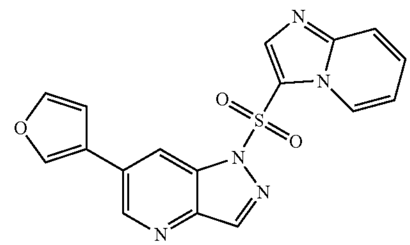 [SMILES: O=S(=O)(c1cnc2ccccn12)n1ncc2ncc(-c3ccoc3)cc21] |
| 32 | 1-(imidazo[1,2-a]pyridine-3-sulfonyl)-6-(4-trifluoromethylphenyl]-1-H-pyrazolo[4,3-b]pyridine | 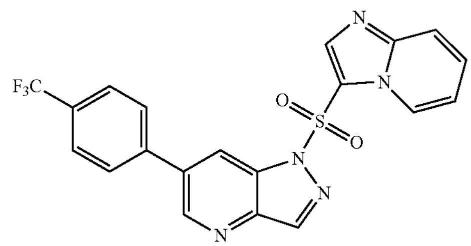 [SMILES: O=S(=O)(c1cnc2ccccn12)n1ncc2ncc(-c3ccc(C(F)(F)F)cc3)cc21] |
| 33 | 1-(imidazo[1,2-a]pyridine-3-sulfonyl)-6-(2-naphthyl)-1-H-pyrazolo[4,3-b]pyridine | 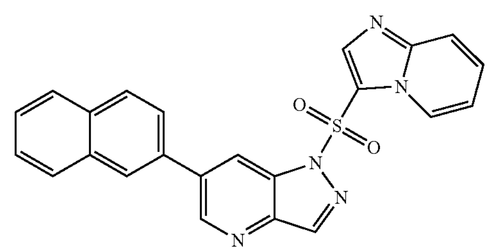 [SMILES: O=S(=O)(c1cnc2ccccn12)n1ncc2ncc(-c3ccc4ccccc4c3)cc21] |
| 34 | 1-(imidazo[1,2-a]pyridine-3-sulfonyl)-6-(4-methylsulfamidophenyl]-1-H-pyrazolo[4,3-b]pyridine | 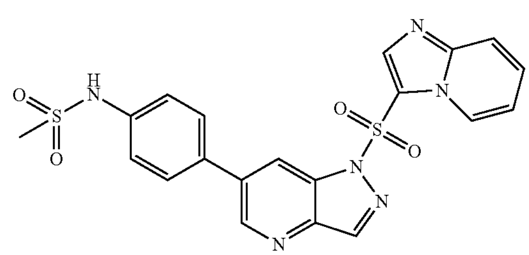 [SMILES: CS(=O)(=O)Nc1ccc(-c2cnc3cnn(S(=O)(=O)c4cnc5ccccn45)c3c2)cc1] |
| 35 | 1-(imidazo[1,2-a]pyridine-3-sulfonyl)-6-[(1-t-butoxycarbonyl)-4-(1,2,3,6-tetrahydropyridinyl)]-1-H-pyrazolo[4,3-b]pyridine | 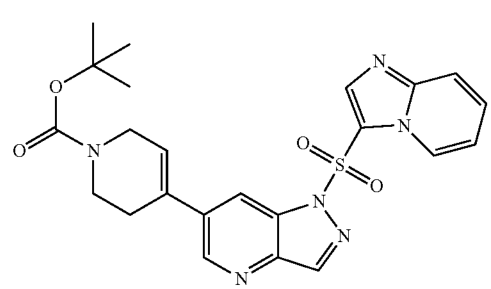 [SMILES: CC(C)(C)OC(=O)N1CC=C(c2cnc3cnn(S(=O)(=O)c4cnc5ccccn45)c3c2)CC1] |
| 36 | 1-(imidazo[1,2-a]pyridine-3-sulfonyl)-6-[6-(1,4-benzodioxanyl)]-1-H-pyrazolo[4,3-b]pyridine | 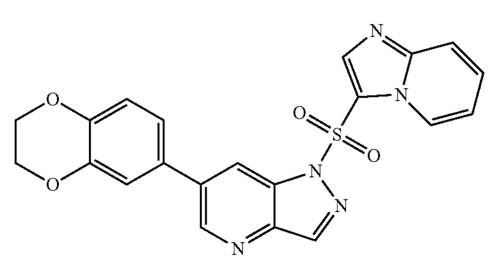 [SMILES: O=S(=O)(c1cnc2ccccn12)n1ncc2ncc(-c3ccc4c(c3)OCCO4)cc21] |

| No. | Compound | Structure |
| --- | --- | --- |
| 37 | 1-(imidazo[1,2-a]pyridine-3-sulfonyl)-6-[4-(4-methylpiperazine-1-carbonyl)phenyl]-1-H-pyrazolo[4,3-b]pyridine | 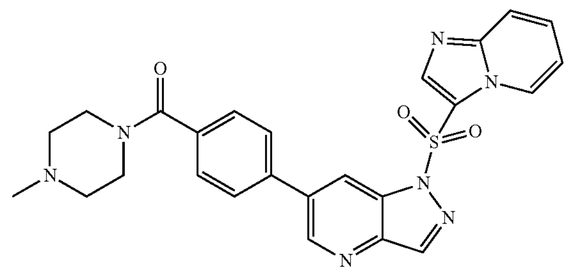 [SMILES: CN1CCN(C(=O)c2ccc(-c3cnc4cnn(S(=O)(=O)c5cnc6ccccn56)c4c3)cc2)CC1] |
| 38 | 1-(imidazo[1,2-a]pyridine-3-sulfonyl)-6-(4-morpholinomethylphenyl)-1-H-pyrazolo[4,3-b]pyridine | 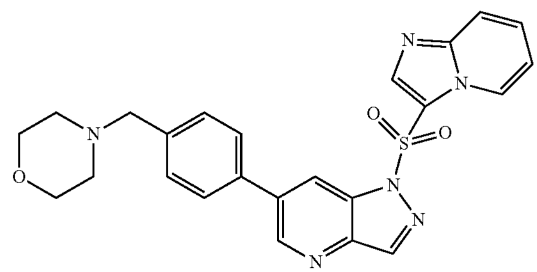 [SMILES: O=S(=O)(c1cnc2ccccn12)n1ncc2ncc(-c3ccc(CN4CCOCC4)cc3)cc21] |
| 39 | 1-(imidazo[1,2-a]pyridine-3-sulfonyl)-6-(4-morpholinylphenyl)-1-H-pyrazolo[4,3-b]pyridine | 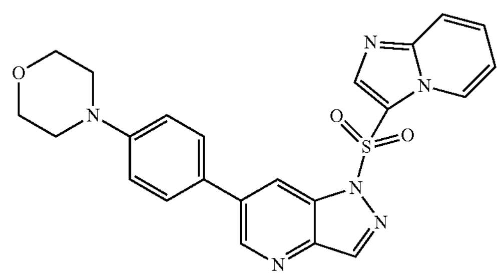 [SMILES: O=S(=O)(c1cnc2ccccn12)n1ncc2ncc(-c3ccc(N4CCOCC4)cc3)cc21] |
| 40 | 1-(imidazo[1,2-a]pyridine-3-sulfonyl)-6-(4-acetyl-phenyl)-1-H-pyrazolo[4,3-b]pyridine | 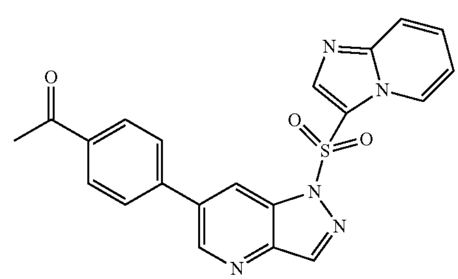 [SMILES: CC(=O)c1ccc(-c2cnc3cnn(S(=O)(=O)c4cnc5ccccn45)c3c2)cc1] |
| 41 | 1-(imidazo[1,2-a]pyridine-3-sulfonyl)-6-(4-dimethylaminocarbonylphenyl)-1-H-pyrazolo[4,3-b]pyridine | 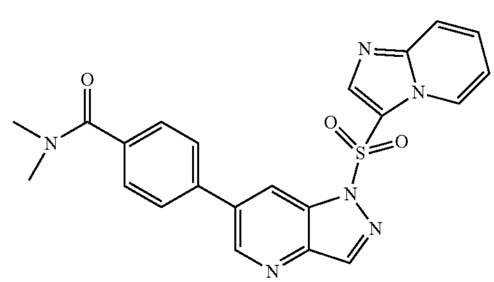 [SMILES: CN(C)C(=O)c1ccc(-c2cnc3cnn(S(=O)(=O)c4cnc5ccccn45)c3c2)cc1] |

-continued

| No. | Compound | Structure |
|---|---|---|
| 42 | 1-(imidazo[1,2-a]pyridine-3-sulfonyl)-6-(4-dimethylaminophenyl)-1-H-pyrazolo[4,3-b]pyridine | 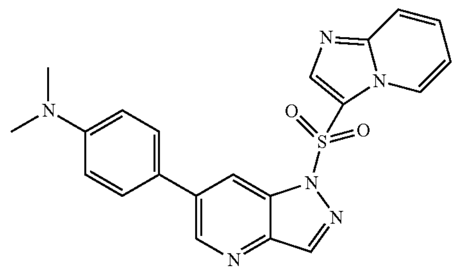 [SMILES: CN(C)c1ccc(-c2cnc3cnn(S(=O)(=O)c4cnc5ccccn45)c3c2)cc1] |
| 43 | 1-(imidazo[1,2-a]pyridine-3-sulfonyl)-6-(2,5-dimethoxyphenyl)-1-H-pyrazolo[4,3-b]pyridine | 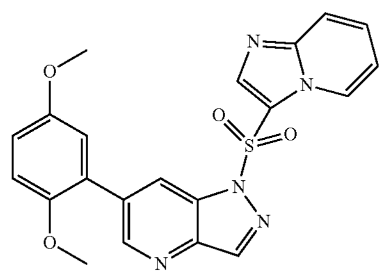 [SMILES: COc1ccc(OC)c(-c2cnc3cnn(S(=O)(=O)c4cnc5ccccn45)c3c2)c1] |
| 44 | 1-(imidazo[1,2-a]pyridine-3-sulfonyl)-6-{{1-[(1-t-butoxycarbonyl)-4-piperidinyl]}-4-pyrazolyl}-1-H-pyrazolo[4,3-b]pyridine | 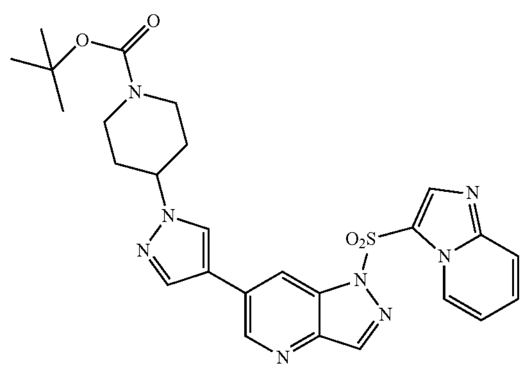 [SMILES: CC(C)(C)OC(=O)N1CCC(n2cc(-c3cnc4cnn(S(=O)(=O)c5cnc6ccccn56)c4c3)cn2)CC1] |
| 45 | 1-(imidazo[1,2-a]pyridine-3-sulfonyl)-6-{[1-(4-piperidinyl)]-4-pyrazolyl}-1-H-pyrazolo[4,3-b]pyridine | 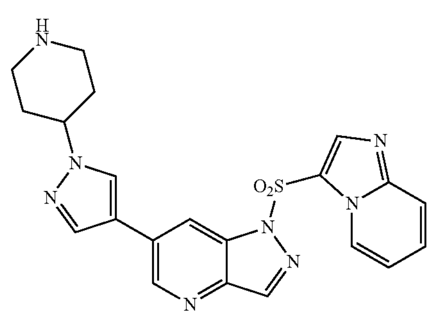 [SMILES: O=S(=O)(c1cnc2ccccn12)n1ncc2ncc(-c3cnn(C4CCNCC4)c3)cc21] |

| No. | Compound | Structure |
|---|---|---|
| 46 | 1-(pyrazolo[1,5-a]pyrimidine-3-sulfonyl)-6-{{1-[(1-t-butoxycarbonyl)-4-piperidinyl]}-4-pyrazol-yl}-1-H-pyrazolo[4,3-b]pyridine | 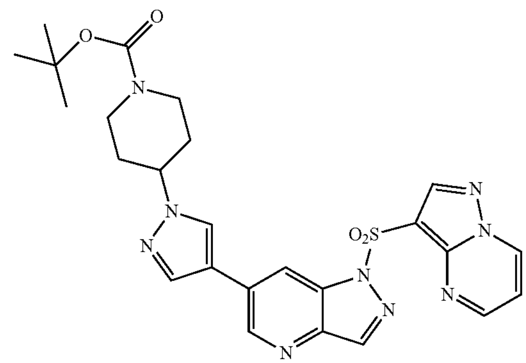 [SMILES: CC(C)(C)OC(=O)N1CCC(n2cc(-c3cnc4cnn(S(=O)(=O)c5cnn6cccnc56)c4c3)cn2)CC1] |
| 47 | 1-(imidazo[1,2-a]pyrimidine-3-sulfonyl)-6-{[1-(4-piperidinyl)]-4-pyrazolyl}-1-H-pyrazolo[4,3-b]pyridine | 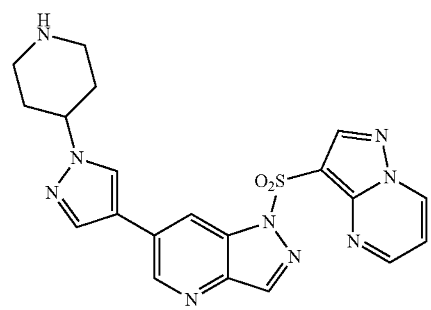 [SMILES: O=S(=O)(c1cnn2cccnc12)n1ncc2ncc(-c3cnn(C4CCNCC4)c3)cc21] |
| 48 | 1-[(6-chloro-imidazo[2,1-b]thiazole)-5-sulfonyl)]-6-{[1-(4-piperidinyl)]-4-pyrazolyl}-1-H-pyrrolo[4,3-b]pyridine | 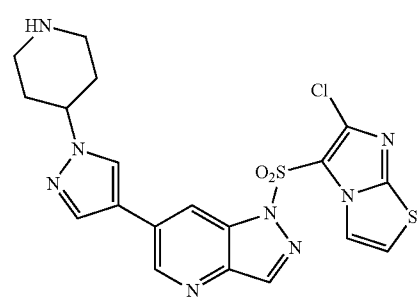 [SMILES: O=S(=O)(c1c(Cl)nc2sccn12)n1ncc2ncc(-c3cnn(C4CCNCC4)c3)cc21] |
| 49 | 1-(imidazo[1,2-b]pyridazine-3-sulfonyl)-6-{{1-[(1-t-butoxycarbonyl)-4-piperidinyl]}-4-pyrazolyl}-1-H-pyrazolo[4,3-b]pyridine | 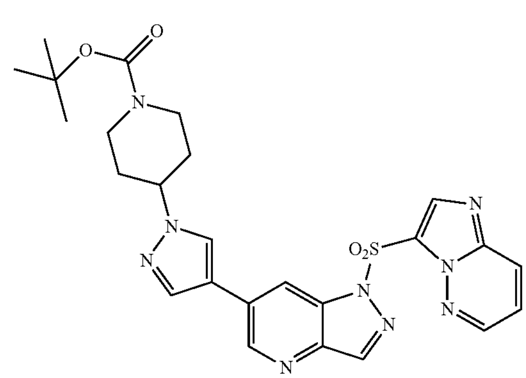 [SMILES: CC(C)(C)OC(=O)N1CCC(n2cc(-c3cnc4cnn(S(=O)(=O)c5cnc6cccnn56)c4c3)cn2)CC1] |

| No. | Compound | Structure |
|---|---|---|
| 50 | 1-(imidazo[1,4-b]pyridazine-3-sulfonyl)-6-{[1-(4-piperidinyl)]-4-pyrazolyl}-4-pyrazolyl}-1-H-pyrazolo[4,3-b]pyridine chloride | 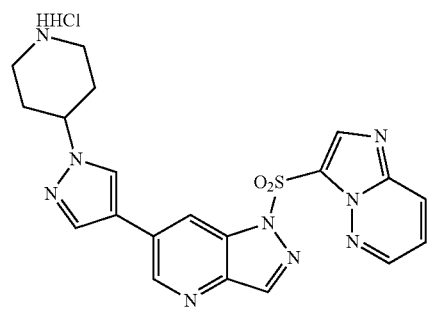 |
| 51 | 1-(imidazo[1,2-b]pyridazine-3-sulfonyl)-6-{[1-(4-piperidinyl)]-4-pyrazolyl}-4-pyrazolyl}-1-H-pyrazolo[4,3-b]pyridine | 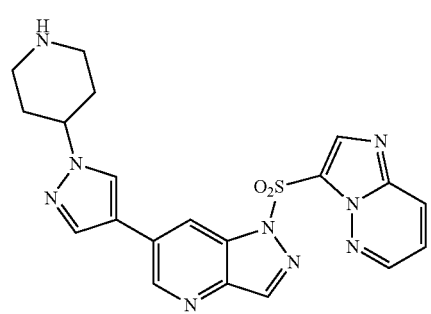 [SMILES: O=S(=O)(c1cnc2cccnn12)n1ncc2ncc(-c3cnn(C4CCNCC4)c3)cc21] |
| 52 | 1-(imidazo[1,2-a]pyrimidine-3-sulfonyl)-6-{{1-[(1-t-butoxycarbonyl)-4-piperidinyl]}-4-pyrazolyl}-1-H-pyrazolo[4,3-b]pyridine | 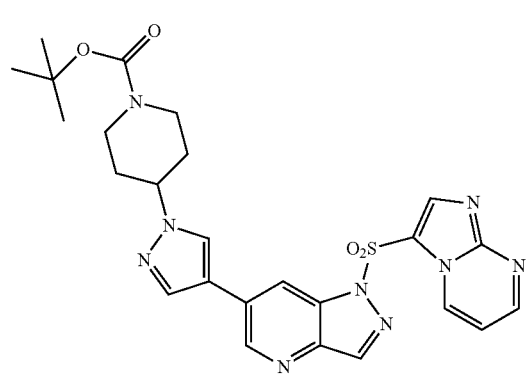 [SMILES: CC(C)(C)OC(=O)N1CCC(n2cc(-c3cnc4cnn(S(=O)(=O)c5cnc6ncccn56)c4c3)cn2)CC1] |
| 53 | 1-(imidazo[1,2-a]pyridine-3-sulfonyl)-6-{{1-[(1-ethyl)-4-piperidinyl]}-4-pyrazolyl}-1-H-pyrazolo[4,3-b]pyridine | 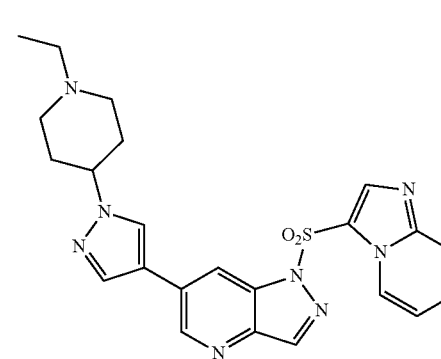 |

| No. | Compound | Structure |
|---|---|---|
| 54 | 1-(imidazo[1,2-a]pyridine-3-sulfonyl)-6-{{1-[(1-acetyl)-4-piperidinyl]}-4-pyrazolyl}-1-H-pyrazolo[4,3-b]pyridine | 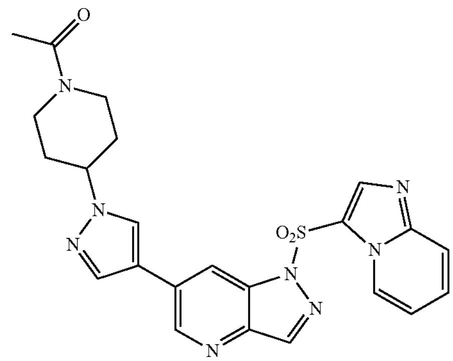 [SMILES: CC(=O)N1CCC(n2cc(-c3cnc4cnn(S(=O)(=O)c5cnc6ccccn56)c4c3)cn2)CC1] |
| 55 | 1-(imidazo[1,2-a]pyridine-3-sulfonyl)-6-{{1-[(1-cylcopropylcarbonyl)-4-piperidinyl]}-4-pyrazolyl}-1-H-pyrazolo[4,3-b]pyridine | 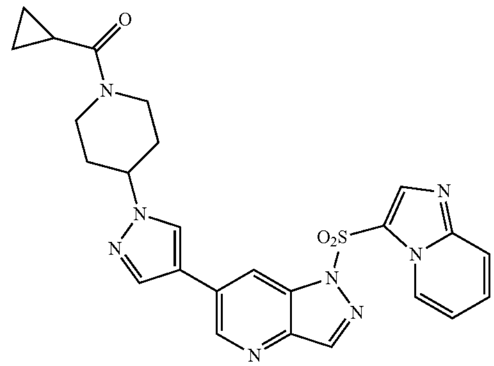 [SMILES: O=C(C1CC1)N1CCC(n2cc(-c3cnc4cnn(S(=O)(=O)c5cnc6ccccn56)c4c3)cn2)CC1] |
| 56 | 1-(imidazo[1,2-a]pyridine-3-sulfonyl)-6-{{1-[(1-cylcopentylcarbonyl)-4-piperidinyl]}-4-pyrazolyl}-1-H-pyrazolo[4,3-b]pyridine | 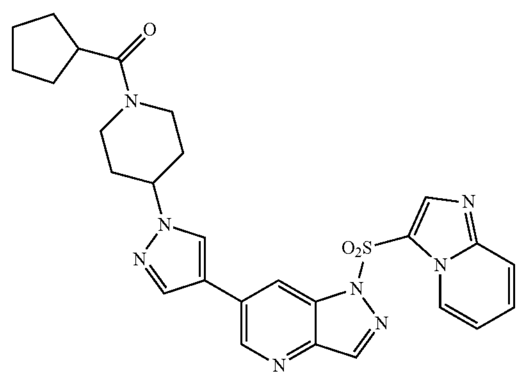 [SMILES: O=C(C1CCCC1)N1CCC(n2cc(-c3cnc4cnn(S(=O)(=O)c5cnc6ccccn56)c4c3)cn2)CC1] |
| 57 | 1-(imidazo[1,2-a]pyridine-3-sulfonyl)-6-{{1-[(1-cyclohexylcarbonyl)-4-piperidinyl]}-4-pyrazolyl}-1-H-pyrazolo[4,3-b]pyridine | 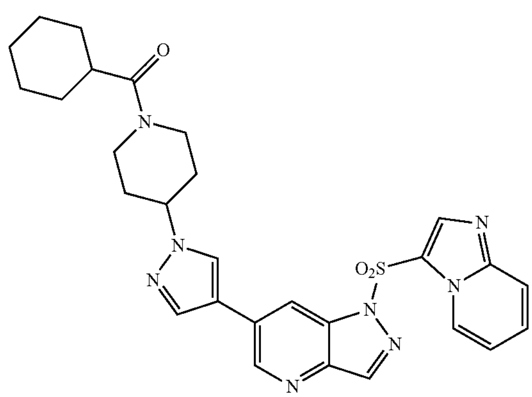 [SMILES: O=C(C1CCCCC1)N1CCC(n2cc(-c3cnc4cnn(S(=O)(=O)c5cnc6ccccn56)c4c3)cn2)CC1] |

-continued

| No. | Compound | Structure |
|---|---|---|
| 58 | 1-(imidazo[1,2-a]pyridine-3-sulfonyl)-6-{{1-[(1-p-trifluoroformyl)-4-piperidinyl]}-4-pyrazolyl}-1-H-pyrazolo[4,3-b]pyridine | 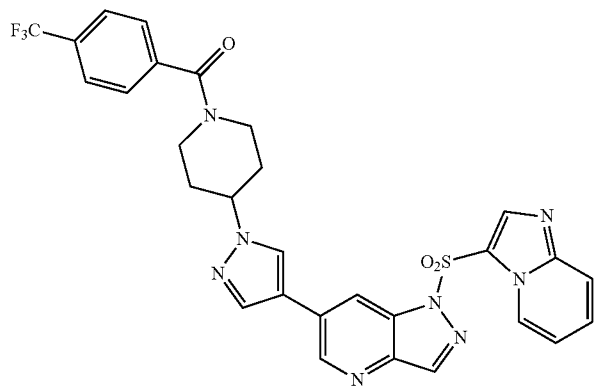 [SMILES: O=C(c1ccc(C(F)(F)F)cc1)N1CCC(n2cc(-c3cnc4cnn(S(=O)(=O)c5cnc6ccccn56)c4c3)cn2)CC1] |
| 59 | 1-(imidazo[1,2-a]pyridine-3-sulfonyl)-6-{{1-[(1-isopropyl)-4-piperidinyl]}-4-pyrazolyl}-1-H-pyrazolo[4,3-b]pyridine | 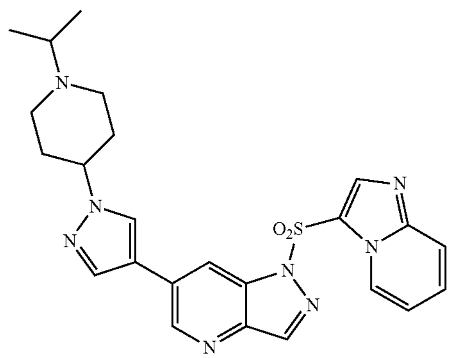 [SMILES: CC(C)N1CCC(n2cc(-c3cnc4cnn(S(=O)(=O)c5cnc6ccccn56)c4c3)cn2)CC1] |
| 60 | 1-(imidazo[1,2-a]pyridine-3-sulfonyl)-6-{{1-[(1-cylcopentyl)-4-piperidinyl]}-4-pyrazolyl}-1-H-pyrazolo[4,3-b]pyridine | 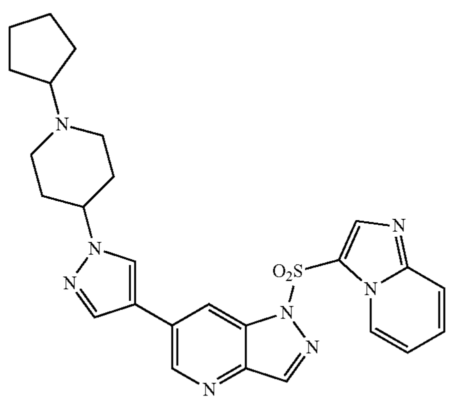 [SMILES: O=S(=O)(c1cnc2ccccn12)n1ncc2ncc(-c3cnn(C4CCN(C5CCCC5)CC4)c3)cc21] |
| 61 | 1-[(6-chloro-imidazo[1,2-b]pyridazine)-3-sulfonyl)]-6-{{1-[(1-t-butoxycarbonyl)-4-piperidinyl]}-4-pyrazolyl}-1-H-pyrazolo[4,3-b]pyridine | 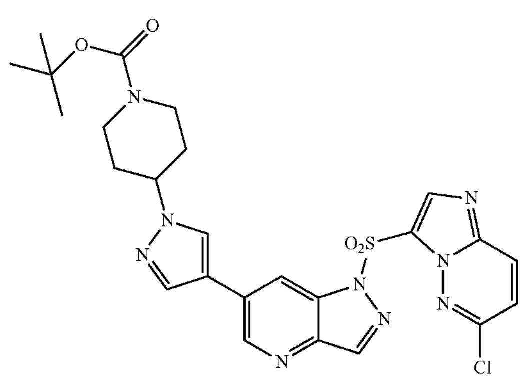 [SMILES: CC(C)(C)OC(=O)N1CCC(n2cc(-c3cnc4cnn(S(=O)(=O)c5cnc6ccc(Cl)nn56)c4c3)cn2)CC1] |

-continued

| No. | Compound | Structure |
|---|---|---|
| 62 | 1-{(6-{{1-[(1-t-butoxycarbonyl)-4-piperidinyl]}-4-pyrazolyl}-imidazo[1,2-b]pyridazine)-3-sulfonyl}-6-{{1-[(1-t-butoxycarbonyl)-4-piperidinyl]}-4-pyrazolyl}-1-H-pyrazolo[4,3-b]pyridine | 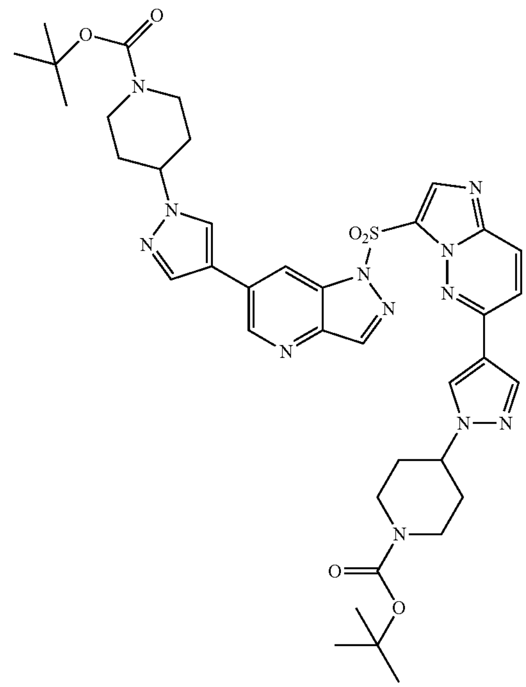 [SMILES: CC(C)(C)OC(=O)N1CCC(n2cc(-c3cnc4cnn(S(=O)(=O)c5cnc6ccc(-c7cnn(C8CCN(C(=O)OC(C)(C)C)CC8)c7)nn56)c4c3)cn2)CC1] |
| 63 | 1-[(6-trifluoromethyl-imidazo[1,2-a]pyridine)-3-sulfonyl)]-6-{{1-[(1-t-butoxycarbonyl)-4-piperidinyl]}-4-pyrazolyl}-1-H-pyrazolo[4,3-b]pyridine | 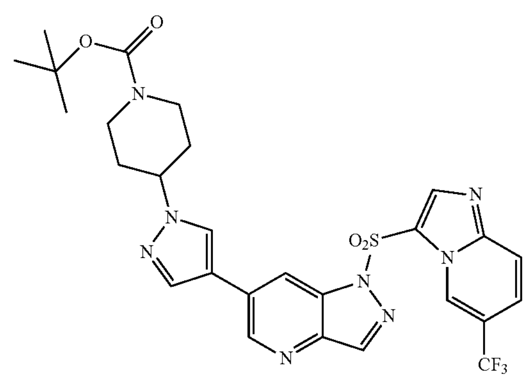 [SMILES: CC(C)(C)OC(=O)N1CCC(n2cc(-c3cnc4cnn(S(=O)(=O)c5cnc6ccc(C(F)(F)F)cn56)c4c3)cn2)CC1] |
| 64 | 1-[(6-trifluoromethyl-imidazo[1,2-a]pyridine)-3-sulfonyl)]-6-{[1-(4-piperidinyl)]-4-pyrazolyl}-4-pyrazolyl}-1-H-pyrazolo[4,3-b]pyridine chloride | 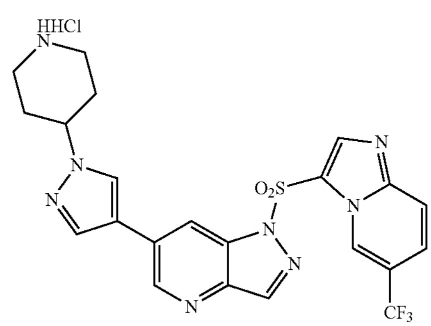 |

-continued

| No. | Compound | Structure |
|---|---|---|
| 65 | 1-[(6-trifluoromethyl-imidazo[1,2-a]pyridine)-3-sulfonyl)]-6-{[1-(4-piperidinyl)]-4-pyrazolyl}-4-pyrazolyl}-1-H-pyrazolo[4,3-b]pyridine | 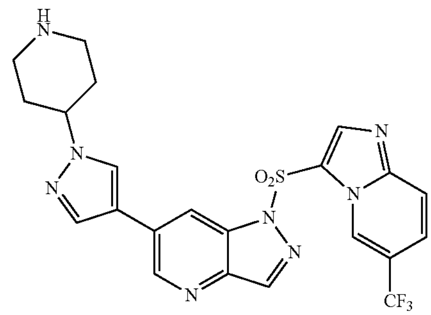 [SMILES: O=S(=O)(c1cnc2ccc(C(F)(F)F)cn12)n1ncc2ncc(-c3cnn(C4CCNCC4)c3)cc21] |
| 66 | 1-(imidazo[1,2-a]pyridine-3-sulfonyl)-6-{[1-(4-piperidinyl)]-4-pyrazolyl}-1-H-pyrazolo[4,3-b]pyridine chloride | 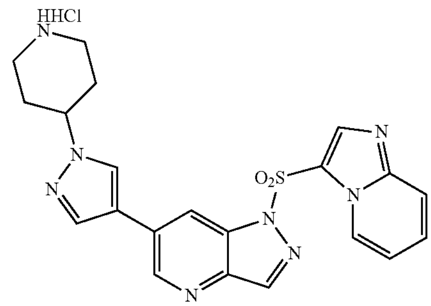 |
| 67 | 1-[(6-chloro-imidazo[1,2-a]pyridine)-3-sulfonyl)]-6-{{1-[(1-t-butoxycarbonyl)-4-piperidinyl]}-4-pyrazolyl}-1-H-pyrazolo[4,3-b]pyridine | 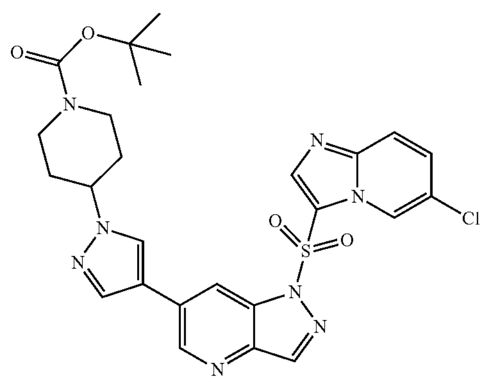 [SMILES: CC(C)(C)OC(=O)N1CCC(n2cc(-c3cnc4cnn(S(=O)(=O)c5cnc6ccc(Cl)cn56)c4c3)cn2)CC1] |
| 68 | 1-{(6-{{1-[(1-t-butoxycarbonyl)-4-piperidinyl]}-4-pyrazolyl}-imidazo[1,2-a]pyridine)-3-sulfonyl}-6-{{1-[(1-t-butoxycarbonyl)-4-piperidinyl]}-4-pyrazolyl}-1-H-pyrazolo[4,3-b]pyridine | 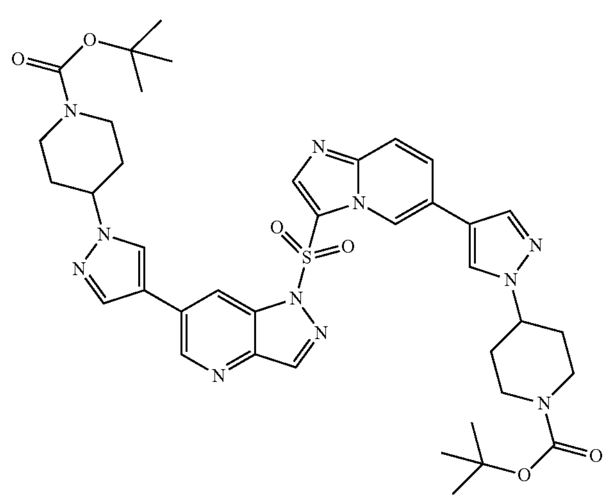 [SMILES: CC(C)(C)OC(=O)N1CCC(n2cc(-c3cnc4cnn(S(=O)(=O)c5cnc6ccc(-c7cnn(C8CCN(C(=O)OC(C)(C)C)CC8)c7)cn56)c4c3)cn2)CC1] |

-continued

| No. | Compound | Structure |
|---|---|---|
| 69 | 1-[(6-trifluoromethyl-imidazo[1,2-a]pyridine)-3-sulfonyl)]-6-{{1-[(1-isopropyl)-4-piperidinyl]}-4-pyrazolyl}-1-H-pyrazolo[4,3-b]pyridine | 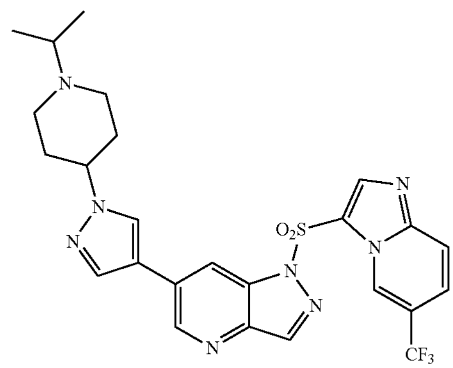 [SMILES: CC(C)N1CCC(n2cc(-c3cnc4cnn(S(=O)(=O)c5cnc6ccc(C(F)(F)F)cn56)c4c3)cn2)CC1] |
| 70 | 1-[(6-bromo-imidazo[1,2-a]pyridine)-3-sulfonyl]-6-[(1-methyl)-4-pyrazolyl]-1H-pyrazolo[4,3-b]pyridine | 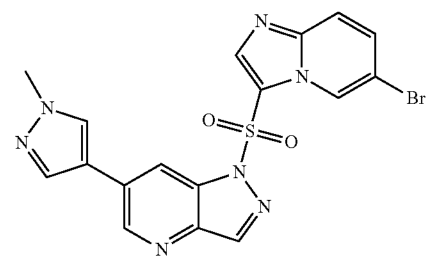 [SMILES: Cn1cc(-c2cnc3cnn(S(=O)(=O)c4cnc5ccc(Br)cn45)c3c2)cn1] |
| 71 | 1-[(6-phenyl-imidazo[1,2-a]pyridine)-3-sulfonyl]-6-[(1-methyl)-4-pyrazolyl]-1-H-pyrazolo[4,3-b]pyridine | 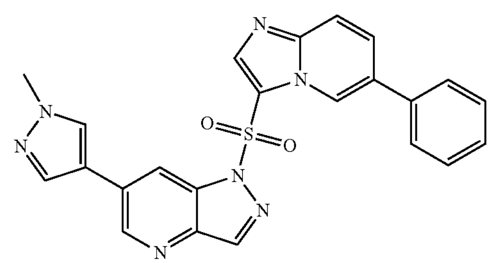 [SMILES: Cn1cc(-c2cnc3cnn(S(=O)(=O)c4cnc5ccc(-c6ccccc6)cn45)c3c2)cn1] |
| 72 | 1-{[6-(3-thiophene)-imidazo[1,2-a]pyridine]-3-sulfonyl}-6-[(1-methyl)-4-pyrazolyl]-1-H-pyrazolo[4,3-b]pyridine | 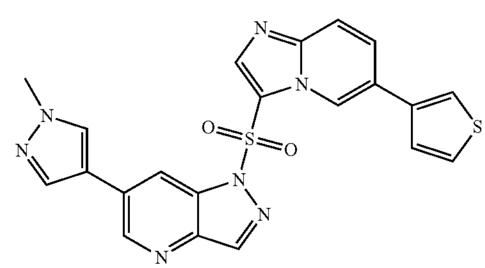 [SMILES: Cn1cc(-c2cnc3cnn(S(=O)(=O)c4cnc5ccc(-c6ccsc6)cn45)c3c2)cn1] |
| 73 | 1-{[6-(4-dimethylaminocarbonylphenyl)-imidazo[1,2-a]pyridine]-3-sulfonyl}-6-[(1-methyl)-4-pyrazolyl]-1-H-pyrazolo[4,3-b]pyridine | 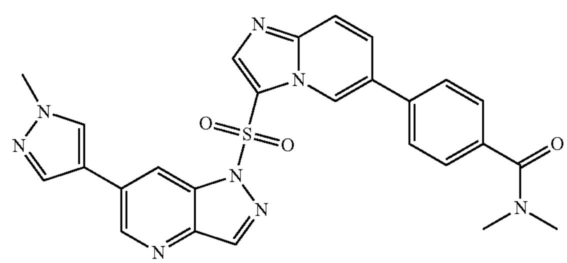 [SMILES: CN(C)C(=O)c1ccc(-c2ccc3ncc(S(=O)(=O)n4ncc5ncc(-c6cnn(C)c6)cc54)n3c2)cc1] |

| No. | Compound | Structure |
|---|---|---|
| 74 | 1-{[6-(5-pyrimidine)-imidazo[1,2-a]pyridine]-3-sulfonyl}-6-[(1-methyl)-4-pyrazolyl]-1-H-pyrazolo[4,3-b]pyridine | 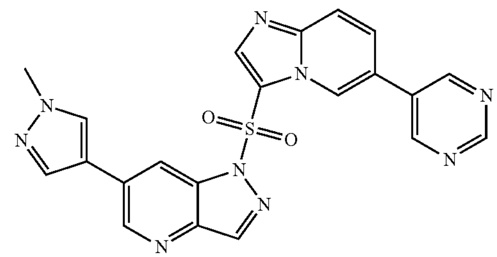 [SMILES: Cn1cc(-c2cnc3cnn(S(=O)(=O)c4cnc5ccc(-c6cncnc6)cn45)c3c2)cn1] |
| 75 | 1-{[6-(4-morpholinylphenyl)-imidazo[1,2-a]pyridine]-3-sulfonyl}-6-[(1-methyl)-4-pyrazolyl]-1-H-pyrazolo[4,3-b]pyridine | 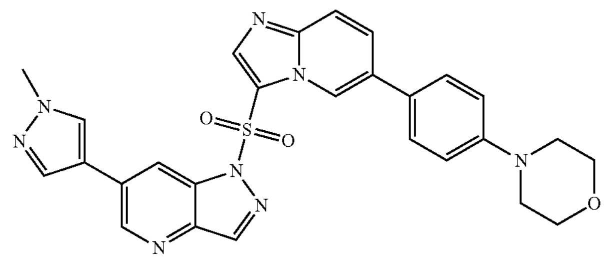 [SMILES: Cn1cc(-c2cnc3cnn(S(=O)(=O)c4cnc5ccc(-c6ccc(N7CCOCC7)cc6)cn45)c3c2)cn1] |
| 76 | 1-{(6-{{1-[(1-t-butoxycarbonyl)-4-piperidinyl]}-4-pyrazolyl}-imidazo[1,2-a]pyridine)-3-sulfonyl}-6-[(1-methyl)-4-pyrazolyl]-1-H-pyrazolo[4,3-b]pyridine | 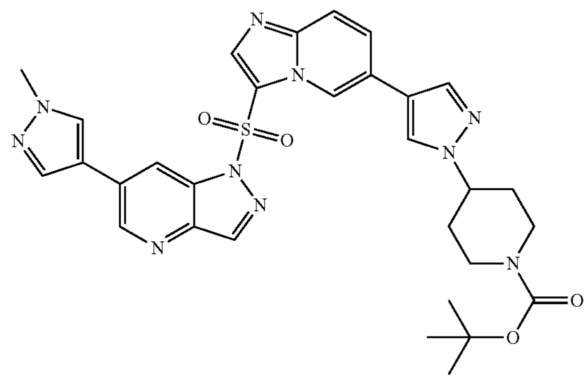 [SMILES: Cn1cc(-c2cnc3cnn(S(=O)(=O)c4cnc5ccc(-c6cnn(C7CCN(C(=O)OC(C)(C)C)CC7)c6)cn45)c3c2)cn1] |
| 77 | 1-{[6-(4-trifluoromethylphenyl)-imidazo[1,2-a]pyridine]-3-sulfonyl}-6-[(1-methyl)-4-pyrazolyl]-1-H-pyrazolo[4,3-b]pyridine | 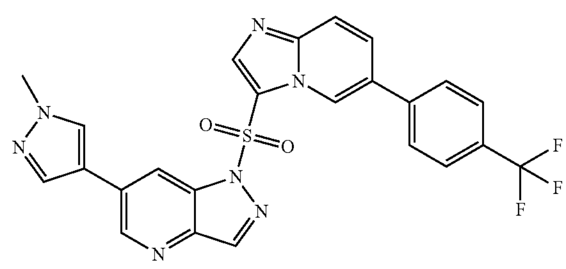 [SMILES: Cn1cc(-c2cnc3cnn(S(=O)(=O)c4cnc5ccc(-c6ccc(C(F)(F)F)cc6)cn45)c3c2)cn1] |
| 78 | 1-{[6-(3-fluoro-4-methylphenyl)-imidazo[1,2-a]pyridine]-3-sulfonyl}-6-[(1-methyl)-4-pyrazolyl]-1-H-pyrazolo[4,3-b]pyridine | 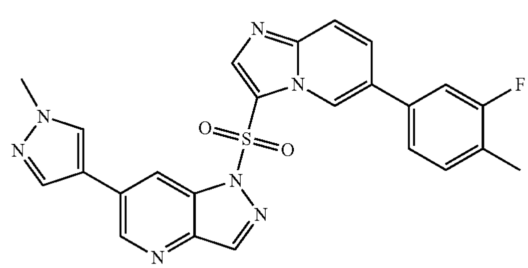 [SMILES: Cc1ccc(-c2ccc3ncc(S(=O)(=O)n4ncc5ncc(-c6cnn(C)c6)cc54)n3c2)cc1F] |

| No. | Compound | Structure |
|---|---|---|
| 79 | 1-{[6-(4-isopropoxyl)phenyl)-imidazo[1,2-a]pyridine]-3-sulfonyl}-6-[(1-methyl)-4-pyrazolyl]-1-H-pyrazolo[4,3-b]pyridine | 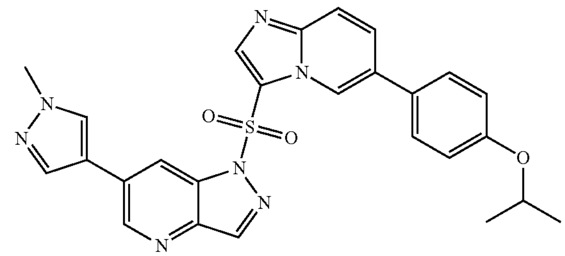 [SMILES: CC(C)Oc1ccc(-c2ccc3ncc(S(=O)(=O)n4ncc5ncc(-c6cnn(C)c6)cc54)n3c2)cc1] |
| 80 | 1-{[6-[4-(4-methylpiperazine-1-carbonyl)phenyl]-imidazo[1,2-a]pyridine]-3-sulfonyl}-6-[(1-methyl)-4-pyrazolyl]-1-H-pyrazolo[4,3-b]pyridine | 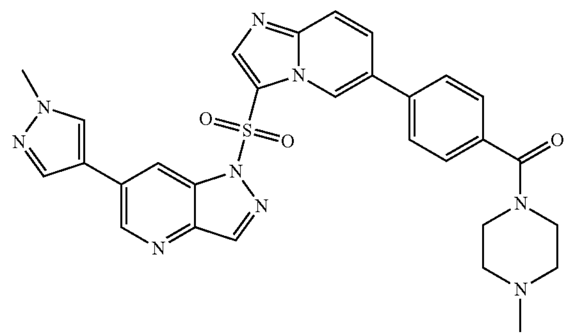 [SMILES: CN1CCN(C(=O)c2ccc(-c3ccc4ncc(S(=O)(=O)n5ncc6ncc(-c7cnn(C)c7)cc65)n4c3)cc2)CC1] |
| 81 | 1-{[6-(4-fluorophenyl)-imidazo[1,2-a]pyridine]-3-sulfonyl}-6-[(1-methyl)-4-pyrazolyl]-1-H-pyrazolo[4,3-b]pyridine | 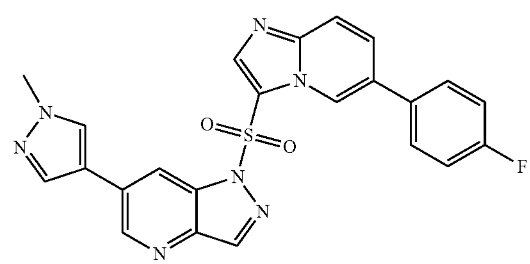 [SMILES: Cn1cc(-c2cnc3cnn(S(=O)(=O)c4cnc5ccc(-c6ccc(F)cc6)cn45)c3c2)cn1] |
| 82 | 1-{[6-([1-(4-piperidinyl)]-4-pyrazolyl)-imidazo[1,2-a]pyridine]-3-sulfonyl}-6-[(1-methyl)-4-pyrazolyl]-1-H-pyrazolo[4,3-b]pyridine chloride | 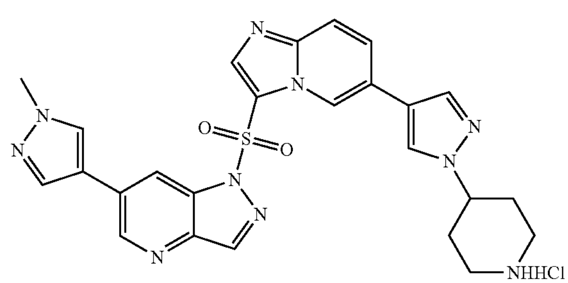 |
| 83 | 1-{[6-(3-trifluoromethylphenyl)-imidazo[1,2-a]pyridine]-3-sulfonyl}-6-[(1-methyl)-4-pyrazolyl]-1-H-pyrazolo[4,3-b]pyridine | 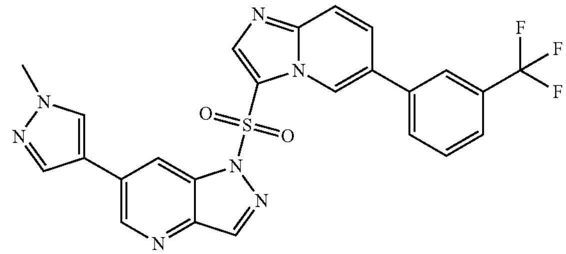 [SMILES: Cn1cc(-c2cnc3cnn(S(=O)(=O)c4cnc5ccc(-c6cccc(C(F)(F)F)c6)cn45)c3c2)cn1] |

| No. | Compound | Structure |
|---|---|---|
| 84 | 1-{[6-(2-trifluoromethylphenyl)-imidazo[1,2-a]pyridine]-3-sulfonyl}-6-[(1-methyl)-4-pyrazolyl]-1-H-pyrazolo[4,3-b]pyridine | 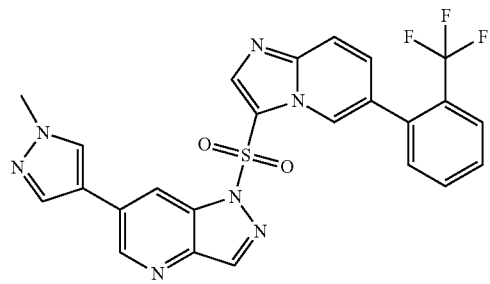 [SMILES: Cn1cc(-c2cnc3cnn(S(=O)(=O)c4cnc5ccc(-c6ccccc6C(F)(F)F)cn45)c3c2)cn1] |
| 85 | 1-{[6-(4-dimethylaminophenyl)-imidazo[1,2-a]pyridine]-3-sulfonyl}-6-[(1-methyl)-4-pyrazolyl]-1-H-pyrazolo[4,3-b]pyridine | 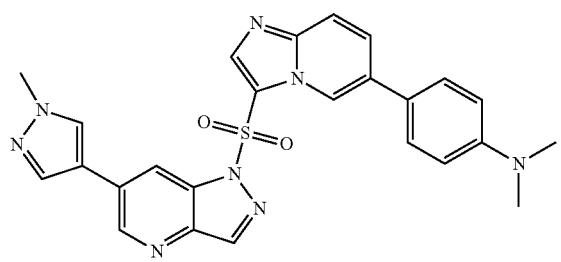 [SMILES: CN(C)c1ccc(-c2ccc3ncc(S(=O)(=O)n4ncc5ncc(-c6cnn(C)c6)cc54)n3c2)cc1] |
| 86 | 1-{[6-(3-fluorophenyl)-imidazo[1,2-a]pyridine]-3-sulfonyl}-6-[(1-methyl)-4-pyrazolyl]-1-H-pyrazolo[4,3-b]pyridine | 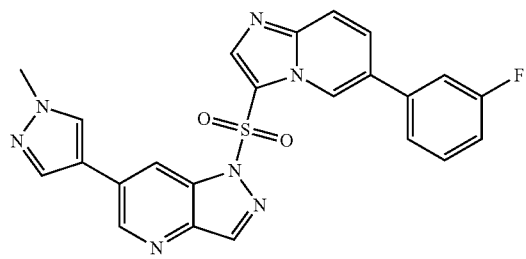 [SMILES: Cn1cc(-c2cnc3cnn(S(=O)(=O)c4cnc5ccc(-c6cccc(F)c6)cn45)c3c2)cn1] |
| 87 | 1-{[6-(2,4-difluorophenyl)-imidazo[1,2-a]pyridine]-3-sulfonyl}-6-[(1-methyl)-4-pyrazolyl]-1-H-pyrazolo[4,3-b]pyridine | 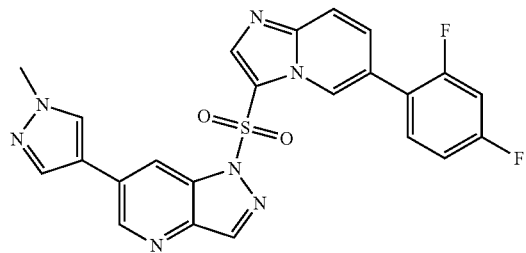 [SMILES: Cn1cc(-c2cnc3cnn(S(=O)(=O)c4cnc5ccc(-c6ccc(F)cc6F)cn45)c3c2)cn1] |
| 88 | 1-{[6-(3,4,5-trifluorophenyl)-imidazo[1,2-a]pyridine]-3-sulfonyl}-6-[(1-methyl)-4-pyrazolyl]-1-H-pyrazolo[4,3-b]pyridine | 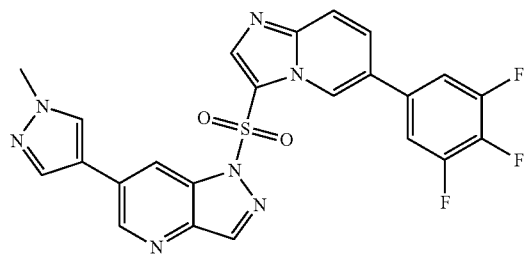 [SMILES: Cn1cc(-c2cnc3cnn(S(=O)(=O)c4cnc5ccc(-c6cc(F)c(F)c(F)c6)cn45)c3c2)cn1] |

-continued

| No. | Compound |
|-----|----------|
| 89 | 1-{[6-(4-methoxyphenyl)-imidazo[1,2-a]pyridine]-3-sulfonyl}-6-[(1-methyl)-4-pyrazolyl]-1-H-pyrazolo[4,3-b]pyridine |
| 90 | 1-{[6-(4-methylphenyl)-imidazo[1,2-a]pyridine]-3-sulfonyl}-6-[(1-methyl)-4-pyrazolyl]-1-H-pyrazolo[4,3-b]pyridine |
| 91 | 1-{[6-(4-morpholinomethylphenyl)-imidazo[1,2-a]pyridine]-3-sulfonyl}-6-[(1-methyl)-4-pyrazolyl]-1-H-pyrazolo[4,3-b]pyridine |
| 92 | 1-{[6-(4-cyanophenyl)-imidazo[1,2-a]pyridine]-3-sulfonyl}-6-[(1-methyl)-4-pyrazolyl]-1-H-pyrazolo[4,3-b]pyridine |
| 93 | 1-{[6-[6-(1,4-benzodioxanyl)]-imidazo[1,2-a]pyridine]-3-sulfonyl}-6-[(1-methyl)-4-pyrazolyl]-1-H-pyrazolo[4,3-b]pyridine |

| No. | Compound | Structure |
|---|---|---|
| 94 | 1-{[6-(4-chlorophenyl)-imidazo[1,2-a]pyridine]-3-sulfonyl}-6-[(1-methyl)-4-pyrazolyl]-1-H-pyrazolo[4,3-b]pyridine | 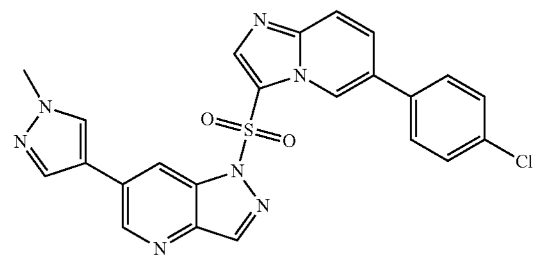 [SMILES: Cn1cc(-c2cnc3cnn(S(=O)(=O)c4cnc5ccc(-c6ccc(Cl)cc6)cn45)c3c2)cn1] |
| 95 | 1-{[6-(3-fluoro-4-pyridinyl)-imidazo[1,2-a]pyridine]-3-sulfonyl}-6-[(1-methyl)-4-pyrazolyl]-1-H-pyrazolo[4,3-b]pyridine | 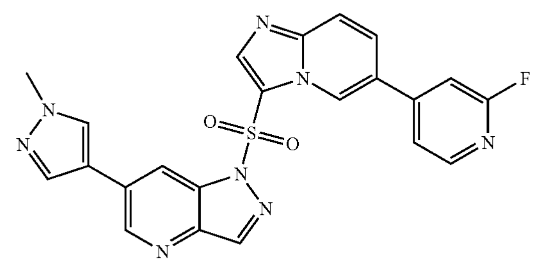 [SMILES: Cn1cc(-c2cnc3cnn(S(=O)(=O)c4cnc5ccc(-c6ccnc(F)c6)cn45)c3c2)cn1] |
| 96 | 1-{[6-(3,4-dimethoxyphenyl)-imidazo[1,2-a]pyridine]-3-sulfonyl}-6-[(1-methyl)-4-pyrazolyl]-1-H-pyrazolo[4,3-b]pyridine | 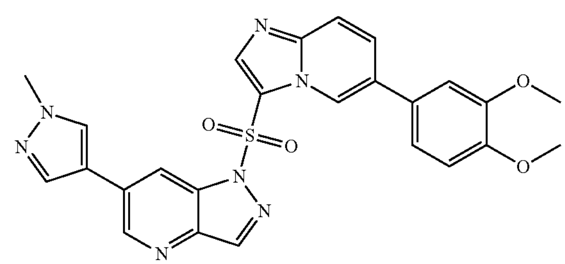 [SMILES: COc1ccc(-c2ccc3ncc(S(=O)(=O)n4ncc5ncc(-c6cnn(C)c6)cc54)n3c2)cc1OC] |
| 97 | 1-{[6-(2-methoxyphenyl)-imidazo[1,2-a]pyridine]-3-sulfonyl}-6-[(1-methyl)-4-pyrazolyl]-1-H-pyrazolo[4,3-b]pyridine | 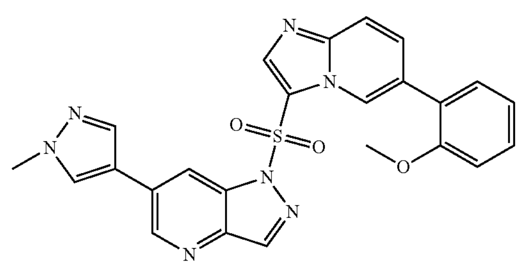 [SMILES: COc1ccccc1-c1ccc2ncc(S(=O)(=O)n3ncc4ncc(-c5cnn(C)c5)cc43)n2c1] |
| 98 | 1-{[6-[5-(1,2-methylenedioxyphenyl)]-imidazo[1,2-a]pyridine]-3-sulfonyl}-6-[(1-methyl)-4-pyrazolyl]-1-H-pyrazolo[4,3-b]pyridine | 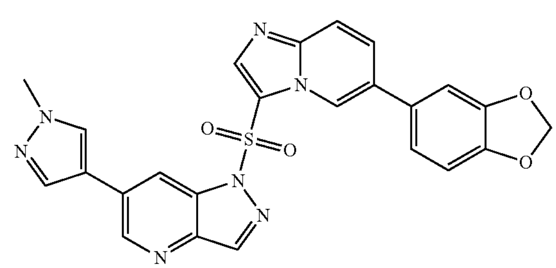 [SMILES: Cn1cc(-c2cnc3cnn(S(=O)(=O)c4cnc5ccc(-c6ccc7c(c6)OCO7)cn45)c3c2)cn1] |

-continued

| No. | Compound |
|---|---|
| 99 | 1-{[6-(2-fluoro-5-pyridinyl)-imidazo[1,2-a]pyridine]-3-sulfonyl}-6-[(1-methyl)-4-pyrazolyl]-1-H-pyrazolo[4,3-b]pyridine |
| 100 | 1-{[6-(3-cyanophenyl)-imidazo[1,2-a]pyridine]-3-sulfonyl}-6-[(1-methyl)-4-pyrazolyl]-1-H-pyrazolo[4,3-b]pyridine |
| 101 | 1-{(6-(3-fluoro-4-methylaminocarbonylphenyl)-imidazo[1,2-a]pyridine)-3-sulfonyl}-6-[(1-methyl)-4-pyrazolyl]-1-H-pyrazolo[4,3-b]pyridine |
| 102 | 1-{(6-(3-fluoro-4-methylaminocarbonylphenyl)-imidazo[1,2-a]pyridine)-3-sulfonyl}-6-[(2-dimethylaminoethyl)-4-pyrazolyl]-1-H-pyrazolo[4,3-b]pyridine |
| 118 | 1-[(6-amino-imidazo[1,2-a]pyridine)-3-sulfonyl]-6-(4-fluorophenyl)-1-H-pyrazolo[4,3-b]pyridine |
| 119 | 1-[(6-n-butylamino-imidazo[1,2-a]pyridine)-3-sulfonyl]-6-[(1-methyl)-4-pyrazolyl]-1-H-pyrazolo[4,3-b]pyridine |

-continued

| No. | Compound |
|---|---|
| 120 | 1-[(6-acetylamino-imidazo[1,2-a]pyridine)-3-sulfonyl]-6-[(1-methyl)-4-pyrazolyl]-1-H-pyrazolo[4,3-b]pyridine |
| 121 | 1-[(6-methoxy-imidazo[1,2-a]pyridine)-3-sulfonyl]-6-[(1-methyl)-4-pyrazolyl]-1-H-pyrazolo[4,3-b]pyridine |
| 122 | 1-[(6-methoxy-imidazo[1,2-a]pyridine)-3-sulfonyl]-6-(4-isoquinolinyl)-1-H-pyrazolo[4,3-b]pyridine |
| 123 | 1-[(6-methoxy-imidazo[1,2-a]pyridine)-3-sulfonyl]-6-(6-methoxy-2-naphthyl)-1-H-pyrazolo[4,3-b]pyridine |
| 124 | 1-[(6-methoxy-imidazo[1,2-a]pyridine)-3-sulfonyl]-6-(4-morpholinylphenyl)-1-H-pyrazolo[4,3-b]pyridine |
| 125 | 1-[(6-methoxy-imidazo[1,2-a]pyridine)-3-sulfonyl]-6-(3-trifluoromethylphenyl)-1-H-pyrazolo[4,3-b]pyridine |

| No. | Compound | Structure |
|---|---|---|
| 126 | 1-[(6-hydroxy-imidazo[1,2-a]pyridine)-3-sulfonyl]-6-(4-methoxyphenyl)-1-H-pyrazolo[4,3-b]pyridine | 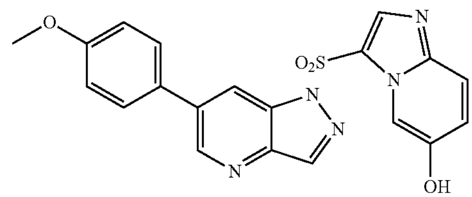 |
| 127 | 1-[(6-hydroxy-imidazo[1,2-a]pyridine)-3-sulfonyl]-6-phenyl-1-H-pyrazolo[4,3-b]pyridine | 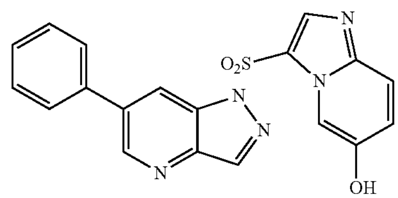 |
| 128 | 1-[(6-isobutyryloxy-imidazo[1,2-a]pyridine)-3-sulfonyl]-6-[(1-methyl)-4-pyrazolyl]-1-H-pyrazolo[4,3-b]pyridine | 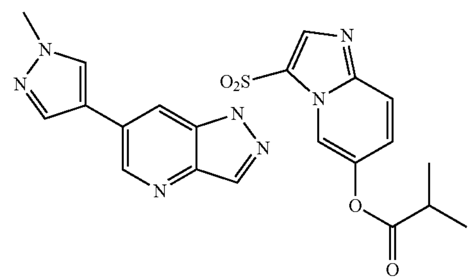 |
| 129 | 1-[(6-furan-2-acyloxy-imidazo[1,2-a]pyridine)-3-sulfonyl]-6-[(1-methyl)-4-pyrazolyl]-1-H-pyrazolo[4,3-b]pyridine | 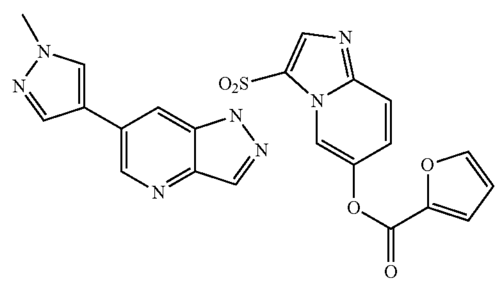 |
| 130 | 1-[(6-bromo-imidazo[1,2-a]pyridine)-3-sulfonyl]-6-ethoxycarbonyl-1-H-pyrazolo[4,3-b]pyridine | 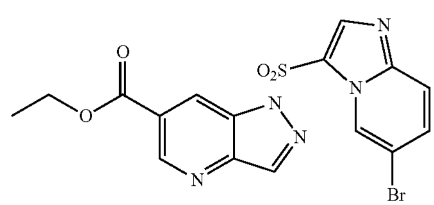 |
| 131 | 1-[(6-bromo-imidazo[1,2-a]pyridine)-3-sulfonyl]-6-benzamido-1-H-pyrazolo[4,3-b]pyridine | 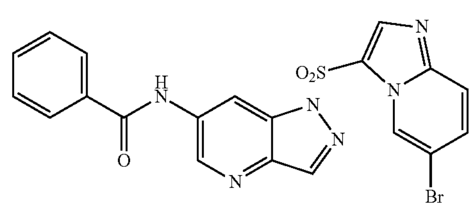 |

-continued

| No. | Compound | Structure |
|---|---|---|
| 132 | 1-[(6-bromo-imidazo[1,2-a]pyridine)-3-sulfonyl]-6-propionamido-1-H-pyrazolo[4,3-b]pyridine | 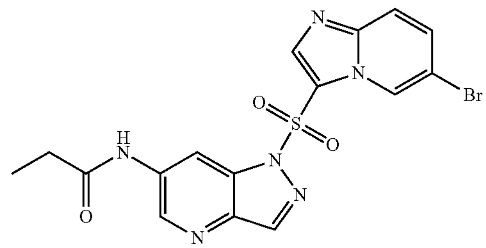 [SMILES: CCC(=O)Nc1cnc2cnn(S(=O)(=O)c3cnc4ccc(Br)cn34)c2c1] |
| 133 | 1-{(6-[(1-methyl)-4-pyrazolyl]-imidazo[1,2-a]pyridine)-3-sulfonyl}-6-benzamido-1-H-pyrazolo[4,3-b]pyridine | 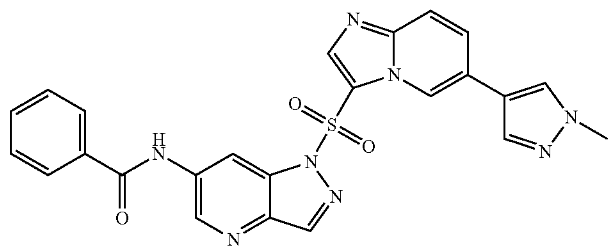 [SMILES: Cn1cc(-c2ccc3ncc(S(=O)(=O)n4ncc5ncc(NC(=O)c6ccccc6)cc54)n3c2)cn1] |
| 134 | 1-[(6-methoxy-imidazo[1,2-a]pyridine)-3-sulfonyl]-6-(3-methoxybenzamido)-1-H-pyrazolo[4,3-b]pyridine | 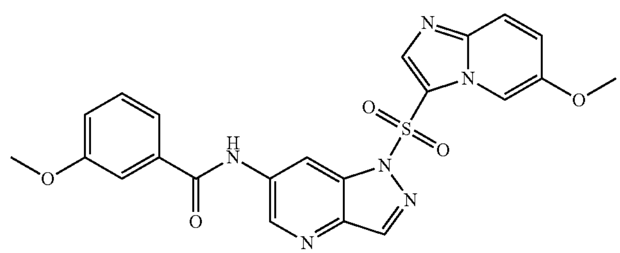 |
| 135 | 1-{(6-[(1-methyl)-4-pyrazolyl]-imidazo[1,2-a]pyridine)-3-sulfonyl}-6-[(1-cyclopentyl)-4-(1,2,3,6-tetrahydropyridinyl)]-1-H-pyrazolo[4,3-b]pyridine | 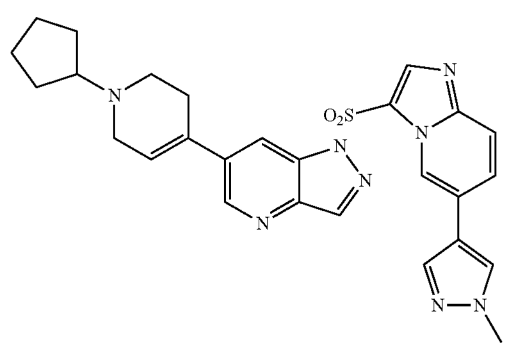 |

| No. | Compound | Structure |
|---|---|---|
| 136 | 1-{(6-[(1-methyl)-4-pyrazolyl]-imidazo[1,2-a]pyridine)-3-sulfonyl}-6-{{1-[(1-cyclopentyl)-4-piperidinyl]}-4-pyrazolyl}-1-H-pyrazolo[4,3-b]pyridine | 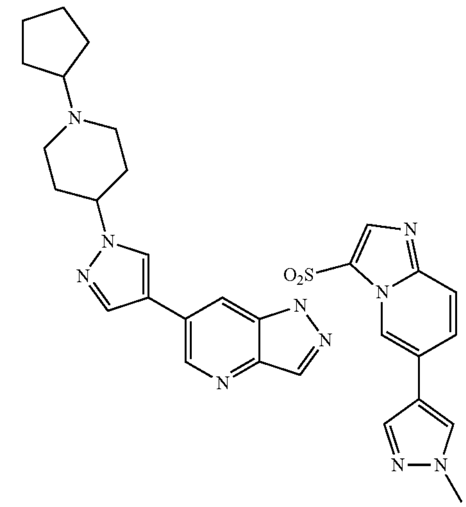 |
| 137 | 1-{(6-[(1-methyl)-4-pyrazolyl]-imidazo[1,2-a]pyridine)-3-sulfonyl}-6-[(1-isopropyl)-4-(1,2,3,6-tetrahydropyridinyl)]-1-H-pyrazolo[4,3-b]pyridine | 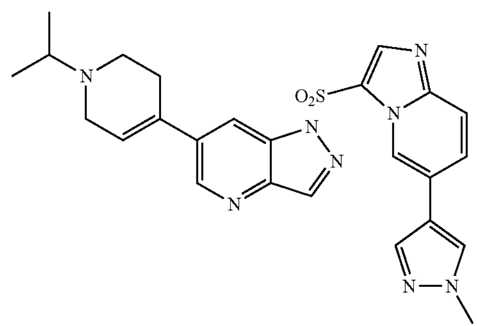 |
| 138 | 1-{(6-[(1-methyl)-4-pyrazolyl]-imidazo[1,2-a]pyridine)-3-sulfonyl}-6-{{1-[(1-ethyl)-4-piperidinyl]}-4-pyrazolyl}-1-H-pyrazolo[4,3-b]pyridine | 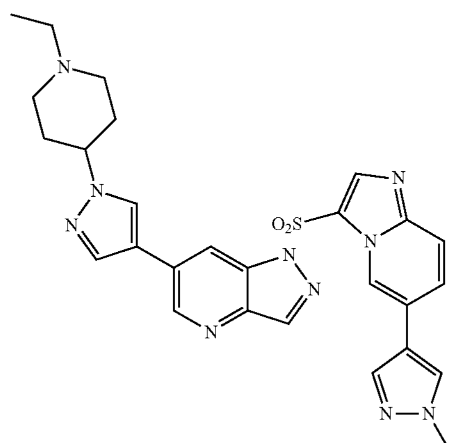 |
| 139 | 1-{(6-[(1-methyl)-4-pyrazolyl]-imidazo[1,2-a]pyridine)-3-sulfonyl}-6-[4-(1,2,3,6-tetrahydropyridinyl)]-1-H-pyrazolo[4,3-b]pyridine | 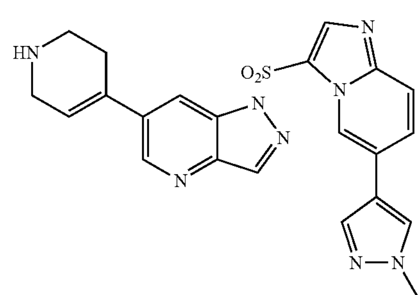 |

| No. | Compound | Structure |
|---|---|---|
| 140 | 1-{(6-[(1-methyl)-4-pyrazolyl]-imidazo[1,2-a]pyridine)-3-sulfonyl}-6-{[1-(4-piperidinyl)]-4-pyrazolyl}-1-H-pyrazolo[4,3-b]pyridine | 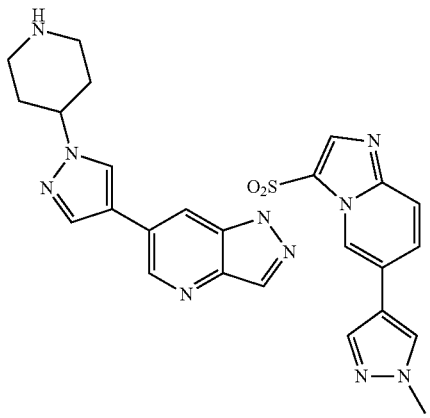 |
| 141 | 1-{(6-[(1-methyl)-4-pyrazolyl]-imidazo[1,2-a]pyridine)-3-sulfonyl}-6-{{1-[(1-t-butoxycarbonyl)-4-piperidinyl]}-4-pyrazolyl}-1-H-pyrazolo[4,3-b]pyridine | 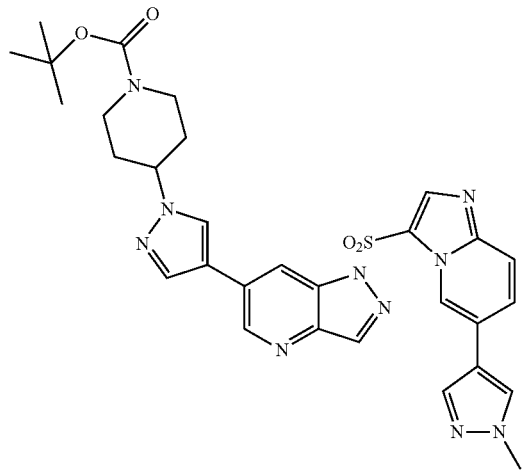 |
| 142 | 1-{(6-[(1-methyl)-4-pyrazolyl]-imidazo[1,2-a]pyridine)-3-sulfonyl}-6-[4-(4-methylpiperazine-1-carbonyl)phenyl]-1-H-pyrazolo[4,3-b]pyridine | 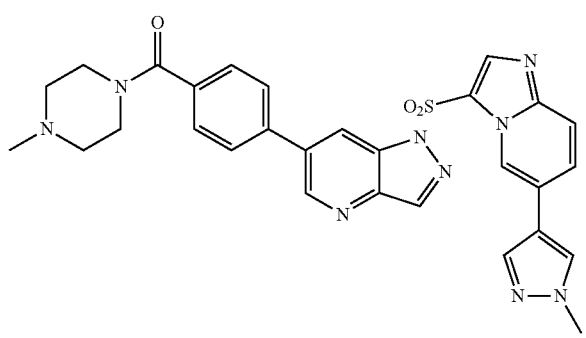 |
| 143 | 1-{(6-[(1-methyl)-4-pyrazolyl]-imidazo[1,2-a]pyridine)-3-sulfonyl}-6-(4-morpholinomethyl-phenyl)-1-H-pyrazolo[4,3-b]pyridine | 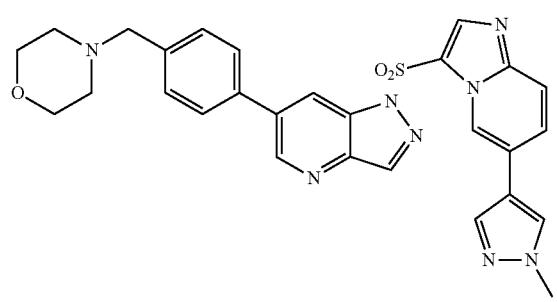 |

| No. | Compound | Structure |
|---|---|---|
| 144 | 1-{(6-[(1-methyl)-4-pyrazolyl]-imidazo[1,2-a]pyridine)-3-sulfonyl}-6-phenyl-1-H-pyrazolo[4,3-b]pyridine | 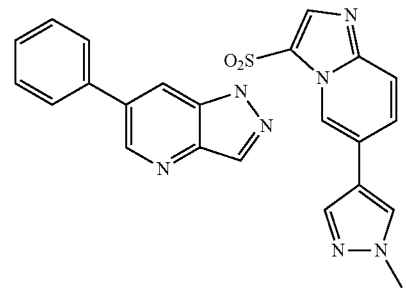 |
| 145 | 1-{(6-[(1-methyl)-4-pyrazolyl]-imidazo[1,2-a]pyridine)-3-sulfonyl}-6-{{1-[(1-isopropyl)-4-piperidinyl]}-4-pyrazolyl}-1-H-pyrazolo[4,3-b]pyridine | 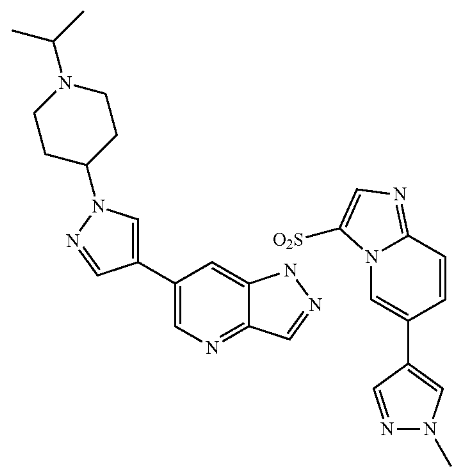 |

The pharmaceutical salt of said 5-member-heterocycle fused pyridine compound according to the present invention can be produced by reacting the compound of Formula (X) with inorganic acid or organic acid, wherein said inorganic acid includes hydrochloride, hydrobromide, phosphoric acid, sulphuric acid and others, said organic acid includes ascorbic acid, nicotinic acid, citric acid, tartaric acid, lactic acid, maleic acid, malonic acid, fumaric acid, oxalic acid, malic acid, glycolic acid, succinic acid, propionic acid, acetic acid, methanesulfonic acid, trifluoromethanesulfonic acid, benzenesulfonic acid, p-toluenesulfonic acid, and others.

The pharmaceutical salt of said 5-member-heterocycle fused pyridine compound according to the present invention can be produced by dissolving said compound into alcohol solution saturated by corresponding acid and carrying out the reaction, for instance, the 5-member-heterocycle fused pyridine compound of this invention may be dissolved by saturated HCl solution in dioxane, stirring for 30 minutes at room temperature, filtering to obtain the resultant hydrochloride salt.

Furthermore, the compound of this invention may have one or more chiral centers. In this circumstance, the compound of this invention also covers individual diastereomer, racemate, as well as individual R and S enantiomer. In this specification, when a racemate mixture is disclosed, two optical isomers (including diastereomer and enantiomer) or stereoisomers each substantially free of the other isomer are explicitly disclosed and claimed at the same time.

Another goal of this invention is to provide a process for the production of said 5-member-heterocycle fused pyridine compound, said process produces the 5-member-heterocycle fused pyridine compound by reaction paths shown in the schemes below, which may comprise steps as following;

Reaction path I:

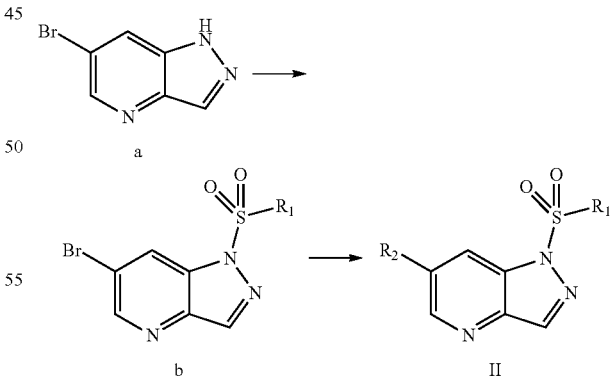

1) Reacting a starting compound a, synthesized referring to prior patent applications (WO2012056372; WO2010056999; WO201208778), with corresponding sulfonyl chloride under the action of a base to produce a compound of Formula b.

2) Reacting the compound of Formula b with corresponding boric acid or boric acid ester in a coupling reaction catalyzed by metal catalyst and under the action of a base, such that a compound of Formula II is produced.

Wherein, $R_1$ and $R_2$ are defined as above;

In step 1) described above, the suitable reaction condition, for the sulfonamide condensation reaction between said corresponding sulfonyl chloride and the starting compound a, is a routine choice for a person skilled in the art. Generally, methanol, ethanol, dioxane, tetrahydrofuran, methylene chloride, chloroform and others may be chosen as the solvent. The base is well known to a person skilled in the art, non-limiting examples include triethylamine, sodium hydroxide, potassium hydroxide, sodium hydride, potassium t-butoxide, and others. In step 2) described above, the suitable condition for the coupling reaction involving the compound of Formula b is a routine choice for a person skilled in the art. The metal catalyst is well known to a person skilled in the art, non-limiting examples include 1,1'-Bis (diphenylphosphino) ferrocene palladium (II) dichloride, tetrakis (triphenylphosphine) palladium (0), bis (acetonitrile) palladium (II) chloride, and others. The base is a base well known to a person skilled in the art, non-limiting examples include $Cs_2CO_3$, $Na_2CO_3$, $K_2CO_3$, $K_3PO_4$, $NaHCO_3$ and others.

Reaction path II:

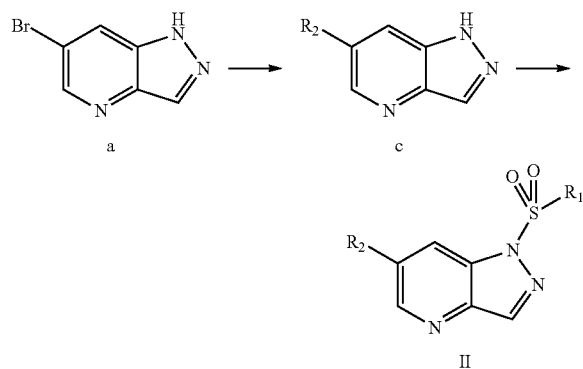

1) Reacting a starting compound a, synthesized referring to prior patent applications (WO2012056372; WO2010056999; WO201208778), with corresponding boric acid or boric acid ester in a coupling reaction catalyzed by metal catalyst and under the action of a base, such that a compound of Formula c is produced.

2) Reacting the compound of Formula c with corresponding sulfonyl chloride under the action of a base to produce a compound of Formula II.

In step 1) described above, the suitable condition for the coupling reaction involving the compound of Formula a and corresponding boric acid or boric acid ester is a routine choice for a person skilled in the art. The metal catalyst is well known to a person skilled in the art, non-limiting examples include 1,1'-Bis (diphenylphosphino) ferrocene palladium (II) dichloride, tetrakis (triphenylphosphine) palladium (0), bis (acetonitrile) palladium (II) dichloride, and others. The base is a base well known to a person skilled in the art, non-limiting examples include $Cs_2CO_3$, $Na_2CO_3$, $K_2CO_3$, $K_3PO_4$, $NaHCO_3$ and others. In step 2) described above, the suitable reaction condition, for the sulfonamide condensation reaction between said corresponding sulfonyl chloride and the compound of Formula c, is a routine choice for a person skilled in the art. Generally, methanol, ethanol, dioxane, tetrahydrofuran, methylene chloride, chloroform and others may be chosen as the solvent. The base is well known to a person skilled in the art, non-limiting examples include triethylamine, sodium hydroxide, potassium hydroxide, sodium hydride, potassium t-butoxide, and others.

Reaction path III:

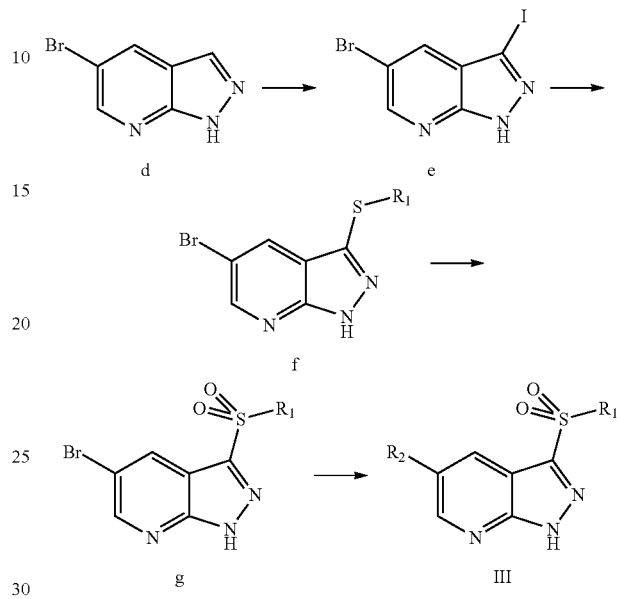

1) Subjecting starting compound d to halogenation reaction with iodine under the action of a base to produce a compound e;

2) Subjecting the compound e to a metal-catalyzed coupling reaction with corresponding thiol compound to produce the compound of Formula f;

3) Subjecting the compound of Formula f to oxidation under the action of an oxidizer to produce a compound of Formula g;

4) Subjecting the compound of Formula g to a metal-catalyzed coupling reaction with corresponding boric acid or boric acid ester to produce the compound of Formula III;

wherein, $R_1$ and $R_2$ are defined as above;

Reaction path IV:

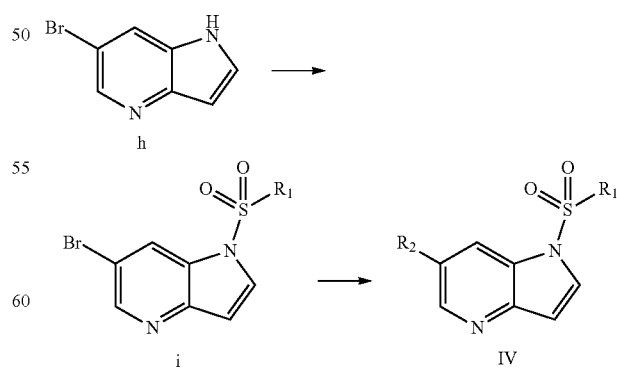

1) Reacting a starting compound h with corresponding sulfonyl chloride under the action of a base to produce a compound of Formula i.

2) Subjecting the compound of Formula i to a metal-catalyzed coupling reaction with corresponding boric acid or boric acid ester under the action of a base to produce a compound of Formula IV;

wherein, $R_1$ and $R_2$ are defined as above.

Reaction path V:

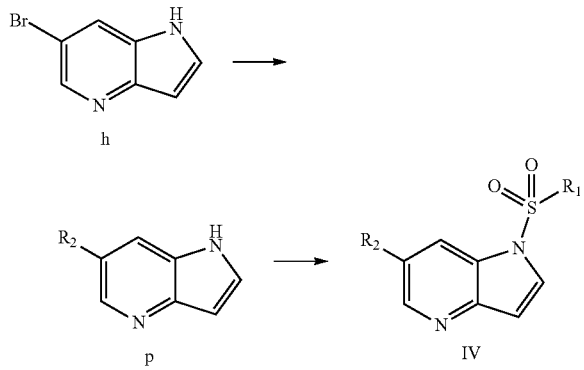

1) Subjecting a starting compound h to a metal-catalyzed coupling reaction with corresponding boric acid or boric acid ester under the action of a base to produce a compound of Formula p;

2) Reacting the compound of Formula p with corresponding sulfonyl chloride under the action of a base to produce a compound of Formula IV;

wherein, $R_1$ and $R_2$ are defined as above.

Reaction path VI:

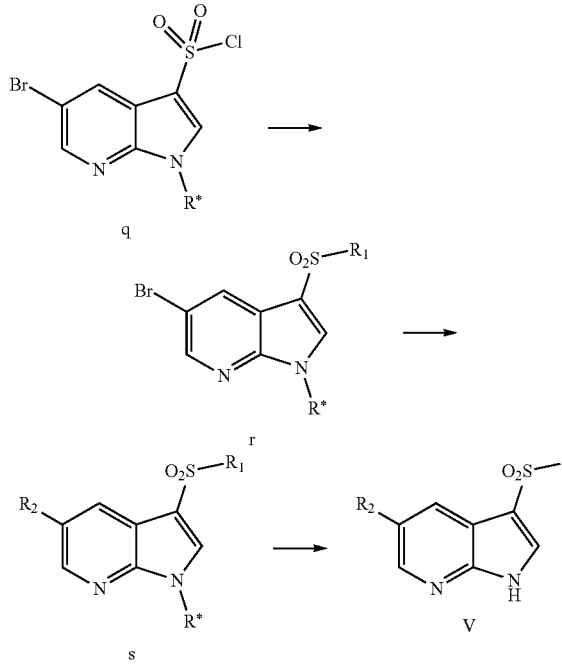

1) Reacting a starting compound q having a protection group R* with corresponding amine under the action of a base to produce compound r.

2) Subjecting the compound of Formula r to a metal-catalyzed coupling reaction with corresponding boric acid or boric acid ester under the action of a base to produce a compound of Formula s;

3) Removing the protection group from the compound of Formula s to produce a compound of Formula V.

Wherein, $R_1$ and $R_2$ are defined as above. The R* is a protection group for N atom that is well known to a person skilled in the art, non-limiting examples include t-butoxycarbonyl, 2-nitrobenzenesulfonyl, benzyl, and others.

The scope of this invention covers any new intermediates disclosed herein as well.

In a third aspect, this invention provides a pharmaceutical composition comprising a prophylactically or therapeutically effective amount of any one of the 5-member-heterocycle fused pyridine compound described above, one or more of pharmaceutically acceptable salts or pharmaceutically acceptable solvates thereof, and a pharmaceutically acceptable excipient. The term "prophylactically or therapeutically effective amount" refers to an amount of the compound that is sufficient to induce the desired prophylactic or therapeutic effect, such as inhibiting protein lysine kinase and/or anti-tumor activity, while the particular amount will vary with factors known to a person skilled in the art, such as the physical and chemical properties of the compound, and characteristics of the vehicle, as well as the dosing regime to be applied. Moreover, the pharmaceutical composition of this invention may further comprise other active agents, such as other lysine kinase inhibitor and/or antitumor substance, for an improved effect.

Pharmaceutically acceptable excipients suitable for this invention include, for example, saccharides, such as lactose, glucose and sucrose; starches, such as corn starch and potato starch; cellulose and its derivatives such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil, and cocoa bean oil; polyols, such as propylene glycol, glycerine, sorbitol, mannitol and polyethylene glycol; alginic acid; emulsifiers, such as Tween; wetting agents, such as sodium dodecyl sulfate; coloring agents; flavoring agents; tabletting agent; stabilizers; antioxidants; preservatives; pyrogen-free water; isotonic saline; and phosphate buffer solution.

The pharmaceutical composition of this invention can be administrated in any conventional dosage and mode.

The 5-member-heterocycle fused pyridine compound, pharmaceutical acceptable salts thereof, pharmaceutical acceptable solvates thereof, or pharmaceutical composition as described above can be used to prevent or treat disorders associated with abnormal cell proliferation, morphological change and hyperkinesis related to abnormal in vivo protein tyrosine kinase, or diseases associated with angiogenesis or cancer metastasis, particularly, diseases associated with the over-expression or over-activation of receptor protein tyrosine kinase c-Met, such as liver cancer, bile duct cancer, pancreatic cancer, lung cancer, thyroid cancer, pleural mesothelioma, lung cancer, stomach cancer, breast cancer, colon cancer, prostate cancer, pancreatic cancer, esophageal cancer, ovarian cancer, renal cancer, glioma, melanoma, etc.

Therefore, in another aspect, this invention is further related to a method for preventing or treating disorders associated with abnormal cell proliferation, morphological change and hyperkinesis related to abnormal in vivo protein tyrosine kinase, and diseases related to angiogenesis or metastasis in an individual in need thereof, said method comprises administering a prophylactically or therapeutically effective amount of the compound or pharmaceutical composition of this invention to said individual. In a preferred embodiment, the diseases are associated with the over-expression or over-activation of receptor protein tyrosine kinase c-Met. More preferably, said disease is selected from cancers associated with the over-expression or over-activation of receptor protein tyrosine kinase c-Met, such as liver cancer, bile duct cancer, pancreatic cancer, lung cancer, thyroid cancer, pleural mesothelioma, lung cancer, stomach cancer, breast cancer, colon cancer, prostate cancer, pancreatic cancer, esophageal cancer, ovarian cancer, renal cancer, glioma, and melanoma.

The following examples are provided to specifically describe the preparation of the compounds of this invention, and their biological activity as inhibitor against tyrosine kinase, particularly c-Met, but this invention is not limited to these examples.

H-NMR measurements were made on Bruker AMX-300 or 400. Microwave irradiation was carried out using Biotage Initiator Microwave Reactor. All solvents for reactions are purified according to routine methods. Silica gel (200-300 mesh or 300-400 mesh) for column chromatography was manufactured by Branch of Qingdao Haiyang Chemical Co., Ltd. Flash preparative chromatography was performed on Parallel Frac FR-260 of YAMAZEN, Japan. Thin layer chromatography plate and preparative plate HSGF-254 is manufactured by Jiangyou Silica Development Co., Ltd. of Yantai. All solvents were of analytical grade solvents. All reagents were purchased from Sinopharm Chemical Reagent Co., Ltd. Color development was performed by means of iodine, ultraviolet fluorescence, and others. Removing organic solvent by evaporation under reduced pressure was performed in a rotary evaporator.

Example 1

Preparation of 1-(2-nitrobenzenesulfonyl)-6-[(1-methyl)-4-pyrazolyl]-1-H-pyrrolo[3,2-b]pyridine

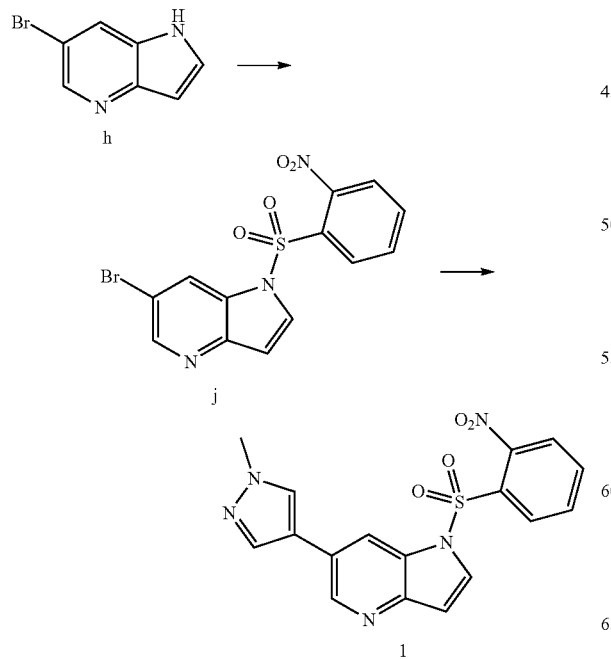

Step 1: Preparation of Compound j

Sixty five milligrams of sodium anhydride was dissolved into 15 ml anhydrous tetrahydrofuran, stirred for 5 minutes at room temperature. One hundred and sixty milligrams of compound h was dissolved into 15 ml anhydrous tetrahydrofuran, then slowly and dropwisely added into tetrahydrofuran solution of sodium hydride, stirred for 30 minutes at room temperature after the addition was completed. One hundred and ninety eight milligrams of 2-nitrophenylsulfonyl chloride was dissolved into 15 ml anhydrous tetrahydrofuran, then slowly and dropwisely added into reaction solution, stirred overnight at room temperature after the addition was completed, the reaction was then completed. Tetrahydrofuran was removed by evaporation, the remainder was dissolved into dichloromethane, washed three times with water, the organic layer was dried over anhydrous sodium sulfate then concentrated, and isolated by flash preparative chromatography to obtain the target compound j (m=256 mg, yield: 82%).

$^1$H NMR (400 MHz, CDCl$_3$) δ 8.64 (d, J=2.0 Hz, 1H), 8.34 (d, J=1.3 Hz, 1H), 7.92 (d, J=7.4 Hz, 1H), 7.86-7.79 (m, 3H), 7.79-7.73 (m, 1H), 6.93 (d, J=3.9 Hz, 1H).

Step 2: Preparation of 1-(2-nitrobenzenesulfonyl)-6-[(1-methyl)-4-pyrazolyl]-1-H-pyrrolo[3,2-b]pyridine Into a microwave reaction tube were disposed 80 mg compound j, 65 mg 1-methyl-1H-pyrazolo-4-borate pinacol ester and 87 mg potassium carbonate, into the microwave reaction tube were added 5 ml dioxane, 2.5 ml ethanol and 2.5 ml water, air was displaced for three times, under a nitrogen atmosphere, 8.5 mg complex of 1,1'-bis(diphenylphosphino) ferrocene palladium (II) dichloride and dichloromethane was added into said microwave tube, then the microwave tube was sealed and placed in microwave reactor, reaction was conducted at a temperature of 120° C. for 30 minutes, till the reaction was completed. The reactant liquid was poured into 15 ml water, extracted three times with dichloromethane, the organic layer was dried over anhydrous sodium sulfate then concentrated, and isolated by flash preparative chromatography to obtain the target compound 1 (m=62 mg, yield: 77%).

$^1$H NMR (400 MHz, DMSO) δ 8.87 (d, J=1.5 Hz, 1H), 8.38 (s, 1H), 8.27 (d, J=8.4 Hz, 1H), 8.21 (d, J=1.8 Hz, 1H), 8.13 (d, J=7.8 Hz, 1H), 8.05 (s, 1H), 8.00 (d, J=3.7 Hz, 2H), 7.92 (t, J=7.9 Hz, 1H), 7.06 (d, J=3.5 Hz, 1H), 3.91 (s, 3H).

Example 2

Preparation of 3-(2-nitrobenzenesulfonyl)-5-[(1-methyl)-4-pyrazolyl]-1-H-pyrazolo[3,4-b]pyridine

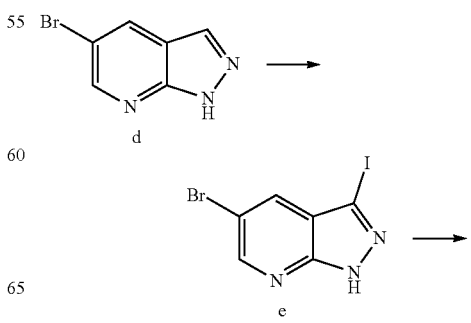

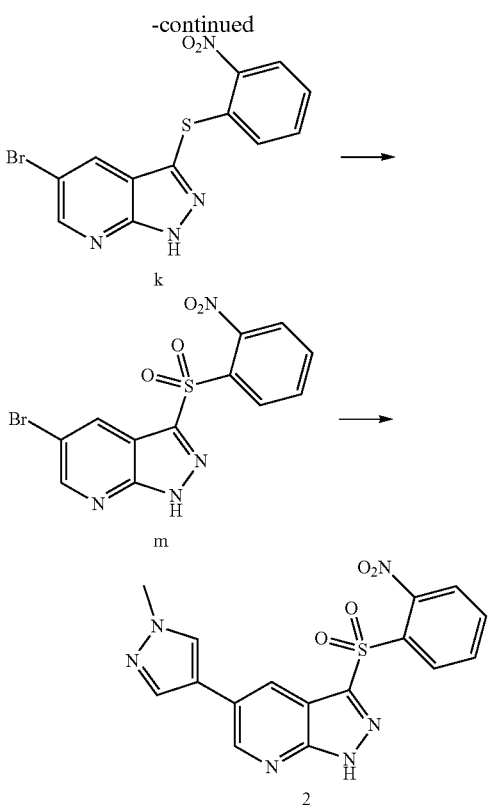

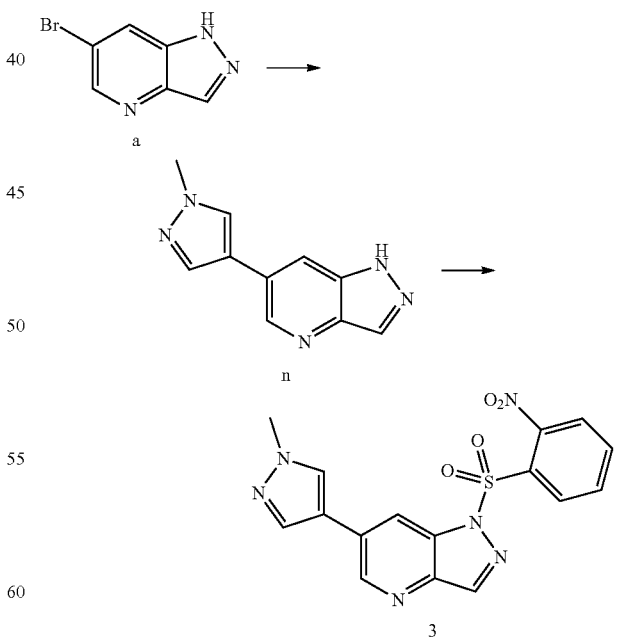

washed three times with water, the organic layer was dried over anhydrous sodium sulfate then concentrated, and isolated by flash preparative chromatography to obtain the target compound m (m=268 mg, yield: 40.1%).

$^1$H NMR (400 MHz, DMSO) δ 8.82 (d, J=2.2 Hz, 1H), 8.53 (d, J=2.2 Hz, 1H), 8.46-8.42 (m, 1H), 8.10-8.06 (m, 1H), 8.05-7.99 (m, 2H).

Step 4: Preparation of 3-(2-nitrobenzenesulfonyl)-5-[(1-methyl)-4-pyrazolyl]-1-H-pyrazolo[3,4-b]pyridine Into a microwave reaction tube, 70 mg compound 15, 57 mg 1-methyl-1H-pyrazolo-4-borate pinacol ester and 76 mg potassium carbonate were disposed, 5 ml dioxane, 2.5 ml ethanol and 2.5 ml water were added into the microwave reaction tube, air was displaced for three times, under a nitrogen atmosphere, 7.5 mg complex of 1,1'-bis(diphenylphosphino) ferrocene palladium (II) dichloride and dichloromethane was added into the microwave tube, then the microwave tube was sealed. The microwave tube was placed into a microwave reactor, reaction was conducted at a temperature of 120° C. for 30 minutes, till the reaction was completed. The aforementioned reactant liquid was poured into 15 ml water, extracted three times with dichloromethane, the organic layer was dried over anhydrous sodium sulfate then concentrated, and isolated by flash preparative chromatography to obtain the target compound 2 (m=58 mg, yield: 83%).

$^1$H NMR (400 MHz, DMSO) δ 9.03 (d, J=2.0 Hz, 1H), 8.47-8.44 (m, 1H), 8.41 (s, 1H), 8.40 (d, J=2.1 Hz, 1H), 8.08 (s, 1H), 8.07-8.05 (m, 1H), 8.01 (m, 2H), 3.92 (s, 3H).

Example 3

Preparation of 1-(2-nitrobenzenesulfonyl)-6-[(1-methyl)-4-pyrazolyl]-1-H-pyrazolo[4,3-b]pyridine Step 1: Preparation of Compound e Four grams of compound d and 10.25 g of iodine were dissolved into 50 ml N,N-dimethylformamide, stirred for 5 minutes at room temperature. Slowly, 2.83 g of potassium hydroxide was added into the above solution, and further stirred at room temperature for 3 hours, the reaction was completed. The reactant liquid was poured into 1000 ml water, solid was precipitated, filtered, the filter cake was washed three times by water immersion, vacuum dried to obtain compound e (m=1.35 g, yield: 41.3%).

$^1$H NMR (400 MHz, CDCl$_3$) δ 8.47 (d, J=2.1 Hz, 1H), 7.93 (d, J=2.1 Hz, 1H).

Step 2: Preparation of Compound k

Into 30 ml isopropanol, 1.5 g of compound e, 1.44 g of 2-nitrophenylsulfonyl chloride, 88 mg cuprous iodide and 516 ml glycol were dissolved, air was displaced for three times, heated at 140° C. to react overnight under a nitrogen atmosphere. After the reaction was completed, the reactant liquid was cooled to room temperature, added 250 ml of dichloromethane, and filtered. The filtrate was washed three times with water, the organic layer was dried over anhydrous sodium sulfate then concentrated, and isolated by flash preparative chromatography to obtain the target compound k (m=832 mg, yield: 51.2%).

$^1$H NMR (400 MHz, CDCl$_3$) δ 8.69 (d, J=2.2 Hz, 1H), 8.30 (d, J=9.7 Hz, 1H), 8.14 (d, J=2.1 Hz, 1H), 7.32 (t, J=8.6 Hz, 2H), 6.82 (d, J=7.9 Hz, 1H).

Step 3: Preparation of Compound m

Into 20 ml trichloromethane, 612 mg compound k and 601 mg m-chloroperbenzoic acid was dissolved, stirred at room temperature for 3 hours, the reaction was completed. The reactant liquid was diluted by 30 ml dichloromethane, Step 1: Preparation of Compound n Into a microwave reaction tube, 300 mg compound a, 473 mg 1-methyl-1H-pyrazolo-4-borate pinacol ester and 628 mg potassium carbonate were disposed, 5 ml dioxane, 2.5 ml ethanol and 2.5 ml water were added into the microwave reaction tube, air was displaced for three times, under a nitrogen atmosphere, 62 mg complex of 1,1'-bis(diphenylphosphino) ferrocene palladium (II) dichloride and dichloromethane was added into the microwave tube, then the microwave tube was sealed, The microwave tube was placed into a microwave reactor, reaction was conducted at a temperature of 120° C. for 30 minutes, till the reaction was completed. The aforementioned reactant liquid was poured into 15 ml water, extracted three times with dichloromethane, the organic layer was dried over anhydrous sodium sulfate then concentrated, isolated by flash preparative chromatography to obtain compound n (m=275 mg, yield: 91%).

$^1$H NMR (300 MHz, DMSO-$d_6$) δ 13.29 (s, 1H), 8.80 (s, 1H), 8.36 (s, 1H), 8.24 (s, 1H), 8.07 (s, 2H), 3.90 (s, 3H).

Step 2: Preparation of 1-(2-nitrobenzenesulfonyl)-6-[(1-methyl)-4-pyrazolyl]-1-H-pyrazolo[4,3-b]pyridine Sixty five mg sodium hydride was dissolved into 15 ml anhydrous DMF, stirred for 5 minutes at room temperature. One hundred and sixty mg compound n was dissolved in 15 ml anhydrous DMF, then slowly and dropwisely added into sodium hydride solution in DMF, and stirred for 30 minutes at room temperature after the addition was finished. One hundred and ninety eight mg 2-nitrophenylsulfonyl chloride was dissolved in 15 ml anhydrous DMF, slowly and dropwisely added into reaction solution, stirred overnight at room temperature after the addition was finished, till the reaction was completed. DMF was removed by evaporation, the remainder was dissolved into dichloromethane, washed three times with water, the organic layer was dried over anhydrous sodium sulfate then concentrated, and isolated by flash preparative chromatography to obtain the target compound 3 (m=256 mg, yield: 82%).

$^1$H NMR (400 MHz, CDCl$_3$) δ 8.90 (d, J=1.9 Hz, 1H), 8.47-8.42 (m, 1H), 8.41 (d, J=0.9 Hz, 1H), 8.38 (dd, J=1.9, 0.9 Hz, 1H), 7.96 (d, J=0.7 Hz, 1H), 7.88 (s, 1H), 7.87-7.82 (m, 2H), 7.80-7.72 (m, 1H), 4.03 (s, 3H).

Example 4

Preparation of 1-benzenesulfonyl-6-[(1-methyl)-4-pyrazolyl]-1-H-pyrazolo[4,3-b]pyridine

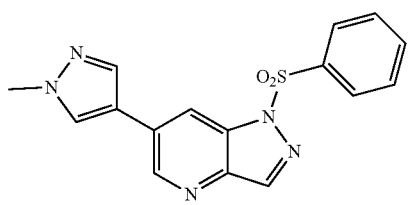 [SMILES: Cn1cc(-c2cnc3cnn(S(=O)(=O)c4ccccc4)c3c2)cn1]

Except for phenylsulfonyl chloride was used instead of 2-nitrophenylsulfonyl chloride, compound 1-benzenesulfonyl-6-[(1-methyl)-4-pyrazolyl]-1-H-pyrazolo[4,3-b]pyridine was prepared by the same process as Example 3.

$^1$H NMR (400 MHz, CDCl$_3$) δ 8.84 (d, J=1.7 Hz, 1H), 8.49 (s, 1H), 8.38 (s, 1H), 8.02 (d, J=7.4 Hz, 2H), 7.94 (s, 1H), 7.86 (s, 1H), 7.62 (t, J=7.4 Hz, 1H), 7.51 (t, J=7.8 Hz, 2H), 4.03 (s, 3H).

Example 5

Preparation of 1-(3-fluorobenzenesulfonyl)-6-[(1-methyl)-4-pyrazolyl]-1-H-pyrazolo[4,3-b]pyridine

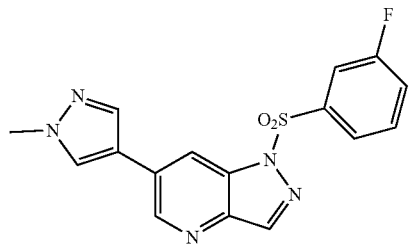 [SMILES: Cn1cc(-c2cnc3cnn(S(=O)(=O)c4cccc(F)c4)c3c2)cn1]

Except for 3-fluorophenylsulfonyl chloride was used instead of 2-nitrophenylsulfonyl chloride, compound 1-(3-fluorobenzenesulfonyl)-6-[(1-methyl)-4-pyrazolyl]-1-H-pyrazolo[4,3-b]pyridine was prepared by the same process as Example 3.

$^1$H NMR (400 MHz, CDCl$_3$) δ 8.86 (s, 1H), 8.46 (s, 1H), 8.40 (s, 1H), 7.94 (s, 1H), 7.91-7.78 (m, 2H), 7.72 (d, J=7.4 Hz, 1H), 7.54-7.41 (m, 1H), 7.32 (s, 1H), 4.03 (s, 3H).

Example 6

Preparation of 1-(2-fluorobenzenesulfonyl)-6-[(1-methyl)-4-pyrazolyl]-1-H-pyrazolo[4,3-b]pyridine

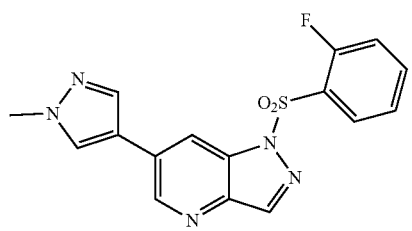 [SMILES: Cn1cc(-c2cnc3cnn(S(=O)(=O)c4ccccc4F)c3c2)cn1]

Except for 2-fluorophenylsulfonyl chloride was used instead of 2-nitrophenylsulfonyl chloride, compound 1-(2-fluorobenzenesulfonyl)-6-[(1-methyl)-4-pyrazolyl]-1-H-pyrazolo[4,3-b]pyridine was prepared by the same process as Example 3.

$^1$H NMR (400 MHz, CDCl$_3$) δ 8.88 (d, J=1.9 Hz, 1H), 8.52 (s, 1H), 8.38 (d, J=0.8 Hz, 1H), 8.24-8.15 (m, 1H), 7.95 (d, J=0.7 Hz, 1H), 7.86 (s, 1H), 7.64 (dd, J=8.3, 3.2 Hz, 1H), 7.43-7.33 (m, 2H), 7.17-7.07 (m, 1H), 4.03 (s, 3H).

Example 7

Preparation of 1-(4-fluorobenzenesulfonyl)-6-[(1-methyl)-4-pyrazolyl]-1-H-pyrazolo[4,3-b]pyridine

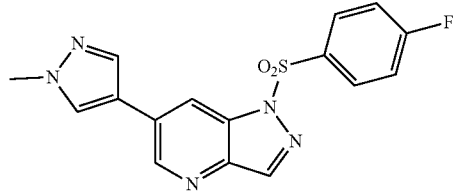 [SMILES: Cn1cc(-c2cnc3cnn(S(=O)(=O)c4ccc(F)cc4)c3c2)cn1]

Except for 4-fluorophenylsulfonyl chloride was used instead of 2-nitrophenylsulfonyl chloride, compound 1-(4-fluorobenzenesulfonyl)-6-[(1-methyl)-4-pyrazolyl]-1-H-pyrazolo[4,3-b]pyridine was prepared by the same process as Example 3.

¹H NMR (400 MHz, CDCl₃) δ 8.85 (d, J=1.9 Hz, 1H), 8.47 (dd, J=1.9, 0.9 Hz, 1H), 8.38 (d, J=0.9 Hz, 1H), 8.09-8.01 (m, 2H), 7.94 (d, J=0.8 Hz, 1H), 7.85 (s, 1H), 7.23-7.14 (m, 2H), 4.03 (s, 3H).

Example 8

Preparation of 1-(2-cyanobenzenesulfonyl)-6-[(1-methyl)-4-pyrazolyl]-1-H-pyrazolo[4,3-b]pyridine

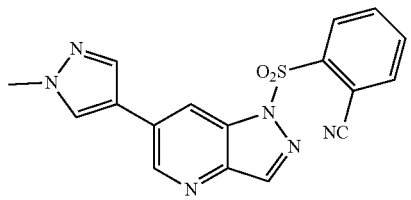 [SMILES: Cn1cc(-c2cnc3cnn(S(=O)(=O)c4ccccc4C#N)c3c2)cn1]

Except for 2-cyanophenylsulfonyl chloride was used instead of 2-nitrophenylsulfonyl chloride, compound 1-(2-cyanobenzenesulfonyl)-6-[(1-methyl)-4-pyrazolyl]-1-H-pyrazolo[4,3-b]pyridine was prepared by the same process as Example 3.

¹H NMR (400 MHz, CDCl₃) δ 8.89 (d, J=1.9 Hz, 1H), 8.71 (dd, J=1.9, 0.9 Hz, 1H), 8.42 (dd, J=8.3, 1.1 Hz, 1H), 8.39 (d, J=0.9 Hz, 1H), 7.96 (d, J=0.7 Hz, 1H), 7.89 (s, 1H), 7.81 (m, 31H), 4.01 (s, 3H).

Example 9

Preparation of 1-(4-nitrobenzenesulfonyl)-6-[(1-methyl)-4-pyrazolyl]-1-H-pyrazolo[4,3-b]pyridine

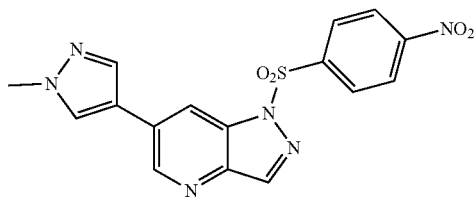 [SMILES: Cn1cc(-c2cnc3cnn(S(=O)(=O)c4ccc([N+](=O)[O-])cc4)c3c2)cn1]

Except for 4-nitrophenylsulfonyl chloride was used instead of 2-nitrophenylsulfonyl chloride, compound 1-(4-nitrobenzenesulfonyl)-6-[(1-methyl)-4-pyrazolyl]-1-H-pyrazolo[4,3-b]pyridine was prepared by the same process as Example 3.

¹H NMR (400 MHz, CDCl₃) δ 8.87 (d, J=1.9 Hz, 1H), 8.49-8.38 (m, 2H), 8.38-8.31 (m, 2H), 8.26-8.18 (m, 2H), 7.95 (d, J=0.7 Hz, 1H), 7.86 (s, 1H), 4.04 (s, 3H).

Example 10

Preparation of 1-(3,4-dimethoxybenzenesulfonyl)-6-[(1-methyl)-4-pyrazolyl]-1-H-pyrazolo[4,3-b]pyridine

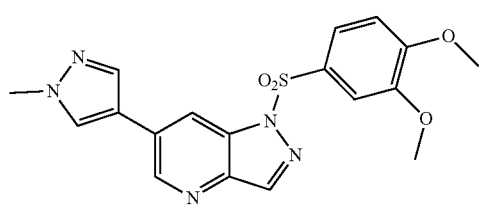

Except for 3,4-dimethoxyphenylsulfonyl chloride was used instead of 2-nitrophenylsulfonyl chloride, compound 1-(3,4-dimethoxybenzenesulfonyl)-6-[(1-methyl)-4-pyrazolyl]-1-H-pyrazolo[4,3-b]pyridine was prepared by the same process as Example 3.

¹H NMR (400 MHz, CDCl₃) δ 8.84 (d, J=1.9 Hz, 1H), 8.48 (dd, J=1.9, 0.9 Hz, 1H), 8.37 (d, J=0.9 Hz, 1H), 7.94 (d, J=0.8 Hz, 1H), 7.86 (s, 1H), 7.63 (dd, J=8.6, 2.2 Hz, 1H), 7.46 (d, J=2.2 Hz, 1H), 6.89 (d, J=8.7 Hz, 1H), 4.03 (s, 3H), 3.90 (s, 3H), 3.89 (s, 3H).

Example 11

Preparation of 1-(3,5-dimethylisoxazolesulfonyl)-6-[(1-methyl)-4-pyrazolyl]-1-H-pyrazolo[4,3-b]pyridine

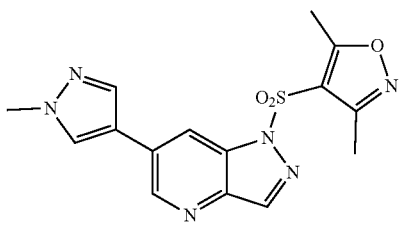 [SMILES: Cc1noc(C)c1S(=O)(=O)n1ncc2ncc(-c3cnn(C)c3)cc21]

Except for 3,5-dimethylisoxazolesulfonyl chloride was used instead of 2-nitrophenylsulfonyl chloride, compound 1-(3,5-dimethylisoxazolesulfonyl)-6-[(1-methyl)-4-pyrazolyl]-1-H-pyrazolo[4,3-b]pyridine was prepared by the same process as Example 3.

¹H NMR (400 MHz, CDCl₃) δ 8.88 (d, J=1.8 Hz, 1H), 8.46-8.38 (m, 2H), 7.92 (s, 1H), 7.84 (s, 1H), 4.03 (s, 3H).

Example 12

Preparation of 1-(2,4-difluorobenzenesulfonyl)-6-[(1-methyl)-4-pyrazolyl]-1-H-pyrazolo[4,3-b]pyridine

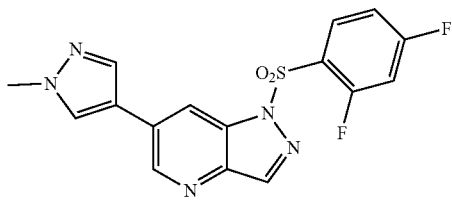 [SMILES: Cn1cc(-c2cnc3cnn(S(=O)(=O)c4ccc(F)cc4F)c3c2)cn1]

Except for 2,4-difluorophenylsulfonyl chloride was used instead of 2-nitrophenylsulfonyl chloride, compound 1-(2,4-difluorobenzenesulfonyl)-6-[(1-methyl)-4-pyrazolyl]-1-H-pyrazolo[4,3-b]pyridine was prepared by the same process as Example 3.

¹H NMR (400 MHz, CDCl₃) δ 8.89 (d, J=1.6 Hz, 1H), 8.50 (s, 1H), 8.38 (s, 1H), 8.23 (dd, J=14.3, 8.4 Hz, 1H), 7.95 (s, 1H), 7.86 (s, 1H), 7.10 (t, J=8.4 Hz, 1H), 6.87 (t, J=9.2 Hz, 1H), 4.03 (s, 3H).

Example 13

Preparation of 1-(4-acetylbenzenesulfonyl)-6-[(1-methyl)-4-pyrazolyl]-H-pyrazolo[4,3-b]pyridine

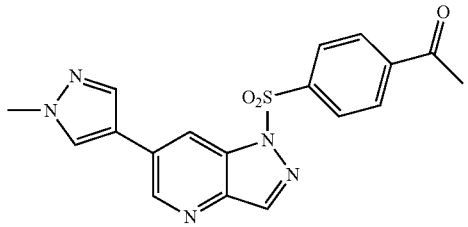 [SMILES: CC(=O)c1ccc(S(=O)(=O)n2ncc3ncc(-c4cnn(C)c4)cc32)cc1]

Except for 4-acetylphenylsulfonyl chloride, compound 1-(4-acetylbenzenesulfonyl)-6-[(1-methyl)-4-pyrazolyl]-1-H-pyrazolo[4,3-b]pyridine was prepared by the same process as Example 3.

$^1$H NMR (400 MHz, CDCl$_3$) δ 8.86 (d, J=1.9 Hz, 1H), 8.48 (dd, J=1.9, 0.9 Hz, 1H), 8.39 (d, J=0.8 Hz, 1H), 8.14-8.09 (m, 2H), 8.06-8.02 (m, 2H), 7.95 (s, 1H), 7.86 (s, 1H), 4.03 (s, 3H).

Example 14

Preparation of 1-(2-trifluoromethylbenzenesulfonyl)-6-[(1-methyl)-4-pyrazolyl]-1-H-pyrazolo[4,3-b]pyridine

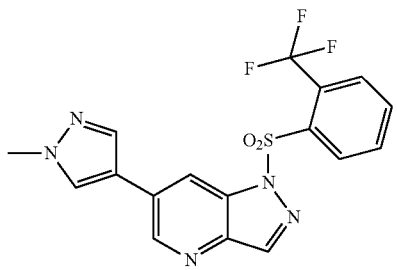 [SMILES: Cn1cc(-c2cnc3cnn(S(=O)(=O)c4ccccc4C(F)(F)F)c3c2)cn1]

Except for 2-trifluoromethylphenylsulfonyl chloride was used instead of 2-nitrophenylsulfonyl chloride, compound 1-(2-trifluoromethylbenzenesulfonyl)-6-[(1-methyl)-4-pyrazolyl]-1-H-pyrazolo[4,3-b]pyridine was prepared by the same process as Example 3.

$^1$H NMR (400 MHz, CDCl$_3$) δ 8.87 (d, J=1.9 Hz, 1H), 8.50-8.46 (m, 2H), 8.36 (d, J=0.8 Hz, 1H), 7.94 (s, 1H), 7.91-7.87 (m, 1H), 7.86-7.80 (m, 3H), 4.03 (s, 3H).

Example 15

Preparation of 1-(4-trifluoromethylbenzenesulfonyl)-6-[(1-methyl)-4-pyrazolyl]-1-H-pyrazolo[4,3-b]pyridine

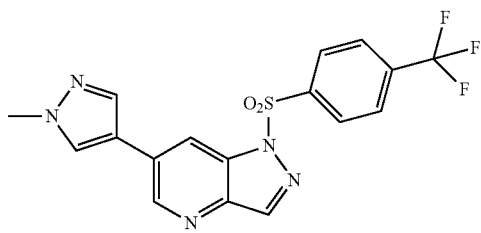 [SMILES: Cn1cc(-c2cnc3cnn(S(=O)(=O)c4ccc(C(F)(F)F)cc4)c3c2)cn1]

Except for 4-trifluoromethylphenylsulfonyl chloride was used instead of 2-nitrophenylsulfonyl chloride, compound 1-(4-trifluoromethylbenzenesulfonyl)-6-[(1-methyl)-4-pyrazolyl]-1-H-pyrazolo[4,3-b]pyridine was prepared by the same process as Example 3.

$^1$H NMR (400 MHz, CDCl$_3$) δ 8.86 (d, J=1.9 Hz, 1H), 8.47 (d, J=1.0 Hz, 1H), 8.40 (d, J=0.8 Hz, 1H), 8.15 (d, J=8.2 Hz, 2H), 7.94 (s, 1H), 7.86 (s, 1H), 7.77 (d, J=8.3 Hz, 2H), 4.03 (s, 3H).

Example 16

Preparation of 1-(3-trifluoromethylbenzenesulfonyl)-6-[(1-methyl)-4-pyrazolyl]-1-H-pyrazolo[4,3-b]pyridine

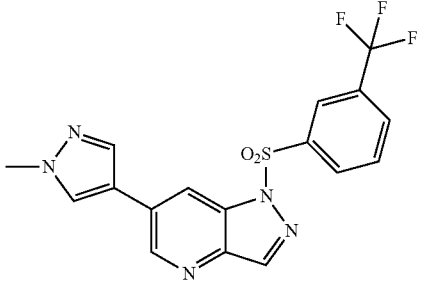 [SMILES: Cn1cc(-c2cnc3cnn(S(=O)(=O)c4cccc(C(F)(F)F)c4)c3c2)cn1]

Except for 3-trifluoromethylphenylsulfonyl chloride was used instead of 2-nitrophenylsulfonyl chloride, compound 1-(3-trifluoromethylbenzenesulfonyl)-6-[(1-methyl)-4-pyrazolyl]-1-H-pyrazolo[4,3-b]pyridine was prepared by the same process as Example 3.

$^1$H NMR (400 MHz, CDCl$_3$) δ 8.87 (s, 1H), 8.47 (s, 1H), 8.41 (s, 1H), 8.31 (s, 1H), 8.22 (d, J=8.2 Hz, 1H), 7.95 (s, 1H), 7.93-7.83 (m, 2H), 7.68 (t, J=8.0 Hz, 1H), 4.03 (s, 3H).

Example 17

Preparation of 1-(4-methoxybenzenesulfonyl)-6-[(1-methyl)-4-pyrazolyl]-1-H-pyrazolo[4,3-b]pyridine

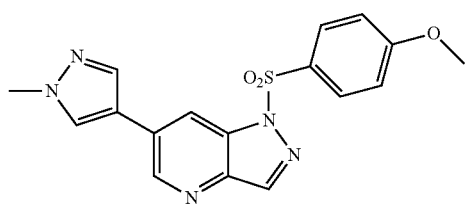

Except for 4-methoxyphenylsulfonyl chloride was used instead of 2-nitrophenylsulfonyl chloride, compound 1-(4-methoxybenzenesulfonyl)-6-[(1-methyl)-4-pyrazolyl]-1-H-pyrazolo[4,3-b]pyridine was prepared by the same process as Example 3.

$^1$H NMR (400 MHz, CDCl$_3$) δ 8.84 (s, 1H), 8.49 (d, J=1.0 Hz, 1H), 8.36 (d, J=0.6 Hz, 1H), 7.96 (d, J=2.1 Hz, 1H), 7.94 (s, 2H), 7.85 (s, 1H), 6.94 (d, J=9.1 Hz, 2H), 4.03 (s, 3H), 3.83 (s, 3H).

Example 18

Preparation of 1-[(6-chloro-imidazo[2,1-b]thiazole)-5-sulfonyl)]-6-[(1-methyl)-4-pyrazolyl]-1-H-pyrazolo[4,3-b]pyridine

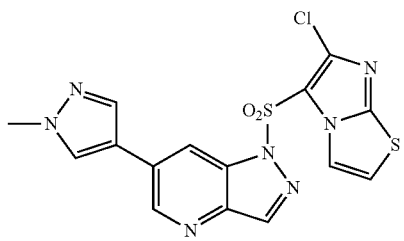 [SMILES: Cn1cc(-c2cnc3cnn(S(=O)(=O)c4c(Cl)nc5sccn45)c3c2)cn1]

Except for (6-chloro-imidazo[2,1-b]thiazole)-5-sulfonyl chloride was used instead of 2-nitrophenylsulfonyl chloride, compound 1-[(6-chloro-imidazo[2,1-b]thiazole)-5-sulfonyl)]-6-[(1-methyl)-4-pyrazolyl]-1-H-pyrazolo[4,3-b]pyridine was prepared by the same process as Example 3.

$^1$H NMR (400 MHz, CDCl$_3$) δ 8.88 (d, J=1.8 Hz, 1H), 8.54 (s, 1H), 8.35 (s, 1H), 8.21 (d, J=4.6 Hz, 1H), 7.93 (s, 1H), 7.84 (s, 1H), 7.17 (d, J=4.5 Hz, 1H), 4.03 (s, 3H).

Example 19

Preparation of 1-(imidazo[1,2-a]pyridine-3-sulfonyl)-6-[(1-methyl)-4-pyrazolyl]-1-H-pyrazolo[4,3-b]pyridine

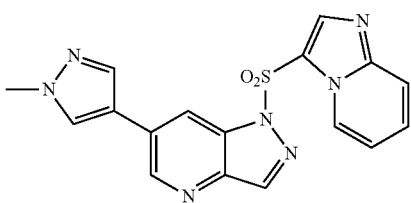 [SMILES: Cn1cc(-c2cnc3cnn(S(=O)(=O)c4cnc5ccccn45)c3c2)cn1]

Except for imidazo[1,2-a]pyridine-3-sulfonyl chloride was used instead of 2-nitrophenylsulfonyl chloride, compound 1-(imidazo[1,2-a]pyridine-3-sulfonyl)-6-[(1-methyl)-4-pyrazolyl]-1-H-pyrazolo[4,3-b]pyridine was prepared by the same process as Example 3.

$^1$H NMR (400 MHz, CDCl$_3$) δ 9.13 (d, J=6.9 Hz, 1H), 8.85 (d, J=1.5 Hz, 1H), 8.46 (s, 1H), 8.32 (d, J=3.4 Hz, 2H), 7.94 (s, 1H), 7.86 (s, 1H), 7.74 (d, J=9.2 Hz, 1H), 7.61-7.46 (m, 1H), 7.17 (t, J=6.9 Hz, 1H), 4.03 (s, 3H).

Example 20

Preparation of 1-(benzo[1,2,5]oxadiazole-4-sulfonyl)-6-[(1-methyl)-4-pyrazolyl]-1-H-pyrazolo[4,3-b]pyridine

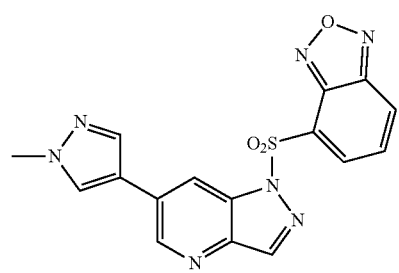 [SMILES: Cn1cc(-c2cnc3cnn(S(=O)(=O)c4cccc5nonc45)c3c2)cn1]

Except for benzo[1,2,5]oxadiazole-4-sulfonyl chloride was used instead of 2-nitrophenylsulfonyl chloride, compound 1-(benzo[1,2,5]oxadiazole-4-sulfonyl)-6-[(1-methyl)-4-pyrazolyl]-1-H-pyrazolo[4,3-b]pyridine was prepared by the same process as Example 3.

$^1$H NMR (400 MHz, CDCl$_3$) δ 8.89 (d, J=1.9 Hz, 1H), 8.74 (dd, J=1.9, 0.8 Hz, 1H), 8.45 (dd, J=6.9, 0.7 Hz, 1H), 8.35 (d, J=0.8 Hz, 1H), 8.18 (dd, J=9.0, 0.7 Hz, 1H), 8.00 (s, 1H), 7.93 (s, 1H), 7.65 (dd, J=9.1, 6.9 Hz, 1H), 4.05 (s, 3H).

Example 21

Preparation of 1-(imidazo[1,2-b]pyridazine-3-sulfonyl)-6-[(1-methyl)-4-pyrazolyl]-1-H-pyrazolo[4,3-b]pyridine

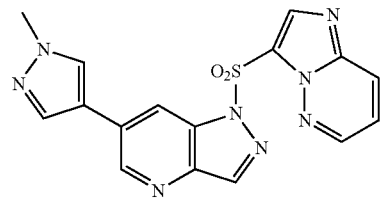 [SMILES: Cn1cc(-c2cnc3cnn(S(=O)(=O)c4cnc5cccnn45)c3c2)cn1]

Except for imidazo[1,2-b]pyridazine-3-sulfonyl chloride was used instead of 2-nitrophenylsulfonyl chloride, compound 1-(imidazo[1,2-b]pyridazine-3-sulfonyl)-6-[(1-methyl)-4-pyrazolyl]-1-H-pyrazolo[4,3-b]pyridine was prepared by the same process as Example 3.

$^1$H NMR (400 MHz, CDCl$_3$) δ 8.87 (d, J=1.9 Hz, 1H), 8.64 (dd, J=1.9, 0.9 Hz, 1H), 8.58 (s, 1H), 8.35 (d, J=0.9 Hz, 1H), 8.30 (dd, J=4.5, 1.6 Hz, 1H), 8.08 (dd, J=9.3, 1.6 Hz, 1H), 7.98 (d, J=0.8 Hz, 1H), 7.89 (s, 1H), 7.26-7.23 (m, 1H), 4.04 (s, 3H).

Example 22

Preparation of 1-(pyrazolo[1,5-a]pyrimidine-3-sulfonyl)-6-[(1-methyl)-4-pyrazolyl]-1-H-pyrazolo[4,3-b]pyridine

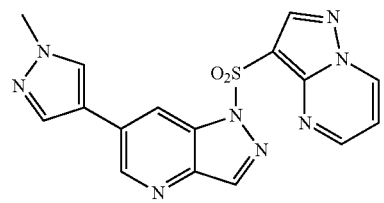 [SMILES: Cn1cc(-c2cnc3cnn(S(=O)(=O)c4cnn5cccnc45)c3c2)cn1]

Except for pyrazolo[1,5-a]pyrimidine-3-sulfonyl chloride was used instead of 2-nitrophenylsulfonyl chloride, compound 1-(pyrazolo[1,5-a]pyrimidine-3-sulfonyl)-6-[(1-methyl)-4-pyrazolyl]-1-H-pyrazolo[4,3-b]pyridine was prepared by the same process as Example 3.

$^1$H NMR (400 MHz, CDCl$_3$) δ 8.83 (d, J=1.8 Hz, 1H), 8.76 (dd, J=7.0, 1.7 Hz, 1H), 8.71 (d, J=4.1 Hz, 2H), 8.66 (s, 1H), 8.35 (s, 1H), 7.97 (s, 1H), 7.88 (s, 1H), 7.11 (dd, J=6.9, 4.3 Hz, 1H), 4.03 (s, 3H).

Example 23

Preparation of 1-(imidazo[1,2-a]pyrimidine-3-sulfonyl)-6-[(1-methyl)-4-pyrazolyl]-1-H-pyrazolo[4,3-b]pyridine

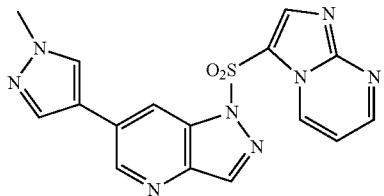 [SMILES: Cn1cc(-c2cnc3cnn(S(=O)(=O)c4cnc5ncccn45)c3c2)cn1]

Except for imidazo[1,2-a]pyrimidine-3-sulfonyl chloride was used instead of 2-nitrophenylsulfonyl chloride, compound 1-(imidazo[1,2-a]pyrimidine-3-sulfonyl)-6-[(1-methyl)-4-pyrazolyl]-1-H-pyrazolo[4,3-b]pyridine was prepared by the same process as Example 3.

$^1$H NMR (400 MHz, CDCl$_3$) δ 8.82 (d, J=1.8 Hz, 1H), 8.74 (dd, J=7.0, 1.8 Hz, 1H), 8.71 (d, J=4.2 Hz, 2H), 8.63 (s, 1H), 8.37 (s, 1H), 7.95 (s, 1H), 7.83 (s, 1H), 7.12 (dd, J=7.0, 4.3 Hz, 1H), 4.04 (s, 3H).

Example 24

Preparation of 1-[(6-chloro-imidazo[1,2-a]pyridine)-3-sulfonyl]-6-[(1-methyl)-4-pyrazolyl]-1-H-pyrazolo[4,3-b]pyridine

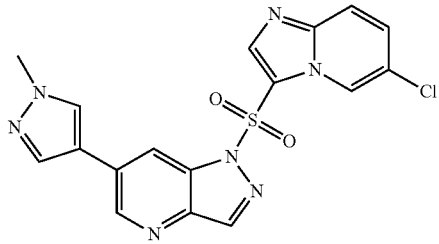 [SMILES: Cn1cc(-c2cnc3cnn(S(=O)(=O)c4cnc5ccc(Cl)cn45)c3c2)cn1]

Except for (6-chloro-imidazo[1,2-a]pyridine)-3-sulfonyl chloride was used instead of 2-nitrophenylsulfonyl chloride, compound 1-[(6-chloro-imidazo[1,2-a]pyridine)-3-sulfonyl]-6-[(1-methyl)-4-pyrazolyl]-1-H-pyrazolo[4,3-b]pyridine was prepared by the same process as Example 3.

$^1$H NMR (400 MHz, CDCl$_3$) δ 9.20 (d, J=1.1 Hz, 1H), 8.87 (d, J=1.9 Hz, 1H), 8.44 (d, J=1.0 Hz, 1H), 8.37 (d, J=0.8 Hz, 1H), 8.28 (s, 1H), 7.95 (s, 1H), 7.86 (s, 1H), 7.68 (d, J=8.8 Hz, 1H), 7.50 (dd, J=9.5, 2.0 Hz, 1H), 4.04 (s, 3H).

Example 25

Preparation of 1-[(6-chloro-imidazo[1,2-b]pyridazine)-3-sulfonyl]-6-[(1-methyl)-4-pyrazolyl]-1-H-pyrazolo[4,3-b]pyridine

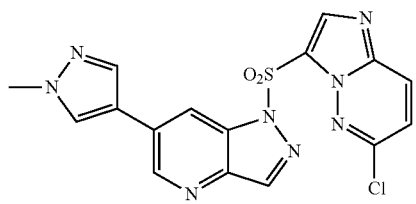 [SMILES: Cn1cc(-c2cnc3cnn(S(=O)(=O)c4cnc5ccc(Cl)nn45)c3c2)cn1]

Except for (6-chloro-imidazo[1,2-b]pyridazine)-3-sulfonyl chloride was used instead of 2-nitrophenylsulfonyl chloride, compound 1-[(6-chloro-imidazo[1,2-b]pyridazine)-3-sulfonyl]-6-[(1-methyl)-4-pyrazolyl]-1-H-pyrazolo[4,3-b]pyridine was prepared by the same process as Example 3.

$^1$H NMR (400 MHz, CDCl$_3$) δ 8.89 (d, J=1.9 Hz, 1H), 8.72 (d, J=1.0 Hz, 1H), 8.54 (s, 1H), 8.37 (d, J=0.6 Hz, 1H), 8.04-7.96 (m, 2H), 7.92 (s, 1H), 7.21 (d, J=9.5 Hz, 1H), 4.04 (s, 3H).

Example 26

Preparation of 1-[(6-trifluoromethyl-imidazo[1,2-a]pyridine)-3-sulfonyl]-6-[(1-methyl)-4-pyrazolyl]-1-H-pyrazolo[4,3-b]pyridine

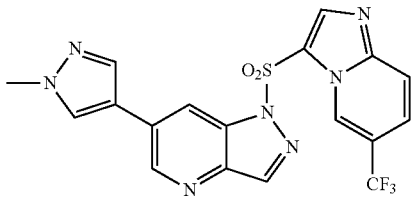 [SMILES: Cn1cc(-c2cnc3cnn(S(=O)(=O)c4cnc5ccc(C(F)(F)F)cn45)c3c2)cn1]

Except for (6-trifluoromethyl-imidazo[1,2-a]pyridine)-3-sulfonyl chloride was used instead of 2-nitrophenylsulfonyl chloride, compound 1-[(6-trifluoromethyl-imidazo[1,2-a]pyridine)-3-sulfonyl]-6-[(1-methyl)-4-pyrazolyl]-1-H-pyrazolo[4,3-b]pyridine was prepared by the same process as Example 3.

$^1$H NMR (400 MHz, CDCl$_3$) δ 9.53 (s, 1H), 8.87 (d, J=1.9 Hz, 1H), 8.45 (s, 1H), 8.37 (d, J=6.4 Hz, 2H), 7.95 (s, 1H), 7.85 (d, J=8.4 Hz, 2H), 7.67 (d, J=8.1 Hz, 1H), 4.04 (s, 3H).

Example 27

Preparation of 1-{(6-[(1-methyl)-4-pyrazolyl]-imidazo[1,2-a]pyridine)-3-sulfonyl}-6-[(1-methyl)-4-pyrazolyl]-1-H-pyrazolo[4,3-b]pyridine

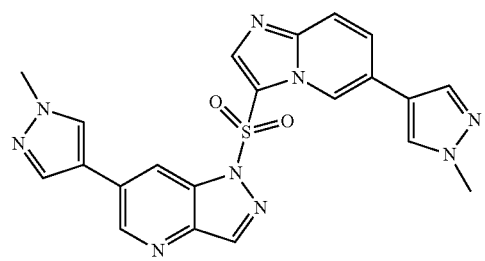 [SMILES: Cn1cc(-c2cnc3cnn(S(=O)(=O)c4cnc5ccc(-c6cnn(C)c6)cn45)c3c2)cn1]

Into a microwave reaction tube were charged 120 mg Compound of Example 24, 64 mg 1-methyl-1H-pyrazolo-4-borate pinacol ester and 120 mg potassium carbonate, and 5 ml dioxane, 2.5 ml ethanol and 2.5 ml water were added into the microwave reaction tube, air was displaced for three times, under a nitrogen atmosphere, 11.8 mg complex of 1,1'-bis(diphenylphosphino) ferrocene palladium (II) dichloride and dichloromethane was added into the microwave tube, then the microwave tube was sealed. The microwave tube was placed into a microwave reactor, reacted at 90° C. for 30 minutes, the reaction was completed. The aforementioned reactant liquid was poured into 15 ml water, extracted three times with dichloromethane, the organic layer was dried over anhydrous sodium sulfate then concentrated, and isolated by flash preparative chromatography to obtain the target compound (m=23 mg, yield: 17.3%).

$^1$H NMR (400 MHz, CDCl$_3$) δ 9.17 (dd, J=1.5, 0.9 Hz, 1H), 8.85 (d, J=1.9 Hz, 1H), 8.46 (dd, J=1.8, 0.8 Hz, 1H), 8.33 (d, J=0.8 Hz, 1H), 8.28 (s, 1H), 7.95 (d, J=0.4 Hz, 1H), 7.86 (s, 1H), 7.82 (d, J=0.6 Hz, 1H), 7.74 (s, 1H), 7.72 (dd, J=9.3, 0.8 Hz, 1H), 7.63 (dd, J=9.3, 1.7 Hz, 1H), 4.04 (s, 3H), 4.00 (s, 3H).

Example 28

Preparation of 1-(imidazo[1,2-a]pyridine-3-sulfonyl)-6-phenyl-1-H-pyrazolo[4,3-b]pyridine

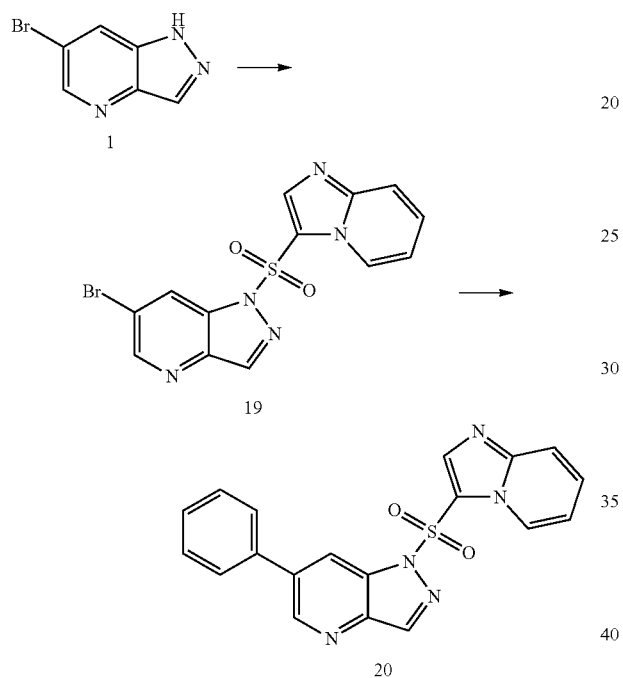

Step 1: Preparation of 1-(imidazo[1,2-a]pyridine-3-sulfonyl)-6-bromo-1-H-pyrazolo[4,3-b]pyridine Forty six mg sodium hydride was dissolved in 15 ml anhydrous tetrahydrofuran, stirred for 5 minutes at room temperature. One hundred and sixty mg compound 1 was dissolved in 15 ml anhydrous tetrahydrofuran, then slowly and dropwisely added into sodium hydride solution in tetrahydrofuran, stirred overnight at room temperature after the addition was finished. One hundred and sixty seven mg imidazo[1,2-a]pyridine-3-sulfonyl chloride was dissolved in 15 ml anhydrous tetrahydrofuran, slowly and dropwisely added into the reactant liquid, stirred overnight at room temperature after the addition was finished, the reaction was completed. Tetrahydrofuran was removed by evaporation, and the remainder was dissolved in dichloromethane, washed three times with water, the organic layer was dried over anhydrous sodium sulfate then concentrated, isolated by flash preparative chromatography to obtain compound 19 (m=231 mg, yield: 79%).

$^1$H NMR (400 MHz, CDCl$_3$) δ 9.10 (d, J=6.9 Hz, 1H), 8.74 (d, J=1.9 Hz, 1H), 8.68 (dd, J=1.9, 0.9 Hz, 1H), 8.34 (d, J=7.6 Hz, 2H), 7.76 (d, J=9.1 Hz, 1H), 7.60-7.50 (m, 1H), 7.19 (dd, J=7.5, 6.4 Hz, 1H).

Step 2: Preparation of 1-(imidazo[1,2-a]pyridine-3-sulfonyl)-6-phenyl-1-H-pyrazolo[4,3-b]pyridine Eighty mg 1-(imidazo[1,2-a]pyridine-3-sulfonyl)-6-bromo-1-H-pyrazolo[4,3-b]pyridine, 31 mg phenylboronic acid and 88 mg potassium carbonate were charged into a microwave reaction tube, 5 ml dioxane, 2.5 ml ethanol and 2.5 ml water were added into the microwave reaction tube, air was displaced for three times, under a nitrogen atmosphere, 8.6 mg complex of 1,1'-bis(diphenylphosphino) ferrocene palladium (II) dichloride and dichloromethane was added into the microwave tube, then the microwave tube was sealed. The microwave tube was placed into a microwave reactor, reaction was conducted at a temperature of 120° C. for 30 minutes, till the reaction was completed. The aforementioned reactant liquid was poured into 15 ml water, extracted three times with dichloromethane, the organic layer was dried over anhydrous sodium sulfate then concentrated, and isolated by flash preparative chromatography to obtain the target compound (m=54 mg, yield: 68%).

$^1$H NMR (400 MHz, CDCl$_3$) δ 9.14 (dd, J=5.8, 1.1 Hz, 1H), 8.95 (d, J=1.9 Hz, 1H), 8.62 (dd, J=1.9, 0.9 Hz, 11H), 8.39 (d, J=0.8 Hz, 1H), 8.33 (s, 1H), 7.78-7.67 (m, 3H), 7.62-7.47 (m, 4H), 7.21-7.13 (m, 1H).

Example 29

Preparation of 1-(imidazo[1,2-a]pyridine-3-sulfonyl)-6-(3-thienyl)-1-H-pyrazolo[4,3-b]pyridine

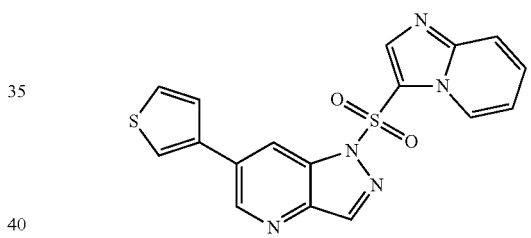

Except for 3-thiopheneboronic acid was used instead of phenylboronic acid, compound 1-(imidazo[1,2-a]pyridine-3-sulfonyl)-6-(3-thienyl)-1-H-pyrazolo[4,3-b]pyridine was prepared by the same process as Example 28.

$^1$H NMR (400 MHz, CDCl$_3$) δ 9.13 (dt, J=6.9, 1.2 Hz, 1H), 8.87 (d, J=1.9 Hz, 1H), 8.48 (dd, J=1.9, 0.9 Hz, 1H), 8.35 (d, J=0.9 Hz, 1H), 8.33 (s, 1H), 7.99-7.94 (m, 1H), 7.75 (dt, J=9.1, 1.1 Hz, 1H), 7.64-7.58 (m, 1H), 7.54 (ddd, J=9.0, 7.0, 1.3 Hz, 1H), 7.18 (td, J=7.0, 1.2 Hz, 1H), 6.87 (dd, J=1.9, 0.9 Hz, 1H).

Example 30

Preparation of 1-(imidazo[1,2-a]pyridine-3-sulfonyl)-6-(3-pyridinyl)-1-H-pyrazolo[4,3-b]pyridine

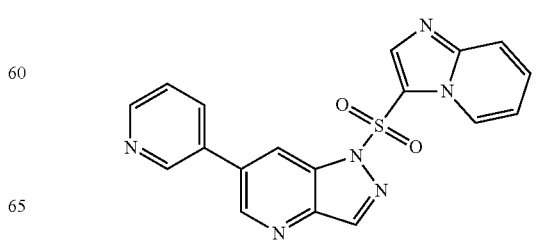

Except for 3-pyridineboronic acid was used instead of phenylboronic acid, compound 1-(imidazo[1,2-a]pyridine-3-sulfonyl)-6-(3-pyridinyl)-1-H-pyrazolo[4,3-b]pyridine was prepared by the same process as Example 28.

$^1$H NMR (400 MHz, CDCl$_3$) δ 9.15 (d, J=6.9 Hz, 1H), 9.03-8.91 (m, 2H), 8.77 (d, J=3.9 Hz, 1H), 8.64 (dd, J=1.8, 0.8 Hz, 1H), 8.43 (d, J=0.7 Hz, 1H), 8.34 (s, 1H), 8.06-7.97 (m, 1H), 7.76 (d, J=9.0 Hz, 1H), 7.60-7.46 (m, 2H), 7.20 (td, J=7.0, 1.0 Hz, 1H).

Example 31

Preparation of 1-(imidazo[1,2-a]pyridine-3-sulfon)-6-(3-furanyl)-1-H-pyrazolo[4,3-b]pyridine

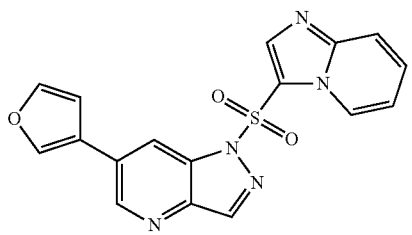 [SMILES: O=S(=O)(c1cnc2ccccn12)n1ncc2ncc(-c3ccoc3)cc21]

Except for 3-furanboronic acid was used instead of phenylboronic acid, compound 1-(imidazo[1,2-a]pyridine-3-sulfonyl)-6-(3-furanyl)-1-H-pyrazolo[4,3-b]pyridine was prepared by the same process as Example 28.

$^1$H NMR (400 MHz, CDCl$_3$) δ 9.13 (dt, J=6.9, 1.2 Hz, 1H), 8.98 (d, J=1.9 Hz, 1H), 8.60 (dd, J=1.9, 0.9 Hz, 1H), 8.36 (d, J=0.9 Hz, 1H), 8.33 (s, 1H), 7.78-7.69 (m, 2H), 7.58-7.49 (m, 3H), 7.17 (td, J=7.0, 1.2 Hz, 1H).

Example 32

Preparation of 1-(imidazo[1,2-a]pyridine-3-sulfonyl)-6-(4-trifluoromethylphenyl]-1-H-pyrazolo[4,3-b]pyridine

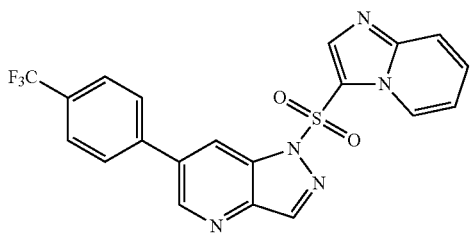 [SMILES: O=S(=O)(c1cnc2ccccn12)n1ncc2ncc(-c3ccc(C(F)(F)F)cc3)cc21]

Except for 4-trifluoromethylphenylboronic acid was used instead of phenylboronic acid, compound 1-(imidazo[1,2-a]pyridine-3-sulfonyl)-6-(4-trifluoromethylphenyl)-1-H-pyrazolo[4,3-b]pyridine was prepared by the same process as Example 28.

$^1$H NMR (400 MHz, CDCl$_3$) δ 9.15 (d, J=6.9 Hz, 1H), 8.95 (d, J=1.8 Hz, 1H), 8.64 (s, 1H), 8.42 (s, 1H), 8.33 (s, 1H), 7.89-7.79 (m, 4H), 7.76 (d, J=9.1 Hz, 1H), 7.60-7.50 (m, 1H), 7.19 (t, J=7.0 Hz, 1H).

Example 33

Preparation of 1-(imidazo[1,2-a]pyridine-3-sulfonyl)-6-(2-naphthyl)-1-H-pyrazolo[4,3-b]pyridine

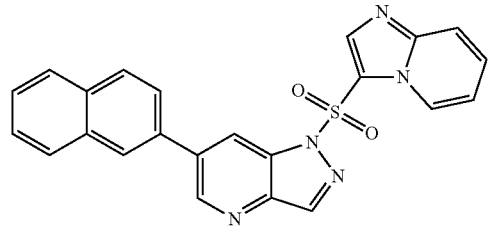 [SMILES: O=S(=O)(c1cnc2ccccn12)n1ncc2ncc(-c3ccc4ccccc4c3)cc21]

Except for 2-naphthylboronic acid was used instead of phenylboronic acid, compound 1-(imidazo[1,2-a]pyridine-3-sulfonyl)-6-(2-naphthyl)-1-H-pyrazolo[4,3-b]pyridine was prepared by the same process as Example 28.

$^1$H NMR (400 MHz, CDCl$_3$) δ 9.15 (dt, J=6.9, 1.2 Hz, 1H), 9.08 (d, J=1.9 Hz, 1H), 8.74 (dd, J=1.9, 0.9 Hz, 1H), 8.42 (d, J=0.9 Hz, 1H), 8.36 (s, 1H), 8.17 (s, 1H), 8.04 (d, J=8.7 Hz, 1H), 8.02-7.97 (m, 1H), 7.97-7.92 (m, 1H), 7.81 (dd, J=8.5, 1.9 Hz, 1H), 7.78-7.72 (m, 1H), 7.63-7.57 (m, 2H), 7.57-7.49 (m, 1H), 7.18 (td, J=7.0, 1.1 Hz, 1H).

Example 34

Preparation of 1-(imidazo[1,2-a]pyridine-3-sulfonyl)-6-(4-methylsulfamidophenyl)-1-H-pyrazolo[4,3-b]pyridine

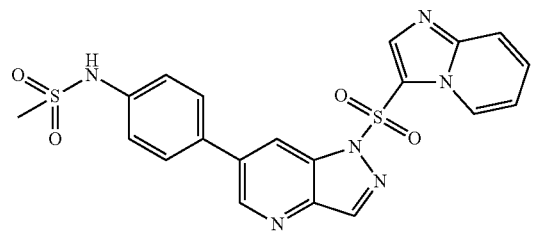 [SMILES: CS(=O)(=O)Nc1ccc(-c2cnc3cnn(S(=O)(=O)c4cnc5ccccn45)c3c2)cc1]

Except for 4-methylsulfamidophenylboronic acid was used instead of phenylboronic acid, compound 1-(imidazo[1,2-a]pyridine-3-sulfonyl)-6-(4-methylsulfamidophenyl)-1-H-pyrazolo[4,3-b]pyridine was prepared by the same process as Example 28.

$^1$H NMR (400 MHz, DMSO) δ 10.08 (s, 1H), 9.06 (d, J=1.9 Hz, 1H), 8.98 (d, J=6.8 Hz, 1H), 8.81 (d, J=0.8 Hz, 1H), 8.71 (s, 1H), 8.60 (d, J=1.1 Hz, 1H), 7.91 (d, J=8.7 Hz, 2H), 7.86 (d, J=9.0 Hz, 1H), 7.74-7.65 (m, 1H), 7.41 (dd, J=11.3, 4.5 Hz, 3H).

Example 35

Preparation of 1-(imidazo[1,2-a]pyridine-3-sulfonyl)-6-[(1-t-butoxycarbonyl)-4-(1,2,3,6-tetrahydropyridinyl)]-1-H-pyrazolo[4,3-b]pyridine

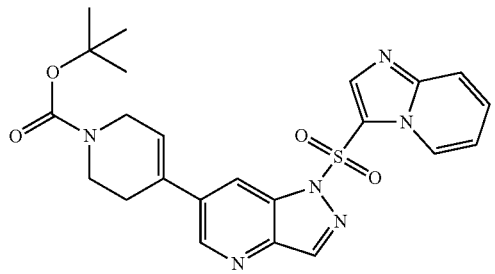 [SMILES: CC(C)(C)OC(=O)N1CC=C(c2cnc3cnn(S(=O)(=O)c4cnc5ccccn45)c3c2)CC1]

Except for (1-t-butoxycarbonyl)-4-1,2,3,6-tetrahydropyridineborate pinacol ester was used instead of phenylboronic acid, compound 1-(imidazo[1,2-a]pyridine-3-sulfonyl)-6-[(1-t-butoxycarbonyl)-4-(1,2,3,6-tetrahydropyridinyl)]-1-H-pyrazolo[4,3-b]pyridine was prepared by the same process as Example 28.

$^1$H NMR (400 MHz, CDCl$_3$) δ 9.12 (d, J=6.9 Hz, 1H), 8.77 (d, J=1.7 Hz, 1H), 8.33 (t, J=8.0 Hz, 3H), 7.74 (d, J=9.0 Hz, 1H), 7.58-7.49 (m, 1H), 7.17 (t, J=6.9 Hz, 1H), 6.40-6.21 (m, 1H), 4.25-4.13 (m, 2H), 3.74 (t, J=5.6 Hz, 2H), 2.72-2.56 (m, 2H), 1.52 (s, 9H).

Example 36

Preparation of 1-(imidazo[1,2-a]pyridine-3-sulfonyl)-6-[6-(1,4-benzodioxanyl)]-1-H-pyrazolo[4,3-b]pyridine

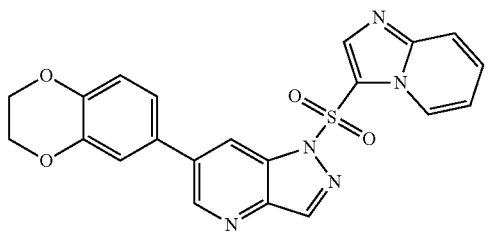 [SMILES: O=S(=O)(c1cnc2ccccn12)n1ncc2ncc(-c3ccc4c(c3)OCCO4)cc21]

Except for 6-(1,4-benzodioxanyl)boronic acid was used instead of phenylboronic acid, compound 1-(imidazo[1,2-a]pyridine-3-sulfonyl)-6-[6-(1,4-benzodioxanyl)]-1-H-pyrazolo[4,3-b]pyridine was prepared by the same process as Example 28.

$^1$H NMR (400 MHz, CDCl$_3$) δ 9.12 (d, J=6.9 Hz, 1H), 8.89 (d, J=1.9 Hz, 1H), 8.53 (dd, J=1.9, 0.9 Hz, 1H), 8.36 (d, J=0.9 Hz, 1H), 8.32 (s, 1H), 7.74 (d, J=9.0 Hz, 1H), 7.57-7.48 (m, 1H), 7.25-7.12 (m, 3H), 7.04 (d, J=8.3 Hz, 1H), 4.36 (s, 4H).

Example 37

Preparation of 1-(imidazo[1,2-a]pyridine-3-sulfonyl)-6-[4-(4-methylpiperazine-1-carbonyl)phenyl]-1-H-pyrazolo[4,3-b]pyridine

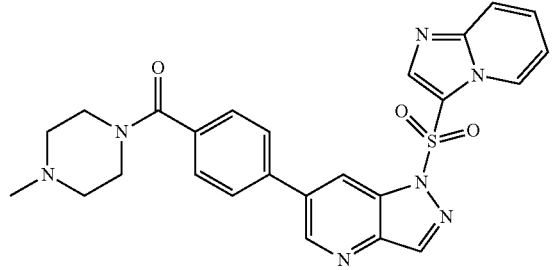 [SMILES: CN1CCN(C(=O)c2ccc(-c3cnc4cnn(S(=O)(=O)c5cnc6ccccn56)c4c3)cc2)CC1]

Except for 4-(4-methylpiperazine-1-carbonyl)phenylboronic acid was used instead of phenylboronic acid, compound 1-(imidazo[1,2-a]pyridine-3-sulfonyl)-6-[4-(4-methylpiperazine-1-carbonyl)phenyl)]-1-H-pyrazolo[4,3-b]pyridine was prepared by the same process as Example 28.

$^1$H NMR (400 MHz, CDCl$_3$) δ 9.14 (d, J=6.9 Hz, 1H), 8.94 (d, J=1.9 Hz, 1H), 8.61 (d, J=1.1 Hz, 1H), 8.41 (d, J=0.8 Hz, 1H), 8.33 (s, 1H), 7.75 (d, J=8.3 Hz, 3H), 7.61 (d, J=8.3 Hz, 2H), 7.58-7.51 (m, 1H), 7.19 (t, J=6.4 Hz, 1H), 3.95-3.80 (m, 2H), 3.63-3.48 (m, 2H), 2.66-2.51 (m, 2H), 2.51-2.39 (m, 2H), 2.38 (s, 3H).

Example 38

Preparation of 1-(imidazo[1,2-a]pyridine-3-sulfonyl)-6-(4-morpholinomethylphenyl)-1-H-pyrazolo[4,3-b]pyridine

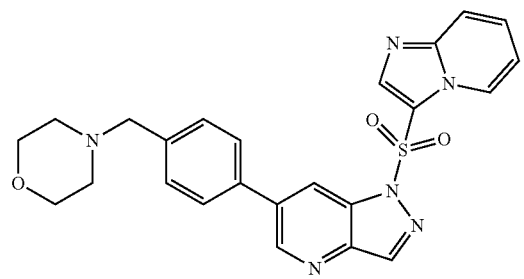 [SMILES: O=S(=O)(c1cnc2ccccn12)n1ncc2ncc(-c3ccc(CN4CCOCC4)cc3)cc21]

Except for 4-morpholinomethylphenylboronic acid was used instead of phenylboronic acid, compound 1-(imidazo[1,2-a]pyridine-3-sulfonyl)-6-(4-morpholinomethylphenyl)-1-H-pyrazolo[4,3-b]pyridine was prepared by the same process as Example 28.

$^1$H NMR (400 MHz, CDCl$_3$) δ 9.14 (dt, J=6.9, 1.1 Hz, 1H), 8.94 (d, J=1.9 Hz, 1H), 8.60 (dd, J=1.9, 0.9 Hz, 1H), 8.39 (d, J=0.9 Hz, 1H), 8.33 (s, 1H), 7.74 (dt, J=9.1, 1.1 Hz, 1H), 7.66 (d, J=8.2 Hz, 2H), 7.61-7.49 (m, 3H), 7.18 (td, J=6.9, 1.1 Hz, 1H), 3.83-3.72 (m, 4H), 3.61 (s, 2H), 2.61-2.45 (m, 4H).

Example 39

Preparation of 1-(imidazo[1,2-a]pyridine-3-sulfonyl)-6-(4-morpholinylphenyl)-1-H-pyrazolo[4,3-b]pyridine

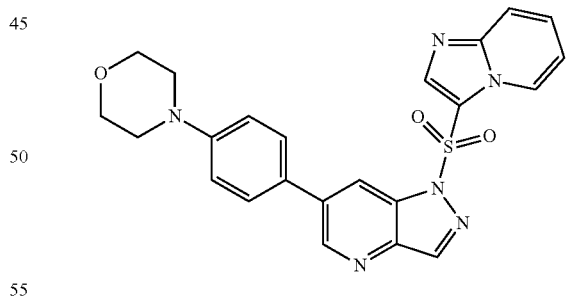

Except for 4-morpholinylphenylboronic acid was used instead of phenylboronic acid, compound 1-(imidazo[1,2-a]pyridine-3-sulfonyl)-6-(4-morpholinylphenyl)-1-H-pyrazolo[4,3-b]pyridine was prepared by the same process as Example 28.

$^1$H NMR (400 MHz, CDCl$_3$) δ 9.18-9.11 (m, 1H), 8.94 (dd, J=1.9, 0.8 Hz, 1H), 8.57 (dt, J=1.7, 0.8 Hz, 1H), 8.38 (t, J=0.8 Hz, 1H), 8.34 (d, J=0.7 Hz, 1H), 7.75 (dd, J=9.0, 1.1 Hz, 1H), 7.70-7.62 (m, 2H), 7.59-7.50 (m, 1H), 7.18 (t, J=7.0 Hz, 1H), 7.09 (d, J=8.7 Hz, 2H), 4.05-3.85 (m, 4H), 3.30 (dd, J=5.9, 3.8 Hz, 4H).

Example 40

Preparation of 1-(imidazo[1,2-a]pyridine-3-sulfonyl)-6-(4-acetylphenyl)-1-H-pyrazolo[4,3-b]pyridine

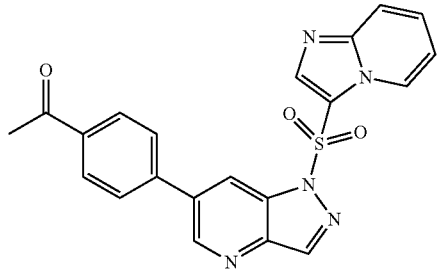 [SMILES: CC(=O)c1ccc(-c2cnc3cnn(S(=O)(=O)c4cnc5ccccn45)c3c2)cc1]

Except for 4-acetylphenylboronic acid was used instead of phenylboronic acid, compound 1-(imidazo[1,2-a]pyridine-3-sulfonyl)-6-(4-acetylphenyl)-1-H-pyrazolo[4,3-b]pyridine was prepared by the same process as Example 28.

$^1$H NMR (400 MHz, CDCl$_3$) δ 9.15 (dt, J=6.9, 1.1 Hz, 1H), 8.97 (d, J=1.9 Hz, 1H), 8.66 (dd, J=1.9, 0.9 Hz, 1H), 8.41 (d, J=0.8 Hz, 1H), 8.33 (s, 1H), 8.19-8.12 (m, 2H), 7.83-7.79 (m, 2H), 7.75 (dt, J=9.1, 1.1 Hz, 1H), 7.55 (ddd, J=9.0, 7.0, 1.2 Hz, 1H), 7.19 (td, J=6.9, 1.0 Hz, 1H), 2.70 (s, 3H).

Example 41

Preparation of 1-(imidazo[1,2-a]pyridine-3-sulfonyl)-6-(4-dimethylaminocarbonylphenyl)-1-H-pyrazolo[4,3-b]pyridine

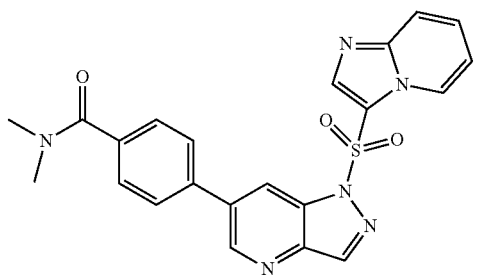 [SMILES: CN(C)C(=O)c1ccc(-c2cnc3cnn(S(=O)(=O)c4cnc5ccccn45)c3c2)cc1]

Except for 4-dimethylaminocarbonylphenylboronic acid was used instead of phenylboronic acid, compound 1-(imidazo[1,2-a]pyridine-3-sulfonyl)-6-(4-dimethylaminocarbonylphenyl)-1-H-pyrazolo[4,3-b]pyridine was prepared by the same process as Example 28.

$^1$H NMR (400 MHz, CDCl$_3$) δ 9.14 (d, J=6.9 Hz, 1H), 8.95 (d, J=1.9 Hz, 1H), 8.62 (d, J=1.8 Hz, 1H), 8.41 (s, 1H), 8.34 (s, 1H), 7.75 (dd, J=8.5, 2.0 Hz, 3H), 7.63 (d, J=8.1 Hz, 2H), 7.59-7.50 (m, 1H), 7.19 (t, 0.1=6.6 Hz, 1H), 3.18 (s, 3H), 3.08 (s, 3H).

Example 42

Preparation of 1-(imidazo[1,2-a]pyridine-3-sulfonyl)-6-(4-dimethylaminophenyl)-1-H-pyrazolo[4,3-b]pyridine

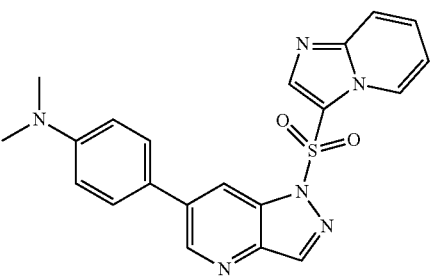 [SMILES: CN(C)c1ccc(-c2cnc3cnn(S(=O)(=O)c4cnc5ccccn45)c3c2)cc1]

Except for 4-dimethylaminophenylboronic acid was used instead of phenylboronic acid, compound 1-(imidazo[1,2-a]pyridine-3-sulfonyl)-6-(4-dimethylaminophenyl)-1-H-pyrazolo[4,3-b]pyridine was prepared by the same process as Example 28.

$^1$H NMR (400 MHz, CDCl$_3$) δ 9.11 (d, J=6.9 Hz, 1H), 8.85 (d, J=1.8 Hz, 1H), 8.61 (dd, J=1.8, 0.9 Hz, 1H), 8.38 (d, J=0.9 Hz, 1H), 8.32 (s, 1H), 7.77-7.70 (m, 2H), 7.65-7.59 (m, 1H), 7.56-7.47 (m, 2H), 7.16 (td, J=6.9, 1.2 Hz, 2H), 3.86 (s, 3H), 3.82 (s, 3H).

Example 43

Preparation of 1-(imidazo[1,2-a]pyridine-3-sulfonyl)-6-(2,5-dimethoxyphenyl)-1-H-pyrazolo[4,3-b]pyridine

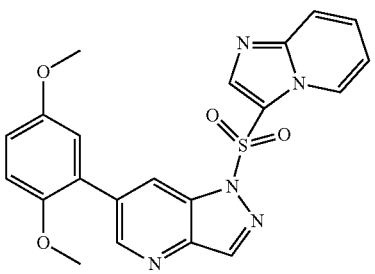 [SMILES: COc1ccc(OC)c(-c2cnc3cnn(S(=O)(=O)c4cnc5ccccn45)c3c2)c1]

Except for 2,5-dimethoxyphenylboronic acid was used instead of phenylboronic acid, compound 1-(imidazo[1,2-a]pyridine-3-sulfonyl)-6-(2,5-dimethoxyphenyl)-1-H-pyrazolo[4,3-b]pyridine was prepared by the same process as Example 28.

$^1$H NMR (400 MHz, CDCl$_3$) δ 9.11 (d, J=6.9 Hz, 1H), 8.85 (d, J=1.8 Hz, 1H), 8.61 (d, J=0.9 Hz, 1H), 8.38 (s, 1H), 8.32 (s, 1H), 7.74 (d, J=9.0 Hz, 1H), 7.57-7.46 (m, 1H), 7.20-7.10 (m, 1H), 7.02-6.89 (m, 3H), 3.86 (s, 3H), 3.82 (s, 3H).

Example 44

Preparation of 1-(imidazo[1,2-a]pyridine-3-sulfonyl)-6-{{1-[(1-t-butoxycarbonyl)-4-piperidinyl]}-4-pyrazolyl}-1-H-pyrazolo[4,3-b]pyridine

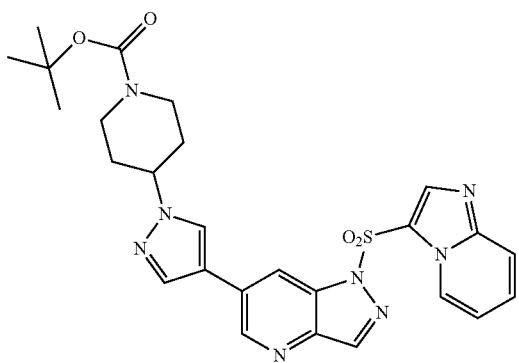

Except for {1-[(1-t-butoxycarbonyl)-4-piperidinyl]}-4-pyrazoloborate pinacol ester was used instead of phenylboronic acid, compound 1-(imidazo[1,2-a]pyridine-3-sulfonyl)-6-{{1-[(1-t-butoxycarbonyl)-4-piperidinyl]}-4-pyrazolyl}-1-H-pyrazolo[4,3-b]pyridine was prepared by the same process as Example 28.

$^1$H NMR (400 MHz, CDCl$_3$) δ 9.13 (d, J=7.0 Hz, 1H), 8.86 (d, J=1.9 Hz, 1H), 8.45 (dd, J=1.9, 0.9 Hz, 1H), 8.33 (d, J=0.9 Hz, 2H), 7.96 (d, J=0.7 Hz, 1H), 7.90 (s, 1H), 7.75 (d, J=9.1 Hz, 1H), 7.58-7.49 (m, 1H), 7.17 (dd, J=7.4, 6.5 Hz, 1H), 4.44-4.33 (m, 3H), 3.04-2.83 (m, 2H), 2.23 (d, J=10.9 Hz, 2H), 2.10-1.93 (m, 2H), 1.50 (s, 9H).

Example 45

Preparation of 1-(imidazo[1,2-a]pyridine-3-sulfonyl)-6-{[1-(4-piperidinyl)]-4-pyrazolyl}-1-H-pyrazolo[4,3-b]pyridine

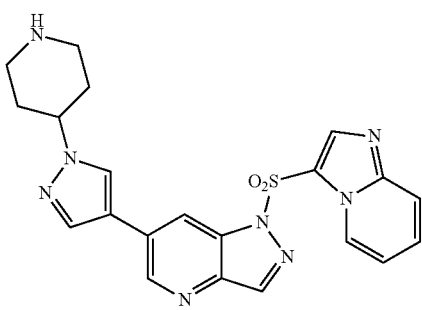

Fifty mg compound of Example 44 was dissolved in 5 ml dioxane saturated with hydrochloric acid, stirred for 30 minutes at room temperature. The reaction was completed, the pH was adjusted to 8-9 using saturated sodium carbonate solution, and diluted by adding 20 ml dichloromethane, washed three times with water, the organic layer was dried over anhydrous sodium sulfate then concentrated, and isolated by flash preparative chromatography to obtain the target compound (m=37 mg, yield: 91%).

$^1$H NMR (400 MHz, CDCl$_3$) δ 9.14 (d, J=7.0 Hz, 1H), 8.87 (s, 1H), 8.51 (s, 1H), 8.35 (s, 1H), 8.34 (s, 1H), 8.16 (s, 1H), 7.99 (s, 1H), 7.75 (d, J=9.0 Hz, 1H), 7.60-7.54 (m, 1H), 7.21 (t, J=7.2 Hz, 1H), 3.75-3.58 (m, 3H), 3.33-3.18 (m, 2H), 2.50-2.45 (m, 2H), 2.08-2.03 (m, 2H).

Example 46

Preparation of 1-(pyrazolo[1,5-a]pyrimidine-3-sulfonyl)-6-{{1-[(1-t-butoxycarbonyl)-4-piperidinyl]}-4-pyrazolyl}-1-H-pyrazolo[4,3-b]pyridine

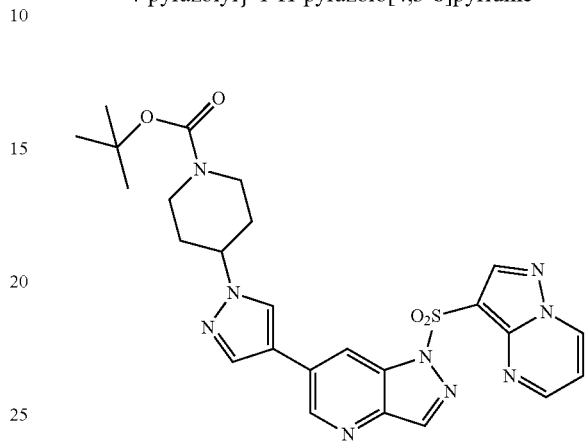

Except for {1-[(1-t-butoxycarbonyl)-4-piperidinyl]}-4-pyrazoloborate pinacol ester was used instead of 1-methyl-1H-pyrazolo-4-boronic acid pinacol ester, compound 1-(pyrazolo[1,5-a]pyrimidine-3-sulfonyl)-6-{{1-[(1-t-butoxycarbonyl)-4-piperidinyl]}-4-pyrazolyl}-1-H-pyrazolo[4,3-b]pyridine was prepared by the same process as Example 22.

$^1$H NMR (400 MHz, CDCl$_3$) δ 8.84 (d, J=1.9 Hz, 1H), 8.76 (dd, J=7.0, 1.6 Hz, 1H), 8.72-8.68 (m, 2H), 8.67 (s, 1H), 8.34 (s, 1H), 7.99 (s, 1H), 7.92 (s, 1H), 7.11 (dd, J=7.0, 4.2 Hz, 1H), 4.44-4.23 (m, 3H), 3.03-2.86 (m, 2H), 2.28-2.18 (m, 2H), 2.12-1.93 (m, 2H), 1.50 (s, 9H).

Example 47

Preparation of 1-(imidazo[1,2-a]pyrimidine-3-sulfonyl)-6-{[1-(4-piperidinyl)]-4-pyrazolyl}-1-H-pyrazolo[4,3-b]pyridine

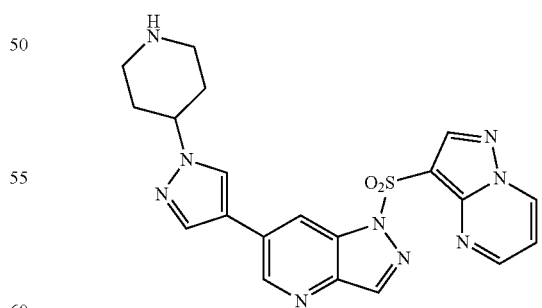

Fifty mg compound of Example 46 was dissolved in 5 ml dioxane saturated with hydrochloric acid, stirred for 30 minutes at room temperature. The reaction was completed, and filtered to obtain filter cake, which was washed three times by ether immersion, dried at vacuum to produce the target compound (m=37 mg, yield: 91%).

¹H NMR (400 MHz, CDCl₃) δ 8.84 (d, J=1.9 Hz, 1H), 8.77 (dd, J=7.0, 1.6 Hz, 1H), 8.72-8.64 (m, 2H), 8.65 (s, 1H), 8.31 (s, 1H), 7.79 (s, 1H), 7.91 (s, 1H), 7.01 (dd, J=7.0, 4.2 Hz, 1H), 4.44-4.35 (m, 3H), 3.23-2.96 (m, 2H), 2.33-2.28 (m, 2H), 2.02-1.93 (m, 2H).

Example 48

Preparation of 1-[(6-chloro-imidazo[2,1-b]thiazole)-5-sulfonyl)]-6-{[1-(4-piperidinyl)]-4-pyrazolyl}-1-H-pyrazolo[4,3-b]pyridine

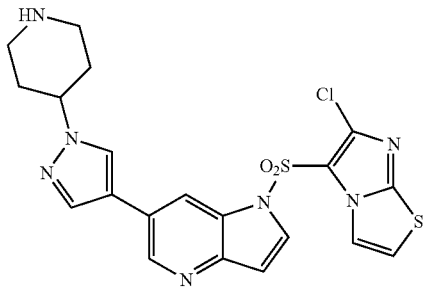 [SMILES: O=S(=O)(c1c(Cl)nc2sccn12)n1ccc2ncc(-c3cnn(C4CCNCC4)c3)cc21]

Except for {1-[(1-t-butoxycarbonyl)-4-piperidinyl]}-4-pyrazoloborate pinacol ester was used instead of 1-methyl-1H-pyrazolo-4-borate pinacol ester, compound 1-[(6-chloro-imidazo[2,1-b]thiazole)-5-sulfonyl)]-6-{{1-[(1-t-butoxycarbonyl)-4-piperidinyl]}-4-pyrazolyl}-1-H-pyrazolo[4,3-b]pyridine was prepared by the same process as Example 18. Eighty seven mg 1-[(6-chloro-imidazo[2,1-b]thiazole)-5-sulfonyl)]-6-{{1-[(1-t-butoxycarbonyl)-4-piperidinyl]}-4-pyrazolyl}-1-H-pyrazolo[4,3-b]pyridine was dissolved in 5 ml dioxane saturated with hydrochloric acid, stirred for 30 minutes at room temperature. The reaction was completed, and filtered to obtain filter cake, which was washed three times by ether immersion, dried at vacuum to produce the target compound (m=65 mg, yield: 90%).

¹H NMR (400 MHz, CDCl₃) δ 8.71 (d, J=1.9 Hz, 1H), 8.21 (dd, J=1.9, 0.7 Hz, 1H), 8.12 (d, J=4.5 Hz, 1H), 7.84 (d, J=3.8 Hz, 1H), 7.82 (s, 1H), 7.81 (s, 1H), 7.53 (d, J=4.5 Hz, 1H), 7.50 (t, J=2.0 Hz, 1H), 6.87 (dd, J=3.8, 0.7 Hz, 1H), 4.67-4.52 (m, 1H), 3.71-3.57 (m, 2H), 2.70-2.53 (m, 2H), 2.53-2.39 (m, 4H).

Example 49

Preparation of 1-(imidazo[1,2-b]pyridazine-3-sulfo-nyl)-6-{{1-[(1-t-butoxycarbonyl)-4-piperidinyl]}-4-pyrazolyl}-1-H-pyrazolo[4,3-b]pyridine

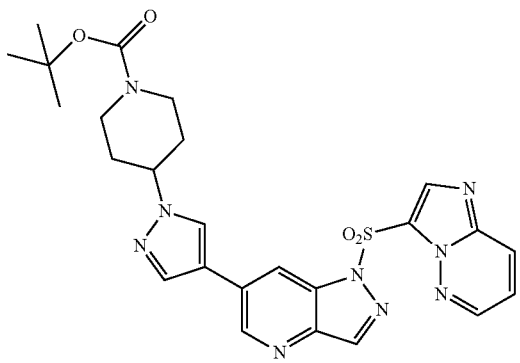

Except for {1-[(1-t-butoxycarbonyl)-4-piperidinyl]}-4-pyrazoloborate pinacol ester was used instead of 1-methyl-1H-pyrazolo-4-borate pinacol ester, compound 1-(imidazo[1,2-b]pyridazine-3-sulfonyl)-6-{{1-[(1-t-butoxycarbonyl)-4-piperidinyl]}-4-pyrazolyl}-1-H-pyrazolo[4,3-b]pyridine was prepared by the same process as Example 21.

¹H NMR (400 MHz, CDCl₃) δ 8.88 (d, J=1.9 Hz, 1H), 8.64 (dd, J=1.9, 0.8 Hz, 1H), 8.58 (s, 1H), 8.35 (d, J=0.8 Hz, 1H), 8.31 (dd, J=4.5, 1.6 Hz, 1H), 8.08 (dd, J=9.3, 1.6 Hz, 1H), 8.00 (d, J=0.6 Hz, 1H), 7.94 (s, 1H), 7.26 (dd, J=9.3, 4.5 Hz, 1H), 4.46-4.23 (m, 3H), 3.04-2.85 (m, 2H), 2.28-2.19 (m, 2H), 2.10-1.95 (m, 2H), 1.50 (s, 9H).

Example 50

Preparation of 1-(imidazo[1,2-b]pyridazine-3-sulfo-nyl)-6-{[1-(4-piperidinyl)]-4-pyrazolyl}-4-pyra-zolyl}-1-H-pyrazolo[4,3-b]pyridine chloride

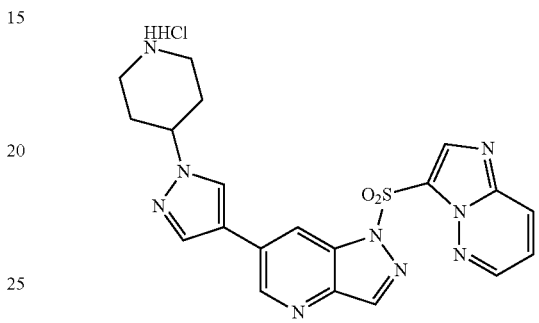

Fifty mg compound of Example 49 was dissolved in 5 ml dioxane saturated with hydrochloric acid, stirred for 30 minutes at room temperature. The reaction was completed, and filtered to obtain filter cake, which was washed three times by ether immersion, dried at 5 vacuum to obtain the target compound (m=35 mg, yield: 89%).

¹H NMR (400 MHz, CDCl₃) δ 8.88 (d, J=1.8 Hz, 1H), 8.65 (s, 1H), 8.59 (s, 1H), 8.36 (s, 2H), 8.08 (dd, J=9.3, 1.4 Hz, 1H), 8.03 (s, 1H), 8.00 (s, 1H), 7.30-7.25 (m, 1H), 4.67-4.54 (m, 1H), 3.77-3.66 (m, 2H), 3.32-3.20 (m, 2H), 2.70-2.51 (m, 4H).

Example 51

Preparation of 1-(imidazo[1,2-b]pyridazine-3-sulfo-nyl)-6-{[1-(4-piperidinyl)]-4-pyrazolyl}-4-pyra-zolyl}-1-H-pyrazolo[4,3-b]pyridine

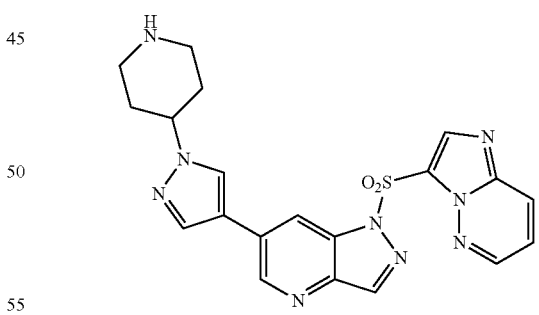

Fifty mg compound of Example 50 was dissolved in 10 ml saturated sodium bicarbonate solution, stirred for 5 minutes. The aqueous solution was extracted three times with dichloromethane, evaporated to dry, the organic layer was dried over anhydrous sodium sulfate then concentrated, dried at vacuum to obtain the target compound (m=45 mg, yield: 98%).

¹H NMR (400 MHz, CDCl₃) δ 8.88 (d, J=1.8 Hz, 1H), 8.65 (s, 1H), 8.59 (s, 1H), 8.36 (s, 2H), 8.08 (dd, J=9.3, 1.4 Hz, 1H), 8.03 (s, 1H), 8.00 (s, 1H), 7.30-7.25 (m, 1H), 4.67-4.54 (m, 1H), 3.77-3.66 (m, 2H), 3.32-3.20 (m, 2H), 2.70-2.51 (m, 4H).

Example 52

Preparation of 1-(imidazo[1,2-a]pyrimidine-3-sulfonyl)-6-{{1-[(1-t-butoxycarbonyl)-4-piperidinyl]}-4-pyrazolyl}-1-H-pyrazolo[4,3-b]pyridine

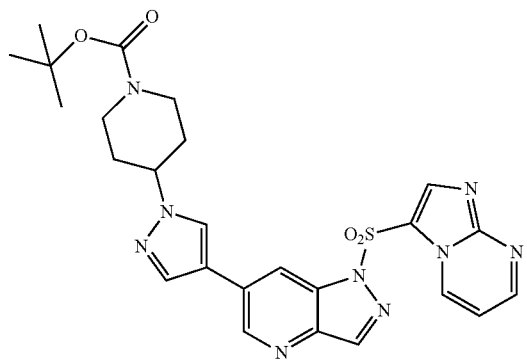 [SMILES: CC(C)(C)OC(=O)N1CCC(n2cc(-c3cnc4cnn(S(=O)(=O)c5cnc6ncccn56)c4c3)cn2)CC1]

Except for {1-[(1-t-butoxycarbonyl)-4-piperidinyl]}-4-pyrazoloborate pinacol ester was used instead of 1-methyl-1H-pyrazolo-4-boronic acid pinacol ester, compound 1-(imidazo[1,2-a]pyrimidine-3-sulfonyl)-6-{{1-[(1-t-butoxycarbonyl)-4-piperidinyl]}-4-pyrazolyl}-1-H-pyrazolo[4,3-b]pyridine was prepared by the same process as Example 23.

$^1$H NMR (400 MHz, CDCl$_3$) δ 8.87 (d, J=1.9 Hz, 1H), 8.68 (dd, J=4.0, 2.0 Hz, 1H), 8.65 (dd, J=1.8, 0.8 Hz, 1H), 8.54 (dd, J=6.9, 2.0 Hz, 1H), 8.37 (s, 1H), 8.37 (d, J=0.8 Hz, 1H), 7.97 (s, 1H), 7.94 (s, 1H), 7.06 (dd, J=6.9, 4.0 Hz, 1H), 4.44-4.28 (m, 3H), 3.02-2.83 (m, 2H), 2.27-2.16 (m, 2H), 2.10-1.94 (m, 2H).

Example 53

Preparation of 1-(imidazo[1,2-a]pyridine-3-sulfonyl)-6-{{1-[(1-ethyl)-4-piperidinyl]}-4-pyrazolyl}-1-H-pyrazolo[4,3-b]pyridine

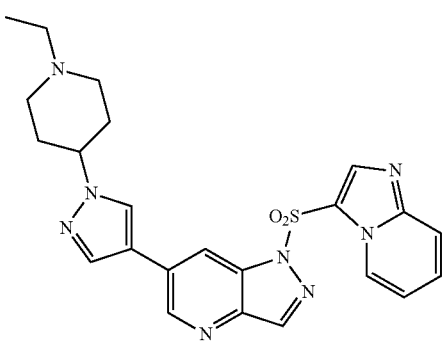 [SMILES: CCN1CCC(n2cc(-c3cnc4cnn(S(=O)(=O)c5cnc6ccccn56)c4c3)cn2)CC1]

Fifty milligrams compound of Example 45 was dissolved in 5 ml methanol, then 12.5 µl acetalaldehyde, 319 µl acetic acid and 17.5 mg sodium cyanoborohydride were sequentially added, stirred at room temperature for 5 hours, the reaction was completed. The reactant liquid was diluted with 20 ml dichloromethane, washed three times with water, the organic layer was dried over anhydrous sodium sulfate then concentrated, and isolated by flash preparative chromatography to obtain the target compound (m=47 mg, yield: 88%).

$^1$H NMR (400 MHz, CDCl$_3$) δ 9.02 (d, J=7.1 Hz, 1H), 8.78 (s, 1H), 8.42 (s, 1H), 8.29-8.22 (m, 3H), 7.87 (s, 1H), 7.63 (dt, J=9.0, 1.2 Hz, 1H), 7.48 (t, J=8.0 Hz, 1H), 7.13 (td, J=7.0, 1.2 Hz, 1H), 4.82 (d, J=13.6 Hz, 1H), 4.52-4.40 (m, 1H), 4.03 (d, J=13.6 Hz, 1H), 3.36-3.25 (m, 1H), 2.81 (dd, J=18.6, 7.3 Hz, 1H), 2.29 (dd, J=24.4, 12.2 Hz, 2H), 2.18 (m, 2H), 2.13-1.96 (m, 2H), 1.35 (t, J=6.6 Hz, 3H).

Example 54

Preparation of 1-(imidazo[1,2-a]pyridine-3-sulfonyl)-6-{{1-[(1-acetyl)-4-piperidinyl]}-4-pyrazolyl}-1-H-pyrazolo[4,3-b]pyridine

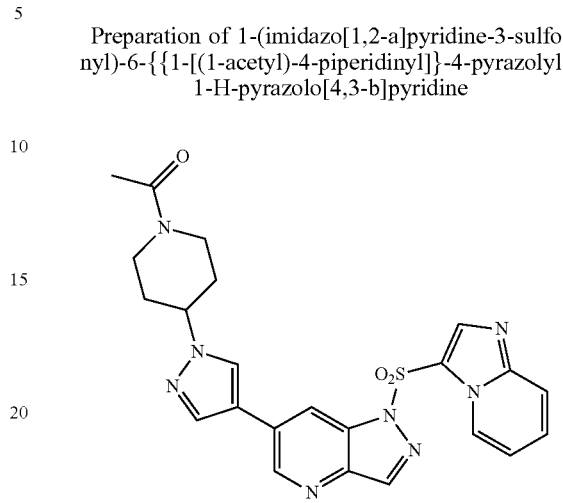

Fifty milligrams compound of Example 45 and 46.6 µl triethylamine were dissolved in 10 ml dichloromethane, then 8.7 µl acetyl chloride was added dropwise, stirred for 30 minutes at room temperature, the reaction was completed. The reactant liquid was washed three times with water, the organic layer was dried over anhydrous sodium sulfate then concentrated, and isolated by flash preparative chromatography to obtain the target compound (m=48 mg, yield: 88%).

$^1$H NMR (400 MHz, CDCl$_3$) δ 9.13 (d, J=6.9 Hz, 1H), 8.85 (d, J=1.8 Hz, 1H), 8.46 (d, J=1.0 Hz, 1H), 8.32 (d, J=4.7 Hz, 2H), 7.97 (s, 1H), 7.91 (s, 1H), 7.74 (d, J=9.0 Hz, 1H), 7.58-7.48 (m, 1H), 7.18 (t, J=6.9 Hz, 1H), 4.82 (d, J=13.6 Hz, 1H), 4.52-4.40 (m, 1H), 4.03 (d, J=13.6 Hz, 1H), 3.36-3.25 (m, 1H), 2.81 (dd, J=18.6, 7.3 Hz, 1H), 2.29 (dd, J=24.4, 12.2 Hz, 2H), 2.18 (s, 3H), 2.13-1.96 (m, 2H).

Example 55

Preparation of 1-(imidazo[1,2-a]pyridine-3-sulfonyl)-6-{{1-[(1-cyclopropylcarbonyl)-4-piperidinyl]}-4-pyrazolyl}-1-H-pyrazolo[4,3-b]pyridine

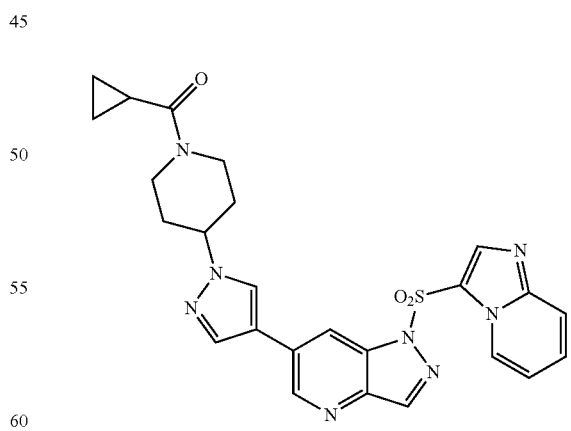

Except for cyclopropylcarbonyl chloride was used instead of acetyl chloride, compound 1-(imidazo[1,2-a]pyridine-3-sulfonyl)-6-{{1-[(1-cyclopropylcarbonyl)-4-piperidinyl]}-4-pyrazolyl}-1-H-pyrazolo[4,3-b]pyridine was prepared by the same process as Example 54.

$^1$H NMR (400 MHz, CDCl$_3$) δ 9.14 (d, J=6.8 Hz, 1H), 8.86 (s, 1H), 8.46 (s, 1H), 8.34 (s, 2H), 7.97 (s, 1H), 7.93 (s,

1H), 7.77 (d, J=9.1 Hz, 1H), 7.56 (t, J=7.7 Hz, 1H), 7.20 (t, J=6.9 Hz, 1H), 4.88-4.66 (m, 1H), 4.57-4.35 (m, 2H), 3.44-3.26 (m, 1H), 2.95-2.75 (m, 1H), 2.42-2.20 (m, 2H), 2.20-1.95 (m, 2H), 1.87-1.75 (m, 1H), 1.11-0.96 (m, 2H), 0.87-0.74 (m, 2H).

Example 56

Preparation of 1-(imidazo[1,2-a]pyridine-3-sulfonyl)-6-{{1-[(1-cyclopentylcarbonyl)-4-piperidinyl]}-4-pyrazolyl}-1-H-pyrazolo[4,3-b]pyridine

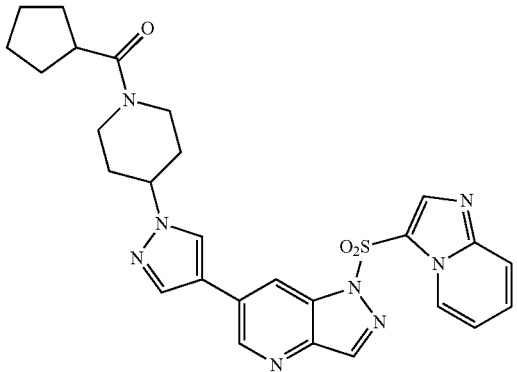 [SMILES: O=C(C1CCCC1)N1CCC(n2cc(-c3cnc4cnn(S(=O)(=O)c5cnc6ccccn56)c4c3)cn2)CC1]

Except for cyclopentylcarbonyl chloride was used instead of acetyl chloride, compound 1-(imidazo[1,2-a]pyridine-3-sulfonyl)-6-{{1-[(1-cyclopentylcarbonyl)-4-piperidinyl]}-4-pyrazolyl}-1-H-pyrazolo[4,3-b]pyridine was prepared by the same process as Example 54.

$^1$H NMR (400 MHz, CDCl$_3$) δ 9.16-9.08 (m, 1H), 8.85 (d, J=0.8 Hz, 1H), 8.45 (s, 1H), 8.32 (d, J=4.4 Hz, 2H), 7.97 (s, 1H), 7.91 (s, 1H), 7.80-7.67 (m, 1H), 7.54 (dd, J=8.5, 7.6 Hz, 1H), 7.18 (t, J=7.0 Hz, 1H), 4.85 (d, J=13.5 Hz, 1H), 4.56-4.38 (m, 1H), 4.14 (d, J=13.3 Hz, 1H), 3.25 (t, J=12.9 Hz, 1H), 2.78 (t, J=12.4 Hz, 1H), 2.64-2.46 (m, 1H), 2.36-2.24 (m, 2H), 2.07-1.96 (m, 2H), 1.81-1.72 (m, 3H), 1.61-1.50 (m, 2H), 1.32-1.24 (m, 3H).

Example 57

Preparation of 1-(imidazo[1,2-a]pyridine-3-sulfonyl)-6-{{1-[(1-cyclohexylcarbonyl)-4-piperidinyl]}-4-pyrazolyl}-1-H-pyrazolo[4,3-b]pyridine

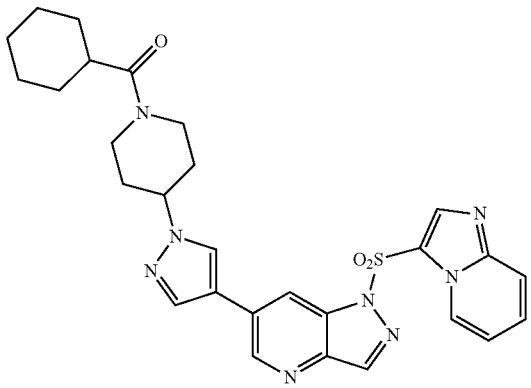 [SMILES: O=C(C1CCCCC1)N1CCC(n2cc(-c3cnc4cnn(S(=O)(=O)c5cnc6ccccn56)c4c3)cn2)CC1]

Except for cyclohexylcarbonyl chloride was used instead of acetyl chloride, compound 1-(imidazo[1,2-a]pyridine-3-sulfonyl)-6-{{1-[(1-cyclohexylcarbonyl)-4-piperidinyl]}-4-pyrazolyl}-1-H-pyrazolo[4,3-b]pyridine was prepared by the same process as Example 54.

$^1$H NMR (400 MHz, CDCl$_3$) δ 9.13 (d, J=6.9 Hz, 1H), 8.85 (d, J=1.8 Hz, 1H), 8.46 (d, J=1.5 Hz, 1H), 8.32 (d, J=4.1 Hz, 2H), 7.97 (s, 1H), 7.91 (s, 1H), 7.75 (d, J=9.0 Hz, 1H), 7.58-7.50 (m, 1H), 7.18 (t, J=6.5 Hz, 1H), 4.85 (d, J=13.7 Hz, 1H), 4.54-4.41 (m, 1H), 4.20 (d, J=14.4 Hz, 1H), 3.26 (t, J=12.0 Hz, 1H), 2.96 (p, J=8.0 Hz, 1H), 2.81 (t, J=11.8 Hz, 1H), 2.38-2.21 (m, 2H), 2.08-1.98 (m, 2H), 1.95-1.81 (m, 5H), 1.79-1.73 (m, 2H), 1.69-1.51 (m, 3H).

Example 58

Preparation of 1-(imidazo[1,2-a]pyridine-3-sulfonyl)-6-{{1-[(1-p-trifluoromethylbenzoyl)-4-piperidinyl]}-4-pyrazolyl}-1-H-pyrazolo[4,3-b]pyridine

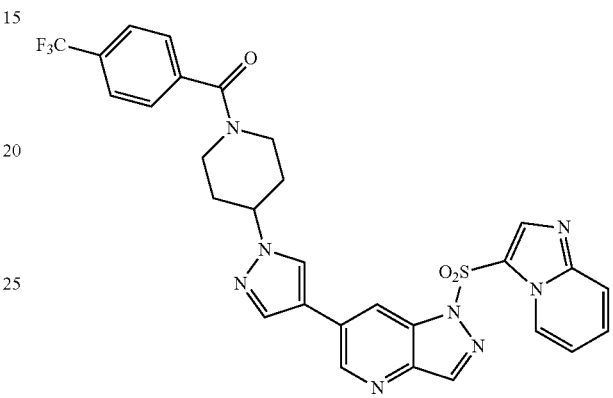

Except for p-trifluoromethyl benzoyl chloride was used instead of acetyl chloride, compound 1-(imidazo[1,2-a]pyridine-3-sulfonyl)-6-{{1-[(1-p-trifluoromethylbenzoyl)-4-piperidinyl]}-4-pyrazolyl}-1-H-pyrazolo[4,3-b]pyridine was prepared by the same process as Example 54.

$^1$H NMR (400 MHz, CDCl$_3$) δ 9.16 (d, J=6.7 Hz, 1H), 8.87 (s, 1H), 8.47 (s, 1H), 8.34 (s, 2H), 7.98 (s, 1H), 7.95 (s, 1H), 7.79 (d, J=8.3 Hz, 1H), 7.72 (d, J=7.9 Hz, 2H), 7.60 (d, J=8.0 Hz, 3H), 7.22 (t, J=6.8 Hz, 1H), 5.01-4.82 (m, 1H), 4.59-4.44 (m, 1H), 4.01-3.81 (m, 1H), 3.35-3.18 (m, 1H), 3.17-2.99 (m, 1H), 2.44-2.01 (m, 4H).

Example 59

Preparation of 1-(imidazo[1,2-a]pyridine-3-sulfonyl)-6-{{1-[(1-isopropyl)-4-piperidinyl]}-4-pyrazolyl}-1-H-pyrazolo[4,3-b]pyridine

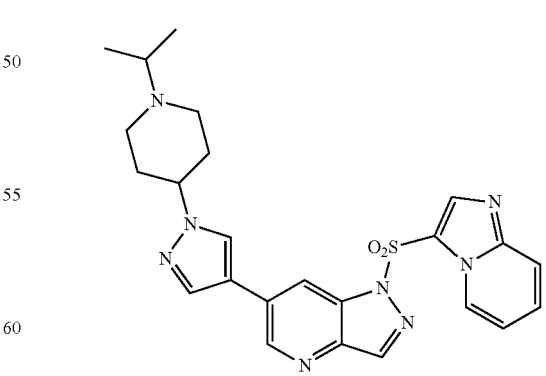

Except for acetone was used instead of acetaldehyde, compound 1-(imidazo[1,2-a]pyridine-3-sulfonyl)-6-{{1-[(1-isopropyl)-4-piperidinyl]}-4-pyrazolyl}-1-H-pyrazolo[4,3-b]pyridine was prepared by the same process as Example 53.

¹H NMR (400 MHz, CDCl₃) δ 9.12 (dt, J=6.9, 1.1 Hz, 1H), 8.85 (d, J=1.9 Hz, 1H), 8.46 (dd, J=1.9, 0.9 Hz, 1H), 8.35-8.31 (m, 2H), 8.00 (s, 1H), 7.94 (d, J=0.6 Hz, 1H), 7.77-7.70 (m, 1H), 7.58-7.49 (m, 1H), 7.18 (td, J=7.0, 1.2 Hz, 1H), 4.57-4.44 (m, 1H), 3.53-3.41 (m, 2H), 3.38-3.23 (m, 1H), 2.99-2.84 (m, 2H), 2.70-2.53 (m, 2H), 2.53-2.37 (m, 2H), 1.35 (d, J=6.6 Hz, 6H).

Example 60

Preparation of 1-(imidazo[1,2-a]pyridine-3-sulfonyl)-6-{{1-[(1-cyclopentyl)-4-piperidinyl]}-4-pyrazolyl}-1-H-pyrazolo[4,3-b]pyridine

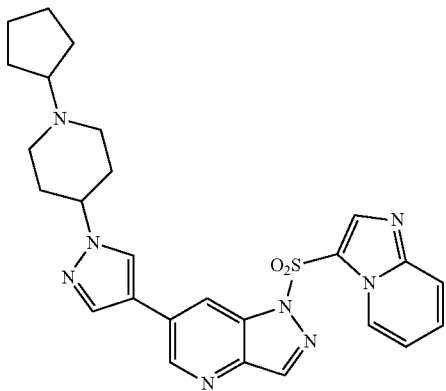 [SMILES: O=S(=O)(c1cnc2ccccn12)n1ncc2ncc(-c3cnn(C4CCN(C5CCCC5)CC4)c3)cc21]

Except for cyclopentanone was used instead of acetaldehyde, compound 1-(imidazo[1,2-a]pyridine-3-sulfonyl)-6-{{1-[(1-cyclopentyl)-4-piperidinyl]}-4-pyrazolyl}-1-H-pyrazolo[4,3-b]pyridine was prepared by the same process as Example 53.

¹H NMR (400 MHz, CDCl₃) δ 9.13 (dd, J=6.9, 1.1 Hz, 1H), 8.88-8.82 (m, 1H), 8.46 (s, 1H), 8.33 (s, 2H), 7.96 (d, J=15.3 Hz, 2H), 7.75 (dd, J=9.1, 1.0 Hz, 1H), 7.58-7.49 (m, 1H), 7.18 (t, J=7.0 Hz, 1H), 4.52-4.37 (m, 1H), 3.52-3.39 (m, 2H), 3.08-2.90 (m, 1H), 2.86-2.62 (m, 2H), 2.59-2.32 (m, 4H), 2.05-1.94 (m, 2H), 1.90-1.72 (m, 4H), 1.70-1.53 (m, 2H).

Example 61

Preparation of 1-[(6-chloro-imidazo[1,2-b]pyridazine)-3-sulfonyl)]-6-{{1-[(1-t-butoxycarbonyl)-4-piperidinyl]}-4-pyrazolyl}-1-H-pyrazolo[4,3-b]pyridine

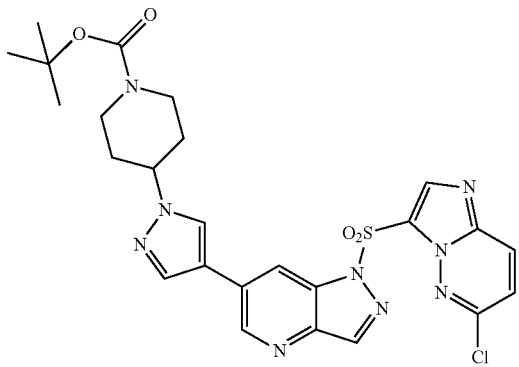 [SMILES: CC(C)(C)OC(=O)N1CCC(n2cc(-c3cnc4cnn(S(=O)(=O)c5cnc6ccc(Cl)nn56)c4c3)cn2)CC1]

Except for {1-[(1-t-butoxycarbonyl)-4-piperidinyl]}-4-pyrazoloborate pinacol ester was used instead of 1-methyl-1H-pyrazolo-4-borate pinacol ester, compound 1-[(6-chloro-imidazo[1,2-b]pyridazine)-3-sulfonyl)]-6-{{1-[(1-t-butoxycarbonyl)-4-piperidinyl]}-4-pyrazolyl}-1-H-pyrazolo[4,3-b]pyridine was prepared by the same process as Example 25.

¹H NMR (400 MHz, CDCl₃) δ 8.89 (d, J=1.8 Hz, 1H), 8.75-8.69 (m, 1H), 8.54 (s, 1H), 8.37 (d, J=0.6 Hz, 1H), 8.00 (dd, J=17.0, 7.4 Hz, 3H), 7.22 (d, J=9.5 Hz, 1H), 4.44-4.24 (m, 3H), 3.03-2.86 (m, 2H), 2.31-2.17 (m, 2H), 2.01 (qd, J=12.4, 4.4 Hz, 2H), 1.50 (s, 9H).

Example 62

Preparation of 1-{(6-{{1-[(1-t-butoxycarbonyl)-4-piperidinyl]}-4-pyrazolyl}-imidazo[1,2-b]pyridazine)-3-sulfonyl}-6-{{1-[(1-t-butoxycarbonyl)-4-piperidinyl]}-4-pyrazolyl}-1-H-pyrazolo[4,3-b]pyridine

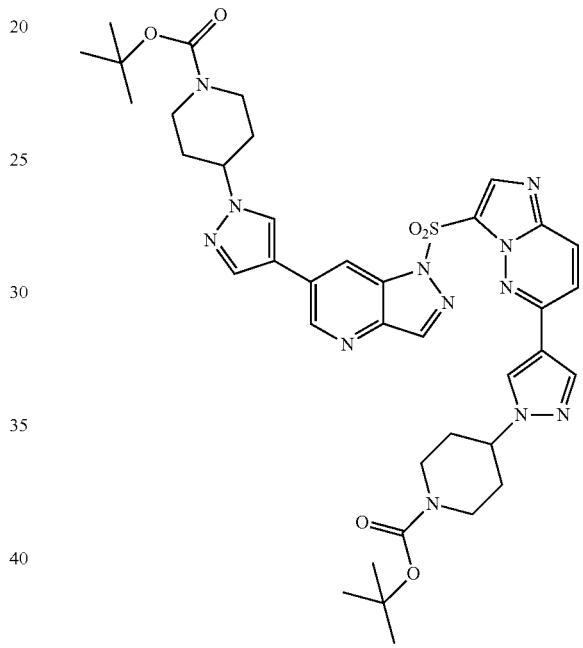

Into a microwave reaction tube were charged 141 mg compound of Example 61, 100 mg {1-[(1-t-butoxycarbonyl)-4-piperidinyl]}-4-pyrazoloborate pinacol ester and 100 mg potassium carbonate, 5 ml dioxane, 2.5 ml ethanol and 2.5 ml water were added into the microwave reaction tube, air was displaced for three times, under a nitrogen atmosphere, 9.8 mg complex of 1,1'-bis(diphenylphosphino) ferrocene palladium (II) dichloride and dichloromethane was added into the microwave tube, then the microwave tube was sealed. The microwave tube was placed into a microwave reactor, reacted at 90° C. for 10 minutes, the reaction was completed. The aforementioned reactant liquid was poured into 15 ml water, extracted three times with dichloromethane, the organic layer was dried over anhydrous sodium sulfate then concentrated, and isolated by flash preparative chromatography to obtain the target compound (m=154 mg, yield: 80%).

¹H NMR (400 MHz, CDCl₃) δ 8.94 (d, J=1.8 Hz, 1H), 8.68 (d, J=1.0 Hz, 1H), 8.55 (s, 1H), 8.35 (d, J=0.7 Hz, 1H), 8.02 (dd, J=6.8, 5.2 Hz, 3H), 7.57 (s, 1H), 7.40 (d, J=9.6 Hz, 1H), 7.22 (s, 1H), 4.47-4.11 (m, 5H), 4.04-3.87 (m, 1H), 3.02-2.86 (m, 2H), 2.84-2.66 (m, 2H), 2.22 (d, J=10.3 Hz, 2H), 2.03 (qd, J=12.3, 4.4 Hz, 2H), 1.92-1.73 (m, 4H), 1.50 (d, J=4.5 Hz, 18H).

Example 63

Preparation of 1-[(6-trifluoromethyl-imidazo[1,2-a]pyridine)-3-sulfonyl)]-6-{{1-[(1-t-butoxycarbonyl)-4-piperidinyl]}-4-pyrazolyl}-1-H-pyrazolo[4,3-b]pyridine

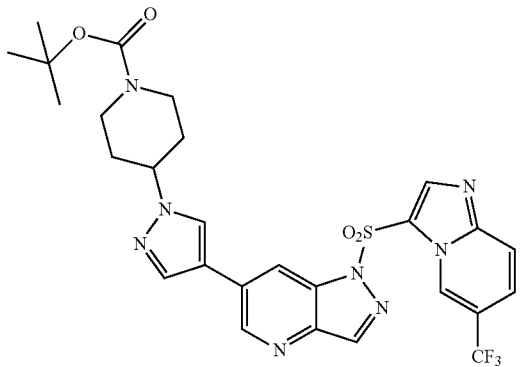 [SMILES: CC(C)(C)OC(=O)N1CCC(n2cc(-c3cnc4cnn(S(=O)(=O)c5cnc6ccc(C(F)(F)F)cn56)c4c3)cn2)CC1]

Except for {1-[(1-t-butoxycarbonyl)-4-piperidinyl]}-4-pyrazoloborate pinacol ester was used instead of 1-methyl-1H-pyrazolo-4-borate pinacol ester, compound 1-[(6-trifluoromethyl-imidazo[1,2-a]pyridine)-3-sulfonyl)]-6-{{1-[(1-t-butoxycarbonyl)-4-piperidinyl]}-4-pyrazolyl}-1-H-pyrazolo[4,3-b]pyridine was prepared by the same process as Example 26.

$^1$H NMR (400 MHz, CDCl$_3$) δ 9.53 (dd, J=1.7, 1.1 Hz, 1H), 8.87 (d, J=1.9 Hz, 1H), 8.45 (dd, J=1.9, 0.9 Hz, 1H), 8.37 (s, 1H), 8.36 (d, J=0.9 Hz, 1H), 7.97 (d, J=0.7 Hz, 1H), 7.91 (d, J=0.6 Hz, 1H), 7.86 (d, J=9.5 Hz, 1H), 7.68 (dd, J=9.5, 1.8 Hz, 1H), 4.46-4.25 (m, 3H), 3.03-2.86 (m, 2H), 2.29-2.18 (m, 2H), 2.02 (tt, J=12.4, 6.2 Hz, 2H), 1.50 (s, 9H).

Example 64

Preparation of 1-[(6-trifluoromethyl-imidazo[1,2-a]pyridine)-3-sulfonyl)]-6-{[1-(4-piperidinyl)]-4-pyrazolyl}-1-H-pyrazolo[4,3-b]pyridine chloride

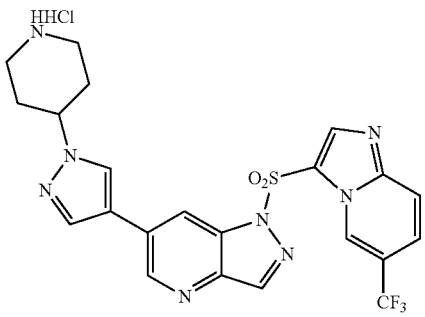

Fifty milligrams compound of Example 63 was dissolved in 5 ml dioxane saturated with hydrochloric acid, stirred for 30 minutes at room temperature. The reaction was completed, and filtered to obtain filter cake, which was washed three times by ether immersion, dried at vacuum to obtain the target compound (m=37 mg, yield: 83%).

$^1$H NMR (400 MHz, CDCl$_3$) δ 9.54 (s, 1H), 8.88 (s, 1H), 8.46 (s, 1H), 8.42 (s, 1H), 8.36 (s, 1H), 8.04 (s, 1H), 7.96 (s, 1H), 7.86 (d, J=9.4 Hz, 1H), 7.68 (d, J=9.5 Hz, 1H), 4.69-4.53 (m, 1H), 3.83-3.63 (m, 2H), 3.38-3.19 (m, 2H), 2.75-2.47 (m, 4H).

Example 65

Preparation of 1-[(6-trifluoromethyl-imidazo[1,2-a]pyridine)-3-sulfonyl)]-6-{[1-(4-piperidinyl)]-4-pyrazolyl}-4-pyrazolyl}-1-H-pyrazolo[4,3-b]pyridine

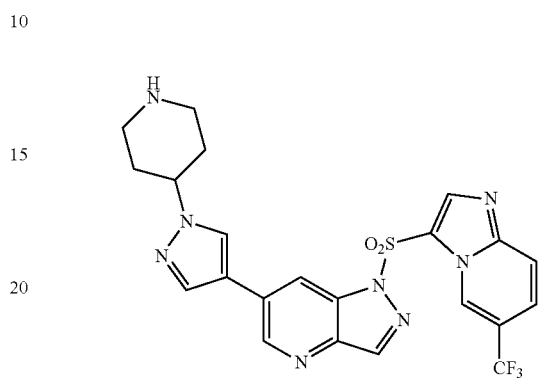

Fifty milligrams compound of Example 64 was added into 10 ml saturated sodium bicarbonate solution, stirred for 5 minutes. The aqueous solution was extracted three times with dichloromethane, evaporated to dry, the organic layer was dried over anhydrous sodium sulfate then concentrated, dried at vacuum to obtain the target compound (m=42 mg, yield: 97%).

$^1$H NMR (400 MHz, CDCl$_3$) δ 9.54 (s, 1H), 8.88 (s, 1H), 8.46 (s, 1H), 8.42 (s, 1H), 8.36 (s, 1H), 8.04 (s, 1H), 7.96 (s, 1H), 7.86 (d, J=9.4 Hz, 1H), 7.68 (d, J=9.5 Hz, 1H), 4.69-4.53 (m, 1H), 3.83-3.63 (m, 2H), 3.38-3.19 (m, 2H), 2.75-2.47 (m, 4H).

Example 66

Preparation of 1-(imidazo[1,2-a]pyridine-3-sulfonyl)-6-{[1-(4-piperidinyl)]-4-pyrazolyl}-1-H-pyrazolo[4,3-b]pyridine chloride

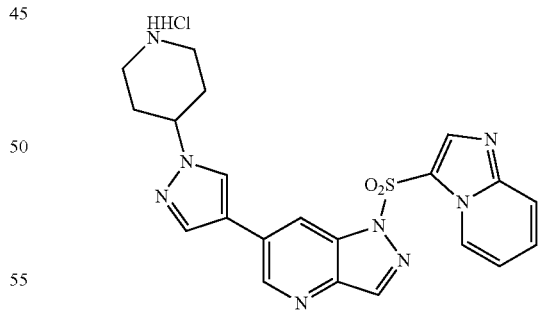

Fifty milligrams compound of Example 44 was dissolved in 5 ml dioxane saturated with hydrochloric acid, stirred for 30 minutes at room temperature. The reaction was completed, and filtered to obtain filter cake, which was washed three times by ether immersion, vacuum dried to obtain the target compound (m=36 mg, yield: 86%).

$^1$H NMR (400 MHz, CDCl$_3$) δ 9.14 (d, J=7.0 Hz, 1H), 8.87 (s, 1H), 8.51 (s, 1H), 8.35 (s, 1H), 8.34 (s, 1H), 8.16 (s, 1H), 7.99 (s, 1H), 7.75 (d, J=9.0 Hz, 1H), 7.60-7.54 (m, 1H), 7.21 (t, J=7.2 Hz, 1H), 3.75-3.58 (m, 3H), 3.33-3.18 (m, 2H), 2.50-2.45 (m, 2H), 2.08-2.03 (m, 2H).

Example 67

Preparation of 1-[(6-chloro-imidazo[1,2-a]pyridine)-3-sulfonyl)]-6-{{1-[(1-t-butoxycarbonyl)-4-piperidinyl]}-4-pyrazolyl}-1-H-pyrazolo[4,3-b]pyridine

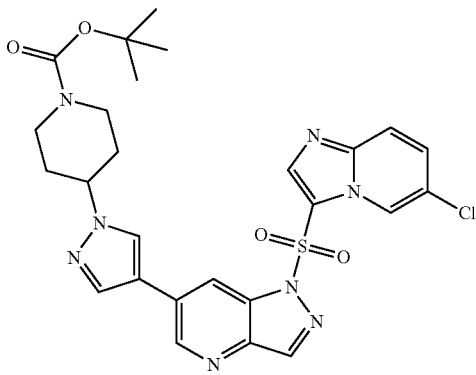 [SMILES: CC(C)(C)OC(=O)N1CCC(n2cc(-c3cnc4cnn(S(=O)(=O)c5cnc6ccc(Cl)cn56)c4c3)cn2)CC1]

Except for {1-[(1-t-butoxycarbonyl)-4-piperidinyl]}-4-pyrazoloborate pinacol ester was used instead of 1-methyl-1H-pyrazolo-4-borate pinacol ester, compound 1-[(6-chloro-imidazo[1,2-a]pyridine)-3-sulfonyl)]-6-{{1-[(1-t-butoxycarbonyl)-4-piperidinyl]}-4-pyrazolyl}-1-H-pyrazolo[4,3-b]pyridine was prepared by the same process as Example 24.

$^1$H NMR (400 MHz, CDCl$_3$) δ 9.19 (dd, J=5.3, 4.4 Hz, 1H), 8.89-8.76 (m, 1H), 8.43 (d, J=6.5 Hz, 1H), 8.36 (d, J=7.0 Hz, 1H), 8.30-8.21 (m, 1H), 7.96 (d, J=5.6 Hz, 1H), 7.91 (s, 1H), 7.72-7.58 (m, 1H), 7.54-7.39 (m, 1H), 4.46-4.16 (m, 3H), 3.06-2.79 (m, 2H), 2.31-2.13 (m, 2H), 2.09-1.90 (m, 2H), 1.49 (s, 9H).

Example 68

Preparation of 1-{(6-{{1-[(1-t-butoxycarbonyl)-4-piperidinyl]}-4-pyrazolyl}-imidazo[1,2-a]pyridine)-3-sulfonyl}-6-{{1-[(1-t-butoxycarbonyl)-4-piperidinyl]}-4-pyrazolyl}-1-H-pyrazolo[4,3-b]pyridine

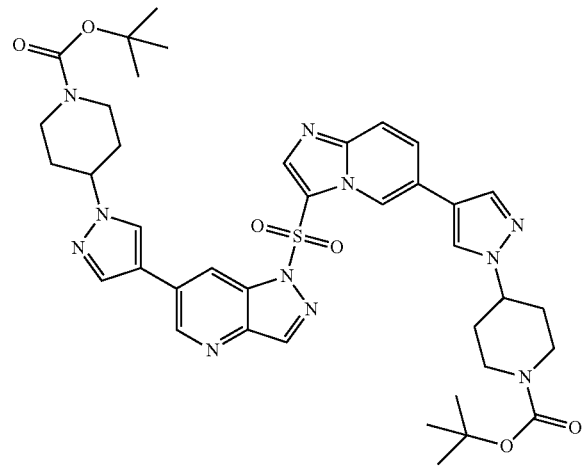 [SMILES: CC(C)(C)OC(=O)N1CCC(n2cc(-c3cnc4cnn(S(=O)(=O)c5cnc6ccc(-c7cnn(C8CCN(C(=O)OC(C)(C)C)CC8)c7)cn56)c4c3)cn2)CC1]

Into a microwave reaction tube were charged 150 mg compound of Example 67, 103 mg {1-[(1-t-butoxycarbonyl)-4-piperidinyl]}-4-pyrazoloborate pinacol ester and 103 mg potassium carbonate, 5 ml dioxane, 2.5 ml ethanol and 2.5 ml water were added into the microwave reaction tube, air was displaced for three times, under a nitrogen atmosphere, 9.9 mg complex of 1,1'-bis(diphenylphosphino) ferrocene palladium (II) dichloride and dichloromethane was added into the microwave tube, then the microwave tube was sealed. The microwave tube was placed into a microwave reactor, reacted at 90° C. for 10 minutes, the reaction was completed. The aforementioned reactant liquid was poured into 15 ml water, extracted three times with dichloromethane, the organic layer was dried over anhydrous sodium sulfate then concentrated, and isolated by flash preparative chromatography to obtain the target compound (m=159 mg, yield: 80%).

$^1$H NMR (400 MHz, CDCl$_3$) δ 9.19 (s, 1H), 8.86 (d, J=1.8 Hz, 1H), 8.46 (s, 1H), 8.33 (d, J=0.8 Hz, 1H), 8.28 (s, 1H), 7.96 (s, 1H), 7.90 (s, 1H), 7.85 (s, 1H), 7.79 (s, 1H), 7.75-7.71 (m, 1H), 7.64 (dd, J=9.3, 1.7 Hz, 1H), 4.44-4.21 (m, 6H), 3.01-2.83 (m, 4H), 2.28-2.16 (m, 4H), 2.09-1.94 (m, 4H), 1.50 (s, 18H).

Example 69

1-[(6-trifluoromethyl-imidazo[1,2-a]pyridine)-3-sulfonyl)]-6-{-[(1-isopropyl)-4-piperidinyl]}-4-pyrazolyl}-1-H-pyrazolo[4,3-b]pyridine

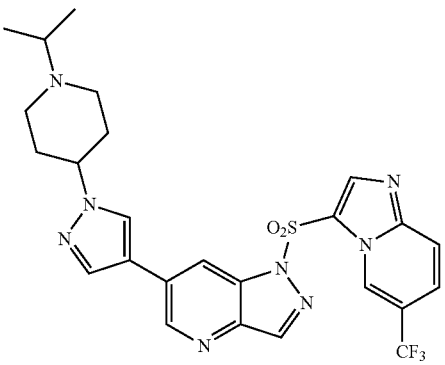 [SMILES: CC(C)N1CCC(n2cc(-c3cnc4cnn(S(=O)(=O)c5cnc6ccc(C(F)(F)F)cn56)c4c3)cn2)CC1]

Except for the compound of Example 65 was used instead of the compound of Example 45, compound 1-[(6-trifluoromethyl-imidazo[1,2-a]pyridine)-3-sulfonyl)]-6-{{1-[(1-isopropyl)-4-piperidinyl]}-4-pyrazolyl}-1-H-pyrazolo[4,3-b]pyridine was prepared by the same process as Example 59.

$^1$H NMR (400 MHz, CDCl$_3$) δ 9.53 (s, 1H), 8.87 (d, J=1.8 Hz, 1H), 8.46 (s, 1H), 8.40 (s, 1H), 8.37 (s, 1H), 8.03 (s, 1H), 7.95 (s, 1H), 7.86 (d, J=9.4 Hz, 1H), 7.68 (d, J=7.8 Hz, 1H), 4.72-4.55 (m, 1H), 3.71-3.57 (m, 2H), 3.57-3.42 (m, 1H), 3.06-2.79 (m, 2H), 2.31-2.13 (m, 2H), 2.09-1.90 (m, 2H), 1.49 (s, 3H), 1.48 (s, 3H).

Example 70

Preparation of 1-[(6-bromo-imidazo[1,2-a]pyridine)-3-sulfonyl]-6-[(1-methyl)-4-pyrazolyl]-1-H-pyrazolo[4,3-b]pyridine

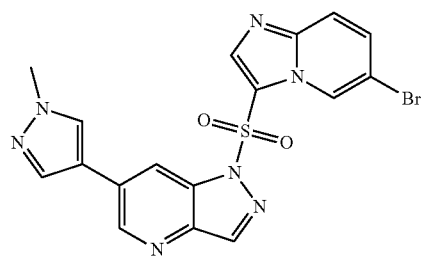 [SMILES: Cn1cc(-c2cnc3cnn(S(=O)(=O)c4cnc5ccc(Br)cn45)c3c2)cn1]

Except for (6-bromo-imidazo[1,2-a]pyridine)-3-sulfonyl chloride was used instead of (6-chloro-imidazo[1,2-a]pyridine)-3-sulfonyl chloride, compound 1-[(6-bromo-imidazo[1,2-a]pyridine)-3-sulfonyl]-6-[(1-methyl)-4-pyrazolyl]-1-H-pyrazolo[4,3-b]pyridine was prepared by the same process as Example 24.

$^1$H NMR (400 MHz, CDCl$_3$) δ 9.28 (dd, J=1.7, 1.0 Hz, 1H), 8.86 (d, J=1.9 Hz, 1H), 8.44 (dd, J=1.8, 0.8 Hz, 1H), 8.37 (d, J=0.8 Hz, 1H), 8.26 (s, 1H), 7.95 (d, J=0.7 Hz, 1H), 7.86 (s, 1H), 7.63 (dd, J=9.5, 0.9 Hz, 1H), 7.59 (dd, J=9.5, 1.7 Hz, 1H), 4.03 (s, 1H).

Example 71

Preparation of 1-[(6-phenyl-imidazo[1,2-a]pyridine)-3-sulfonyl]-6-[(1-methyl)-4-pyrazolyl]-1-H-pyrazolo[4,3-b]pyridine

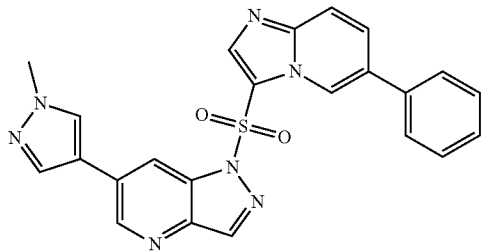 [SMILES: Cn1cc(-c2cnc3cnn(S(=O)(=O)c4cnc5ccc(-c6ccccc6)cn45)c3c2)cn1]

Into a microwave reaction tube were charged 80 mg compound of Example 70, 25.7 mg phenylboronic acid and 87 mg potassium carbonate, 2 ml dioxane, 1 ml ethanol and 1 ml water were added into the microwave reaction tube, air was displaced for three times, under a nitrogen atmosphere, 8.6 mg complex of 1,1'-bis(diphenylphosphino) ferrocene palladium (II) dichloride and dichloromethane was added into the microwave tube, then the microwave tube was sealed. The microwave tube was placed into a microwave reactor, reacted at 90° C. for 30 minutes, the reaction was completed. The aforementioned reactant liquid was poured into 15 ml water, extracted three times with dichloromethane, the organic layer was dried over anhydrous sodium sulfate then concentrated, and isolated by flash preparative chromatography to obtain the target compound (m=83 mg, yield: 86%).

$^1$H NMR (400 MHz, CDCl$_3$) δ 9.27 (t, J=1.3 Hz, 1H), 8.86 (d, J=1.9 Hz, 1H), 8.48 (dd, J=1.8, 0.8 Hz, 1H), 8.35 (m, 2H), 7.95 (d, J=0.7 Hz, 1H), 7.85 (s, 1H), 7.78 (m, 2H), 7.61 (m, 2H), 7.50 (m, 3H), 4.04 (s, 3H).

Example 72

Preparation of 1-{[6-(3-thiophene)-imidazo[1,2-a]pyridine]-3-sulfonyl}-6-[(1-methyl)-4-pyrazolyl]-1-H-pyrazolo[4,3-b]pyridine

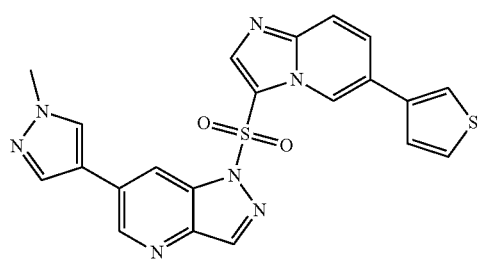 [SMILES: Cn1cc(-c2cnc3cnn(S(=O)(=O)c4cnc5ccc(-c6ccsc6)cn45)c3c2)cn1]

Except for thiophene-3-boronic acid was used instead of phenylboronic acid, compound 1-{[6-(3-thiophene)-imidazo[1,2-a]pyridine]-3-sulfonyl}-6-[(1-methyl)-4-pyrazolyl]-1-H-pyrazolo[4,3-b]pyridine was prepared by the same process as Example 71.

$^1$H NMR (400 MHz, CDCl$_3$) δ 9.30 (s, 1H), 8.86 (d, J=1.8 Hz, 1H), 8.48 (dd, J=1.8, 0.8 Hz, 1H), 8.34 (d, J=0.7 Hz, 1H), 8.32 (s, 1H), 7.95 (d, J=0.6 Hz, 1H), 7.86 (s, 1H), 7.76 (d, J=1.6 Hz, 2H), 7.57 (dd, J=2.9, 1.4 Hz, 1H), 7.50 (dd, J=5.0, 2.9 Hz, 1H), 7.43 (dd, J=5.0, 1.4 Hz, 1H), 4.04 (s, 3H).

Example 73

Preparation of 1-{[6-(4-dimethylaminocarbonylphenyl)-imidazo[1,2-a]pyridine]-3-sulfonyl}-6-[(1-methyl)-4-pyrazolyl]-1-H-pyrazolo[4,3-b]pyridine

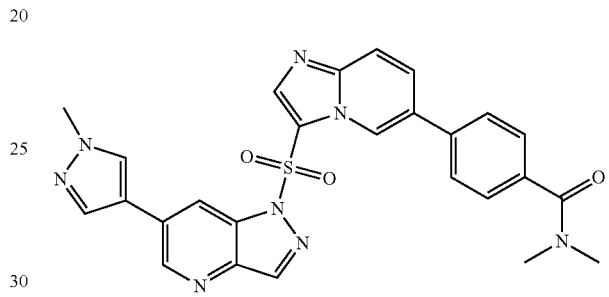

Except for 4-dimethylaminocarbonylphenylboronic acid was used instead of phenylboronic acid, compound 1-{[6-(4-dimethylaminocarbonylphenyl)-imidazo[1,2-a]pyridine]-3-sulfonyl}-6-[(1-methyl)-4-pyrazolyl]-1-H-pyrazolo[4,3-b]pyridine was prepared by the same process as Example 71.

$^1$H NMR (400 MHz, CDCl$_3$) δ 9.30 (dd, J=1.5, 1.0 Hz, 1H), 8.86 (d, J=1.9 Hz, 1H), 8.48 (dd, J=1.8, 0.8 Hz, 1H), 8.35 (m, 2H), 7.94 (d, J=0.6 Hz, 1H), 7.86 (s, 1H), 7.81 (dd, J=9.3, 0.9 Hz, 1H), 7.76 (dd, J=9.3, 1.7 Hz, 1H), 7.65 (d, J=8.4 Hz, 2H), 7.56 (d, J=8.4 Hz, 2H), 4.03 (s, 3H), 3.12 (d, J=40.7 Hz, 6H).

Example 74

Preparation of 1-{[6-(5-pyrimidine)-imidazo[1,2-a]pyridine]-3-sulfonyl}-6-[(1-methyl)-4-pyrazolyl]-1-H-pyrazolo[4,3-b]pyridine

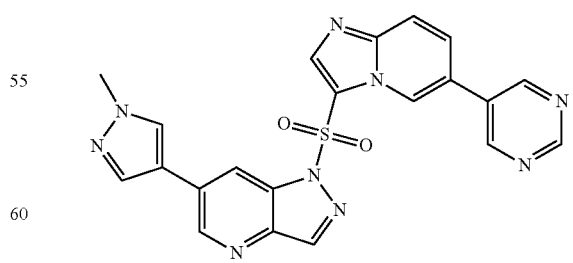

Except for pyrimidine-5-boronic acid was used instead of phenylboronic acid, compound 1-{[6-(5-pyrimidine)-imidazo[1,2-a]pyridine]-3-sulfonyl}-6-[(1-methyl)-4-pyrazolyl]-1-H-pyrazolo[4,3-b]pyridine was prepared by the same process as Example 71.

¹H NMR (400 MHz, CDCl₃) δ 9.43 (dd, J=1.8, 1.1 Hz, 1H), 9.36 (s, 1H), 9.07 (s, 2H), 8.87 (d, J=1.9 Hz, 1H), 8.46 (dd, J=1.8, 0.8 Hz, 1H), 8.35 (m, 2H), 7.95 (d, J=0.8 Hz, 1H), 7.90 (dd, J=9.4, 0.9 Hz, 1H), 7.87 (s, 1H), 7.73 (dd, J=9.3, 1.9 Hz, 1H), 4.04 (s, 3H).

Example 75

Preparation of 1-{[6-(4-morpholinylphenyl)-imidazo[1,2-a]pyridine]-3-sulfonyl}-6-[(1-methyl)-4-pyrazolyl]-1-H-pyrazolo[4,3-b]pyridine

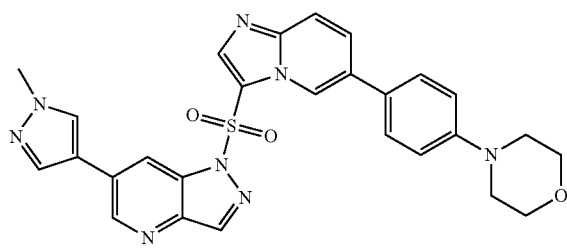 [SMILES: Cn1cc(-c2cnc3cnn(S(=O)(=O)c4cnc5ccc(-c6ccc(N7CCOCC7)cc6)cn45)c3c2)cn1]

Except for 4-morpholinylphenylboronic acid was used instead of phenylboronic acid, compound 1-{[6-(4-morpholinylphenyl)-imidazo[1,2-a]pyridine]-3-sulfonyl}-6-[(1-methyl)-4-pyrazolyl]-1-H-pyrazolo[4,3-b]pyridine was prepared by the same process as Example 71.

¹H NMR (400 MHz, CDCl₃) δ 9.19 (t, J=1.2 Hz, 1H), 8.86 (d, J=1.9 Hz, 1H), 8.49 (dd, J=1.8, 0.7 Hz, 1H), 8.34 (d, J=0.7 Hz, 1H), 8.32 (s, 1H), 7.95 (s, 1H), 7.86 (s, 1H), 7.74 (d, J=1.3 Hz, 2H), 7.52 (d, J=8.7 Hz, 2H), 7.00 (d, J=8.8 Hz, 2H), 4.03 (s, 3H), 3.91 (m, 4H), 3.26 (m, 4H).

Example 76

Preparation of 1-{(6-{{1-[(1-t-butoxycarbonyl)-4-piperidinyl]}-4-pyrazolyl}-imidazo[1,2-a]pyridine)-3-sulfonyl}-6-[(1-methyl)-4-pyrazolyl]-1-H-pyrazolo[4,3-b]pyridine

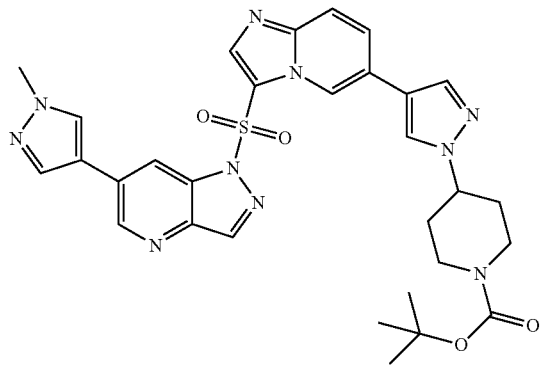 [SMILES: Cn1cc(-c2cnc3cnn(S(=O)(=O)c4cnc5ccc(-c6cnn(C7CCN(C(=O)OC(C)(C)C)CC7)c6)cn45)c3c2)cn1]

Except for 1-[(1-t-butoxycarbonyl)-4-piperidinyl]}-pyrazolo-4-pinacol ester was used instead of phenylboronic acid, compound 1-{(6-{{1-[(1-t-butoxycarbonyl)-4-piperidinyl]}-4-pyrazolyl}-imidazo[1,2-a]pyridine)-3-sulfonyl}-6-[(1-methyl)-4-pyrazolyl]-1-H-pyrazolo[4,3-b]pyridine was prepared by the same process as Example 71.

¹H NMR (400 MHz, CDCl₃) δ 9.17 (s, 1H), 8.86 (d, J=1.9 Hz, 1H), 8.46 (m, 1H), 8.33 (s, 1H), 8.28 (s, 1H), 7.95 (s, 1H), 7.87 (s, 1H), 7.85 (s, 1H), 7.78 (s, 1H), 7.72 (d, J=9.4 Hz, 1H), 7.63 (dd, J=9.3, 1.7 Hz, 1H), 4.35 (m, 3H), 4.04 (s, 3H), 2.95 (m, 2H), 2.20 (m, 2H), 2.00 (m, 4.4 Hz, 2H), 1.50 (s, 9H).

Example 77

Preparation of 1-{[6-(4-trifluoromethylphenyl)-imidazo[1,2-a]pyridine]-3-sulfonyl}-6-[(1-methyl)-4-pyrazolyl]-1-H-pyrazolo[4,3-b]pyridine Except for 4-trifluoromethylphenylboronic acid was used instead of phenylboronic acid, compound 1-{[6-(4-trifluoromethylphenyl)-imidazo[1,2-a]pyridine]-3-sulfonyl}-6-[(1-methyl)-4-pyrazolyl]-1-H-pyrazolo[4,3-b]pyridine was prepared by the same process as Example 71.

¹H NMR (400 MHz, CDCl₃) δ 9.34 (s, 1H), 8.87 (d, J=1.8 Hz, 1H), 8.48 (s, 1H), 8.35 (s, 2H), 7.96 (s, 1H), 7.85 (m, 2H), 7.76 (m, 5H), 4.04 (s, 3H).

Example 78

Preparation of 1-{[6-(3-fluoro-4-methylphenyl)-imidazo[1,2-a]pyridine]-3-sulfonyl}-6-[(1-methyl)-4-pyrazolyl]-1-H-pyrazolo[4,3-b]pyridine Except for 3-fluoro-4-methylphenylboronic acid was used instead of phenylboronic acid, compound 1-{[6-(3-fluoro-4-methylphenyl)-imidazo[1,2-a]pyridine]-3-sulfonyl}-6-[(1-methyl)-4-pyrazolyl]-1-H-pyrazolo[4,3-b]pyridine was prepared by the same process as Example 71.

¹H NMR (400 MHz, CDCl₃) δ 9.25 (s, 1H), 8.86 (d, J=1.7 Hz, 1H), 8.47 (s, 1H), 8.34 (d, J=7.3 Hz, 2H), 7.94 (s, 1H), 7.86 (s, 1H), 7.78 (d, J=9.3 Hz, 1H), 7.72 (dd, J=9.4, 1.7 Hz, 1H), 7.29 (m, 3H), 4.04 (s, 3H), 2.36 (d, J=1.6 Hz, 3H).

Example 79

Preparation of 1-{[6-(4-isopropoxyl)phenyl)-imidazo[1,2-a]pyridine]-3-sulfonyl}-6-[(1-methyl)-4-pyrazolyl]-1-H-pyrazolo[4,3-b]pyridine

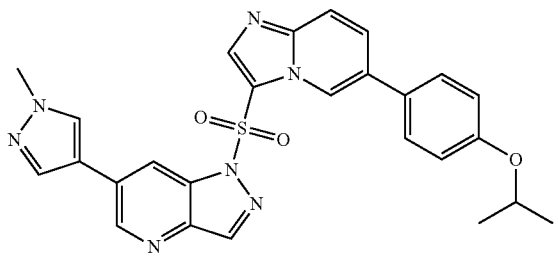 [SMILES: CC(C)Oc1ccc(-c2ccc3ncc(S(=O)(=O)n4ncc5ncc(-c6cnn(C)c6)cc54)n3c2)cc1]

Except for 4-isopropoxylphenylboronic acid was used instead of phenylboronic acid, compound 1-{[6-(4-isopropoxyl)phenyl)-imidazo[1,2-a]pyridine]-3-sulfonyl}-6-[(1-methyl)-4-pyrazolyl]-1-H-pyrazolo[4,3-b]pyridine was prepared by the same process as Example 71.

$^{1}$H NMR (400 MHz, CDCl$_3$) δ 9.27 (m, 1H), 8.85 (d, J=1.9 Hz, 1H), 8.47 (dd, J=1.8, 0.8 Hz, 1H), 8.34 (m, 2H), 7.94 (d, J=0.6 Hz, 1H), 7.85 (s, 1H), 7.76 (m, 2H), 7.39 (t, J=7.9 Hz, 1H), 7.14 (t, J=4.9 Hz, 2H), 6.98 (dd, J=8.0, 2.1 Hz, 1H), 4.66 (dt, J=12.1, 6.1 Hz, 1H), 4.03 (s, 3H), 1.41 (d, J=6.1 Hz, 6-1).

Example 80

Preparation of 1-{[6-[4-(4-methylpiperazine-1-carbonyl)phenyl]-imidazo[1,2-a]pyridine]-3-sulfonyl}-6-[(1-methyl)-4-pyrazolyl]-1-H-pyrazolo[4,3-b]pyridine

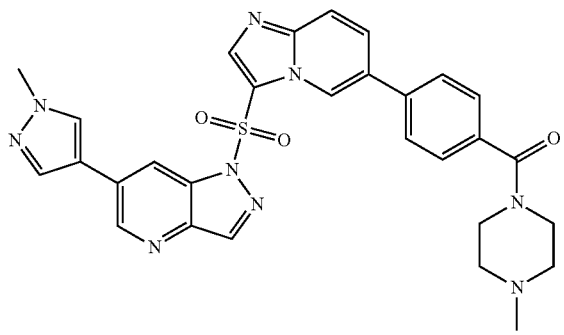 [SMILES: CN1CCN(C(=O)c2ccc(-c3ccc4ncc(S(=O)(=O)n5ncc6ncc(-c7cnn(C)c7)cc65)n4c3)cc2)CC1]

Except for 4-(4-methylpiperazine-1-carbonyl)phenylboronic acid was used instead of 5 phenylboronic acid, compound 1-{[6-[4-(4-methylpiperazine-1-carbonyl)phenyl]-imidazo[1,2-a]pyridine]-3-sulfonyl}-6-[(1-methyl)-4-pyrazolyl]-1-H-pyrazolo[4,3-b]pyridine was prepared by the same process as Example 71.

$^{1}$H NMR (400 MHz, CDCl$_3$) δ 9.31 (m, 1H), 8.86 (d, J=1.9 Hz, 1H), 8.47 (dd, J=1.8, 0.8 Hz, 1H), 8.36 (d, J=0.8 Hz, 1H), 8.34 (s, 1H), 7.95 (d, J=0.6 Hz, 1H), 7.87 (s, 1H), 7.81 (dd, J=9.3, 0.8 Hz, 1H), 7.76 (dd, J=9.3, 1.7 Hz, 1H), 7.67 (d, J=8.3 Hz, 2H), 7.56 (d, J=8.3 Hz, 2H), 4.04 (s, 3H), 3.86 (s, 2H), 3.54 (s, 2H), 2.50 (d, J=47.2 Hz, 4H), 2.38 (s, 3H).

Example 81

Preparation of 1-{[6-(4-fluorophenyl)-imidazo[1,2-a]pyridine]-3-sulfonyl}-6-[(1-methyl)-4-pyrazolyl]-1-H-pyrazolo[4,3-b]pyridine

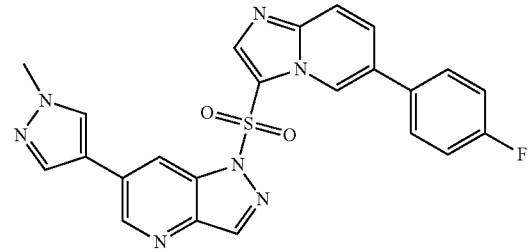 [SMILES: Cn1cc(-c2cnc3cnn(S(=O)(=O)c4cnc5ccc(-c6ccc(F)cc6)cn45)c3c2)cn1]

Except for 4-fluorophenylboronic acid was used instead of phenylboronic acid, compound 1-{[6-(4-fluorophenyl)-imidazo[1,2-a]pyridine]-3-sulfonyl}-6-[(1-methyl)-4-pyrazolyl]-1-H-pyrazolo[4,3-b]pyridine was prepared by the same process as Example 71.

$^{1}$H NMR (400 MHz, CDCl$_3$) δ 9.24 (s, 1H), 8.86 (d, J=1.8 Hz, 0H), 8.48 (d, J=1.1 Hz, 1H), 8.34 (d, J=7.2 Hz, 2H), 7.95 (s, 1H), 7.86 (s, 1H), 7.79 (d, J=9.3 Hz, 1H), 7.72 (dd, J=9.3, 1.8 Hz, 1H), 7.58 (dd, J=8.7, 5.1 Hz, 2H), 7.21 (t, J=8.6 Hz, 2H), 4.04 (s, 3H).

Example 82

Preparation of 1-{[6-([1-(4-piperidinyl)]-4-pyrazolyl)-imidazo[1,2-a]pyridine]-3-sulfonyl}-6-[(1-methyl)-4-pyrazolyl]-1-H-pyrazolo[4,3-b]pyridine chloride

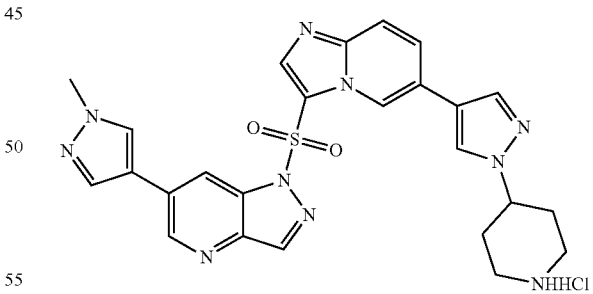

Fifty milligrams compound of Example 76 was dissolved in 5 ml dioxane saturated with hydrochloric acid, stirred for 30 minutes at room temperature. The reaction was completed, and filtered to obtain filter cake, which was washed three times by ether immersion, vacuum dried to obtain the target compound (m=36 mg, yield: 86%).

$^{1}$H NMR (400 MHz, CDCl$_3$) δ 9.05 (d, J=1.8 Hz, 1H), 8.96 (s, 1H), 8.75 (s, 1H), 8.65 (s, 1H), 8.60 (s, 2H), 8.36 (s, 1H), 8.27 (s, 1H), 7.96 (d, J=13.6 Hz, 2H), 7.90 (d, J=8.9 Hz, 1H), 4.51 (m, 2H), 3.95 (s, 3H), 3.40 (m, 3H), 3.06 (m, 3H).

Example 83

Preparation of 1-{[6-(3-trifluoromethylphenyl)-imidazo[1,2-a]pyridine]-3-sulfonyl}-6-[(1-methyl)-4-pyrazolyl]-1-H-pyrazolo[4,3-b]pyridine

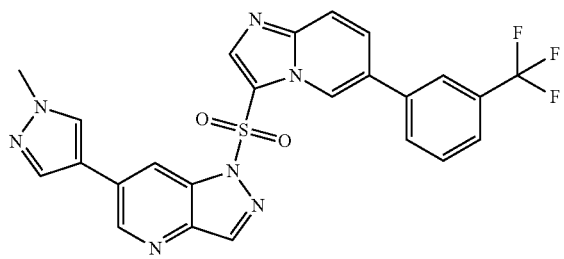 [SMILES: Cn1cc(-c2cnc3cnn(S(=O)(=O)c4cnc5ccc(-c6cccc(C(F)(F)F)c6)cn45)c3c2)cn1]

Except for 3-trifluoromethylphenylboronic acid was used instead of phenylboronic acid, compound 1-{[6-(3-trifluoromethylphenyl)-imidazo[1,2-a]pyridine]-3-sulfonyl}-6-[(1-methyl)-4-pyrazolyl]-1-H-pyrazolo[4,3-b]pyridine was prepared by the same process as Example 71.

$^1$H NMR (400 MHz, CDCl$_3$) δ 9.35 (s, 1H), 8.87 (d, J=1.9 Hz, 1H), 8.47 (d, J=1.0 Hz, 1H), 8.36 (s, 2H), 7.94 (s, 1H), 7.84 (m, 4H), 7.76 (m, 2H), 7.67 (t, J=7.8 Hz, 1H), 4.04 (s, 3H).

Example 84

Preparation of 1-{[6-(2-trifluoromethylphenyl)-imidazo[1,2-a]pyridine]-3-sulfonyl}-6-[(1-methyl)-4-pyrazolyl]-1-H-pyrazolo[4,3-b]pyridine

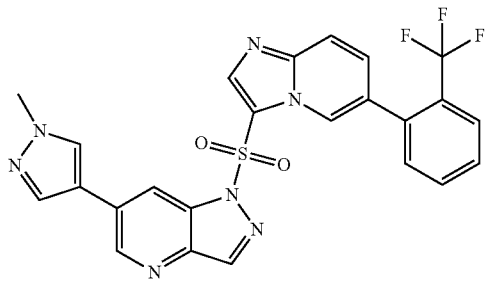 [SMILES: Cn1cc(-c2cnc3cnn(S(=O)(=O)c4cnc5ccc(-c6ccccc6C(F)(F)F)cn45)c3c2)cn1]

Except for 2-trifluoromethylphenylboronic acid was used instead of phenylboronic acid, compound 1-{[6-(2-trifluoromethylphenyl)-imidazo[1,2-a]pyridine]-3-sulfonyl}-6-[(1-methyl)-4-pyrazolyl]-1-H-pyrazolo[4,3-b]pyridine was prepared by the same process as Example 71.

$^1$H NMR (400 MHz, CDCl$_3$) δ 9.10 (s, 1H), 8.85 (d, J=1.9 Hz, 1H), 8.43 (dd, J=1.8, 0.8 Hz, 1H), 8.35 (s, 1H), 8.30 (d, J=0.7 Hz, 1H), 7.92 (d, J=0.7 Hz, 1H), 7.85 (m, 2H), 7.75 (dd, J=9.2, 0.8 Hz, 1H), 7.64 (m, 2H), 7.49 (m, 2H), 7.40 (d, J=7.2 Hz, 1H), 4.03 (s, 2H).

Example 85

Preparation of 1-{[6-(4-dimethylaminophenyl)-imidazo[1,2-a]pyridine]-3-sulfonyl}-6-[(1-methyl)-4-pyrazolyl]-1-H-pyrazolo[4,3-b]pyridine

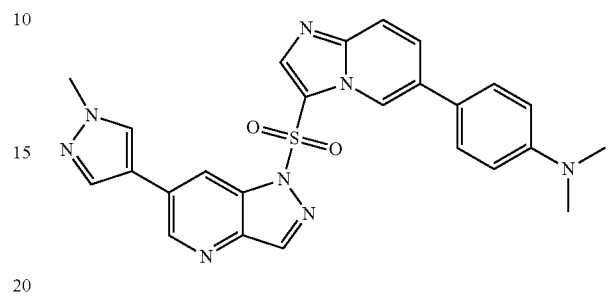

Except for 4-dimethylaminophenylboronic acid was used instead of phenylboronic acid, compound 1-{[6-(4-dimethylaminophenyl)-imidazo[1,2-a]pyridine]-3-sulfonyl}-6-[(1-methyl)-4-pyrazolyl]-1-H-pyrazolo[4,3-b]pyridine was prepared by the same process as Example 71.

$^1$H NMR (400 MHz, CDCl$_3$) δ 9.14 (t, J=1.3 Hz, 1H), 8.86 (d, J=1.9 Hz, 1H), 8.49 (dd, J=1.9, 0.8 Hz, 1H), 8.35 (d, J=0.8 Hz, 1H), 8.31 (s, 1H), 7.96 (d, J=0.6 Hz, 1H), 7.86 (s, 1H), 7.73 (dd, J=3.5, 2.0 Hz, 2H), 7.46 (d, J=8.9 Hz, 2H), 6.78 (d, J=8.9 Hz, 2H), 4.03 (s, 3H), 3.03 (s, 6H).

Example 86

Preparation of 1-{[6-(3-fluorophenyl)-imidazo[1,2-a]pyridine]-3-sulfonyl}-6-[(1-methyl)-4-pyrazolyl]-1-H-pyrazolo[4,3-b]pyridine

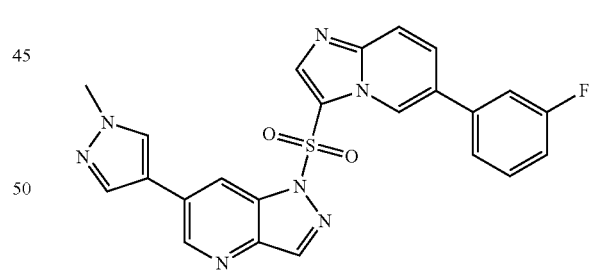

Except for 3-fluorophenylboronic acid was used instead of phenylboronic acid, compound 1-{[6-(3-fluorophenyl)-imidazo[1,2-a]pyridine]-3-sulfonyl}-6-[(1-methyl)-4-pyrazolyl]-1-H-pyrazolo[4,3-b]pyridine was prepared by the same process as Example 71.

$^1$H NMR (400 MHz, CDCl$_3$) δ 9.29 (dd, J=1.7, 1.0 Hz, 1H), 8.86 (d, J=1.9 Hz, 1H), 8.48 (dd, J=1.9, 0.9 Hz, 1H), 8.36 (d, J=0.8 Hz, 1H), 8.34 (s, 1H), 7.94 (d, J=0.7 Hz, 1H), 7.86 (s, 1H), 7.80 (dd, J=9.3, 1.0 Hz, 1H), 7.74 (dd, J=9.3, 1.8 Hz, 1H), 7.49 (m, 1H), 7.41 (m, 1H), 7.32 (m, 11H), 7.18 (tdd, J=8.5, 2.6, 1.0 Hz, 1H), 4.04 (s, 3H).

Example 87

Preparation of 1-{[6-(2,4-difluorophenyl)-imidazo[1,2-a]pyridine]-3-sulfonyl}-6-[(1-methyl)-4-pyrazolyl]-1-H-pyrazolo[4,3-b]pyridine

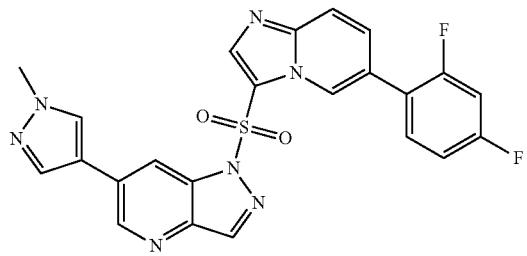 [SMILES: Cn1cc(-c2cnc3cnn(S(=O)(=O)c4cnc5ccc(-c6ccc(F)cc6F)cn45)c3c2)cn1]

Except for 2,4-difluorophenylboronic acid was used instead of phenylboronic acid, compound 1-{[6-(2,4-difluorophenyl)-imidazo[1,2-a]pyridine]-3-sulfonyl}-6-[(1-methyl)-4-pyrazolyl]-1-H-pyrazolo[4,3-b]pyridine was prepared by the same process as Example 71.

$^1$H NMR (400 MHz, CDCl$_3$) δ 9.24 (s, 1H), 8.86 (d, J=1.8 Hz, 1H), 8.46 (dd, J=1.8, 0.8 Hz, 1H), 8.35 (d, J=0.8 Hz, 2H), 7.94 (d, J=0.5 Hz, 1H), 7.86 (s, 1H), 7.79 (dd, J=9.3, 0.8 Hz, 1H), 7.67 (dt, J=9.3, 1.6 Hz, 1H), 7.48 (td, J=8.6, 6.2 Hz, 1H), 7.02 (m, 2H), 4.04 (s, 3H).

Example 88

Preparation of 1-{[6-(3,4,5-trifluorophenyl)-imidazo[1,2-a]pyridine]-3-sulfonyl}-6-[(1-methyl)-4-pyrazolyl]-1-H-pyrazolo[4,3-b]pyridine

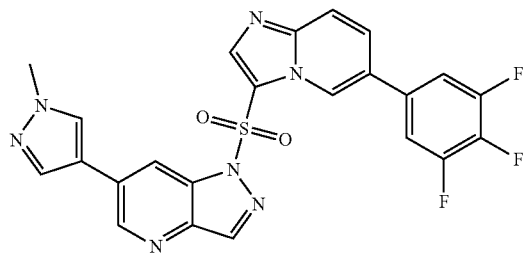 [SMILES: Cn1cc(-c2cnc3cnn(S(=O)(=O)c4cnc5ccc(-c6cc(F)c(F)c(F)c6)cn45)c3c2)cn1]

Except for 3,4,5-trifluorophenylboronic acid was used instead of phenylboronic acid, compound 1-{[6-(3,4,5-trifluorophenyl)-imidazo[1,2-a]pyridine]-3-sulfonyl}-6-[(1-methyl)-4-pyrazolyl]-1-H-pyrazolo[4,3-b]pyridine was prepared by the same process as Example 71.

$^1$H NMR (400 MHz, CDCl$_3$) δ 9.27 (s, 1H), 8.87 (d, J=1.8 Hz, 1H), 8.47 (s, 1H), 8.34 (d, J=6.4 Hz, 2H), 7.95 (s, 1H), 7.86 (s, 1H), 7.81 (d, J=9.3 Hz, 1H), 7.66 (dd, J=9.3, 1.8 Hz, 1H), 7.26 (m, 2H), 4.04 (s, 3H).

Example 89

Preparation of 1-{[6-(4-methoxyphenyl)-imidazo[1,2-a]pyridine]-3-sulfonyl}-6-[(1-methyl-4-pyrazolyl]-1-H-pyrazolo[4,3-b]pyridine

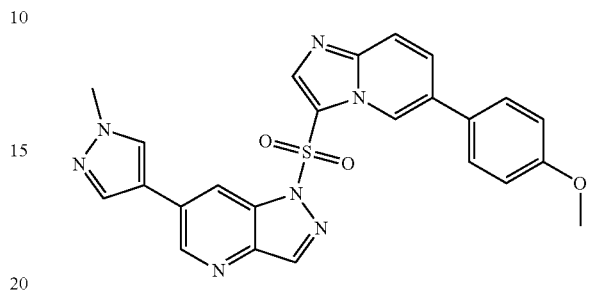

Except for 4-methoxyphenylboronic acid was used instead of phenylboronic acid, compound 1-{[6-(4-methoxyphenyl)-imidazo[1,2-a]pyridine]-3-sulfonyl}-6-[(1-methyl)-4-pyrazolyl]-1-H-pyrazolo[4,3-b]pyridine was prepared by the same process as Example 71.

$^1$H NMR (400 MHz, CDCl$_3$) δ 9.20 (t, J=1.3 Hz, 1H), 8.86 (d, J=1.9 Hz, 1H), 8.48 (m, 1H), 8.35 (s, 1H), 8.32 (s, 1H), 7.95 (s, 1H), 7.85 (s, 1H), 7.75 (m, 2H), 7.54 (d, J=8.8 Hz, 2H), 7.02 (d, J=8.8 Hz, 2H), 4.04 (s, 3H), 3.89 (s, 3H).

Example 90

Preparation of 1-{[6-(4-methylphenyl)-imidazo[1,2-a]pyridine]-3-sulfonyl}-6-[(1-methyl)-4-pyrazolyl]-1-H-pyrazolo[4,3-b]pyridine

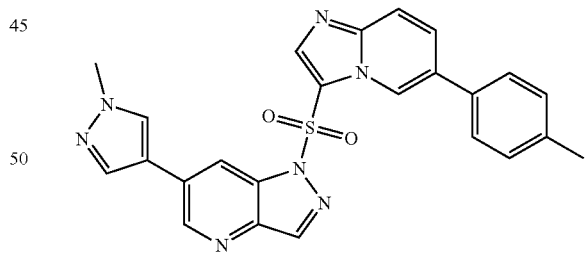

Except for 4-methylphenylboronic acid was used instead of phenylboronic acid, compound 1-{[6-(4-methylphenyl)-imidazo[1,2-a]pyridine]-3-sulfonyl}-6-[(1-methyl)-4-pyrazolyl]-1-H-pyrazolo[4,3-b]pyridine was prepared by the same process as Example 71.

$^1$H NMR (400 MHz, CDCl$_3$) δ 9.24 (t, J=1.3 Hz, 1H), 8.86 (d, J=1.9 Hz, 1H), 8.48 (m, 1H), 8.34 (d, J=7.4 Hz, 2H), 7.95 (s, 1H), 7.85 (s, 1H), 7.76 (d, J=1.3 Hz, 2H), 7.50 (d, J=8.1 Hz, 2H), 7.31 (d, J=8.0 Hz, 2H), 4.04 (s, 3H), 2.44 (s, 3H).

Example 91

Preparation of 1-{[6-(4-morpholinomethylphenyl)-imidazo[1,2-a]pyridine]-3-sulfonyl}-6-[(1-methyl)-4-pyrazolyl]-1-H-pyrazolo[4,3-b]pyridine

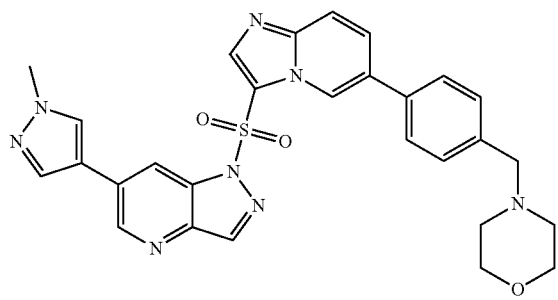 [SMILES: Cn1cc(-c2cnc3cnn(S(=O)(=O)c4cnc5ccc(-c6ccc(CN7CCOCC7)cc6)cn45)c3c2)cn1]

Except for 4-morpholinomethylphenylboronic acid was used instead of phenylboronic acid, compound 1-{[6-(4-morpholinomethylphenyl)-imidazo[1,2-a]pyridine]-3-sulfonyl}-6-[(1-methyl)-4-pyrazolyl]-1-H-pyrazolo[4,3-b]pyridine was 5 prepared by the same process as Example 71.

$^1$H NMR (400 MHz, CDCl$_3$) δ 9.30 (s, 1H), 8.88 (d, J=1.6 Hz, 1H), 8.50 (d, J=1.8 Hz, 1H), 8.37 (s, 1H), 8.34 (s, 1H), 7.97 (s, 1H), 7.88 (s, 1H), 7.79 (t, J=1.5 Hz, 2H), 7.59 (d, J=8.1 Hz, 2H), 7.50 (d, J=8.1 Hz, 2H), 4.06 (s, 3H), 3.78 (m, 4H), 3.60 (s, 2H), 2.52 (m, 4H).

Example 92

Preparation of 1-{[6-(4-cyanophenyl)-imidazo[1,2-a]pyridine]-3-sulfonyl}6-[(1-methyl)-4-pyrazolyl]-1-H-pyrazolo[4,3-b]pyridine

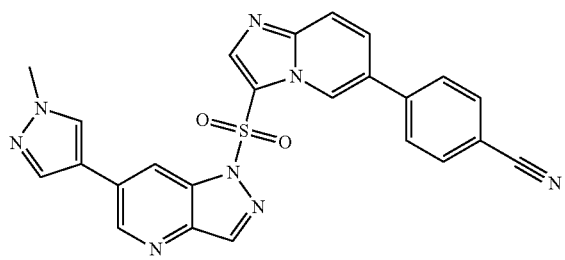 [SMILES: Cn1cc(-c2cnc3cnn(S(=O)(=O)c4cnc5ccc(-c6ccc(C#N)cc6)cn45)c3c2)cn1]

Except for 4-cyanophenylboronic acid was used instead of phenylboronic acid, compound 1-{[6-(4-cyanophenyl)-imidazo[1,2-a]pyridine]-3-sulfonyl}-6-[(1-methyl)-4-pyrazolyl]-1-H-pyrazolo[4,3-b]pyridine was prepared by the same process as Example 71.

$^1$H NMR (400 MHz, CDCl$_3$) δ 9.37 (s, 1H), 8.87 (d, J=1.9 Hz, 1H), 8.47 (dd, J=1.5, 0.5 Hz, 1H), 8.34 (s, 2H), 7.95 (s, 1H), 7.84 (m, 4H), 7.75 (m, 3H), 4.04 (s, 3H).

Example 93

Preparation of 1-{[6-[6-(1,4-benzodioxanyl)]-imidazo[1,2-a]pyridine]-3-sulfonyl}-6-[(1-methyl)-4-pyrazolyl]-1-H-pyrazolo[4,3-b]pyridine

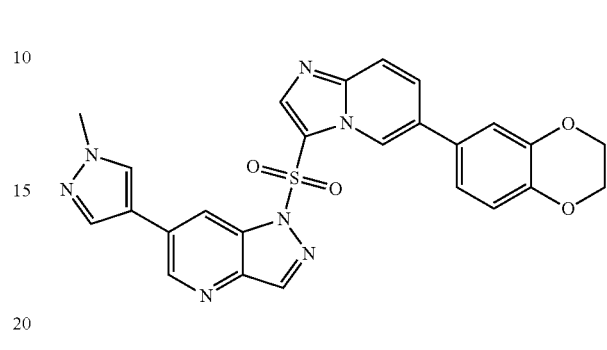

Except for (1,4-benzodioxanyl)-6-boronic acid was used instead of phenylboronic acid, compound 1-{[6-[6-(1,4-benzodioxanyl)]-imidazo[1,2-a]pyridine]-3-sulfonyl}-6-[(1-methyl)-4-pyrazolyl]-1-H-pyrazolo[4,3-b]pyridine was prepared by the same process as Example 71.

$^1$H NMR (400 MHz, CDCl$_3$) δ 9.18 (s, 1H), 8.85 (d, J=1.8 Hz, 1H), 8.47 (d, J=1.1 Hz, 1H), 8.35 (s, 1H), 8.32 (s, 1H), 7.94 (s, 1H), 7.85 (s, 1H), 7.75 (d, J=9.4 Hz, 1H), 7.70 (dd, J=9.2, 1.6 Hz, 1H), 7.12 (d, J=2.1 Hz, 1H), 7.08 (dd, J=8.3, 2.3 Hz, 1H), 6.98 (d, J=8.3 Hz, 1H), 4.34 (s, 4H), 4.03 (s, 3H).

Example 94

Preparation of 1-{[6-(4-chlorophenyl)-imidazo[1,2-a]pyridine]-3-sulfonyl}6-[(1-methyl)-4-pyrazolyl]-1-H-pyrazolo[4,3-b]pyridine

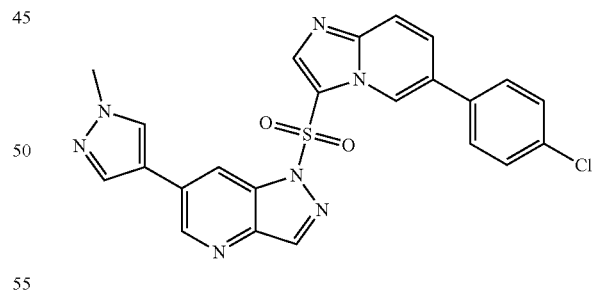

Except for 4-chlorophenylboronic acid was used instead of phenylboronic acid, compound 1-{[6-(4-chlorophenyl)-imidazo[1,2-a]pyridine]-3-sulfonyl}-6-[(1-methyl)-4-pyrazolyl]-1-H-pyrazolo[4,3-b]pyridine was prepared by the same process as Example 71.

$^1$H NMR (400 MHz, CDCl$_3$) δ 9.26 (m, 1H), 8.86 (d, J=1.8 Hz, 1H), 8.47 (m, 1H), 8.34 (d, J=5.4 Hz, 2H), 7.95 (s, 1H), 7.85 (s, 1H), 7.79 (dd, J=9.3 Hz, 0.9 Hz, 1H), 7.72 (dd, J=9.3, 1.7 Hz, 1H), 7.55 (m, 2H), 7.48 (m, 2H), 4.04 (s, 3H).

Example 95

Preparation of 1-{[6-(3-fluoro-4-pyridinyl)-imidazo[1,2-a]pyridine]-3-sulfonyl}-6-[(1-methyl)-4-pyrazolyl]-1-H-pyrazolo[4,3-b]pyridine

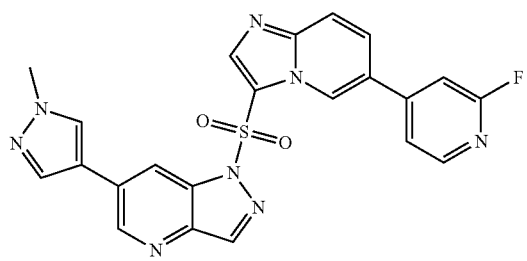 [SMILES: Cn1cc(-c2cnc3cnn(S(=O)(=O)c4cnc5ccc(-c6ccnc(F)c6)cn45)c3c2)cn1]

Except for 3-fluoro-pyridine-4-boronic acid was used instead of phenylboronic acid, compound 1-{[6-(3-fluoro-4-pyridinyl)-imidazo[1,2-a]pyridine]-3-sulfonyl}-6-[(1-methyl)-4-pyrazolyl]-1-H-pyrazolo[4,3-b]pyridine was prepared by the same process as Example 71.

$^1$H NMR (400 MHz, CDCl$_3$) δ 9.47 (dd, J=1.7, 1.0 Hz, 1H), 8.89 (d, J=1.9 Hz, 1H), 8.49 (dd, J=1.8, 0.9 Hz, 1H), 8.42 (d, J=5.4 Hz, 1H), 8.37 (s, 2H), 7.97 (d, J=0.4 Hz, 1H), 7.89 (m, 2H), 7.78 (dd, J=9.3, 1.8 Hz, 1H), 7.51 (dt, J=5.2, 1.4 Hz, 1H), 7.23 (t, J=1.7 Hz, 1H), 4.06 (s, 31H).

Example 96

Preparation of 1-{[6-(3,4-dimethoxyphenyl)-imidazo[1,2-a]pyridine]-3-sulfonyl}-6-[(1-methyl)-4-pyrazolyl]-1-H-pyrazolo[4,3-b]pyridine

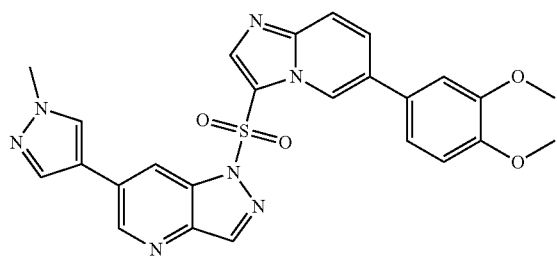 [SMILES: COc1ccc(-c2ccc3ncc(S(=O)(=O)n4ncc5ncc(-c6cnn(C)c6)cc54)n3c2)cc1OC]

Except for 3,4-dimethoxyphenylboronic acid was used instead of phenylboronic acid, compound 1-{[6-(3,4-dimethoxyphenyl)-imidazo[1,2-a]pyridine]-3-sulfonyl}-6-[(1-methyl)-4-pyrazolyl]-1-H-pyrazolo[4,3-b]pyridine was prepared by the same process as Example 71.

$^1$H NMR (400 MHz, CDCl$_3$) δ 9.23 (t, J=1.2 Hz, 1H), 8.86 (d, J=1.9 Hz, 1H), 8.47 (dd, J=1.8, 0.6 Hz, 1H), 8.33 (s, 2H), 7.94 (s, 1H), 7.85 (s, 1H), 7.75 (m, 2H), 7.16 (dd, J=8.3, 2.1 Hz, 1H), 7.10 (d, J=2.1 Hz, 1H), 6.98 (d, J=8.4 Hz, 1H), 4.03 (s, 3H), 3.99 (s, 3H), 3.97 (s, 3H).

Example 97

Preparation of 1-{[6-(2-methoxyphenyl)-imidazo[1,2-a]pyridine]-3-sulfonyl}-6-[(1-methyl)-4-pyrazolyl]-1-H-pyrazolo[4,3-b]pyridine

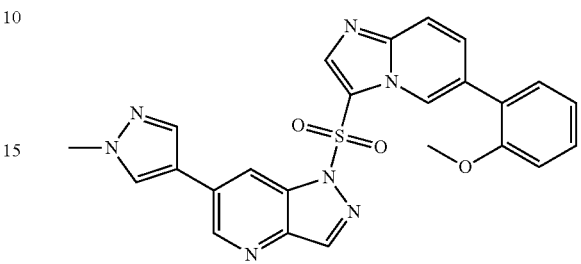

Except for 2-methoxyphenylboronic acid was used instead of phenylboronic acid, compound 1-{[6-(2-methoxyphenyl)-imidazo[1,2-a]pyridine]-3-sulfonyl}-6-[(1-methyl)-4-pyrazolyl]-1-H-pyrazolo[4,3-b]pyridine was prepared by the same process as Example 71.

$^1$H NMR (400 MHz, CDCl$_3$) δ 9.20 (t, J=1.3 Hz, 1H), 8.85 (d, J=1.9 Hz, 1H), 8.47 (dd, J=1.9, 0.8 Hz, 1H), 8.34 (m, 2H), 7.93 (d, J=0.7 Hz, 1H), 7.83 (s, 1H), 7.73 (dd, J=2.5, 1.3 Hz, 2H), 7.43 (m, 1H), 7.35 (dd, J=7.5, 1.7 Hz, 1H), 7.06 (m, 2H), 4.03 (s, 3H), 3.85 (s, 3H).

Example 98

Preparation of 1-{[6-[5-(1,2-methylenedioxyphenyl)]-imidazo[1,2-a]pyridine]-3-sulfonyl}-6-[(1-methyl)-4-pyrazolyl]-1-H-pyrazolo[4,3-b]pyridine

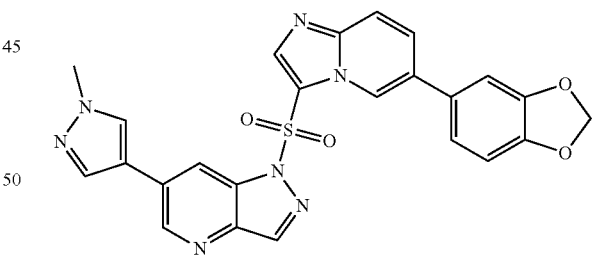

Except for 5-(1,2-methylenedioxyphenyl)boronic acid was used instead of phenylboronic acid, compound 1-{[6-[5-(1,2-methylenedioxyphenyl)]-imidazo[1,2-a]pyridine]-3-sulfonyl}-6-[(1-methyl)-4-pyrazolyl]-1-H-pyrazolo[4,3-b]pyridine was prepared by the same process as Example 71.

$^1$H NMR (400 MHz, CDCl$_3$) δ 9.18 (dd, J=1.6, 1.0 Hz, 1H), 8.86 (d, J=1.9 Hz, 1H), 8.47 (dd, J=1.8, 0.8 Hz, 1H), 8.35 (d, J=0.7 Hz, 1H), 8.32 (s, 1H), 7.94 (d, J=0.6 Hz, 1H), 7.85 (m, 1H), 7.75 (dd, J=9.3, 0.9 Hz, 1H), 7.69 (dd, J=9.4, 1.9 Hz, 1H), 7.07 (m, 2H), 6.93 (d, J=8.5 Hz, 1H), 6.07 (s, 2H), 4.04 (s, 3H).

Example 99

Preparation of 1-{[6-(2-fluoro-5-pyridinyl)-imidazo[1,2-a]pyridine]-3-sulfonyl}-6-[(1-methyl)-4-pyrazolyl]-1-H-pyrazolo[4,3-b]pyridine

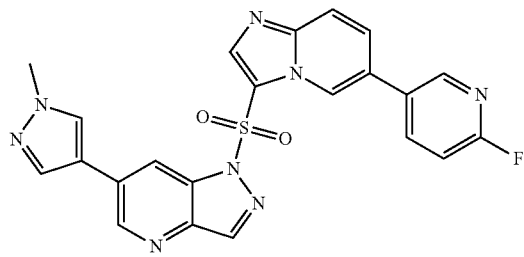 [SMILES: Cn1cc(-c2cnc3cnn(S(=O)(=O)c4cnc5ccc(-c6ccc(F)nc6)cn45)c3c2)cn1]

Except for 2-fluoro-pyridine-5-boronic acid was used instead of phenylboronic acid, compound 1-{[6-(2-fluoro-5-pyridinyl)-imidazo[1,2-a]pyridine]-3-sulfonyl}-6-[(1-methyl)-4-pyrazolyl]-1-H-pyrazolo[4,3-b]pyridine was prepared by the same process as Example 71.

$^1$H NMR (400 MHz, CDCl$_3$) δ 9.34 (s, 1H), 8.89 (d, J=1.8 Hz, 1H), 8.53 (d, J=2.6 Hz, 1H), 8.48 (d, J=1.0 Hz, 1H), 8.36 (s, 2H), 8.08 (ddd, J=8.2, 7.5, 2.6 Hz, 1H), 7.97 (s, 1H), 7.87 (m, 2H), 7.72 (dd, J=9.3, 1.8 Hz, 1H), 7.15 (dd, J=8.7, 3.0 Hz, 1H), 4.06 (s, 3H).

Example 100

Preparation of 1-{[6-(3-cyanophenyl)-imidazo[1,2-a]pyridine]-3-sulfonyl}-6-[(1-methyl)-4-pyrazolyl]-1-H-pyrazolo[4,3-b]pyridine

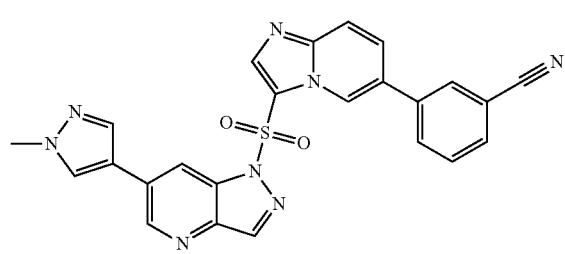 [SMILES: Cn1cc(-c2cnc3cnn(S(=O)(=O)c4cnc5ccc(-c6cccc(C#N)c6)cn45)c3c2)cn1]

Except for 3-cyanophenylboronic acid was used instead of phenylboronic acid, compound 1-{[6-(3-cyanophenyl)-imidazo[1,2-a]pyridine]-3-sulfonyl}-6-[(1-methyl)-4-pyrazolyl]-1-H-pyrazolo[4,3-b]pyridine was prepared by the same process as Example 71.

$^1$H NMR (400 MHz, CDCl$_3$) δ 9.33 (s, 1H), 8.87 (d, J=1.8 Hz, 1H), 8.47 (dd, J=1.8, 0.8 Hz, 1H), 8.35 (m, 2H), 7.95 (d, J=2.9 Hz, 1H), 7.87 (m, 4H), 7.78 (dt, J=7.8, 1.3 Hz, 1H), 7.72 (dd, J=9.4, 1.8 Hz, 1H), 7.67 (m, 1H), 4.04 (s, 3H).

Example 101

Preparation of 1-{(6-(3-fluoro-4-methylaminocarbonylphenyl)-imidazo[1,2-a]pyridine)-3-sulfonyl}-6-[(1-methyl)-4-pyrazolyl]-1-H-pyrazolo[4,3-b]pyridine

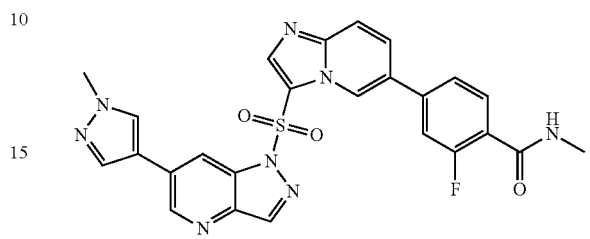

Except for 3-fluoro-4-methylaminocarbonylphenylboronic acid was used instead of phenylboronic acid, compound 1-{(6-(3-fluoro-4-methylaminocarbonylphenyl)-imidazo[1,2-a]pyridine)-3-sulfonyl}-6-[(1-methyl)-4-pyrazolyl]-1-H-pyrazolo[4,3-b]pyridine was prepared by the same process as Example 71.

$^1$H NMR (400 MHz, CDCl$_3$) δ 9.34 (d, J=1.5 Hz, 1H), 8.86 (d, J=1.9 Hz, 1H), 8.47 (d, J=1.9 Hz, 1H), 8.35 (s, 1H), 8.34 (s, 1H), 8.25 (t, J=8.2 Hz, 1H), 7.93 (s, 1H), 7.86 (s, 1H), 7.83 (dd, J=9.3, 0.9 Hz, 1H), 7.75 (dd, J=9.4, 1.8 Hz, 1H), 7.53 (dd, J=8.2, 1.8 Hz, 1H), 7.41 (dd, J=12.6, 1.8 Hz, 1H), 6.84 (s, 1H), 4.04 (s, 3H), 3.10 (d, J=5.1 Hz, 3H).

Example 102

Preparation of 1-{(6-(3-fluoro-4-methylaminocarbonylphenyl)-imidazo[1,2-a]pyridine)-3-sulfonyl}-6-[(2-di methylaminoethyl)-4-pyrazolyl]-1-H-pyrazolo[4,3-b]pyridine

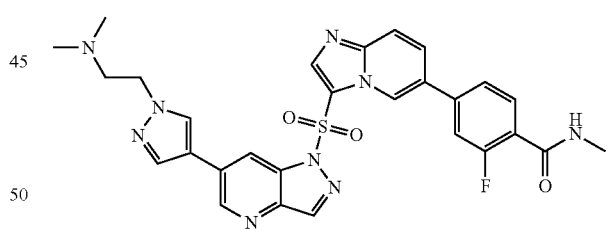

Except for 2-dimethylaminoethyl-1H-pyrazolo-4-borrate pinacol ester was used instead of 1-methyl-1H-pyrazolo-4-boronic acid pinacol ester, compound 1-{(6-(3-fluoro-4-methylaminocarbonylphenyl)-imidazo[1,2-a]pyridine)-3-sulfonyl}-6-[(2-dimethylaminoethyl)-4-pyrazolyl]-1-H-pyrazolo[4,3-b]pyridine was prepared by the same process as Example 71.

$^1$H NMR (400 MHz, CDCl$_3$) δ 9.33 (d, J=1.5 Hz, 1H), 8.86 (d, J=1.9 Hz, 1H), 8.46 (d, J=1.9 Hz, 1H), 8.35 (s, 1H), 8.33 (s, 1H), 8.25 (t, J=8.1 Hz, 1H), 7.91 (s, 1H), 7.84 (s, 1H), 7.83 (dd, J=9.3, 0.9 Hz, 1H), 7.75 (dd, J=9.4, 1.8 Hz, 1H), 7.53 (dd, J=8.1, 1.8 Hz, 1H), 7.41 (dd, J=12.6, 1.8 Hz, 1H), 6.84 (s, 1H), 4.10 (t, J=6.5 Hz, 2H), 3.10 (d, J=5.1 Hz, 3H), 2.64 (t, J=6.5 Hz, 2H), 2.18 (s, 6H).

Example 103

Preparation of 1-{(6-[(1-methyl)-4-pyrazolyl]-imidazo[1,2-a]pyridine)-3-sulfonyl}-6-[(1-methyl)-4-pyrazolyl]-7-isopropyl-1-H-pyrazolo[4,3-b]pyridine

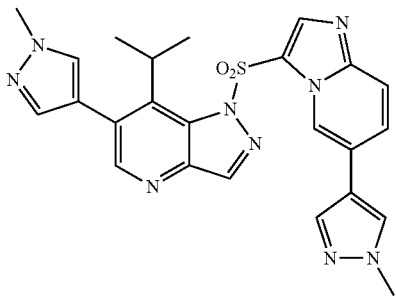 [SMILES: CC(C)c1c(-c2cnn(C)c2)cnc2cnn(S(=O)(=O)c3cnc4ccc(-c5cnn(C)c5)cn34)c12]

Fifty milligrams compound 27, 61 mg zinc bis(isopropyl) sulfinate were dissolved into 5 ml dimethyl sulfoxide, 32 μl t-butyl hydroperoxide was added with vigorous agitation, reaction was conducted at 50° C. for 12 hours. After the reaction was completed, the reactant liquid was cooled to room temperature, 50 ml saturated sodium bicarbonate was added, extracted three times with 30 ml ethyl acetate. The organic layer was dried over anhydrous sodium sulfate then concentrated, and isolated by flash preparative chromatography to obtain the target compound 103 (m=15 mg, yield: 30%).

$^1$H NMR (400 MHz, CDCl$_3$) δ 9.44 (s, 1H), 8.89 (s, 1H), 8.48 (s, 1H), 8.38 (s, 1H), 7.90 (d, J=0.9 Hz, 1H), 7.82 (s, 1H), 7.79 (d, J=9.3 Hz, 1H), 7.72 (d, J=9.1 Hz, 1H), 7.52 (s, 1H), 7.44 (s, 1H), 4.04 (s, 3H), 4.00 (s, 3H), 3.38 (m, 1H), 1.27 (d, J=6.9 Hz, 6H).

Example 104

Preparation of 1-{[6-(4-pyrazolyl)-imidazo[1,2-a]pyridine]-3-sulfonyl}-6-(4-pyrazolyl)-1-H-pyrazolo[4,3-b]pyridine

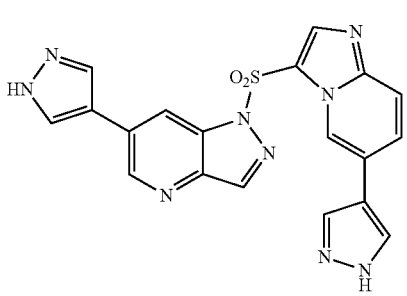 [SMILES: O=S(=O)(c1cnc2ccc(-c3cn[nH]c3)cn12)n1ncc2ncc(-c3cn[nH]c3)cc21]

Eighty milligrams sodium hydride was dissolved in 30 ml anhydrous tetrahydrofuran, stirred for 5 minutes at room temperature. Four hundred and forty milligrams 6-bromoindazole was dissolved in 30 ml anhydrous tetrahydrofuran, then slowly and dropwisely added into the tetrahydrofuran solution of sodium hydride, stirred for 30 minutes at room temperature after the addition was completed. Seven hundred and twenty-three milligrams 6-bromoimidazo[1,2-a]pyridine-3-sulfonyl chloride was dissolved in 30 ml anhydrous tetrahydrofuran, then slowly and dropwisely added into the reactant liquid, stirred overnight at room temperature after the addition was done, the reaction was completed. Tetrahydrofuran was removed by evaporation, and the remainder was dissolved in dichloromethane, washed three times with water, the organic layer was dried over anhydrous sodium sulfate then concentrated, isolated by flash preparative chromatography to obtain 1-[(6-bromo-imidazo[1,2-a]pyridine)-3-sulfonyl]-6-bromo-1-H-pyrazolo[4,3-b]pyridine (m=755 mg, yield: 74.3%). ESI (m/z): 458.0 [M+H]$^+$.

Into a microwave reaction tube were disposed 80 mg 1-[(6-bromo-imidazo[1,2-a]pyridine)-3-sulfonyl]-6-bromo-1-H-pyrazolo[4,3-b]pyridine, 113 mg 1-t-butoxycarbonyl-1H-pyrazolo-4-boronic acid pinacol ester and 97 mg potassium carbonate, 5 ml dioxane, 2.5 ml ethanol and 2.5 ml water were added into the microwave reaction tube, air was displaced for three times, under a nitrogen atmosphere, 7.2 mg 1,1'-bis(diphenylphosphino) ferrocene palladium (II) dichloromethane complex was added into the microwave tube, then the microwave tube was sealed. The microwave tube was placed into a microwave reactor, reaction was conducted at a temperature of 120° C. for 30 minutes, the reaction was completed. The aforementioned reactant liquid was poured into 15 ml water, extracted three times with dichloromethane, the organic layer was dried over anhydrous sodium sulfate then concentrated. The concentrated solid was dissolved in 10 ml dioxane saturated with hydrochloric acid, stirred at room temperature for 3 hours, then evaporated to remove the organic phase, and isolated by flash preparative chromatography to obtain the target compound 104 (m=64 mg, yield: 85%). ESI (m/z): 432.0 [M+H]$^+$.

$^1$H NMR (400 MHz, CDCl$_3$) δ 9.25 (s, 1H), 8.92 (s, 1H), 8.55 (s, 1H), 8.38 (s, 1H), 8.33 (s, 1H), 8.09 (s, 2H), 7.98 (s, 2H), 7.77 (d, J=9.1 Hz, 1H), 7.69 (d, J=9.5 Hz, 1H).

Example 105

Preparation of 1-{[6-(4-pyrazolyl)-imidazo[1,2-a]pyridine]-3-sulfonyl}-6-[(1-methyl)-4-pyrazolyl]-1-H-pyrazolo[4,3-b]pyridine

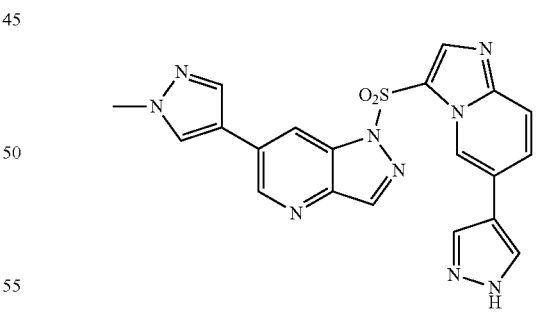

Except for pyrazolo-4-boronic acid was used instead of phenylboronic acid, compound 1-{[6-(4-pyrazolyl)-imidazo[1,2-a]pyridine]-3-sulfonyl}-6-[(1-methyl)-4-pyrazolyl]-1-H-pyrazolo[4,3-b]pyridine was prepared by the same process as Example 71.

$^1$H NMR (400 MHz, DMSO-d$_6$) δ 9.05 (d, J=1.9 Hz, 1H), 8.97 (s, 1H), 8.76 (d, J=0.9 Hz, 1H), 8.64 (s, 1H), 8.61-8.58 (m, 1H), 8.57 (dd, J=1.9, 0.9 Hz, 1H), 8.34 (s, 1H), 8.24 (d, J=0.8 Hz, 1H), 7.96 (dd, J=9.3, 1.8 Hz, 1H), 7.93 (s, 1H), 7.88 (dd, J=9.3, 1.0 Hz, 1H), 3.94 (s, 3H).

Example 106

Preparation of 1-{(6-[(1-methyl)-4-pyrazolyl]-imidazo[1,2-a]pyridine)-3-sulfonyl}-6-(4-pyrazolyl)-1-H-pyrazolo[4,3-b]pyridine

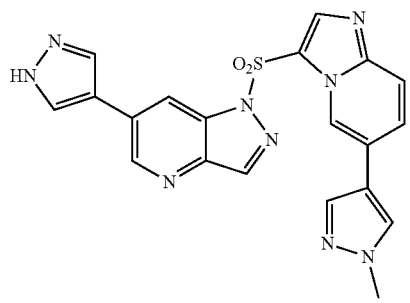 [SMILES: Cn1cc(-c2ccc3ncc(S(=O)(=O)n4ncc5ncc(-c6cn[nH]c6)cc54)n3c2)cn1]

One hundred milligrams sodium hydride was dissolved in 30 ml anhydrous tetrahydrofuran, stirred for 5 minutes at room temperature. Five hundred and fifty milligrams 6-bromoindazole was dissolved in 30 ml anhydrous tetrahydrofuran, then slowly and dropwisely added into the tetrahydrofuran solution of sodium hydride, stirred for 30 minutes at room temperature after the addition was completed. Nine hundred and seven milligrams 6-[(1-methyl)-4-pyrazolyl]-imidazo[1,2-a]pyridine-3-sulfonyl chloride was dissolved in 30 ml anhydrous tetrahydrofuran, slowly and dropwisely added into the reactant liquid, stirred overnight at room temperature after the addition was done, the reaction was completed. Tetrahydrofuran was removed by evaporation, the remainder was dissolved in dichloromethane, washed three times with water, the organic layer was dried over anhydrous sodium sulfate then concentrated, isolated by flash preparative chromatography to obtain compound 1-{(6-[(1-methyl)-4-pyrazolyl]-imidazo[1,2-a]pyridine)-3-sulfonyl}-6-bromo-1-H-pyrazolo[4,3-b]pyridine (m=968 mg, yield: 76%). ESI (m/z): 460.0, 458.0 [M+H]$^+$.

Into a microwave reaction tube were disposed 100 mg 1-{(6-[(1-methyl)-4-pyrazolyl]-imidazo[1,2-a]pyridine)-3-sulfonyl}-6-bromo-1-H-pyrazolo[4,3-b]pyridine, 77 mg 1-t-butoxycarbonyl-1H-pyrazolo-4-borate pinacol ester and 90 mg potassium carbonate, 5 ml dioxane, 2.5 ml ethanol and 2.5 ml water were added into the microwave reaction tube, air was displaced for three times, under a nitrogen atmosphere, 9 mg complex of 1,1'-bis(diphenylphosphino) ferrocene palladium (II) dichloride and dichloromethane was added into the microwave tube, then the microwave tube was sealed. The microwave tube was placed into a microwave reactor, reaction was conducted at a temperature of 120° C. for 30 minutes, the reaction was completed. The aforementioned reactant liquid was poured into 15 ml water, extracted three times with dichloromethane, the organic layer was dried over anhydrous sodium sulfate then concentrated. The concentrated solid was dissolved into 10 ml dioxane saturated with hydrochloric acid, stirred at room temperature for 3 hours, evaporated to remove the organic phase, and isolated by flash preparative chromatography to obtain the target compound 106 (m=80 mg, yield: 82%).

$^1$H NMR (400 MHz, CDCl$_3$) δ 9.30 (s, 1H), 8.88 (dd, J=1.9, 1.0 Hz, 1H), 8.46 (d, J=1.6 Hz, 1H), 8.39 (s, 1H), 8.28 (s, 1H), 7.97 (s, 1H), 7.88 (s, 1H), 7.65 (d, J=9.3 Hz, 1H), 7.60 (d, J=9.7 Hz, 2H), 7.29 (s, 1H), 4.05 (s, 3H).

Example 107

Preparation of 1-{(5-[(1-methyl)-4-pyrazolyl])-1-H-pyrrolo[2,3-b]pyridine-3-sulfonyl}-1-H-pyrazolo[3,4-b]pyridine

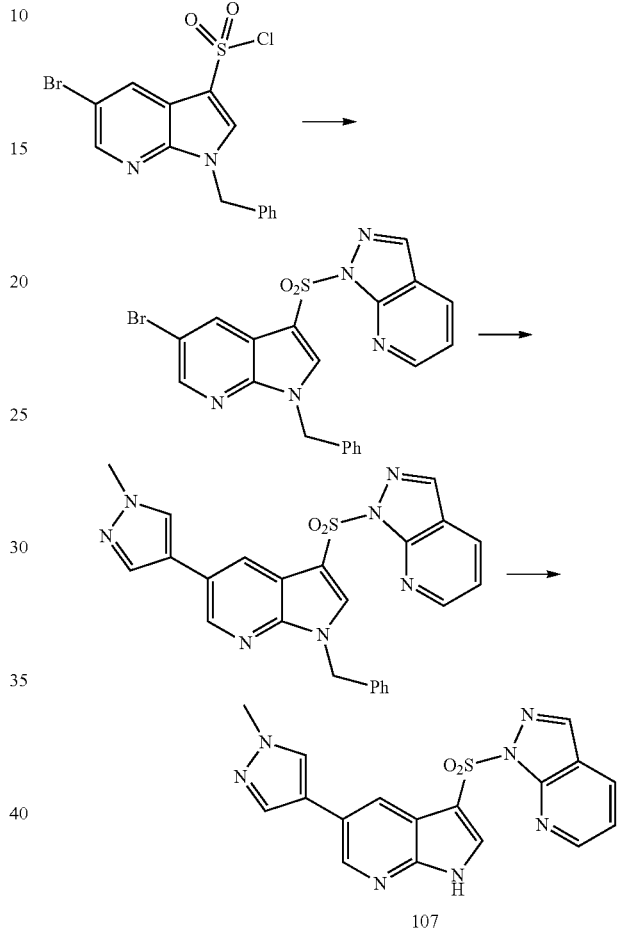

107

Eighty milligrams sodium hydride was dissolved in 30 ml anhydrous tetrahydrofuran, stirred for 5 minutes at room temperature. Two hundred and sixty-five milligrams 1-H-pyrazolo[3,4-b]pyridine was dissolved in 30 ml anhydrous tetrahydrofuran, then slowly and dropwisely added into the tetrahydrofuran solution of sodium hydride, stirred for 30 minutes at room temperature after the addition was completed. Nine hundred and seven milligrams 1-benzyl-5-bromo-1-H-pyrrolo[2,3-b]pyridine-3-sulfonyl chloride was dissolved in 30 ml anhydrous tetrahydrofuran, slowly and dropwisely added into the reactant liquid, stirred overnight at room temperature after the addition was done, the reaction was completed. Tetrahydrofuran was removed by evaporation, the remainder was dissolved in dichloromethane, washed three times with water, the organic layer was dried over anhydrous sodium sulfate then concentrated, isolated by flash preparative chromatography to obtain compound 1-[(1-benzyl-5-bromo-pyrrolo[2,3-b]pyridine)-3-sulfonyl]-1-H-pyrazolo[3,4-b]pyridine (m=697 mg, yield: 67%). ESI (m/z): 470.0, 468.0 [M+H]$^+$.

Into a microwave reaction tube were disposed 90 mg 1-[(1-benzyl-5-bromo-pyrrolo[2,3-b]pyridine)-3-sulfonyl]-1-H-pyrazolo[3,4-b]pyridine, 48 mg 1-methyl-1H-pyrazolo-4-borrate pinacol ester and 80 mg potassium carbonate, 5 ml dioxane, 2.5 ml ethanol and 2.5 ml water were added into the microwave reaction tube, air was displaced for three times, under a nitrogen atmosphere, 7.8 mg 1,1'-bis(diphenylphosphino) ferrocene palladium (II)dichloromethane complex was added into the microwave tube, then the microwave tube was sealed. The microwave tube was placed into a microwave reactor, reaction was conducted at a temperature of 120° C. for 30 minutes, the reaction was completed. The aforementioned reactant liquid was poured into 15 ml water, extracted three times with dichloromethane, the organic layer was dried over anhydrous sodium sulfate then concentrated, isolated by flash preparative chromatography to obtain 1-{(5-[(1-methyl)-4-pyrazolyl])-1-benzyl-pyrrolo[2,3-b]pyridine-3-sulfonyl}-1-H-pyrazolo[3,4-b]pyridine (m=90 mg, yield: 85%). ESI (m/z): 549.4 [M+H]+.

Fifty milligrams 1-{(5-[(1-methyl)-4-pyrazolyl])-1-benzyl-pyrrolo[2,3-b]pyridine-3-sulfonyl}-1-H-pyrazolo[3,4-b]pyridine and 17 mg 10% palladium on carbon was dissolved in 30 ml ethanol, reacted at 70° C. under 20 pis hydrogen pressure, filtered to remove the palladium on carbon, the organic layer was dried over anhydrous sodium sulfate then concentrated, isolated by flash preparative chromatography to obtain compound 107 (m=38 mg, yield: 94%). ESI (m/z): 380.0 [M+H]+.

Example 108

Preparation of 1-{[6-[4-(4-methylpiperazine-1-carbonyl)phenyl]-1-H-pyrrolo[2,3-b]pyridine-3-sulfonyl}-6-[(1-methyl)-4-pyrazolyl]-1-H-pyrrolo[2,3-b]pyridine

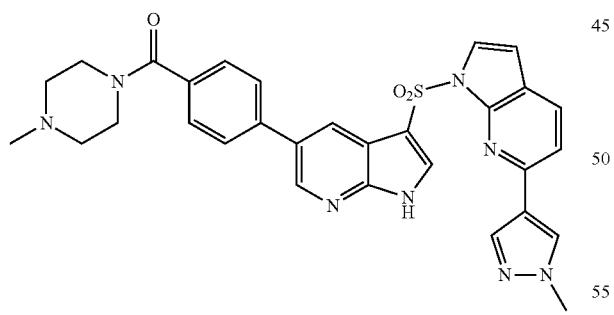

Except for 6-[(1-methyl)-4-pyrazolyl]-1-H-pyrrolo[2,3-b]pyridine was used instead of 1-H-pyrazolo[3,4-b]pyridine, and 4-(4-methylpiperazine-1-carbonyl)phenylboronic acid was used instead of 1-methyl-1H-pyrazolo-4-borate pinacol ester, compound 1-{[6-[4-(4-methylpiperazine-1-carbonyl)phenyl]-1-H-pyrrolo[2,3-b]pyridine-3-sulfonyl}-6-[(1-methyl)-4-pyrazolyl]-1-H-pyrrolo[2,3-b]pyridine was prepared by the same process as Example 107. ESI (m/z): 581.5 [M+H]+.

Example 109

Preparation of 1-[(3-chlorophenyl)-1-H-pyrrolo[2,3-b]pyridine-3-sulfonyl]-1-H-pyrazolo[3,4-b]pyridine

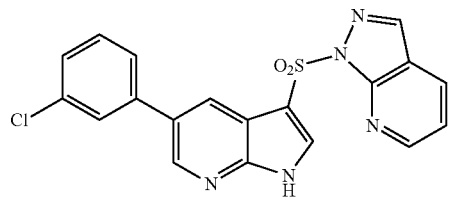 [SMILES: O=S(=O)(c1c[nH]c2ncc(-c3cccc(Cl)c3)cc12)n1ncc2cccnc21]

Except for 3-chlorophenylboronic acid was used instead of 1-methyl-1H-pyrazolo-4-borate pinacol ester, compound 1-[(3-chlorophenyl)-1-H-pyrrolo[2,3-b]pyridine-3-sulfonyl]-1-H-pyrazolo[3,4-b]pyridine was prepared by the same process as Example 107. ESI (m/z): 410.0 [M+H]+.

Example 110

Preparation of 1-[(4-morpholinylphenyl)-1-H-pyrrolo[2,3-b]pyridine-3-sulfonyl]-1-H-pyrazolo[3,4-b]pyridine

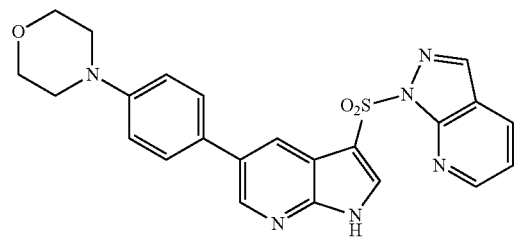 [SMILES: O=S(=O)(c1c[nH]c2ncc(-c3ccc(N4CCOCC4)cc3)cc12)n1ncc2cccnc21]

Except for 4-morpholinylphenylboronic acid was used instead of 1-methyl-1H-pyrazolo-4-borate pinacol ester, compound 1-[(3-chlorophenyl)-1-H-pyrrolo[2,3-b]pyridine-3-sulfonyl]-1-H-pyrazolo[3,4-b]pyridine was prepared by the same process as Example 107. ESI (m/z): 461.1 [M+H]+.

Example 111

Preparation of 1-(naphthalene-1-sulfonyl)-6-[(1-methyl)-4-pyrazolyl]-1-H-pyrazolo[4,3-b]pyridine

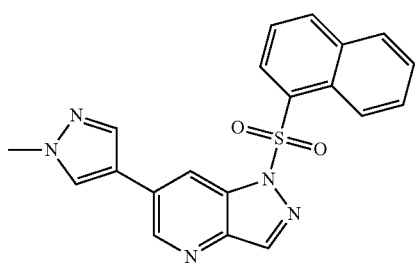 [SMILES: Cn1cc(-c2cnc3cnn(S(=O)(=O)c4cccc5ccccc45)c3c2)cn1]

Except for naphthalene-1-sulfonyl chloride was used instead of 2-nitrophenylsulfonyl chloride, compound 1-(naphthalene-1-sulfonyl)-6-[(1-methyl)-4-pyrazolyl]-1-H-pyrazolo[4,3-b]pyridine was prepared by the same process as Example 3.

$^1$H-NMR (400 MHz, CDCl$_3$) δ 8.82 (t, J=4.7 Hz, 2H), 8.53 (dd, J=7.4, 1.0 Hz, 2H), 8.30 (s, 1H), 8.14 (d, J=8.3 Hz, 1H), 7.91 (m, 3H), 7.60 (m, 3H), 4.03 (s, 3H).

Example 112

Preparation of 1-(naphthalene-2-sulfonyl)-6-[(1-methyl)-4-pyrazolyl]-1-H-pyrazolo[4,3-b]pyridine

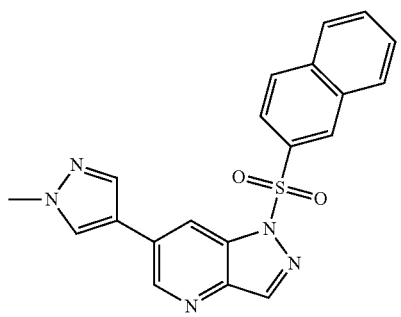 [SMILES: Cn1cc(-c2cnc3cnn(S(=O)(=O)c4ccc5ccccc5c4)c3c2)cn1]

Except for naphthalene-2-sulfonyl chloride was used instead of 2-nitrophenylsulfonyl chloride, compound 1-(naphthalene-2-sulfonyl)-6-[(1-methyl)-4-pyrazolyl]-1-H-pyrazolo[4,3-b]pyridine was prepared by the same process as Example 3.

$^1$H-NMR (400 MHz, CDCl$_3$) δ 8.83 (d, J=1.7 Hz, 1H), 8.65 (s, 1H), 8.55 (s, 1H), 8.36 (s, 1H), 7.97 (m, 2H), 7.88 (m, 4H), 7.64 (m, 2H), 4.04 (s, 3H).

Example 113

Preparation of 1-[(6-nitro-imidazo[1,2-a]pyridine)-3-sulfonyl]-6-(3-ethoxyphenyl)-1-H-pyrazolo[4,3-b]pyridine

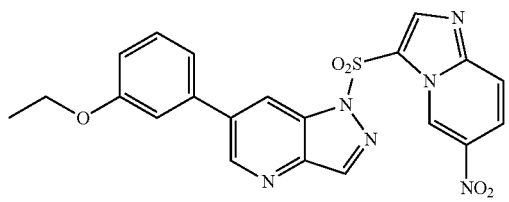 [SMILES: CCOc1cccc(-c2cnc3cnn(S(=O)(=O)c4cnc5ccc([N+](=O)[O-])cn45)c3c2)c1]

Except for 6-nitro-imidazo[1,2-a]pyridine-3-sulfonyl chloride was used instead of imidazo[1,2-a]pyridine-3-sulfonyl chloride, and 3-ethoxyphenylboronic acid was used instead of phenylboronic acid, compound 1-[(6-nitro-imidazo[1,2-a]pyridine)-3-sulfonyl]-6-(3-ethoxyphenyl)-1-H-pyrazolo[4,3-b]pyridine was prepared by the same process as Example 28.

$^1$H NMR (400 MHz, DMSO-d$_6$) δ 9.83 (s, 1H), 9.11 (d, J=6.3 Hz, 2H), 8.89 (s, 1H), 8.59 (s, 1H), 8.12-8.05 (m, 1H), 7.77 (d, J=9.5 Hz, 1H), 7.56-7.48 (m, 2H), 7.40 (s, 1H), 7.13-7.07 (m, 1H), 4.22-4.10 (m, 2H), 1.39 (t, J=7.1 Hz, 3H).

Example 114

Preparation of 1-[(6-amino-imidazo[1,2-a]pyridine)-3-sulfonyl]-6-(3,5-dichlorophenyl)-1-H-pyrazolo[4,3-b]pyridine

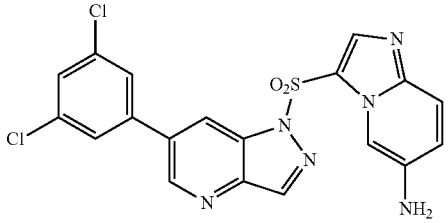 [SMILES: Nc1ccc2ncc(S(=O)(=O)n3ncc4ncc(-c5cc(Cl)cc(Cl)c5)cc43)n2c1]

Except for 3,5-dichlorophenylboronic acid was used instead of 3-ethoxyphenylboronic acid, compound 1-[(6-nitro-imidazo[1,2-a]pyridine)-3-sulfonyl]-6-(3,5-dichlorophenyl)-1-H-pyrazolo[4,3-b]pyridine was prepared by the same process as Example 113. Eighty milligrams 1-[(6-nitro-imidazo[1,2-a]pyridine)-3-sulfonyl]-6-(3,5-dichlorophenyl)-1-H-pyrazolo[4,3-b]pyridine, 58 mg reduced iron powder and 28 mg ammonium formate were dissolved in toluene, reacted at 90° C. for 8 hours, filtered while still hot, evaporated to remove the organic phase, the solid obtained from evaporation was dissolved in dichloromethane, washed three times with water, the organic layer was dried over anhydrous sodium sulfate then concentrated, isolated by flash preparative chromatography to obtain compound 114 (m=42 mg, yield: 56%).

$^1$H NMR (400 MHz, DMSO-d$_6$) δ 9.82 (s, 1H), 9.14 (d, J=2.1 Hz, 1H), 9.11 (s, 1H), 8.92 (s, 1H), 8.67 (s, 1H), 8.08 (dd, J=10.1, 2.5 Hz, 1H), 8.00 (d, J=1.8 Hz, 2H), 7.82-7.79 (m, 1H), 7.77 (d, J=9.9 Hz, 1H), 5.89 (br, 2H).

Example 115

Preparation of 1-[(6-nitro-imidazo[1,2-a]pyridine)-3-sulfonyl]-6-(4-trifluoromethylphenyl)-1-H-pyrazolo[4,3-b]pyridine

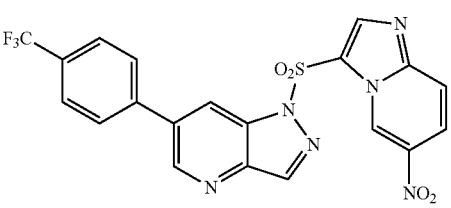 [SMILES: O=[N+]([O-])c1ccc2ncc(S(=O)(=O)n3ncc4ncc(-c5ccc(C(F)(F)F)cc5)cc43)n2c1]

Except for 4-trifluoromethylphenylboronic acid was used instead of phenylboronic acid, compound 1-[(6-nitro-imidazo[1,2-a]pyridine)-3-sulfonyl]-6-(4-trifluoromethylphenyl)-1-H-pyrazolo[4,3-b]pyridine was prepared by the same process as Example 113.

$^1$H NMR (400 MHz, DMSO-d$_6$) δ 9.82 (s, 1H), 9.18 (s, 1H), 9.10 (s, 1H), 8.92 (s, 1H), 8.69 (s, 1H), 8.25-8.17 (m, 2H), 8.07 (d, J=11.5 Hz, 1H), 7.92 (d, J=8.0 Hz, 1H), 7.86 (d, J=7.6 Hz, 1H), 7.76 (d, J=10.0 Hz, 1H).

Example 116

Preparation of 1-[(6-nitro-imidazo[1,2-a]pyridine)-3-sulfonyl]-6-(3,4,5-trifluorophenyl)-1-H-pyrazolo[4,3-b]pyridine

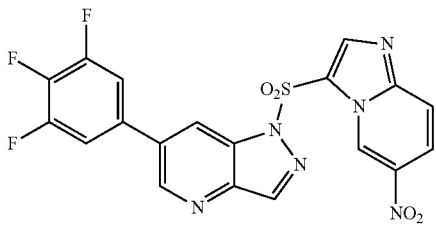 [SMILES: O=[N+]([O-])c1ccc2ncc(S(=O)(=O)n3ncc4ncc(-c5cc(F)c(F)c(F)c5)cc43)n2c1]

Except for 3,4,5-trifluorophenylboronic acid was used instead of phenylboronic acid, compound 1-[(6-nitro-imidazo[1,2-a]pyridine)-3-sulfonyl]-6-(3,4,5-trifluorophenyl)-1-H-pyrazolo[4,3-b]pyridine was prepared by the same process as Example 113.

$^1$H NMR (400 MHz, DMSO-d$_6$) δ 9.82 (s, 1H), 9.12 (d, J=6.0 Hz, 2H), 8.91 (s, 1H), 8.66 (s, 1H), 8.08 (d, J=8.6 Hz, 1H), 8.03-7.92 (m, 2H), 7.77 (d, J=12.2 Hz, 1H).

Example 117

Preparation of 1-[(6-amino-imidazo[1,2-a]pyridine)-3-sulfonyl]-6-phenyl-1-H-pyrazolo[4,3-b]pyridine

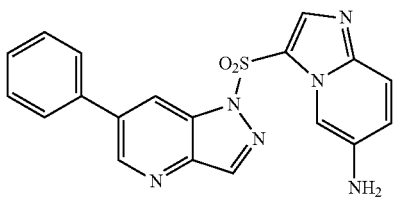 [SMILES: Nc1ccc2ncc(S(=O)(=O)n3ncc4ncc(-c5ccccc5)cc43)n2c1]

Except for phenylboronic acid was used instead of 3,5-dichlorophenylboronic acid, compound 1-[(6-amino-imidazo[1,2-a]pyridine)-3-sulfonyl]-6-phenyl-1-H-pyrazolo[4,3-b]pyridine was prepared by the same process as Example 114.

$^1$H NMR (400 MHz, DMSO-d$_6$) δ 9.86 (s, 1H), 9.14 (s, 1H), 9.12 (d, J=2.0 Hz, 1H), 8.88 (s, 1H), 8.61 (s, 1H), 8.07 (dd, J=10.0, 2.3 Hz, 1H), 7.88 (d, J=7.1 Hz, 2H), 7.86-7.79 (m, 1H), 7.77 (d, J=10.3 Hz, 1H), 7.57-7.50 (m, 2H), 5.39 (br, 2H).

Example 118

Preparation of 1-[(6-amino-imidazo[1,2-a]pyridine)-3-sulfonyl]-6-(4-fluorophenyl)-1-H-pyrazolo[4,3-b]pyridine

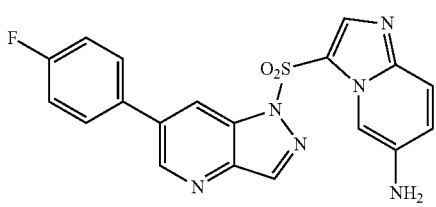 [SMILES: Nc1ccc2ncc(S(=O)(=O)n3ncc4ncc(-c5ccc(F)cc5)cc43)n2c1]

Except for 4-fluorophenylboronic acid was used instead of 3,5-dichlorophenylboronic acid, compound 1-[(6-amino-imidazo[1,2-a]pyridine)-3-sulfonyl]-6-(4-fluorophenyl)-1-H-pyrazolo[4,3-b]pyridine was prepared by the same process as Example 114.

$^1$H NMR (400 MHz, CDCl$_3$) δ 9.33 (s, 1H), 8.96 (d, J=1.9 Hz, 1H), 8.74 (s, 1H), 8.60 (s, 1H), 8.48 (s, 1H), 8.10 (dd, J=10.0, 2.2 Hz, 1H), 7.76-7.67 (m, 3H), 7.30 (m, 2H), 6.09 (br, 2H).

Example 119

Preparation of 1-[(6-n-butylamino-imidazo[1,2-a]pyridine)-3-sulfonyl]-6-[(1-methyl)-4-pyrazolyl]-1-H-pyrazolo[4,3-b]pyridine

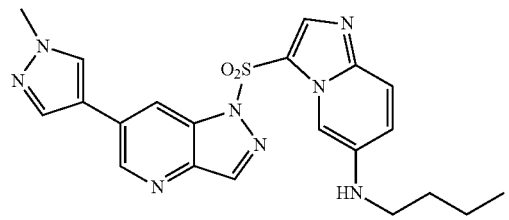 [SMILES: CCCCNc1ccc2ncc(S(=O)(=O)n3ncc4ncc(-c5cnn(C)c5)cc43)n2c1]

Except for 1-methyl-1H-pyrazolo-4-borate pinacol ester was used instead of 3,5-dichlorophenylboronic acid, compound 1-[(6-amino-imidazo[1,2-a]pyridine)-3-sulfonyl]-6-[(1-methyl)-4-pyrazolyl]-1-H-pyrazolo[4,3-b]pyridine was prepared by the same process as Example 114. Fifty milligrams 1-[(6-amino-imidazo[1,2-a]pyridine)-3-sulfonyl]-6-[(1-methyl)-4-pyrazolyl]-1-H-pyrazolo[4,3-b]pyridine, 18 mg n-butylaldehyde, 32 mg sodium cyanoborohydride and 8 μl acetic acid were dissolved in 30 ml methanol, reacted at 50° C. for 8 hours, evaporated to remove the organic phase, the solid obtained by evaporation was dissolved in dichloromethane, washed three times with water, the organic layer was dried over anhydrous sodium sulfate then concentrated, isolated by flash preparative chromatography to obtain compound 119 (m=48 mg, yield: 85%).

$^1$H NMR (400 MHz, CDCl$_3$) δ 8.86 (d, J=1.9 Hz, 1H), 8.63 (dd, J=2.0, 1.0 Hz, 1H), 8.38 (d, J=1.0 Hz, 1H), 8.20 (s, 1H), 7.96 (d, J=0.9 Hz, 1H), 7.88 (s, 1H), 7.33 (d, J=9.7 Hz, 1H), 7.20 (d, J=2.1 Hz, 1H), 6.81 (dd, J=9.7, 2.2 Hz, 1H), 4.03 (s, 3H), 3.01 (t, J=7.0 Hz, 2H), 1.66 (p, J=7.2 Hz, 2H), 1.46 (h, J=7.4 Hz, 2H), 0.99 (t, J=7.3 Hz, 3H).

Example 120

Preparation of 1-[(6-acetylamino-imidazo[1,2-a]pyridine)-3-sulfonyl]-6-[(1-methyl)-4-pyrazolyl]-1-H-pyrazolo[4,3-b]pyridine

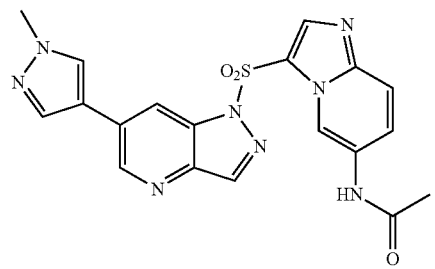 [SMILES: CC(=O)Nc1ccc2ncc(S(=O)(=O)n3ncc4ncc(-c5cnn(C)c5)cc43)n2c1]

Except for 1-methyl-1H-pyrazolo-4-borate pinacol ester was used instead of 3,5-dichlorophenylboronic acid, compound 1-[(6-amino-imidazo[1,2-a]pyridine)-3-sulfonyl]-6-[(1-methyl)-4-pyrazolyl]-1-H-pyrazolo[4,3-b]pyridine was prepared by the same process as Example 114. Fifty milligrams 1-[(6-amino-imidazo[1,2-a]pyridine)-3-sulfonyl]-6-[(1-methyl)-4-pyrazolyl]-1-H-pyrazolo[4,3-b]pyridine, 11 mg acetyl chloride and 18.5 mg 4-dimethylaminopyridine was dissolved in 30 ml dichloromethane, stirred at room temperature for 3 hours, the organic phase was washed three times with water, the organic layer was dried over anhydrous sodium sulfate then concentrated, isolated by flash preparative chromatography to obtain compound 120 (m=53 mg, yield: 95%).

$^{1}$H NMR (400 MHz, DMSO-d$_{6}$) δ 10.24 (s, 1H), 9.34 (d, J=1.9 Hz, 1H), 9.06 (d, J=1.9 Hz, 1H), 9.03 (s, 1H), 8.71 (s, 1H), 8.54 (s, 1H), 8.48 (d, J=1.4 Hz, 1H), 8.17 (s, 1H), 7.55 (d, J=9.8 Hz, 1H), 7.28 (dd, J=9.9, 2.0 Hz, 1H), 3.93 (s, 3H), 2.08 (s, 3H).

Example 121

Preparation of 1-[(6-methoxy-imidazo[1,2-a]pyridine)-3-sulfonyl]-6-[(1-methyl)-4-pyrazolyl]-1-H-pyrazolo[4,3-b]pyridine

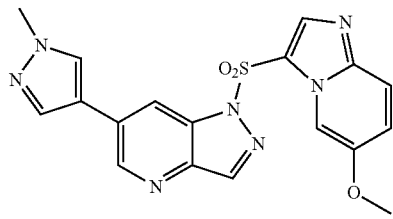 [SMILES: COc1ccc2ncc(S(=O)(=O)n3ncc4ncc(-c5cnn(C)c5)cc43)n2c1]

Except for 6-methoxy-imidazo[1,2-a]pyridine-3-sulfonyl chloride was used instead of imidazo[1,2-a]pyridine-3-sulfonyl chloride, and 1-methyl-1H-pyrazolo-4-borate pinacol ester was used instead of phenylboronic acid, compound 1-[(6-methoxy-imidazo[1,2-a]pyridine)-3-sulfonyl]-6-[(1-methyl)-4-pyrazolyl]-1-H-pyrazolo[4,3-b]pyridine was prepared by the same process as Example 28.

$^{1}$H NMR (400 MHz, CDCl$_{3}$) δ 8.85 (d, J=1.9 Hz, 1H), 8.65-8.62 (m, 1H), 8.44 (dd, J=1.9, 0.9 Hz, 1H), 8.33 (d, J=0.9 Hz, 1H), 8.23 (s, 1H), 7.93 (d, J=0.9 Hz, 1H), 7.85 (s, 1H), 7.59 (dd, J=9.8, 0.7 Hz, 1H), 7.55 (d, J=0.8 Hz, 1H), 7.43 (s, 1H), 7.25 (d, J=2.4 Hz, 1H), 4.03 (s, 3H), 3.95 (s, 3H).

Example 122

Preparation of 1-[(6-methoxy-imidazo[1,2-a]pyridine)-3-sulfonyl]-6-(4-isoquinolinyl)-1-H-pyrazolo[4,3-b]pyridine

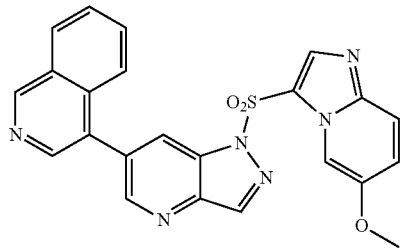 [SMILES: COc1ccc2ncc(S(=O)(=O)n3ncc4ncc(-c5cncc6ccccc56)cc43)n2c1]

Except for isoquinoline-4-boronic acid was used instead of 1-methyl-1H-pyrazolo-4-borate pinacol ester, compound 1-[(6-methoxy-imidazo[1,2-a]pyridine)-3-sulfonyl]-6-(4-isoquinolinyl)-1-H-pyrazolo[4,3-b]pyridine was prepared by the same process as Example 121.

$^{1}$H NMR (400 MHz, CDCl$_{3}$) δ 9.40 (s, 1H), 8.87 (d, J=1.7 Hz, 1H), 8.68 (d, J=2.1 Hz, 1H), 8.64 (s, 1H), 8.57 (s, 1H), 8.49 (s, 1H), 8.23 (s, 1H), 8.14 (d, J=7.9 Hz, 1H), 7.78 (d, J=3.5 Hz, 2H), 7.77-7.70 (m, 1H), 7.61 (d, J=9.7 Hz, 1H), 7.33-7.28 (m, 1H), 3.97 (s, 3H).

Example 123

Preparation of 1-[(6-methoxy-imidazo[1,2-a]pyridine)-3-sulfonyl]-6-(6-methoxy-2-naphthyl)-1-H-pyrazolo[4,3-b]pyridine

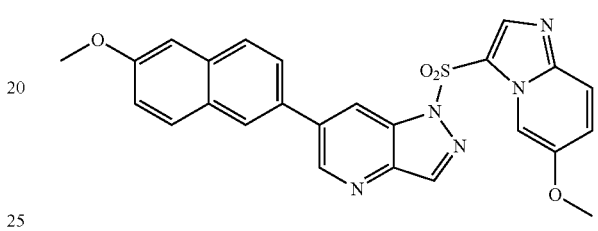

Except for 6-methoxynaphthalene-2-boronic acid was used instead of 1-methyl-1H-pyrazolo-4-borate pinacol ester, compound 1-[(6-methoxy-imidazo[1,2-a]pyridine)-3-sulfonyl]-6-(6-methoxy-2-naphthyl)-1-H-pyrazolo[4,3-b] pyridine was prepared by the same process as Example 121.

$^{1}$H NMR (400 MHz, CDCl$_{3}$) δ 9.06 (d, J=1.9 Hz, 1H), 8.70 (dd, J=1.9, 0.8 Hz, 1H), 8.66 (d, J=2.0 Hz, 1H), 8.41 (d, J=0.8 Hz, 1H), 8.26 (s, 1H), 8.09 (d, J=1.6 Hz, 1H), 7.90 (dd, J=15.5, 8.8 Hz, 2H), 7.77 (dd, J=8.5, 1.9 Hz, 1H), 7.59 (dd, J=9.7, 0.6 Hz, 1H), 7.29-7.24 (m, 2H), 7.24-7.20 (m, 1H), 3.98 (s, 3H), 3.94 (s, 3H).

Example 124

Preparation of 1-[(6-methoxy-imidazo[1,2-a]pyridine)-3-sulfonyl]-6-(4-morpholinylphenyl)-1-H-pyrazolo[4,3-b]pyridine

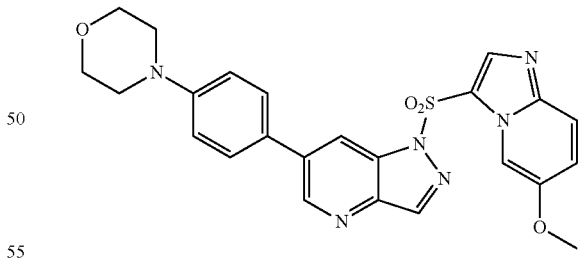

Except for 4-morpholinylphenylboronic acid was used instead of 1-methyl-1H-pyrazolo-4-borate pinacol ester, compound 1-[(6-methoxy-imidazo[1,2-a]pyridine)-3-sulfonyl]-6-(4-morpholinylphenyl)-1-H-pyrazolo[4,3-b]pyridine was prepared by the same process as Example 121.

$^{1}$H NMR (400 MHz, CDCl$_{3}$) δ 8.92 (d, J=1.9 Hz, 1H), 8.64 (dd, J=2.5, 0.8 Hz, 1H), 8.54 (dd, J=2.0, 0.9 Hz, 1H), 8.36 (d, J=0.9 Hz, 1H), 8.23 (s, 1H), 7.66-7.61 (m, 2H), 7.58 (dd, J=9.8, 0.8 Hz, 1H), 7.25 (dd, J=9.8, 2.4 Hz, 1H), 7.09-7.02 (m, 2H), 3.94 (s, 3H), 3.93-3.88 (m, 4H), 3.31-3.25 (m, 4H).

Example 125

Preparation of 1-[(6-methoxy-imidazo[1,2-a]pyridine)-3-sulfonyl]-6-(3-trifluoromethylphenyl)-1-H-pyrazolo[4,3-b]pyridine

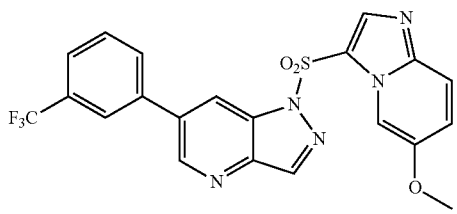 [SMILES: COc1ccc2ncc(S(=O)(=O)n3ncc4ncc(-c5cccc(C(F)(F)F)c5)cc43)n2c1]

Except for 3-trifluoromethylphenylboronic acid was used instead of 1-methyl-1H-pyrazolo-4-borate pinacol ester, compound 1-[(6-methoxy-imidazo[1,2-a]pyridine)-3-sulfonyl]-6-(3-trifluoromethylphenyl)-1-H-pyrazolo[4,3-b]pyridine was prepared by the same process as Example 121.

$^1$H NMR (400 MHz, CDCl$_3$) δ 8.94 (d, J=1.9 Hz, 1H), 8.67 (d, J=2.3 Hz, 1H), 8.64-8.60 (m, 1H), 8.43 (s, 1H), 8.25 (s, 1H), 7.92 (s, 1H), 7.88 (d, J=7.9 Hz, 1H), 7.76 (s, 1H), 7.71 (t, J=7.7 Hz, 1H), 7.60 (d, J=9.7 Hz, 1H), 7.28 (dd, J=9.7, 2.4 Hz, 1H), 3.97 (s, 3H).

Example 126

Preparation of 1-[(6-hydroxy-imidazo[1,2-a]pyridine)-3-sulfonyl]-6-(4-methoxyphenyl)-1-H-pyrazolo[4,3-b]pyridine

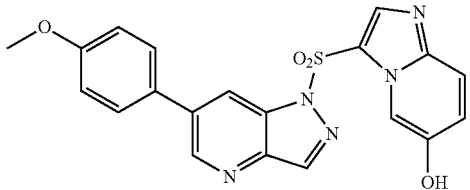 [SMILES: COc1ccc(-c2cnc3cnn(S(=O)(=O)c4cnc5ccc(O)cn45)c3c2)cc1]

Except for 4-methoxyphenylboronic acid was used instead of 1-methyl-1H-pyrazolo-4-borate pinacol ester, compound 1-[(6-methoxy-imidazo[1,2-a]pyridine)-3-sulfonyl]-6-(4-methoxyphenyl)-1-H-pyrazolo[4,3-b]pyridine was prepared by the same process as Example 121. Fifty milligrams 1-[(6-methoxy-imidazo[1,2-a]pyridine)-3-sulfonyl]-6-(4-methoxyphenyl)-1-H-pyrazolo[4,3-b]pyridine was dissolved in 20 ml dichloromethane, at 0° C., 33 μl boron tribromide was slowly and dropwisely added into the reactant liquid, stirred at room temperature for 3 hours after the addition was completed, the reactant liquid was cooled to 0° C. again and 3 ml methanol was slowly added, then the organic phase was evaporated to dry, isolated by flash preparative chromatography to obtain compound 126 (m=16 mg, yield: 34%).

$^1$H NMR (400 MHz, CDCl$_3$) δ 8.91 (d, J=1.9 Hz, 1H), 8.64 (d, J=2.4 Hz, 1H), 8.57-8.53 (m, 1H), 8.37 (s, 1H), 8.24 (s, 1H), 7.63 (d, J=8.8 Hz, 2H), 7.58 (d, J=9.8 Hz, 1H), 7.26 (dd, J=9.7, 2.4 Hz, 1H), 7.08 (d, J=8.8 Hz, 2H), 3.94 (s, 3H).

Example 127

Preparation of 1-[(6-hydroxy-imidazo[1,2-a]pyridine)-3-sulfonyl]-6-phenyl-1H-pyrazolo[4,3-b]pyridine

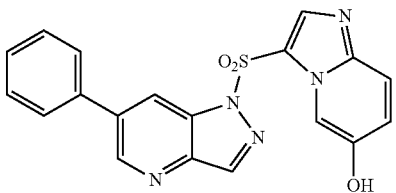 [SMILES: O=S(=O)(c1cnc2ccc(O)cn12)n1ncc2ncc(-c3ccccc3)cc21]

Except for phenylboronic acid was used instead of 4-methoxyphenylboronic acid, compound 1-[(6-hydroxy-imidazo[1,2-a]pyridine)-3-sulfonyl]-6-phenyl-1-H-pyrazolo[4,3-b]pyridine was prepared by the same process as Example 126.

$^1$H NMR (400 MHz, CDCl$_3$) δ 8.95 (d, J=1.9 Hz, 1H), 8.65 (d, J=2.2 Hz, 1H), 8.60 (d, J=1.8 Hz, 1H), 8.40 (s, 1H), 8.24 (s, 1H), 7.69 (d, J=7.2 Hz, 2H), 7.62-7.47 (m, 4H), 7.27 (dd, J=9.7, 2.4 Hz, 1H).

Example 128

Preparation of 1-[(6-isobutyryloxy-imidazo[1,2-a]pyridine)-3-sulfonyl]-6-[(1-methyl)-4-pyrazolyl]-1-H-pyrazolo[4,3-b]pyridine

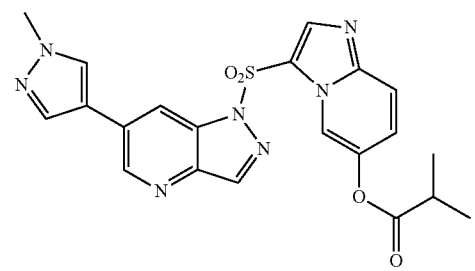 [SMILES: CC(C)C(=O)Oc1ccc2ncc(S(=O)(=O)n3ncc4ncc(-c5cnn(C)c5)cc43)n2c1]

Compound 121 was used in the same process as Example 126 to produce 1-[(6-hydroxy-imidazo[1,2-a]pyridine)-3-sulfonyl]-6-[(1-methyl)-4-pyrazolyl]-1-H-pyrazolo[4,3-b]pyridine. Fifty milligrams 1-[(6-hydroxy-imidazo[1,2-a]pyridine)-3-sulfonyl]-6-[(1-methyl)-4-pyrazolyl]-1-H-pyrazolo[4,3-b]pyridine, 15 mg isobutyryl chloride and 18.5 mg 4-dimethylaminopyridine were dissolved in 30 ml dichloromethane, stirred at room temperature for 3 hours, the organic phase was washed three times with water, the organic layer was dried over anhydrous sodium sulfate then concentrated, isolated by flash preparative chromatography to obtain compound 128 (m=54 mg, yield: 92%).

$^1$H NMR (400 MHz, CDCl$_3$) δ 9.15-9.05 (m, 1H), 8.87 (d, J=1.9 Hz, 1H), 8.46 (dd, 0.1=2.1, 1.1 Hz, 1H), 8.40-8.35 (m, 1H), 8.32 (s, 1H), 7.95 (d, J=5.7 Hz, 1H), 7.88 (d, J=6.2 Hz, 1H), 7.72 (d, J=9.7 Hz, 1H), 7.41-7.32 (m, 1H), 4.04 (s, 3H), 2.90 (p, J=6.9 Hz, 1H), 1.37 (dd, J=7.1, 0.9 Hz, 6H).

Example 129

Preparation of 1-[(6-furan-2-acyloxy-imidazo[1,2-a]pyridine)-3-sulfonyl]-6-[(1-methyl)-4-pyrazolyl]-1-H-pyrazolo[4,3-b]pyridine

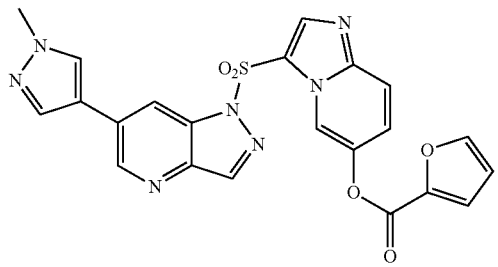 [SMILES: Cn1cc(-c2cnc3cnn(S(=O)(=O)c4cnc5ccc(OC(=O)c6ccco6)cn45)c3c2)cn1]

Except for 6-furan-2-carbonyl chloride was used instead of isobutyryl chloride, compound 1-[(6-furan-2-acyloxy-imidazo[1,2-a]pyridine)-3-sulfonyl]-6-[(1-methyl)-4-pyrazolyl]-1-H-pyrazolo[4,3-b]pyridine was prepared by the same process as Example 128.

$^1$H NMR (400 MHz, CDCl$_3$) δ 9.31-9.20 (m, 1H), 8.94-8.83 (m, 1H), 8.52-8.45 (m, 1H), 8.41 (d, J=0.9 Hz, 1H), 8.39-8.35 (m, 1H), 7.97 (d, J=6.0 Hz, 1H), 7.90 (d, J=8.4 Hz, 1H), 7.82 (d, J=9.8 Hz, 1H), 7.78 (dt, J=1.7, 0.9 Hz, 1H), 7.66-7.63 (m, 1H), 7.56-7.50 (m, 2H), 4.06 (d, J=0.9 Hz, 3H).

Example 130

Preparation of 1-[(6-bromo-imidazo[1,2-a]pyridine)-3-sulfonyl]-6-ethoxycarbonyl-1-H-pyrazolo[4,3-b]pyridine

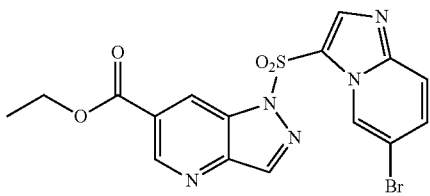 [SMILES: CCOC(=O)c1cnc2cnn(S(=O)(=O)c3cnc4ccc(Br)cn34)c2c1]

Three grams 6-bromopyrazolopyridine was dissolved in 80 ml anhydrous tetrahydrofuran, 3.6 ml n-butyl lithium was added at −78° C., stirred for 5 minutes, 15 ml anhydrous tetrahydrofuran solution of ethyl chloroformate was added at −78° C., further stirred for 30 minutes. The reaction was terminated by saturated sodium bicarbonate solution, ethyl acetate was added for extraction, the organic layer was evaporated to dry, isolated by flash preparative chromatography to obtain compound 6-ethoxycarbonyl-1-H-pyrazolo[4,3-b]pyridine (m=200 mg, yield: 14%). ESI (m/z): 192.0 [M+H]$^+$.

$^1$H NMR (400 MHz, DMSO-d$_6$) 9.02 (s, 1H), 8.53 (s, 1H), 8.45 (s, 1H), 4.39 (q, J=7.1 Hz, 2H), 1.37 (t, J=7.1 Hz, 3H).

Eighty milligrams sodium hydride and 53 mg ethyl pyrazolopyridine-6-formate were dissolved in 10 ml anhydrous tetrahydrofuran, stirred for 30 minutes, 60 mg 6-bromoimidazo[1,2-a]pyridine-3-sulfonyl chloride was dissolved in 10 ml anhydrous tetrahydrofuran, then slowly and dropwisely added into the reactant liquid, stirred at room temperature for 4 hours after the addition was completed. Tetrahydrofuran was removed by evaporation, the remainder was dissolved in dichloromethane, washed three times with water, the organic layer was dried over anhydrous sodium sulfate then concentrated, isolated by flash preparative chromatography to obtain compound 130 (m=15 mg, yield: 12%). ESI (m/z): 450.0 [M+H]$^+$.

$^1$H NMR (400 MHz, CDCl$_3$) δ 9.35 (d, J=1.6 Hz, 2H), 2 9.30 (s, 1H), 9.09 (s, 1H), 8.49 (s, 1H), 8.33 (s, 1H), 7.67 (d, J=9.6 Hz, 1H), 7.63 (t, J=5.6 Hz, 1H), 4.55 (q, J=7.1 Hz, 2H), 1.71 (s, 1H), 1.51 (t, J=7.1 Hz, 3H).

Example 131

Preparation of 1-[(6-bromo-imidazo[1,2-a]pyridine)-3-sulfonyl]-6-benzamido-1-H-pyrazolo[4,3-b]pyridine

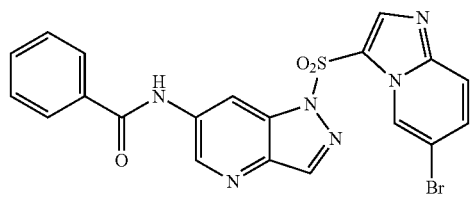 [SMILES: O=C(Nc1cnc2cnn(S(=O)(=O)c3cnc4ccc(Br)cn34)c2c1)c1ccccc1]

6-bromo-1-H-pyrazolo[4,3-b]pyridine (1.07 g) was dissolved in 30 ml DMF, 0.72 g sodium hydride was added at 0° C., stirred for 30 minutes, 1.8 ml 2-(trisilyl)ethoxymethyl chloride was added, stirred at room temperature for 2 hours. Upon terminated with ice water, the reaction liquid was extracted with ethyl acetate, the organic phase was evaporated to dry, isolated by flash preparative chromatography to obtain compound 1-[2-(trimethylsilyl)ethoxymethyl]-6-bromopyrazolo[4,3-b]pyridine (m=1.3 g, yield: 73.3%).

$^1$H NMR (400 MHz, Acetone-d) δ 8.62 (s, 1H), 8.46 (s, 1H), 8.25 (s, 1H), 5.82 (s, 2H), 3.60 (t, J=8.0 Hz, 2H), 0.86 (t, J=8.0 Hz, 2H), −0.06 (d, J=15.5 Hz, 9H).

Two hundred milligrams compound 1-[2-(trimethylsilyl)ethoxymethyl]-6-bromopyrazolo[4,3-b]pyridine and 30 mg copper sulfate pentahydrate were dissolved in 5 ml concentrated aqueous ammonia, reacted overnight at 150° C. in sealed vessel. The reactant liquid was extracted with ethyl acetate, the organic phase was evaporated to dry, isolated by flash preparative chromatography to obtain compound 1-[2-(trimethylsilyl)ethoxymethyl]-6-aminopyrazolo[4,3-b]pyridine (m=56 mg, yield: 34.8%).

$^1$H NMR (400 MHz, Acetone-d) δ 8.14 (d, J=2.3 Hz, 1H), 7.90 (s, 1H), 7.08 (d, J=2.2 Hz, 1H), 5.59 (s, 2H), 3.54 (t, J=8.0 Hz, 2H), 0.85 (t, J=8.0 Hz, 2H), −0.07 (s, 9H).

One hundred milligrams compound 1-[2-(trisilyl)ethoxymethyl]-6-aminopyrazolo[4,3-b]pyridine was dissolved in 6 ml dichloromethane, 44 μl benzoyl chloride was added, stirred overnight at room temperature. The reactant liquid was extracted with ethyl acetate, the organic phase was evaporated to dry, isolated by flash preparative chromatography to obtain compound 1-[2-(trisilyl)ethoxymethyl]-6-benzoylamidopyrazolo[4,3-b]pyridine (m=116 mg, yield: 96%).

$^1$H NMR (400 MHz, CDCl$_3$) δ 8.65 (d, J=16.1 Hz, 2H), 8.34 (s, 1H), 8.20 (s, 1H), 7.92 (d, J=8.1 Hz, 2H), 7.54 (m, 3H), 5.73 (s, 2H), 3.70-3.56 (m, 2H), 1.00-0.89 (m, 2H), −0.03 (s, 9H).

One hundred and thirty-five milligrams compound 1-[2-(trisilyl)ethoxymethyl]-6-benzoylamidopyrazolo[4,3-b]pyridine was added into 2 ml tetrahydrofuran solution of 1N TBAF, refluxed overnight. The reactant liquid was extracted with ethyl acetate, the organic layer was evaporated to dry, isolated by flash preparative chromatography to obtain compound 6-benzamido-1H-pyrazolo[4,3-b]pyridine (m=40 mg, yield: 45.8%). ESI (m/z): 239.0 [M+H]⁺.

Fourteen milligrams sodium hydride was suspended in 5 ml anhydrous tetrahydrofuran, 5 ml tetrahydrofuran solution comprising 40 mg compound 6-benzamido-1H-pyrazolo[4,3-b]pyridine was added, stirred for 30 minutes, 5 ml tetrahydrofuran solution comprising 50 mg compound 6-bromoimidazo[1,2-a]pyridine-3-sulfonyl chloride was added, stirred at room temperature for 4 hours. Ethyl acetate was added for extraction, the organic layer was evaporated to dry, and purified by column chromatography, isolated by flash preparative chromatography to obtain compound 131 (m=50 mg, yield: 59.9%).

¹H NMR (400 MHz, DMSO-d₆) δ 10.93 (s, 1H), 9.18 (s, 1H), 9.07 (s, 1H), 9.03 (s, 1H), 8.77 (s, 1H), 8.48 (s, 1H), 8.06 (d, J=7.7 Hz, 2H), 7.85 (s, 2H), 7.64 (m, 3H).

Example 132

Preparation of 1-[(6-bromo-imidazo[1,2-a]pyridine)-3-sulfonyl]-6-propionamido-1-H-pyrazolo[4,3-b]pyridine

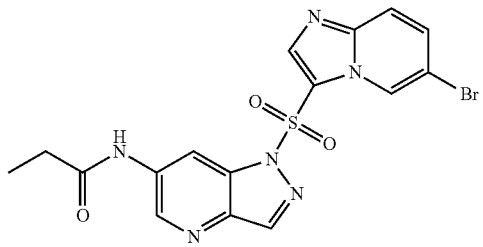 [SMILES: CCC(=O)Nc1cnc2cnn(S(=O)(=O)c3cnc4ccc(Br)cn34)c2c1]

Except for propionyl chloride was used instead of benzoyl chloride, compound 1-[(6-bromo-imidazo[1,2-a]pyridine)-3-sulfonyl]-6-propionamido-1-H-pyrazolo[4,3-b]pyridine was prepared by the same process as Example 131.

¹H NMR (400 MHz, DMSO-d₆) δ 10.64 (s, 1H), 9.05 (d, J=1.1 Hz, 1H), 9.00 (s, 1H), 8.75 (d, J=1.8 Hz, 1H), 8.72 (s, 1H), 8.44 (s, 1H), 7.84 (s, 2H), 2.49-2.42 (q, 2H), 1.14 (t, J=7.5 Hz, 3H).

Example 133

Preparation of 1-{(6-[(1-methyl)-4-pyrazolyl]-imidazo[1,2a]pyridine)-3-sulfonyl}-6-benzamido-1-H-pyrazolo[4,3-b]pyridine

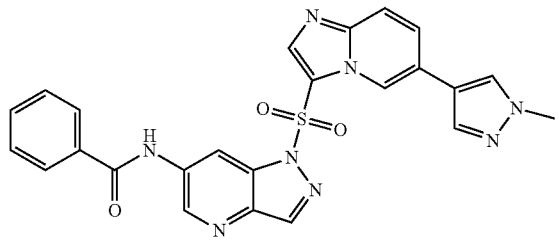 [SMILES: Cn1cc(-c2ccc3ncc(S(=O)(=O)n4ncc5ncc(NC(=O)c6ccccc6)cc54)n3c2)cn1]

Into a microwave reaction tube were disposed 40 mg compound 131, 20 mg 1-methyl-1H-pyrazolo-4-borate pinacol ester and 33 mg potassium carbonate, 5 ml dioxane, 2.5 ml ethanol and 2.5 ml water were added into the microwave reaction tube, air was displaced for three times, under a nitrogen atmosphere, 3.2 mg complex of 1,1'-bis(diphenylphosphino) ferrocene palladium (II) dichloride and dichloromethane was added into the microwave tube, then the microwave tube was sealed. The microwave tube was placed into a microwave reactor, reaction was conducted at a temperature of 120° C. for 30 minutes, the reaction was completed. The aforementioned reactant liquid was poured into 15 ml water, extracted three times with dichloromethane, the organic layer was dried over anhydrous sodium sulfate then concentrated. The concentrated solid was dissolved into 10 ml dioxane saturated with hydrochloric acid, stirred at room temperature for 3 hours, evaporated to remove the organic phase, and isolated by flash preparative chromatography to obtain the target compound 133 (m=20 mg, yield: 50%).

¹H NMR (400 MHz, DMSO-d₆) δ 11.03 (s, 1H), 9.29 (s, 1H), 9.07 (s, 1H), 8.90 (s, 1H), 8.74 (s, 1H), 8.47 (s, 1H), 8.25 (s, 1H), 8.09 (d, J=7.8 Hz, 2H), 7.90 (d, J=7.1 Hz, 2H), 7.73-7.54 (m, 3H), 3.86 (s, 3H).

Example 134

Preparation of 1-[(6-methoxy-imidazo[1,2-a]pyridine)-3-sulfonyl]-6-(3-methoxybenzamido)-1-H-pyrazolo[4,3-b]pyridine

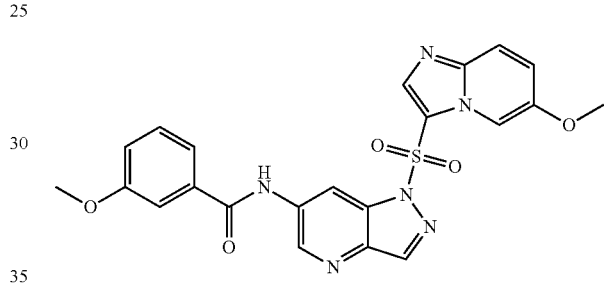

Except for 3-methoxybenzoyl chloride was used instead of benzoyl chloride, and 6-methoxyimidazo[1,2-a]pyridine-3-sulfonyl chloride was used instead of 6-bromoimidazo[1,2-a]pyridine-3-sulfonyl chloride, compound 1-[(6-methoxy-imidazo[1,2-a]pyridine)-3-sulfonyl]-6-(3-methoxybenzamido)-1-H-pyrazolo[4,3-b]pyridine was prepared by the same process as Example 131.

¹H NMR (400 MHz, DMSO-d₆) δ 10.46 (s, 1H), 8.35 (dd, J=9.4, 1.9 Hz, 2H), 8.26 (d, J=1.9 Hz, 1H), 7.87 (s, 1H), 7.63-7.38 (m, 4H), 7.27-7.10 (m, 2H), 3.87 (s, 3H), 3.83 (s, 3H).

Example 135

Preparation of 1-{(6-[(1-methyl)-4-pyrazolyl]-imidazo[1,2-a]pyridine)-3-sulfonyl}-6-[(1-cyclopentyl)-4-(1,2,3,6-tetrahydropyridinyl)]-1-H-pyrazolo[4,3-b]pyridine

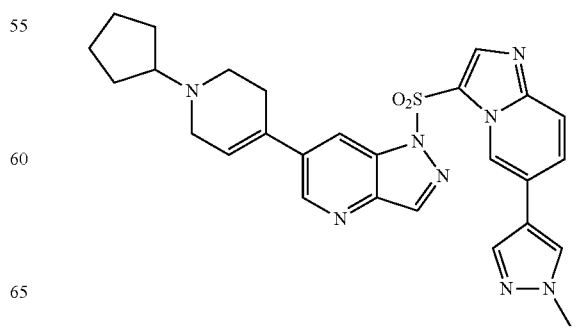

Except for 1-cyclopentyl-1,2,3,6-tetrahydropyridine-4-borate pinacol ester was used instead of 1-t-butoxycarbonyl-1H-pyrazolo-4-borate pinacol ester, compound 1-{(6-[(1-methyl)-4-pyrazolyl]-imidazo[1,2-a]pyridine)-3-sulfonyl}-6-[(1-cyclopentyl)-4-(1,2,3,6-tetrahydropyridinyl)]-1-H-pyrazolo[4,3-b]pyridine was prepared by the same process as Example 106.

$^1$H NMR (400 MHz, CDCl$_3$) δ 9.15 (s, 1H), 8.78 (d, J=1.6 Hz, 1H), 8.39 (s, 1H), 8.34 (s, 1H), 8.28 (s, 1H), 7.81 (s, 1H), 7.77 (s, 1H), 7.72 (d, J=9.2 Hz, 1H), 7.67-7.60 (m, 1H), 6.29 (m, 1H), 4.03 (s, 3H), 3.67 (m, 2H), 3.21 (m, 2H), 3.12 (m, 1H), 2.95 (m, 2H), 2.08 (m, 2H), 1.89 (m, 4H), 1.65 (m, 2H).

Example 136

Preparation of 1-{(6-[(1-methyl)-4-pyrazolyl]-imidazo[1,2-a]pyridine)-3-sulfonyl}-6-{{1-[(1-cyclopentyl)-4-piperidinyl]}-4-pyrazolyl}-1-H-pyrazolo[4,3-b]pyridine

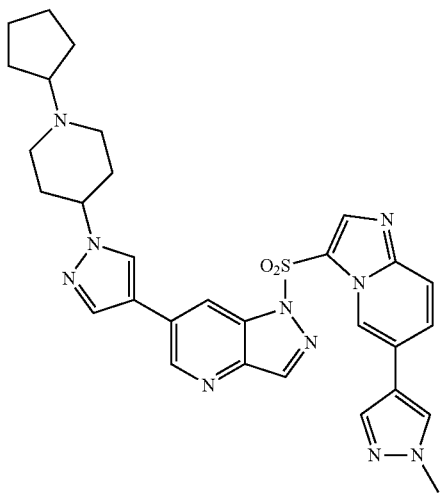 [SMILES: Cn1cc(-c2ccc3ncc(S(=O)(=O)n4ncc5ncc(-c6cnn(C7CCN(C8CCCC8)CC7)c6)cc54)n3c2)cn1]

Except for 1-[(1-cyclopentyl)-4-piperidinyl]pyrazolo-4-borate pinacol ester was used instead of 1-t-butoxycarbonyl-1H-pyrazolo-4-borate pinacol ester, compound 1-{(6-[(1-methyl)-4-pyrazolyl]-imidazo[1,2-a]pyridine)-3-sulfonyl}-6-{{1-[(1-cyclopentyl)-4-piperidinyl]}-4-pyrazolyl}-1-H-pyrazolo[4,3-b]pyridine was prepared by the same process as Example 106.

$^1$H NMR (400 MHz, CDCl$_3$) δ 9.16 (s, 1H), 8.85 (d, J=1.8 Hz, 1H), 8.50-8.44 (m, 1H), 8.34 (s, 1H), 8.30 (s, 1H), 8.00 (s, 1H), 7.94 (s, 1H), 7.80 (s, 1H), 7.76 (s, 1H), 7.72 (d, J=9.2 Hz, 1H), 7.63 (dd, J=9.3, 1.7 Hz, 1H), 4.59-4.46 (m, 1H), 4.01 (s, 3H), 3.55 (q, J=10.0 Hz, 2H), 3.14 (dd, J=21.5, 6.8 Hz, 1H), 2.53-2.42 (m, 2H), 2.06 (dt, J=13.3, 7.1 Hz, 3H), 2.00-1.81 (m, 6H), 1.64 (dd, J=12.8, 4.8 Hz, 3H).

Example 137

Preparation of 1-{(6-[(1-methyl)-4-pyrazolyl]-imidazo[1,2-a]pyridine)-3-sulfonyl}-6-[(1-isopropyl)-4-(1,2,3,6-tetrahydropyridinyl)]-1-H-pyrazolo[4,3-b]pyridine

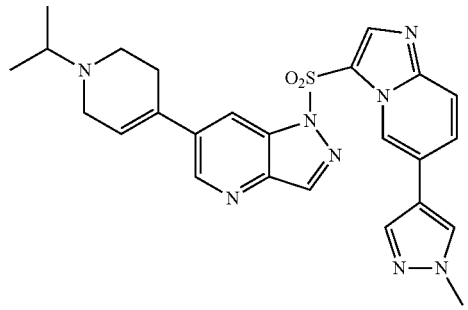 [SMILES: CC(C)N1CC=C(c2cnc3cnn(S(=O)(=O)c4cnc5ccc(-c6cnn(C)c6)cn45)c3c2)CC1]

Except for 1-isopropyl-1,2,3,6-tetrahydropyridine-4-borate pinacol ester was used instead of 1-t-butoxycarbonyl-1H-pyrazolo-4-borate pinacol ester, compound 1-{(6-[(1-methyl)-4-pyrazolyl]-imidazo[1,2-a]pyridine)-3-sulfonyl}-6-[(1-isopropyl)-4-(1,2,3,6-tetrahydropyridinyl)]-1-H-pyrazolo[4,3-b]pyridine was prepared by the same process as Example 106.

$^1$H NMR (400 MHz, CDCl$_3$) δ 9.14 (s, 1H), 8.77 (d, J=1.8 Hz, 1H), 8.40 (s, 1H), 8.34 (s, 1H), 8.30 (s, 1H), 7.80 (s, 1H), 7.77 (s, 1H), 7.72 (d, J=9.4 Hz, 1H), 7.63 (dd, J=9.3, 1.7 Hz, 1H), 6.30 (m, 1H), 4.02 (s, 3H), 3.75-3.68 (m, 2H), 3.37 (m, 1H), 3.25 (m, 2H), 3.01 (m, 2H), 1.41 (d, J=6.6 Hz, 6H).

Example 138

Preparation of 1-{(6-[(1-methyl)-4-pyrazolyl]-imidazo[1,2-a]pyridine)-3-sulfonyl}-6-{{1-[(1-ethyl)-4-piperidinyl]}-4-pyrazolyl}-1-H-pyrazolo[4,3-b]pyridine

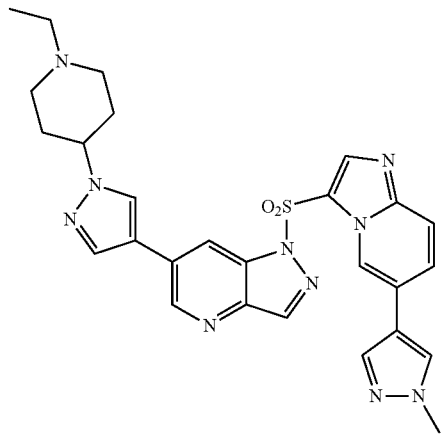 [SMILES: CCN1CCC(n2cc(-c3cnc4cnn(S(=O)(=O)c5cnc6ccc(-c7cnn(C)c7)cn56)c4c3)cn2)CC1]

Except for 1-[(1-ethyl)-4-piperidinyl]pyrazolo-4-borate pinacol ester was used instead of 1-t-butoxycarbonyl-1H-pyrazolo-4-borate pinacol ester, compound 1-{(6-[(1-methyl)-4-pyrazolyl]-imidazo[1,2-a]pyridine)-3-sulfonyl}-6-{{1-[(1-ethyl)-4-piperidinyl]}-4-pyrazolyl}-1-H-pyrazolo[4,3-b]pyridine was prepared by the same process as Example 106.

¹H-NMR (400 MHz, DMSO-d₆) δ 9.05 (d, J=1.8 Hz, 1H), 8.96 (s, 1H), 8.75 (s, 1H), 8.65 (s, 1H), 8.60 (s, 2H), 8.36 (s, 1H), 8.27 (s, 1H), 7.96 (d, J=13.6 Hz, 2H), 7.90 (d, J=8.9 Hz, 1H), 4.82 (d, J=13.6 Hz, 1H), 4.52-4.40 (m, 1H), 4.03 (d, J=13.6 Hz, 1H), 3.36-3.25 (m, 1H), 2.81 (dd, J=18.6, 7.3 Hz, 1H), 2.29 (dd, J=24.4, 12.2 Hz, 2H), 2.18 (m, 2H), 2.13-1.96 (m, 2H), 1.35 (t, J=6.6 Hz, 3H).

Example 139

Preparation of 1-{(6-[(1-methyl)-4-pyrazolyl]-imidazo[1,2-a]pyridine)-3-sulfonyl}-6-[4-(1,2,3,6-tetrahydropyridinyl)]-1-H-pyrazolo[4,3-b]pyridine

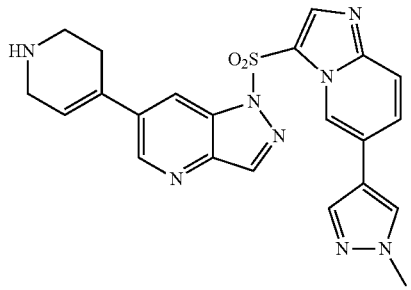 [SMILES: Cn1cc(-c2ccc3ncc(S(=O)(=O)n4ncc5ncc(C6=CCNCC6)cc54)n3c2)cn1]

Except for 1,2,3,6-tetrahydropyridine-4-borate pinacol ester was used instead of 1-t-butoxycarbonyl-1H-pyrazolo-4-borate pinacol ester, compound 1-{(6-[(1-methyl)-4-pyrazolyl]-imidazo[1,2-a]pyridine)-3-sulfonyl}-6-[4-(1,2,3,6-tetrahydropyridinyl)]-1-H-pyrazolo[4,3-b]pyridine was prepared by the same process as Example 106.

¹H NMR (400 MHz, CDCl₃) δ 9.15 (s, 1H), 8.78 (s, 1H), 8.36 (s, 1H), 8.33 (s, 1H), 8.27 (s, 1H), 7.81 (s, 1H), 7.76 (s, 1H), 7.71 (d, J=9.3 Hz, 1H), 7.62 (d, J=9.6 Hz, 1H), 6.39 (m, 1H), 4.02 (s, 3H), 3.70-3.60 (m, 2H), 3.21 (t, J=5.6 Hz, 2H), 2.65-2.53 (m, 2H).

Example 140

Preparation of 1-{(6-[(1-methyl)-4-pyrazolyl]-imidazo[1,2-a]pyridine)-3-sulfonyl}-6-{[1-(4-piperidinyl)]-4-pyrazolyl}-1-H-pyrazolo[4,3-b]pyridine

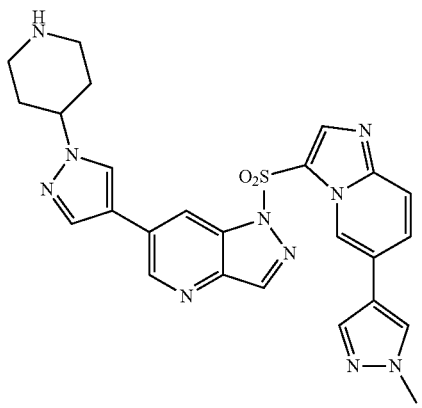 [SMILES: Cn1cc(-c2ccc3ncc(S(=O)(=O)n4ncc5ncc(-c6cnn(C7CCNCC7)c6)cc54)n3c2)cn1]

Except for 1-(4-piperidinyl)-pyrazolo-4-borate pinacol ester was used instead of 1-t-butoxycarbonyl-1H-pyrazolo-4-borate pinacol ester, compound 1-{(6-[(1-methyl)-4-pyrazolyl]-imidazo[1,2-a]pyridine)-3-sulfonyl}-6-{[1-(4-piperidinyl)]-4-pyrazolyl}-1-H-pyrazolo[4,3-b]pyridine was prepared by the same process as Example 106.

¹H-NMR (400 MHz, DMSO-d₆) δ 9.05 (d, J=1.8 Hz, 1H), 8.96 (s, 1H), 8.75 (s, 1H), 8.65 (s, 1H), 8.60 (s, 2H), 8.36 (s, 1H), 8.27 (s, 1H), 7.96 (d, J=13.6 Hz, 2H), 7.90 (d, J=8.9 Hz, 1H), 4.51 (m, 2H), 3.95 (s, 3H), 3.40 (m, 3H), 3.06 (m, 3H).

Example 141

Preparation of 1-{(6-[(1-methyl)-4-pyrazolyl]-imidazo[1,2-a]pyridine)-3-sulfonyl}-6-{{1-[(1-t-butoxycarbonyl)-4-piperidinyl]}-4-pyrazolyl}-1-H-pyrazolo[4,3-b]pyridine

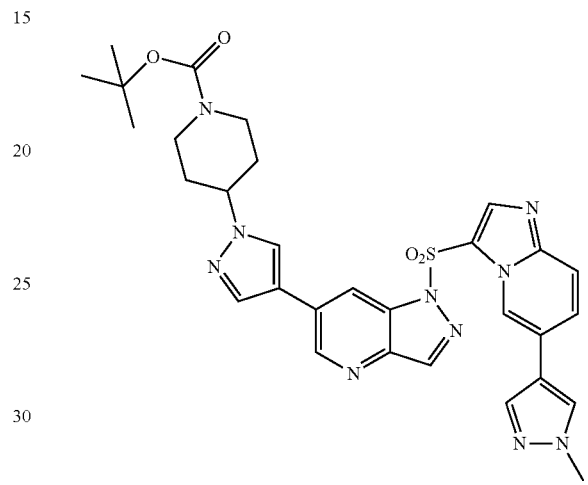

Except for 1-[(1-t-butoxycarbonyl)-4-piperidinyl]-pyrazolo-4-borate pinacol ester was used instead of 1-t-butoxycarbonyl-1H-pyrazolo-4-borate pinacol ester, compound 1-{(6-[(1-methyl)-4-pyrazolyl]-imidazo[1,2-a]pyridine)-3-sulfonyl}-6-{{1-[(1-t-butoxycarbonyl)-4-piperidinyl]}-4-pyrazolyl}-1-H-pyrazolo[4,3-b]pyridine was prepared by the same process as Example 106.

¹H-NMR (400 MHz, CDCl₃) δ 9.17 (s, 1H), 8.86 (d, J=1.9 Hz, 1H), 8.46 (m, 1H), 8.33 (s, 1H), 8.28 (s, 1H), 7.95 (s, 1H), 7.87 (s, 1H), 7.85 (s, 1H), 7.78 (s, 1H), 7.72 (d, J=9.4 Hz, 1H), 7.63 (dd, J=9.3, 1.7 Hz, 1H), 4.35 (m, 3H), 4.04 (s, 3H), 2.95 (m, 2H), 2.20 (m, 2H), 2.00 (m, 4.4 Hz, 2H), 1.50 (s, 9H).

Example 142

Preparation of 1-{(6-[(1-methyl)-4-pyrazolyl]-imidazo[1,2-a]pyridine)-3-sulfonyl}-6-[4-(4-methylpiperazine-1-carbonyl)phenyl]-1-H-pyrazolo[4,3-b]pyridine

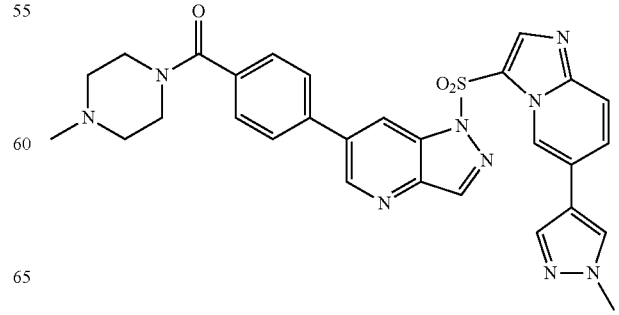

Except for 4-(4-methylpiperazine-1-carbonyl)phenylborate was used instead of 1-t-butoxycarbonyl-1H-pyrazolo-4-borate pinacol ester, compound 1-{(6-[(1-methyl)-4-pyrazolyl]-imidazo[1,2-a]pyridine)-3-sulfonyl}-6-[4-(4-methylpiperazine-1-carbonyl)phenyl]-1-H-pyrazolo[4,3-b]pyridine was prepared by the same process as Example 106.

$^1$H NMR (400 MHz, CDCl$_3$) δ 9.19 (s, 1H), 8.94 (d, J=1.8 Hz, 1H), 8.65-8.59 (m, 1H), 8.41 (s, 1H), 8.29 (s, 1H), 7.83 (s, 1H), 7.77-7.70 (m, 4H), 7.67-7.58 (m, 3H), 4.01 (s, 3H), 3.94-3.80 (m, 2H), 3.61-3.45 (m, 2H), 2.62-2.50 (m, 2H), 2.48-2.39 (m, 2H), 2.36 (s, 3H).

Example 143

Preparation of 1-{(6-[(1-methyl)-4-pyrazolyl]-imidazo[1,2-a]pyridine)-3-sulfonyl}-6-(4-morpholinomethylphenyl)-1-H-pyrazolo[4,3-b]pyridine

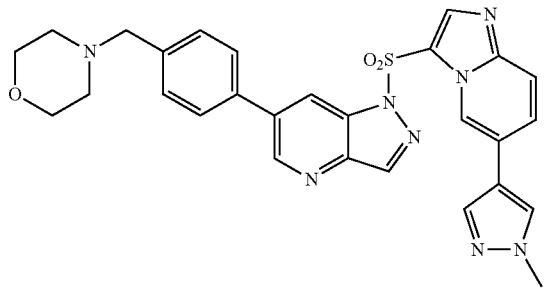 [SMILES: Cn1cc(-c2ccc3ncc(S(=O)(=O)n4ncc5ncc(-c6ccc(CN7CCOCC7)cc6)cc54)n3c2)cn1]

Except for 4-morpholinomethylphenylboronic acid was used instead of 1-t-butoxycarbonyl-1H-pyrazolo-4-borate pinacol ester, compound 1-{(6-[(1-methyl)-4-pyrazolyl]-imidazo[1,2-a]pyridine)-3-sulfonyl}-6-(4-morpholinomethylphenyl)-1-H-pyrazolo[4,3-b]pyridine was prepared by the same process as Example 106.

$^1$H NMR (400 MHz, CDCl$_3$) δ 9.18 (s, 1H), 8.94 (s, 1H), 8.60 (s, 1H), 8.40 (s, 1H), 8.29 (s, 1H), 7.82 (s, 1H), 7.75 (s, 1H), 7.72 (d, J=9.3 Hz, 1H), 7.65 (d, J=7.5 Hz, 3H), 7.53 (d, J=7.9 Hz, 2H), 4.01 (s, 3H), 3.76 (t, J=4.6 Hz, 4H), 3.60 (s, 2H), 2.59-2.44 (m, 4H).

Example 144

Preparation of 1-{(6-[(1-methyl)-4-pyrazolyl]-imidazo[1,2-a]pyridine)-3-sulfonyl}-6-phenyl-1-H-pyrazolo[4,3-b]pyridine

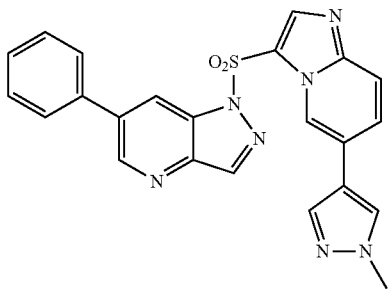 [SMILES: Cn1cc(-c2ccc3ncc(S(=O)(=O)n4ncc5ncc(-c6ccccc6)cc54)n3c2)cn1]

Except for phenylboronic acid was used instead of 1-t-butoxycarbonyl-1H-pyrazolo-4-borate pinacol ester, compound 1-{(6-[(1-methyl)-4-pyrazolyl]-imidazo[1,2-a]pyridine)-3-sulfonyl}-6-phenyl-1-H-pyrazolo[4,3-b]pyridine was prepared by the same process as Example 106.

$^1$H NMR (400 MHz, CDCl$_3$) δ 9.18 (s, 1H), 8.95 (s, 1H), 8.62 (s, 1H), 8.40 (s, 1H), 8.30 (s, 1H), 7.82 (s, 1H), 7.76-7.67 (m, 4H), 7.63 (d, J=9.3 Hz, 1H), 7.57 (t, J=7.4 Hz, 2H), 7.51 (t, J=7.2 Hz, 1H), 4.00 (s, 3H).

Example 145

Preparation of 1-{(6-[(1-methyl)-4-pyrazolyl]-imidazo[1,2-a]pyridine)-3-sulfonyl}-6-{(1-[(1-isopropyl)-4-piperidinyl]}-4-pyrazolyl}-1-H-pyrazolo[4,3-b]pyridine

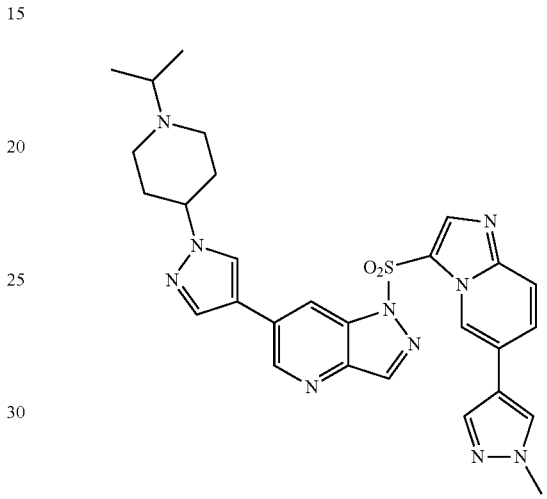

Except for 1-[(1-isopropyl)-4-piperidinyl]pyrazolo-4-borate pinacol ester was used instead of 1-t-butoxycarbonyl-1H-pyrazolo-4-borate pinacol ester, compound 1-{(6-[(1-methyl)-4-pyrazolyl]-imidazo[1,2-a]pyridine)-3-sulfonyl}-6-phenyl-1-H-pyrazolo[4,3-b]pyridine was prepared by the same process as Example 106.

$^1$H NMR (400 MHz, CDCl$_3$) δ 9.16 (s, 1H), 8.85 (s, 1H), 8.46 (s, 1H), 8.33 (s, 1H), 8.29 (s, 1H), 7.94 (d, J=6.8 Hz, 2H), 7.81 (s, 1H), 7.74 (s, 1H), 7.72 (d, J=9.3 Hz, 1H), 7.63 (d, J=9.4 Hz, 1H), 4.27 (td, J=10.9, 5.4 Hz, 1H), 4.00 (s, 3H), 3.12 (dd, J=9.7, 6.1 Hz, 2H), 2.91 (p, J=6.6 Hz, 1H), 2.46 (t, J=11.5 Hz, 2H), 2.40-2.28 (m, 2H), 2.23-2.01 (m, 2H), 1.14 (d, J=6.5 Hz, 6H).

Test I: The Effect of Compounds on c-Met Enzyme Activity at the Molecular Level

1. Test Method

Enzymatic reaction substrate Poly(Glu,Tyr)4:1 was diluted to 20 μg/mL in potassium ion free PBS (10 mM sodium phosphate buffer, 150 mM NaCl, pH7.2-7.4), microplate was coated with this solution at 125 μL per well, and reacted at 37° C. for 12-16 hours. Liquid in wells was discarded. Plate washing: the plate was washed 3 times for 5 minutes each with 200 μL per well of T-PBS (potassium ion free PBS containing 0.1% Tween-20). The microplate was dried in 37° C. oven for 1-2 hours.

Into each well was added 49 μL diluted ATP solution in reaction buffer (50 mM HEPES pH 7.4, 50 mM MgCl$_2$, 0.5 mM MnCl$_2$, 0.2 mM Na$_3$VO$_4$, 1 mM DTT), and 1 μL per well of compound to be tested was added, then 50 μL diluted solution of c-Met kinase domain recombinant protein in reaction buffer was added to initiate the reaction, each test was setup with two wells of ATP free control. Reaction was performed in a 37° C. shaker (100 rpm) for 1 hour. Liquid in the wells was discarded, and the plate was washed three times with T-PBS.

Antibody PY99 was added at 100 μL per well (the antibody was 1:500 diluted in T-PBS containing 5 mg/mL BSA), incubated in a 37° C. shaker for 0.5 hour. Liquid in the wells was discarded, and the plate was washed three times with T-PBS.

Goat anti mouse secondary antibody labeled with horseradish peroxidase was added at 100 μL per well (the antibody was 1:2000 diluted in T-PBS containing 5 mg/mL BSA), incubated in a 37° C. shaker for 0.5 hour. Liquid in the wells was discarded, and the plate was washed three times with T-PBS.

OPD visualization solution (2 mg/ml) was added at 100 μL per well (diluted in 0.1M citric acid-sodium citrate buffer containing 0.03% $H_2O_2$ (pH=5.4)), reacted in dark at 25° C. for 1-10 minutes.

Reaction was terminated by adding 50 μL per well of 2M $H_2SO_4$, the plate was read at 490 nm using a VERSAmax microplate reader with tunable wavelength.

Inhibition rate of the sample was calculated using the following equation:

$$\text{Inhibition rate of sample (\%)} = \left(1 - \frac{OD \text{ of compound} - OD \text{ of enzyme free control}}{OD \text{ of negative control} - OD \text{ of enzyme free control}}\right) \times 100$$

2. Test Result

The enzyme activity test at the molecular level (Table 1) suggests that the compounds of this invention can significantly inhibit c-Met tyrosine kinase activity, some of the compounds exhibited c-Met inhibition activity stronger than the comparative compound 1-(benzo[1,2,5]oxadiazole-4-sulfonyl)-6-[(1-methyl)-4-pyrazolyl]-1-H-pyrazolo[4,3-b]pyridine (an analogue reported in Bioorganic & Medicinal Chemistry Letters 19 (2009) 2780-2784), but weaker than the activity of the positive control PF2341066.

TABLE 1

Receptor tyrosin kinase c-Met inhibition rate by compounds at a concentration of 10 μM

| Compound No. | Inhibition rate at 10 μM (%) | Compound No. | Inhibition rate at 10 μM (%) |
|---|---|---|---|
| 1 | 88.1 | 2 | 92.8 |
| 3 | 84.6 | 4 | 44.1 |
| 5 | 57.5 | 6 | 34.4 |
| 7 | 40.7 | 8 | 72.4 |
| 9 | 22 | 10 | 37.9 |
| 11 | 48.6 | 12 | 37.5 |
| 13 | 52.6 | 14 | 74.3 |
| 15 | 40.6 | 16 | 73.2 |
| 17 | 49.9 | 18 | 64 |
| 19 | 59.3 | 20 | 85.7 |
| 21 | 77.9 | 22 | 69.5 |
| 23 | 65.1 | 24 | 70.5 |
| 25 | 86.2 | 26 | 65.2 |
| 27 | 70.6 | 28 | 70.6 |
| 29 | 65.7 | 30 | 71 |
| 31 | 69 | 32 | 64.2 |
| 33 | 53.7 | 34 | 61.3 |
| 35 | 62.5 | 36 | 66.3 |
| 37 | 73.3 | 38 | 87.1 |
| 39 | 68.8 | 40 | 66 |
| 41 | 68.7 | 42 | 67.5 |
| 43 | 58.4 | 44 | 87.5 |
| 45 | 89.6 | 46 | 81.3 |
| 47 | 79.8 | 48 | 87.3 |
| 49 | 76.7 | 50 | 93.9 |
| 51 | 72.3 | 52 | 54.5 |
| 53 | 65.7 | 54 | 70.7 |
| 55 | 74.1 | 56 | 62.1 |
| 57 | 60.8 | 58 | 58.9 |
| 59 | 60.3 | 60 | 57.4 |
| 61 | 59.8 | 62 | 62.6 |
| 63 | 83.2 | 64 | 80 |
| 65 | 79.3 | 66 | 63 |
| 67 | 66 | 68 | 69.8 |
| 69 | 79.9 | 70 | 68.2 |
| 71 | 62 | 72 | 80.9 |
| 73 | 59.6 | 74 | >67.6 |
| 75 | >77.3 | 76 | >76.3 |
| 77 | >76.9 | 78 | >12.1 |
| 79 | >83.1 | 80 | >75.3 |
| 81 | >68.7 | 82 | >78.5 |
| 83 | >79.8 | 84 | >71.5 |
| 85 | >71.2 | 86 | >67.9 |
| 87 | >76.8 | 88 | >70.2 |
| 89 | >71.7 | 90 | >72.2 |
| 91 | >69.4 | 92 | >71.9 |
| 93 | >64.5 | 94 | >74.3 |
| 95 | >72.1 | 96 | >71.8 |
| 97 | >63.8 | 98 | >77.9 |
| 99 | >73.3 | 100 | >60.4 |
| 101 | >64.5 | 102 | >65.5 |

Test II: Additional Test on the Effect of Compounds on c-Met Enzyme Activity at the Molecular Level 1. Test Method Enzymatic reaction substrate Poly(Glu,Tyr)$_{4:1}$ was diluted to 20 μg/mL in potassium ion free PBS (10 mM sodium phosphate buffer, 150 mM NaCl, pH7.2-7.4), microplate was coated with this solution at 125 μL per well, and reacted at 37° C. for 12-16 hours. Liquid in wells was discarded, then the plate was washed 3 times for 5 minutes each with 200 μL per well of T-PBS (PBS containing 0.1% Tween-20). The microplate was dried in 37° C. oven for 1-2 hours.

Into each well was added 50 μL diluted ATP solution in reaction buffer (50 mM HEPES pH 7.4, 50 mM $MgCl_2$, 0.5 mM $MnCl_2$, 0.2 mM $Na_3VO_4$, 1 mM DTT), the final concentration was 5 μM. Test compound was diluted in DMSO to proper concentration, added at 1 μL per well or corresponding level of DMSO (negative control wells), then 49 μL diluted solution of c-Met kinase domain recombinant protein in reaction buffer was added to initiate the reaction, each test was setup with two wells of ATP free control. Reaction was performed in a 37° C. shaker (100 rpm) for 1 hour. The plate was washed three times with T-PBS. Primary antibody PY99 diluted solution was added at 100 μL per well, incubated in a 37° C. shaker for 0.5 hour.

The plate was washed three times with T-PBS. Goat anti mouse secondary antibody labeled with horseradish peroxidase was added at 100 μL per well, incubated in a 37° C. shaker for 0.5 hour. The plate was washed three times with T-PBS. OPD visualization solution (2 mg/ml) was added at 100 μL per well (diluted in 0.1M citric acid-sodium citrate buffer containing 0.03% $H_2O_2$ (pH=5.4)), reacted in dark at 25° C. for 1-10 minutes (OPD dissolve was accomplished with ultrasound treatment, and the visualization solution was made immediately prior to use). Reaction was terminated by adding 50 μL per well of 2M H$_2$SO$_4$, the plate was read at 490 nm using a SPECTRA MAX 190 microplate reader with tunable wavelength.

Inhibition rate of the sample was calculated using the following equation:

Inhibition rate (%) =
$$\left(1 - \frac{OD \text{ of compound} - OD \text{ of } ATP \text{ free control}}{OD \text{ of negative control} - OD \text{ of } ATP \text{ free control}}\right) \times 100$$

IC$_{50}$ was calculated by fitting the data for a four parameter fit using inhibition curve. Test results are shown below in Table 2.

Test III: Test about the Effect of Compounds on c-Met Mediated Proliferation of Tumor Cell and Engineered Cell Proliferation 1. Test Method Assays on the growth inhibition of the compounds against gastric tumor cell MKN45, non-small cell carcinoma EBC-1 cell (both are MET persistent activated cell lines due to MET gene amplification, and are Met dependent tumor cell lines, MKN45 cell was purchased from JCRB, Japan, EBC-1 cell was purchased from ATCC, USA) were detected using sulforhodamine B (SRB) staining. A certain amount of MKN45 cells and EBC-1 cells at log phase were inoculated into 96-well culture plate at 90 μL per well, incubated overnight and then 10 μL compound at various concentrations or vehicle control (normal saline) was added, each concentration was tested in triplicate. After incubation with compound for 72 hours, the incubation was terminated, adherent cells were retained and medium was discarded, 10% (w/v) trichloroacetic acid (100 μL pre well) was added, the cells were fixed at 4° C. for 1 hour, then rinsed with distilled water for 5 times, after dried at room temperature, SRB solution (4 mg/mL, dissolved in 1% glacial acetic acid) was added at 100 μL per well, incubated and stained at room temperature for 15 minutes, then rinsed with 1% glacial acetic acid for 5 times to remove any unbound SRB, dried at room temperature, then 10 mM Tris solution was added at 100 μL per well, the optical density (OD) value at 515 nm was measured using VERSMax microplate reader.

The inhibition rate of tumor cell growth by the compound was calculated by the following equation: inhibition rate (%)=(OD of control well−OD of administered well)/OD of control well×100%. Experiments were conducted in duplicates. IC$_{50}$ value was calculated by fitting the data for a four parameter fit using inhibition curve, the results are shown below in Table 2.

Assays on the growth inhibition of the compounds against engineered BaF3/TPR-Met cell (engineered cell line having TPR-Met fusion protein stably expressed in cytoplasm, persistently activated, Met dependent sensitive cell line; BaF3 cell was purchased from DSMZ, German) were detected using microculture tetrozolium (MTT) staining. A certain amount of BaF3/TPR-Met cells at log phase were inoculated into 96-well culture plate at 90 L per well, incubated overnight and then 10 μL compound at various concentrations or vehicle control (normal saline) was added, each concentration was tested in triplicate. After incubation with compound for 72 hours, the incubation was terminated, MTT solution (5 mg/mL) was added at 20 μL per well, incubated at 37° C. for 4 hours, then 100 μL triplet solution (10% SDS−5% isobutanol−0.01M HCl) was added, incubated overnight at 37° C., OD value was measured at 570 nm. The inhibition rate of tumor cell growth by the compound was calculated by the following equation: inhibition rate (%)=(OD of control well−OD of administered well)/OD of control well×100%. Experiments were conducted in duplicates. The results are shown below in Table 2.

TABLE 2

| Compound | Average inhibition rate at 10 μM (%) | Average inhibition rate at 1 μM (%) | Average inhibition rate at 0.1 μM (%) | IC50 (nM) | Cell proliferation inhibition rate at 1 μM (%) | Cell proliferation inhibition rate at 200 nM (%) | Cell line |
|---|---|---|---|---|---|---|---|
| 01 | 88.1 | | | | | | |
| 02 | 92.8 | 7 | | | | | |
| 03 | 84.6 | | | | | | |
| 04 | 44.1 | | | | | | |
| 05 | 57.5 | 33.8 | 2.1 | | | | |
| 06 | 34.4 | | | | | | |
| 07 | 40.7 | | | | | | |
| 08 | 72.4 | 51.6 | 9.2 | | | | |
| 09 | 22 | | | | | | |
| 10 | 37.9 | | | | | | |
| 11 | 48.6 | | | | | | |
| 12 | 37.5 | | | | | | |
| 13 | 52.6 | 45.3 | 28.5 | | | | |
| 14 | 74.3 | 54.7 | 39.9 | | | | |
| 15 | 40.6 | | | | | | |
| 16 | 73.2 | 56.1 | 25.2 | | | | |
| 17 | 49.9 | | | | | | |
| 18 | 64 | 60.5 | 52.2 | 4.2 ± 0.6 | 94.4 | 1.8 | BaF3/TPR-Met |
| 19 | 59.3 | 53.5 | 59.2 | 7.8 ± 0.8 | 95.6 | 91.8 | BaF3/TPR-Met |
| 20 | 85.7 | 72.6 | 54.9 | 316.2 ± 141.5 | 2.9 | 3.2 | BaF3/TPR-Met |
| 21 | 77.9 | 59.7 | 59 | | 42.7 | | BaF3/TPR-Met |
| 22 | 69.5 | 58.7 | 24.9 | 39.7 ± 6.3 | | | |
| 23 | 65.1 | 52.7 | 26.9 | 3.7 ± 1.4 | | | |
| 24 | 70.5 | 67.8 | 62.9 | 2.5 ± 1.2 | 90.9 | 65.9 | BaF3/TPR-Met |
| 25 | 86.2 | 78 | 71.7 | 21.3 ± 2.3 | 88.4 | 36.3 | BaF3/TPR-Met |
| 26 | 65.2 | 63.8 | 60 | 33.9 ± 6.9 | | | BaF3/TPR-Met |
| 27 | 70.6 | 59.6 | 56.9 | 0.5 ± 0.1 | | | EBC-1 |
| 28 | 70.6 | 70.3 | 64.6 | 6.7 ± 0.5 | 66.1 | | BaF3/TPR-Met |
| 29 | 65.7 | 63.8 | 55.7 | 4.6 ± 1.0 | 92.6 | | BaF3/TPR-Met |

TABLE 2-continued

| Compound | Average inhibition rate at 10 μM (%) | Average inhibition rate at 1 μM (%) | Average inhibition rate at 0.1 μM (%) | IC50 (nM) | Cell proliferation inhibition rate at 1 μM (%) | Cell proliferation inhibition rate at 200 nM (%) | Cell line |
|---|---|---|---|---|---|---|---|
| 30 | 71 | 59.7 | 48.3 | | | | |
| 31 | 69 | 64.1 | 59 | | | | |
| 32 | 64.2 | 52 | 52.9 | | | | |
| 33 | 53.7 | 47.3 | 39.9 | | | | |
| 34 | 61.3 | 49.3 | 31.3 | | | | |
| 35 | 62.5 | 53.2 | 51.1 | | | | |
| 36 | 66.3 | 60 | 45.6 | | | | |
| 37 | 73.3 | 63.8 | 60.1 | 6.4 ± 2.2 | 96.2 | 59.5 | BaF3/TPR-Met |
| 38 | 87.1 | 63.9 | 63.2 | | | | |
| 39 | 68.8 | 65 | 58.2 | 2.6 ± 0.3 | 96.3 | 74.4 | BaF3/TPR-Met |
| 40 | 66 | 57.4 | 45.7 | | | | |
| 41 | 68.7 | 54.6 | 45.1 | | | | |
| 42 | 67.5 | 58.4 | 45.5 | | | | |
| 43 | 68.7 | 47.6 | 23.1 | | | | |
| 44 | 87.5 | 78.6 | 74.6 | 6.9 ± 1.9 | 95.8 | 95 | BaF3/TPR-Met |
| 45 | 89.6 | 76.5 | 73.4 | 2.9 ± 0.6 | 95.9 | 27.9 | BaF3/TPR-Met |
| 46 | 81.3 | 65 | 55.9 | | 68 | 33.7 | BaF3/TPR-Met |
| 47 | 79.8 | 56.1 | 35.1 | | | | |
| 48 | 87.3 | 77.6 | 65.6 | | | | |
| 49 | 76.7 | 74.5 | 71 | | 90.5 | 28.4 | BaF3/TPR-Met |
| 50 | 93.9 | 67.4 | 66.8 | | 30.5 | 32.7 | BaF3/TPR-Met |
| 51 | 72.3 | 66.7 | 64.6 | | 7.7 | 15.3 | BaF3/TPR-Met |
| 52 | 54.5 | 50.3 | 24.5 | | | | |
| 53 | 74.1 | 68.4 | 67.5 | | 90.9 | | BaF3/TPR-Met |
| 54 | 62.1 | 57.9 | 55.9 | | 89.6 | 88.3 | BaF3/TPR-Met |
| 55 | 60.8 | 58.3 | 58.8 | 1.3 ± 0.1 | 89.8 | 89.3 | BaF3/TPR-Met |
| 56 | 58.9 | 56.3 | 53.3 | | 90.6 | 79.1 | BaF3/TPR-Met |
| 57 | 60.3 | 54.5 | 52.4 | | 89.5 | 86.8 | BaF3/TPR-Met |
| 58 | 57.4 | 55.7 | 52.8 | | | | BaF3/TPR-Met |
| 59 | 59.8 | 51.9 | 51.6 | | 89.8 | 70.6 | BaF3/TPR-Met |
| 60 | 62.6 | 53.4 | 50.1 | | 89.4 | 84.8 | BaF3/TPR-Met |
| 61 | 83.2 | 76 | 73.7 | | 91.7 | 83.1 | BaF3/TPR-Met |
| 62 | 80 | 73.2 | 73.2 | | | | BaF3/TPR-Met |
| 63 | 63 | 60.4 | 59 | | 66.5 | | BaF3/TPR-Met |
| 64 | 66 | 60.4 | 59.1 | | 76.4 | | BaF3/TPR-Met |
| 65 | 69.8 | 65.1 | 60.8 | | | | BaF3/TPR-Met |
| 66 | 79.9 | 75.8 | 73.3 | | 92.7 | | BaF3/TPR-Met |
| 67 | 68.2 | 64.6 | 63.1 | | 91.6 | 90.3 | BaF3/TPR-Met |
| 68 | 62 | 55.8 | 50.2 | | | | BaF3/TPR-Met |
| 69 | 59.6 | 57.7 | 52.3 | | | | |
| 70 | 79.3 | 44.7 | | | | | |
| 71 | 83.8 | 73.4 | 68.5 | 0.1 ± 0.01 | | | MKN45 |
| 72 | 76.5 | 80.3 | 70.1 | 0.04 ± 0.04 | 72.8 | | MKN45 |
| 73 | 76.9 | 72.8 | 78 | | 14.4 | | MKN45 |
| 74 | 12.1 | | | | | | |
| 75 | 83.1 | 75.6 | 74.6 | | | | MKN45 |
| 76 | 78.3 | 75.5 | 78 | | 14.9 | | MKN45 |
| 77 | 85.5 | 64.8 | 55.8 | | | | MKN45 |
| 78 | 89.3 | 69.3 | 64.5 | | | | MKN45 |
| 79 | 77.4 | 30.5 | | | | | |
| 80 | 80.6 | 47.5 | | | | | |
| 81 | 80.2 | 73.6 | 72.9 | | 24.7 | | MKN45 |
| 82 | 77.7 | 63.8 | 54.4 | | | | MKN45 |
| 83 | 77.7 | 44.4 | | | | | |
| 84 | 73.5 | 41.2 | | | | | |
| 85 | 79.4 | 30.1 | | | | | |
| 86 | 77.8 | 66.6 | 45 | | | | |
| 87 | 72.5 | 72.7 | 33.8 | | | | |
| 88 | 64.5 | 59.4 | 1.1 | | | | |
| 89 | 83.4 | 79.9 | 45.3 | | | | |
| 90 | 81.1 | 83 | 69 | | 17.6 | | MKN45 |
| 91 | 74.1 | 85.5 | 77.3 | | 72.9 | | MKN45 |
| 92 | 78.9 | 79.1 | 82.8 | | | | MKN45 |
| 93 | 77.9 | 76.8 | 76.1 | | | | MKN45 |
| 94 | 83.9 | 55.7 | 72.1 | | | | MKN45 |
| 95 | 63.4 | 57.1 | 62.7 | | 65.5 | 42.3 | MKN45 |
| 96 | 68.3 | 61.5 | 56.6 | 0.7 ± 0.1 | | | MKN45 |
| 97 | 65.5 | 62.7 | 51.7 | 0.5 ± 0.1 | 67.8 | | MKN45 |
| 98 | 74.3 | 66.8 | 50.6 | 1.4 ± 0.1 | | | MKN45 |
| 99 | 71.8 | 66.2 | 55.5 | | 67.9 | 48.5 | MKN45 |
| 100 | 85.4 | 87.3 | 83.7 | | 66.6 | 63.8 | MKN45 |
| 101 | | 100 | 100 | 0.3 ± 0.1 | | | |
| 102 | 95.4 | 85.3 | 73.7 | | 67.9 | 63.8 | MKN45 |
| 103 | | 100.7 | 98.5 | 3.2 ± 0.3 | 92.7 | 80.9 | EBC-1 |

TABLE 2-continued

| Compound | Average inhibition rate at 10 μM (%) | Average inhibition rate at 1 μM (%) | Average inhibition rate at 0.1 μM (%) | IC50 (nM) | Cell proliferation inhibition rate at 1 μM (%) | Cell proliferation inhibition rate at 200 nM (%) | Cell line |
|---|---|---|---|---|---|---|---|
| 104 | | 100.5 | 99.8 | 2.1 ± 0.6 | 89.2 | 85.7 | EBC-1 |
| 105 | | 100.3 | 97.8 | 2.6 ± 0.4 | 91.5 | 77.7 | EBC-1 |
| 106 | | 100.6 | 103.9 | 1.9 ± 0.1 | 85.7 | 37.0 | EBC-1 |
| 107 | | 88.2 | 29.1 | | 18.1 | 18.9 | EBC-1 |
| 108 | | 61.4 | 9.1 | | 20.6 | 15.4 | EBC-1 |
| 109 | | 40 | | | | | |
| 110 | | 13.5 | | | | | |
| 111 | | 63.3 | 28.6 | | | | |
| 112 | | 48.8 | | | | | |
| 113 | | 97.7 | 48.6 | | 9 | 7.9 | EBC-1 |
| 114 | | 30.4 | | | | | |
| 115 | | 95.7 | 46.6 | | | | EBC-1 |
| 116 | | 84.6 | 70.8 | 3.6 ± 0.6 | | | EBC-1 |
| 117 | | 15.8 | | | | | |
| 118 | | 75.5 | 62.7 | | | | EBC-1 |
| 119 | | 26.4 | | | | | |
| 120 | | 28.7 | | | | | |
| 121 | | 101.1 | 99 | 9.0 ± 1.0 | 92.5 | 91.6 | EBC-1 |
| 122 | | 100.5 | 72.9 | 189.7 ± 32.7 | | | EBC-1 |
| 123 | | 99.3 | 87 | 51.5 ± 6.0 | | | EBC-1 |
| 124 | | 99.7 | 94.4 | 4.7 ± 1.0 | 92.7 | 43.1 | EBC-1 |
| 125 | | 99.3 | 84.5 | 55.2 ± 5.6 | | | EBC-1 |
| 126 | | 100.1 | 100 | 7.3 ± 1.1 | 87 | 35.1 | EBC-1 |
| 127 | | 99 | 93.9 | 30.0 ± 3.3 | | | EBC-1 |
| 128 | | 99.3 | 99.4 | 2.0 ± 0.2 | 87 | 80.6 | EBC-1 |
| 129 | | 101.2 | 99.6 | 2.7 ± 0.5 | 86.6 | 79 | EBC-1 |
| 130 | | 90.8 | 16.1 | | | | EBC-1 |
| 131 | | 83.6 | 75.1 | | | | EBC-1 |
| 132 | | 100 | 92.1 | | 85.4 | 48.2 | EBC-1 |
| 133 | | 100 | 100 | 2.6 ± 0.2 | 87.8 | 86.4 | EBC-1 |
| 134 | | 56.9 | 66.8 | | | | EBC-1 |
| 135 | | 88.2 | 87.4 | 2.6 ± 0.2 | 91.4 | 89.4 | EBC-1 |
| 136 | | 91.3 | 90.2 | 1.2 ± 0.1 | 92.4 | 91.4 | EBC-1 |
| 137 | | 89.9 | 91.6 | 1.3 ± 0.1 | 92.4 | 73 | EBC-1 |
| 138 | | 90.5 | 87.7 | 0.6 ± 0.01 | 92.9 | 90.9 | EBC-1 |
| 139 | | 88.9 | 90.3 | 1.0 ± 0.1 | 91.6 | 90.7 | EBC-1 |
| 140 | | 89.5 | 92.4 | 0.5 ± 0.03 | 92 | 91.4 | EBC-1 |
| 141 | | 88.5 | 86.3 | 0.3 ± 0.1 | 92.7 | 92.6 | EBC-1 |
| 142 | | 91.3 | 89.4 | 0.5 ± 0.1 | 92.6 | 92.1 | EBC-1 |
| 143 | | 92.1 | 90 | 0.4 ± 0.1 | 92.5 | 92.3 | EBC-1 |
| 144 | | 93.1 | 92.1 | 0.3 ± 0.01 | 91.4 | 91.1 | EBC-1 |
| 145 | | 87.1 | 90.6 | 0.6 ± 0.1 | 92.8 | 92.4 | EBC-1 |

Test IV: Effect of Compounds on Human Non-Small Cell Lung Cancer Cell EBC-1 Xenograft Growth in Nude Mice 1. Test Method EBC-1 cells were implanted subcutaneously in the right axilla of nude mice at 5×10⁶ cells per mouse, xenograft developed thereby was passaged in nude mice for 3 generations prior to use. Tumor tissue at rapid growth phase was taken, minced under sterile condition into pieces of about 1.5 mm³, then implanted subcutaneously in the right axilla of nude mice.

Xenografted tumor diameters were determined by caliper measurements, when the tumor grew to give a tumor volume of 100-200 mm³, the animals were randomized into groups based on the tumor volume, 12 animals in the vehicle control group, and 6 animals in each test group. The test groups were administered orally with compound 142 or 145 (50 mg/kg, 100 mg/kg), the administration was made daily for 21 consecutive days, while the vehicle control group was administered with equivalent amount of solvent (0.5% sodium carboxymethyl cellulose).

Xenografted tumor diameters were measured twice per week, and body weights of the mice were measured at the same time. Tumor Volume (TV) was calculated by the following equation: TV=1/2×a×b², wherein a, b refers to the length and width, respectively. Based on the measurement, Relative Tumor Volume (RTV) was calculated by the following equation: RTV=$V_t/V_0$, wherein $V_0$ is the tumor volume measured when divided for administration (i.e., do), $V_t$ is the tumor volume measured at each timepoint. Antitumor activity is evaluated by the following indices: 1) relative tumor proliferation rate T/C (%), calculated by the following equation: T/C (%)=($T_{RTV}/C_{RTV}$)×100%, $T_{RTV}$: RTV of treatment group; $C_{RTV}$: RTV of negative control group; 2) inhibition rate of tumor volume increase GI %, calculated by the following equation: GI %=[1−(TVt−TV₀)/(CVt−CV₀)]×100%, TVt is the tumor volume of the treatment group measured at each timepoint; TV₀ is the tumor volume of the treatment group measured when divided for administration; CVt is the tumor volume of the control group measured at each timepoint; CV₀ is the tumor volume of the control group measured when divided for administration.

2. Test Result

When administration was completed (d21), compound 142 exhibited very significant dose dependent inhibition against the tumor growth of human lung cancer EBC-1 subcutaneous xenograft in nude mice, 100 mg/kg and 50 mg/kg dosage groups obtained T/C percentages of 1.05% and 16.91%, respectively, at day 21, in 100 mg/kg dosage group, two mice exhibited complete tumor regression at day 11 and four mice exhibited complete tumor regression by the end of the trial. Compound 145 exhibited very significant dose dependent inhibition against the tumor growth of human lung cancer EBC-1 subcutaneous xenograft in nude mice, 100 mg/kg and 50 mg/kg dosage groups obtained T/C percentages of 0.40% and 2.36%, respectively, at day 21; in 100 mg/kg dosage group, two mice exhibited complete tumor regression at day 11 and four mice exhibited complete tumor regression by the end of the trial; in 50 mg/kg dosage group, two mice exhibited complete tumor regression at day 18 and three mice exhibited complete tumor regression by the end of the trial. During the administration period, mice in all treatment groups were in good state and were survived (FIG. 1).

During the trial, tumor diameters and animal weights were measured twice a week. Tumor Volume (TV) was calculated by the following equation: $TV=1/2 \times a \times b^2$, wherein a, b represent length and width, respectively. Based on the measurement, Relative Tumor Volume (RTV) was calculated by the following equation: $RTV=V_t/V_0$, wherein $V_0$ is the tumor volume measured when divided for administration (i.e., $d_0$), $V_t$ is the tumor volume measured at each timepoint. Antitumor activity is evaluated by the following indices: 1) relative tumor proliferation rate T/C (%), calculated by the following equation: T/C (%)=$(T_{RTV}/C_{RTV}) \times 100\%$, $T_{RTV}$: RTV of treatment group; $C_{RTV}$: RTV of negative control group; 2) inhibition rate of tumor volume increase GI %, calculated by the following equation: GI %=$[1-(TVt-TV_0)/(CVt-CV_0)] \times 100\%$, TVt is the tumor volume of the treatment group measured at each timepoint;

TABLE 3

Experimental therapeutic effect of compounds on human lung cancer EBC-1 xenograft in nude mice

| Group | Dosage, mode of administration | Animal number $d_0$ | $d_{21}$ | Weight (g) $d_0$ | $d_{21}$ | TV (mm³, mean ± SD) $d_0$ | $d_{21}$ | RTV (mean ± SD) | T/C (%) | GI (%) |
|---|---|---|---|---|---|---|---|---|---|---|
| Vehicle control | 0.2 ml/animal, po qd/21 | 12 | 12 | 17.9 | 22.8 | 126 ± 31 | 1606 ± 362 | 13.18 ± 3.39 | | |
| 142 | 100 mg/kg po qd/21 | 6 | 6 | 17.8 | 20.9 | 120 ± 30 | 21 ± 34(4) | 0.14 ± 0.21*** | 1.05 | 106.70 |
| | 50 mg/kg po qd/21 | 6 | 6 | 17.7 | 21.0 | 120 ± 25 | 259 ± 421 | 2.23 ± 3.89*** | 16.91 | 90.65 |
| 145 | 100 mg/kg po qd/21 | 6 | 6 | 16.9 | 19.1 | 123 ± 27 | 8 ± 13(4) | 0.05 ± 0.09*** | 0.40 | 107.77 |
| | 50 mg/kg po qd/21 | 6 | 6 | 16.8 | 19.9 | 127 ± 32 | 36 ± 49(3) | 0.31 ± 0.50*** | 2.36 | 106.14 | t student's test vs vehicle control,
***$p < 0.001$ numbers in parenthesis are the numbers of mice exhibiting complete tumor regression Test V: Effect of Compound on Human Malignant Glioblastoma Cell U87MG Xenograft in Nude Mice 1. Test Method U87-MG cells were expanded by in vitro culture, cells at log phase were harvested and resuspended in EMEM, adjusted to a cell density of $2.8 \times 10^7$/mL, then implanted subcutaneously in the right axilla of nude mice. Animals and the growth status of the xenograft were monitored periodically, when tumor volume generally reached 100~300 mm³, animals bearing tumor in too big size, too small size, or in irregular shape were eliminated, and the remaining tumor bearing mice were randomized into 2 groups based on the tumor volume, one vehicle control group (5% DMAC containing 0.5% methylcellulose), and one test group receiving Sample 19 at 50 mg/kg daily for 14 consecutive days.

$TV_0$ is the tumor volume of the treatment group measured when divided for administration; CVt is the tumor volume of the control group measured at each timepoint; $CV_0$ is the tumor volume of the control group measured when divided for administration.

2. Test Result

Figure 2:
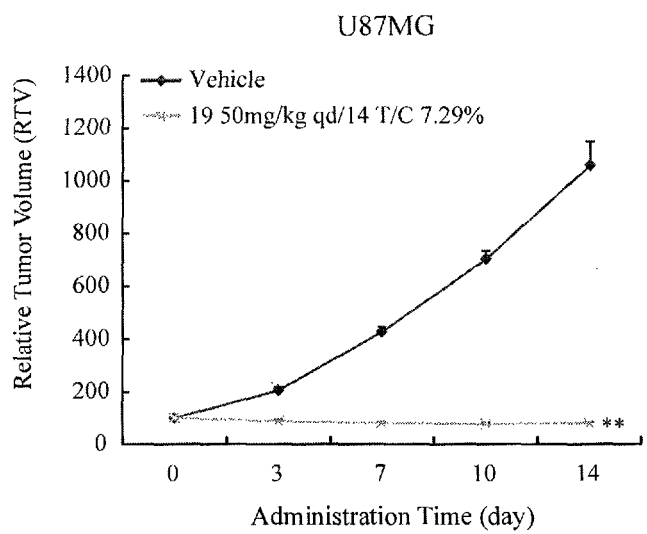
FIG. 2 shows the effect of the compound according to this invention on growth of human malignant glioblastoma cell U87MG xenograft in nude mice.

When administration was completed (d14), test group receiving compound 19 at 50 mg/kg exhibited favorable antitumor activity, relative tumor proliferation rate (% T/C) at the end of the trial was 7.29% (P<0.01), the test group exhibited a very significant difference in relative tumor volume when compared to the vehicle control group. During the administration period, all mice in treatment group were in good state and were survived (FIG. 2).

TABLE 4

Experimental therapeutic effect of compound on U87MG xenograft in nude mice

| Group | Dosage, mode of administration | Animal number $d_0$ | $d_{14}$ | Weight (g) $d_0$ | $d_{21}$ | TV (mm³, mean ± SE) $d_0$ | $d_{21}$ | RTV (mean ± SE) | T/C (%) | GI (%) |
|---|---|---|---|---|---|---|---|---|---|---|
| Vehicle control | 0.25 ml/animal po qd/14 | 12 | 12 | 23.5 | 24.6 | 182 ± 22 | 1846 ± 149 | 1056.3 ± 92.2 | | |
| 19 | 50 mg/kg po qd/14 | 6 | 6 | 24.2 | 24.5 | 180 ± 20 | 140 ± 20 | 77.0 ± 5.2** | 7.29 | 102.41 | t student's test vs vehicle control group,
**$p < 0.01$

Although the present invention is described referring to specific examples, it is obvious to a person skilled in the art that numerous modifications and variations may be made to this invention without departing from the spirit and scope of the present invention. Accordingly, the appended claims cover all these modifications within the scope of this invention. All publications, patents and patent applications cited herein are incorporated herein by reference.

We claim:

1. A 5-member-heterocycle-fused pyridine compound having a structure of Formula II), pharmaceutically acceptable salts or pharmaceutically acceptable solvates thereof,

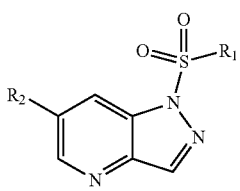 (II)

wherein:
- $R_1$ is substituted or unsubstituted $C_6$-$C_{20}$ aryl; substituted or unsubstituted 5- to 10- membered heteroaryl containing 1-5 heteroatoms selected from the group consisting of N, O, and S; or substituted or unsubstituted 4- to 10-membered heterocyclyl containing 1-5 heteroatoms selected from the group consisting of N, O, and S; wherein, substituent in the substituted group is halogen, nitro, cyano, hydroxyl, unsubstituted or halogen- or morpholinyl-substituted $C_1$-$C_6$ alkyl, $C_1$-$C_6$ alkoxy, $C_1$-$C_6$ alkylcarbonyl, $C_1$-$C_6$ alkoxycarbonyl, —$NR_aR_b$, —C(O)($NR_aR_b$), unsubstituted phenyl or phenyl substituted by 1-4 of $R_3$, or unsubstituted 4- to 7-membered heteroaryl containing 1-5 heteroatoms selected from the group consisting of N, O, and S, or 4- to 7-membered heteroaryl containing 1-5 heteroatoms selected from the group consisting of N, O, and S substituted by 1-4 of $R_4$;
- $R_2$ is substituted or unsubstituted $C_6$-$C_{20}$ aryl; substituted or unsubstituted 5- to 10- membered heteroaryl containing 1-5 heteroatoms selected from the group consisting of N, O, and S; or substituted or unsubstituted 4- to 10-membered heterocyclyl containing 1-5 heteroatoms selected from the group consisting of N, O, and S; wherein, substituent in the substituted group is halogen, nitro, cyano, $C_1$-$C_4$ alkylenedioxy, unsubstituted or halogen- or —$NR_cR_d$-substituted $C_1$-$C_6$ alkyl or $C_3$-$C_6$ cycloalkyl, $C_1$-$C_6$ alkoxy, $C_1$-$C_6$ sulfamido, —$NR_aR_b$, —C(O)R', morpholinyl, or unsubstituted or R"-substituted piperidinyl;
- $R_3$ is halogen, nitro, cyano, $C_1$-$C_4$ alkylenedioxy, unsubstituted or halogen- or morpholinyl-substituted $C_1$-$C_6$ alkyl, $C_1$-$C_6$ alkoxy, —$NR_aR_b$, —C(O)R', or morpholinyl;
- $R_4$ is halogen, nitro, cyano, unsubstituted or halogen-substituted $C_1$-$C_6$ alkyl, $C_1$-$C_6$ alkoxy, —$NR_aR_b$, —C(O)R', or unsubstituted or $C_1$-$C_6$ alkoxycarbonyl-substituted piperidinyl;
- R' is $C_1$-$C_6$ alkyl, $C_1$-$C_6$ alkoxy, —$NR_aR_b$, or unsubstituted or halogen- or $C_1$-$C_6$ alkyl-substituted 4- to 7-membered heterocyclyl;
- R" is $C_1$-$C_6$ alkyl; $C_3$-$C_6$ cycloalkyl; $C_1$-$C_6$ alkylcarbonyl; $C_1$-$C_6$ alkoxycarbonyl; $C_3$-$C_6$cycloalkylcarbonyl; or unsubstituted benzoyl or benzoyl substituted by substituent(s) selected from the group consisting of halogen, $C_1$-$C_6$ alkyl, and halogen-substituted $C_1$-$C_6$ alkyl;
- $R_a$ and $R_b$ are each independently H, $C_1$-$C_6$ alkyl or $C_1$-$C_6$ alkylcarbonyl; and
- $R_c$ and $R_d$ are each independently H or $C_1$-$C_6$ alkyl; or, $R_c$ and $R_d$, together with the N atom to which they are attached, form 3- to 7-membered heterocyclyl.

2. The 5-member-heterocycle-fused pyridine compound, pharmaceutically acceptable salts or pharmaceutically acceptable solvates thereof, according to claim 1, wherein, $R_1$ is selected from phenyl, naphthyl, isoxazolyl, imidazo[2,1-b]thiazolyl, imidazo[1,2-a]pyridinyl, benzo[1,2,5]oxadiazolyl, imidazo[1,2-b]pyridazinyl, pyrazolo[1,5-a]imidazolyl, imidazo[1,2-a]pyrimidinyl; wherein substituent in the substituted group is halogen; nitro; hydroxyl; cyano; unsubstituted or halogen- or morpholinyl-substituted $C_1$-$C_5$ alkyl; $C_1$-$C_5$ alkoxy; $C_1$-$C_5$ alkylcarbonyl; $C_1$-$C_5$ alkoxycarbonyl; —$NR_aR_b$; —C(O)($NR_aR_b$); unsubstituted phenyl or phenyl substituted by 1-3 of $R_3$; or unsubstituted 5-7 membered heteroaryl comprising 1-3 heteroatoms selected from N, O, and S or 5-7 membered heteroaryl comprising 1-3 heteroatoms selected from N, O, and S substituted by 1-3 of $R_4$, wherein said heteroaryl is selected from the group consisting of furanyl, thienyl, pyrrolyl, pyrazolyl, imidazolyl, oxazolyl, isoxazolyl, pyranyl, pyridinyl, morpholinyl, oxazinyl and pyrazinyl;
- $R_2$ is substituted or unsubstituted $C_6$-$C_{10}$ aryl; substituted or unsubstituted 5-10 membered heteroaryl comprising 1-5 heteroatoms selected from N, O, and S; or substituted or unsubstituted 5-10 membered heterocyclyl comprising 1-5 heteroatoms selected from N, O, and S; wherein, substituent in the substituted group is halogen, nitro, cyano, $C_1$-$C_4$ alkylenedioxy; unsubstituted $C_1$-$C_5$ alkyl or $C_1$-$C_5$ alkyl substituted by halogen or —$NR_cR_d$; $C_1$-$C_5$ alkoxy; $C_1$-$C_5$ sulfamido; —$NR_aR_b$; —C(O)R'; morpholinyl; or unsubstituted or R"-substituted piperidinyl;
- $R_3$ is halogen; nitro; cyano; $C_1$-$C_4$ alkylenedioxy; unsubstituted or halogen- or morpholinyl-substituted $C_1$-$C_5$ alkyl; $C_1$-$C_5$ alkoxy; —$NR_aR_b$; —C(O)R'; or morpholinyl;
- $R_4$ is halogen, nitro, cyano, unsubstituted or halogen-substituted $C_1$-$C_5$ alkyl; $C_1$-$C_5$ alkoxy; —$NR_aR_b$; —C(O)R'; or unsubstituted or $C_1$-$C_5$ alkoxycarbonyl-substituted piperidinyl;
- R' is $C_1$-$C_5$ alkyl; $C_1$-$C_5$ alkoxy; —$NR_aR_b$; or unsubstituted or halogen- or $C_1$-$C_5$ alkyl-substituted 5-6 membered heterocyclyl;
- R" is $C_1$-$C_5$ alkyl; $C_3$-$C_6$ cycloalkyl; $C_1$-$C_5$ alkylcarbonyl; $C_1$-$C_5$ alkoxycarbonyl; $C_3$-$C_6$ cycloalkylcarbonyl; or unsubstituted benzoyl or benzoyl substituted by substituent(s) selected from halogen, $C_1$-$C_5$ alkyl, halogen-substituted $C_1$-$C_5$ alkyl;
- $R_a$ and $R_b$ are independently H or $C_1$-$C_5$ alkyl; and
- $R_c$ and $R_d$ are independently H or $C_1$-$C_5$ alkyl; or, $R_c$ and $R_d$, together with the N atom to which they are attached, form 3-7 membered heterocyclyl.

3. The 5-member-heterocycle-fused pyridine compound, pharmaceutically acceptable salts or pharmaceutically acceptable solvates thereof, according to claim 1, wherein $R_1$ is—

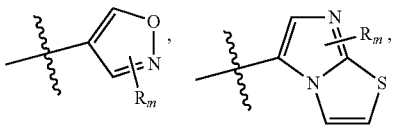

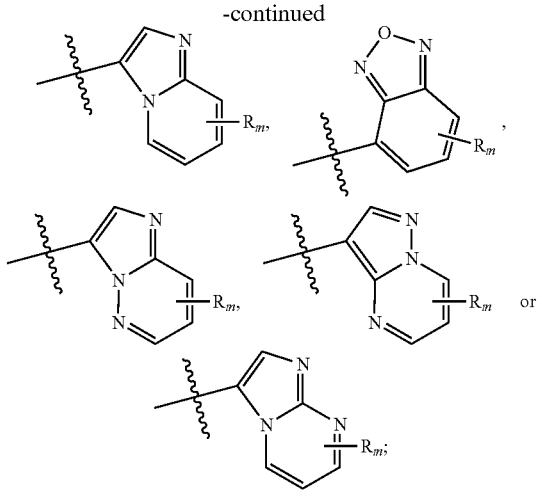

wherein, $R_m$ is H, halogen, nitro, cyano; unsubstituted or halogen- or morpholinyl-substituted $C_1$-$C_4$ alkyl; $C_1$-$C_4$ alkoxy; $C_1$-$C_4$ alkylcarbonyl; $C_1$-$C_4$ alkoxycarbonyl; —$NR_aR_b$; —$C(O)(NR_aR_b)$; unsubstituted phenyl or phenyl substituted by 1-3 of $R_3$; or unsubstituted 5- to 7-membered heteroaryl containing 1-3 heteroatoms selected from the group consisting of N, O, and S or 5- to 7-membered heteroaryl containing 1-3 heteroatoms selected from the group consisting of N, O, and S substituted by 1-3 of $R_4$, wherein said heteroaryl is selected from the group consisting of furanyl, thienyl, pyrrolyl, pyrazolyl, imidazolyl, oxazolyl, isoxazolyl, pyranyl, pyridinyl, morpholinyl, oxazinyl, and pyrazinyl;

$R_2$ is substituted or unsubstituted $C_6$-$C_{20}$ aryl; substituted or unsubstituted 5- to 10- membered heteroaryl containing 1-5 heteroatoms selected from the group consisting of N, O, and S; or substituted or unsubstituted 4- to 10-membered heterocyclyl containing 1-5 heteroatoms selected from the group consisting of N, O, and S; wherein, substituent in the substituted group is halogen, nitro, cyano, $C_1$-$C_4$ alkylenedioxy, unsubstituted or halogen- or —$NR_cR_d$-substituted $C_1$-$C_6$ alkyl, $C_1$-$C_6$ alkoxy, $C_1$-$C_6$ sulfamido, —$NR_aR_b$, —$C(O)R'$, morpholinyl, or unsubstituted or R"-substituted piperidinyl;

$R_3$ is halogen, nitro, cyano, $C_1$-$C_2$ alkylenedioxy, unsubstituted or halogen- or morpholinyl-substituted $C_1$-$C_4$ alkyl, $C_1$-$C_4$ alkoxy, —$NR_aR_b$, —$C(O)R'$, or 4-morpholinyl;

$R_4$ is halogen, nitro, cyano, unsubstituted or halogen-substituted $C_1$-$C_4$ alkyl, $C_1$-$C_4$ alkoxy, —$NR_aR_b$, —$C(O)R'$, 4-piperidinyl, or 1-t-butoxycarbonyl-4-piperidinyl;

$R'$ is $C_1$-$C_4$ alkyl, $C_1$-$C_4$ alkoxy, —$NR_aR_b$, or 4-methylpiperazinyl;

$R''$ is $C_1$-$C_4$ alkyl, $C_3$-$C_6$ cycloalkyl, $C_1$-$C_4$ alkylcarbonyl, $C_1$-$C_4$ alkoxycarbonyl, $C_3$-$C_6$ cycloalkylcarbonyl, or p-trifluoromethylbenzoyl;

$R_a$ and $R_b$ are each independently H, $C_1$-$C_4$ alkyl or $C_1$-$C_4$ alkylcarbonyl; and $R_c$ and $R_d$ are each independently H or $C_1$-$C_6$ alkyl; or, $R_c$ and $R_d$, together with the N atom to which they are attached, form 3- to 7-membered heterocyclyl.

4. The 5-member-heterocycle-fused pyridine compound, pharmaceutically acceptable salts or pharmaceutically acceptable solvates thereof, according to claim 1, wherein $R_1$ is

[structure]

$R_2$ is

[structures]

wherein, $R_m$ is H, halogen, nitro, hydroxyl, $C_1$-$C_4$ alkoxy, unsubstituted phenyl or phenyl substituted by 1-3 of $R_3$, or unsubstituted 5- to 7-membered heteroaryl containing 1-3 heteroatoms selected from the group consisting of N, O, and S, or 5- to 7-membered heteroaryl containing 1-3 heteroatoms selected from the group consisting of N, O, and S substituted by 1-3 of $R_4$, wherein said heteroaryl is selected from the group consisting of furanyl, thienyl, pyrrolyl, pyrazolyl, imidazolyl, oxazolyl, isoxazolyl, pyranyl, pyridinyl, morpholinyl, oxazinyl, and pyrazinyl;

$R_n$ is H, halogen; nitro; cyano; unsubstituted or halogen-, dimethylamino-, 4-morpholinyl-, 1-aziridinyl-, 1-azetidinyl-, 1-tetrahydropyrrolyl-, 1-piperidinyl- or 1-homopiperidinyl- substituted $C_1$-$C_4$ alkyl; $C_1$-$C_4$ alkoxy; $C_1$-$C_4$ sulfamido; —$NR_aR_b$; —$C(O)R'$; 4-morpholinyl; or unsubstituted or R"-substituted piperidinyl;

$R_3$ is halogen, nitro, cyano, $C_1$-$C_4$ alkylenedioxy, unsubstituted or halogen- or morpholinyl- substituted $C_1$-$C_6$ alkyl, $C_1$-$C_6$ alkoxy, —$NR_aR_b$, —$C(O)R'$, or morpholinyl;

$R_4$ is halogen, nitro, cyano, unsubstituted or halogen-substituted $C_1$-$C_6$ alkyl, $C_1$-$C_6$ alkoxy, —$NR_aR_b$, —$C(O)R'$, or unsubstituted or $C_1$-$C_6$ alkoxycarbonyl-substituted piperidinyl; $R'$ is $C_1$-$C_4$ alkyl, $C_1$-$C_4$ alkoxy, —$NR_aR_b$, or 4-methylpiperazinyl;

$R''$ is $C_1$-$C_4$ alkyl, $C_3$-$C_6$ cycloalkyl, $C_1$-$C_4$ alkylcarbonyl, $C_1$-$C_4$ alkoxycarbonyl, $C_3$-$C_6$ cycloalkylcarbonyl, or p-trifluoromethylbenzoyl;

$R_a$ and $R_b$ are independently H, $C_1$-$C_4$ alkyl or $C_1$-$C_4$ alkylcarbonyl.

5. The 5-member-heterocycle-fused pyridine compound, pharmaceutically acceptable salts or pharmaceutically acceptable solvates thereof, according to claim 1, wherein, the 5-member-heterocycle fused pyridine compound is selected from the group consisting of the following compounds:

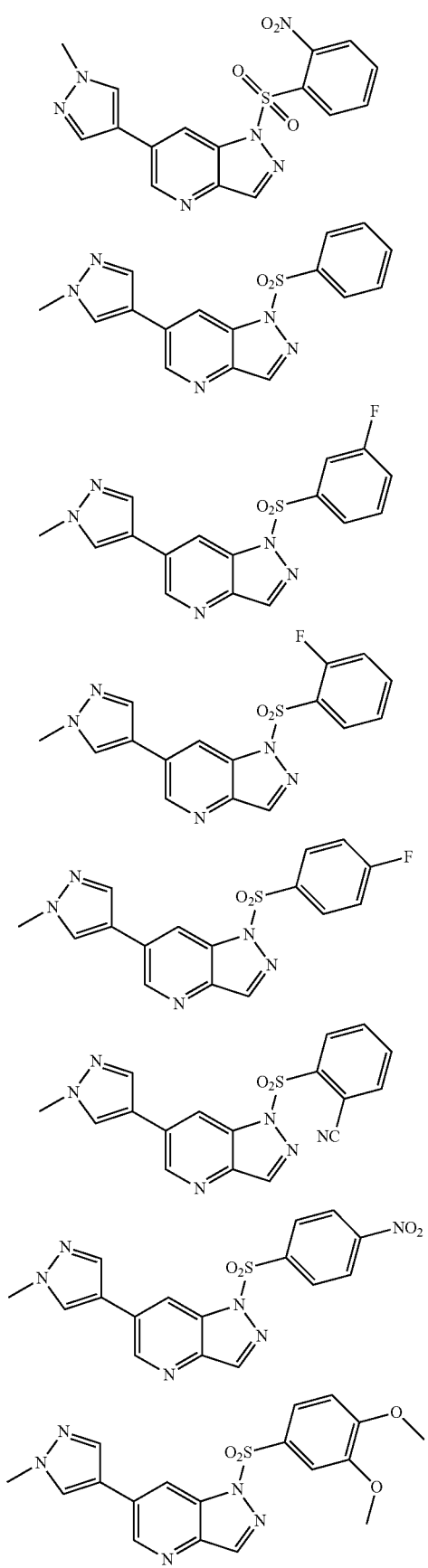
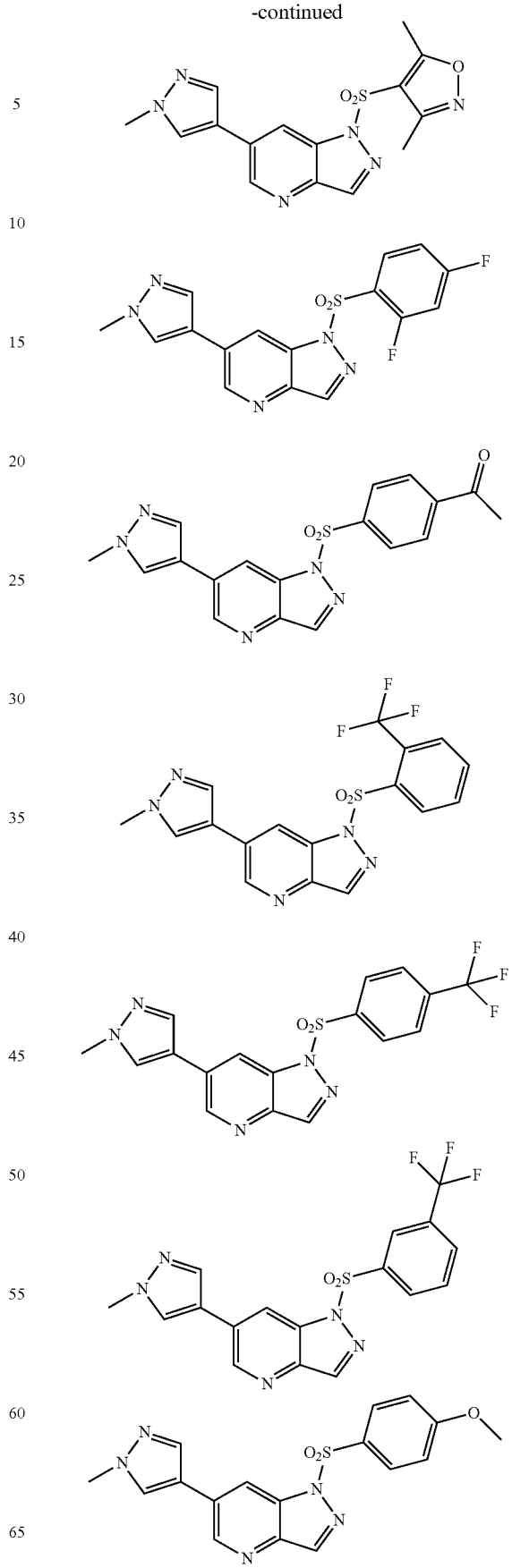

167
-continued
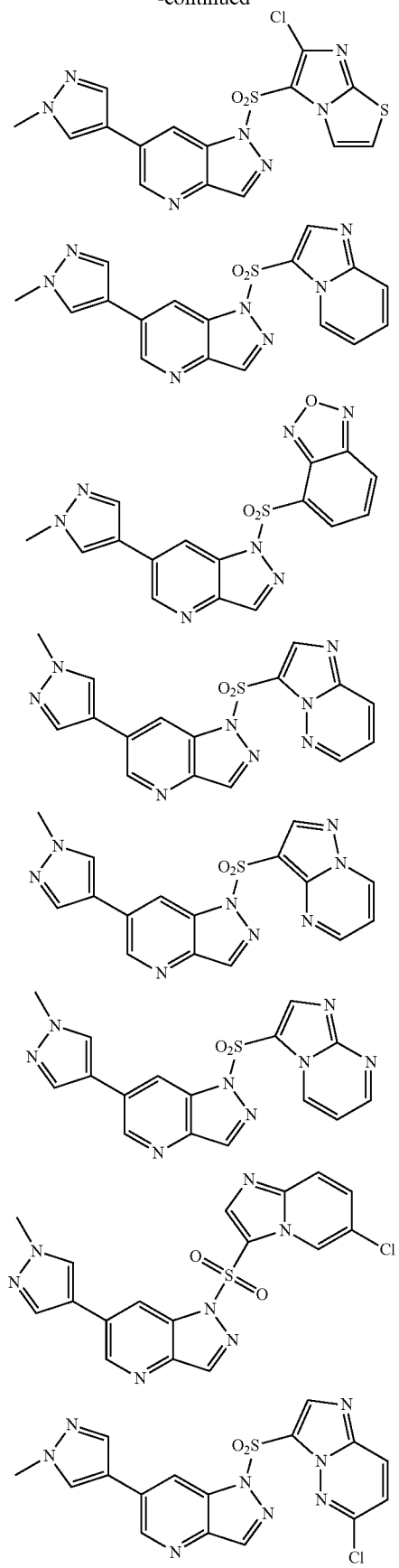
168
-continued
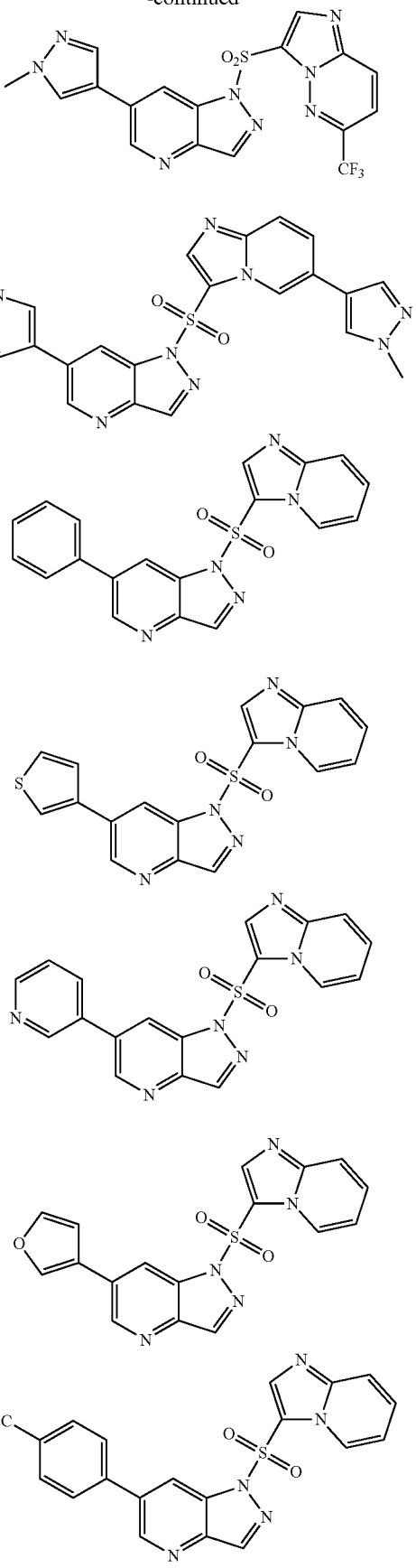

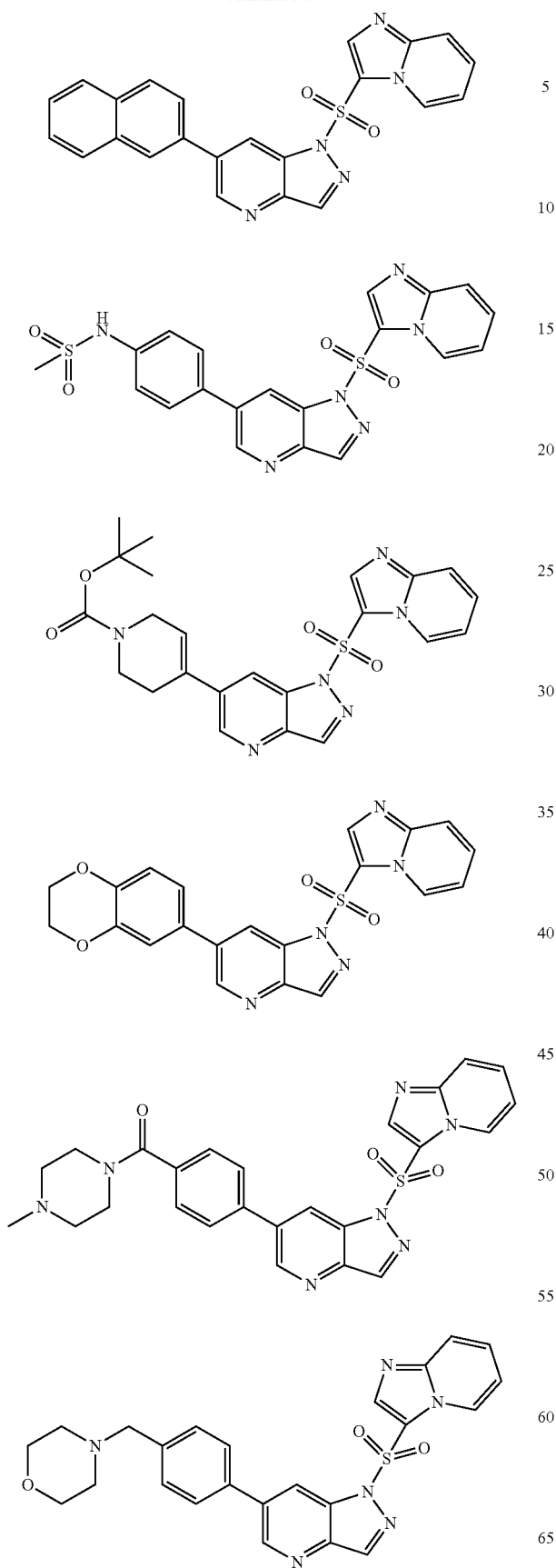
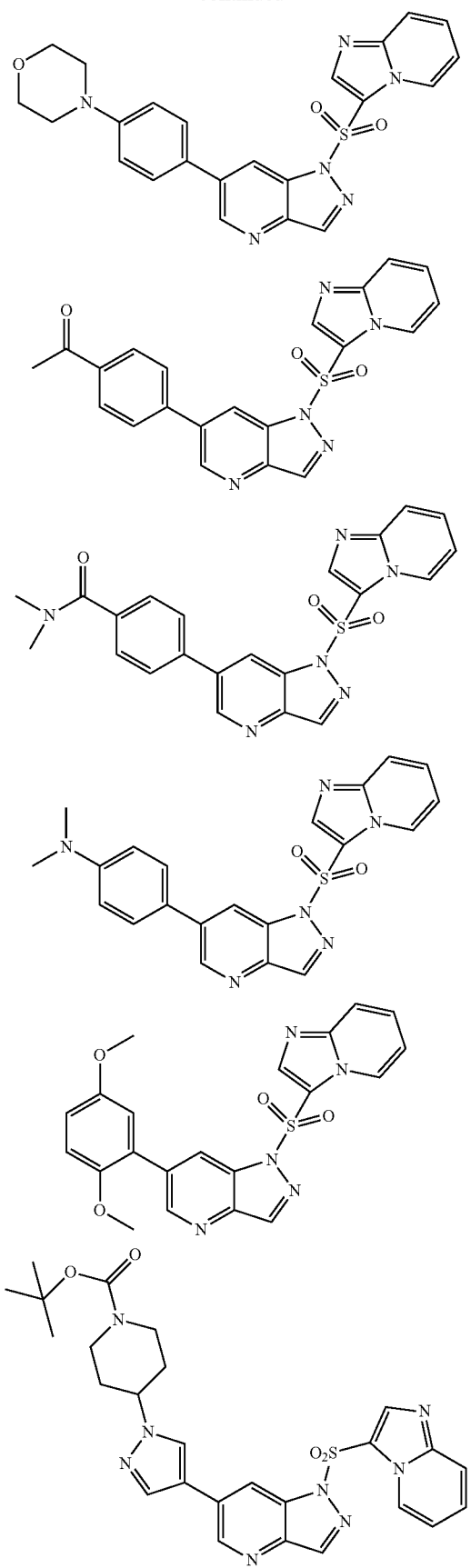

171
-continued
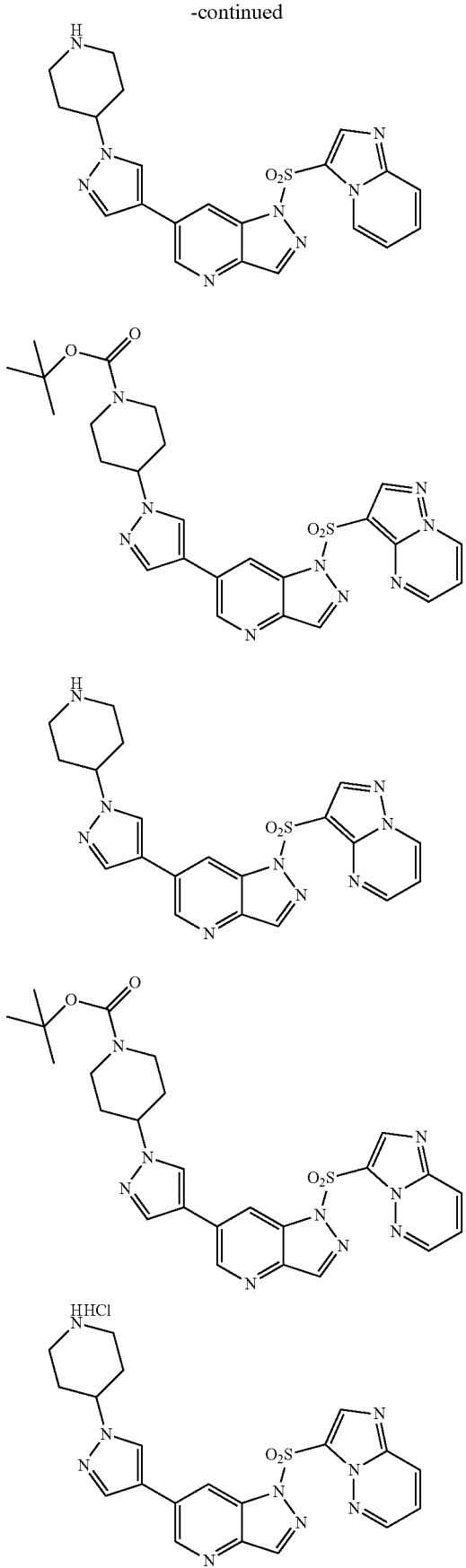
172
-continued
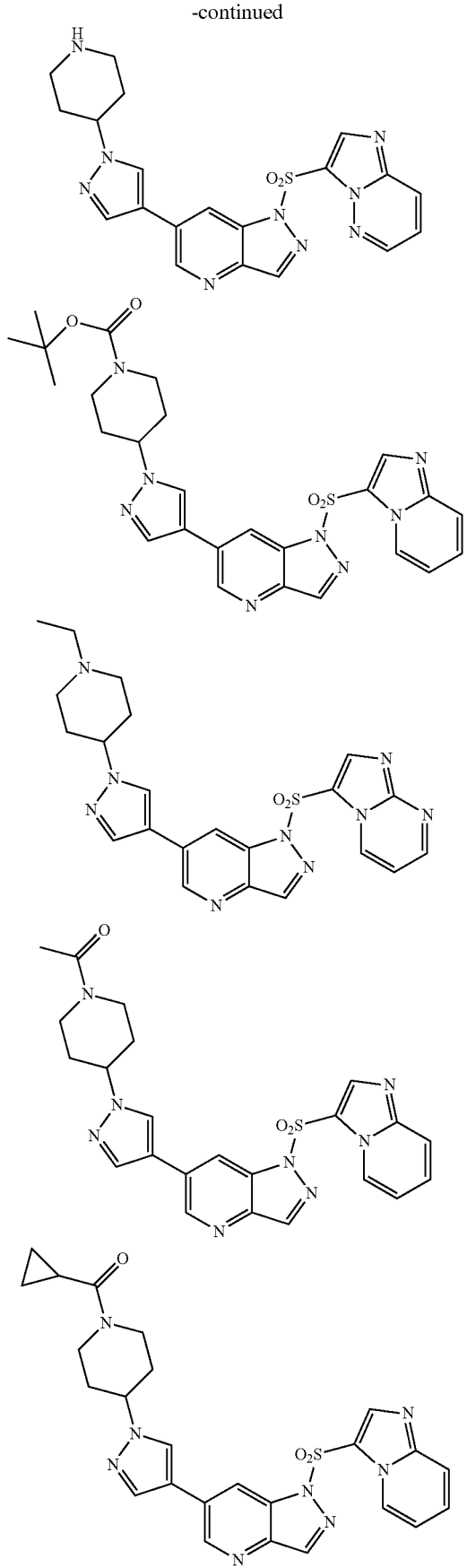

173
-continued
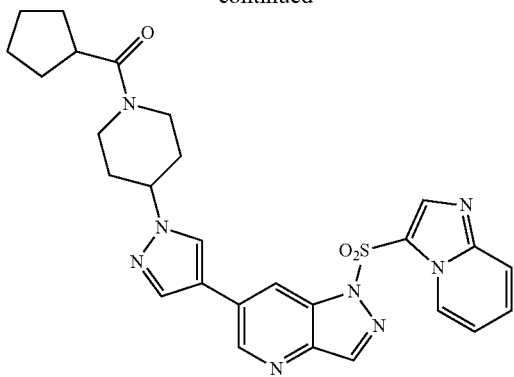
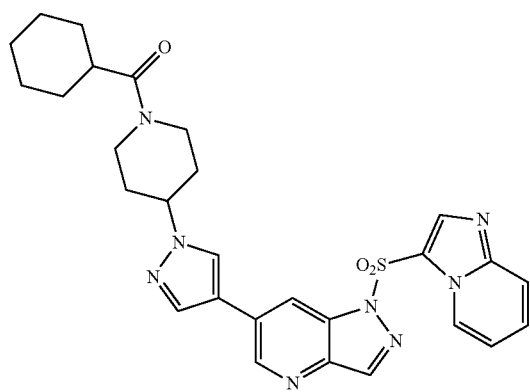
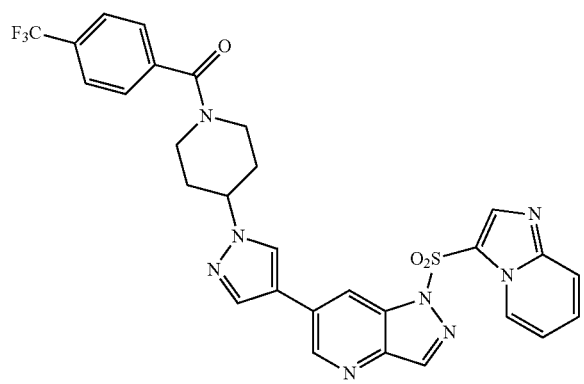
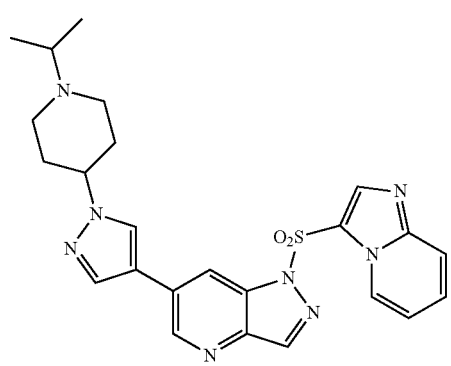
174
-continued
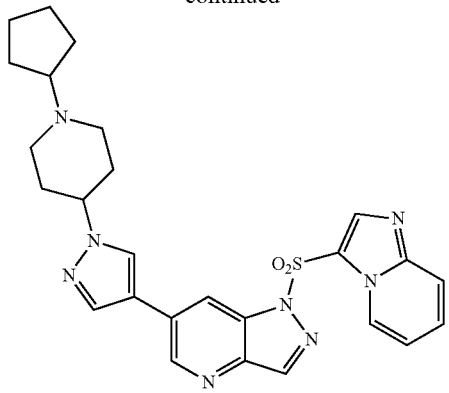
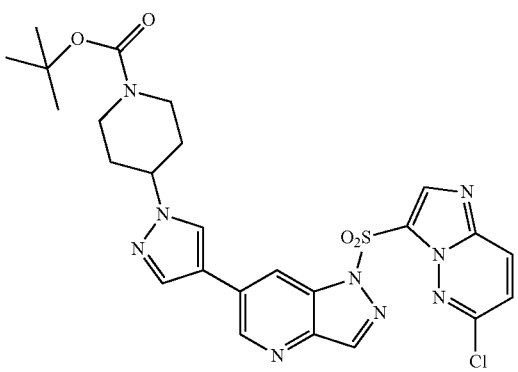
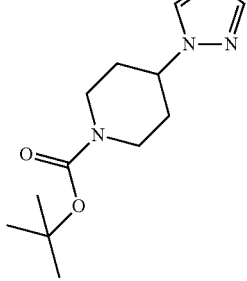

175
-continued
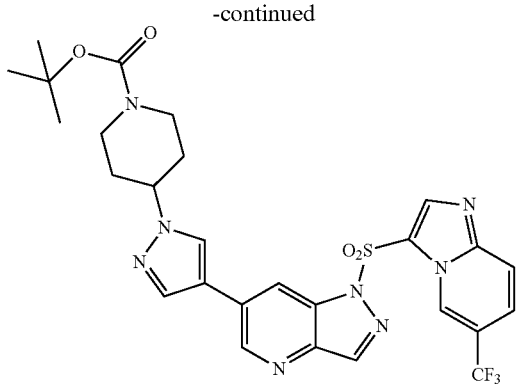
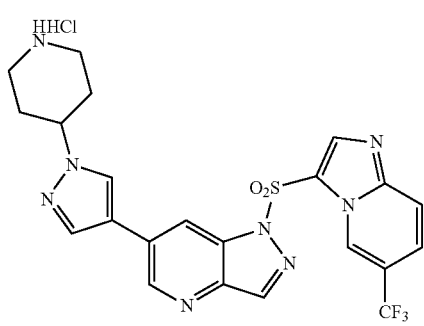
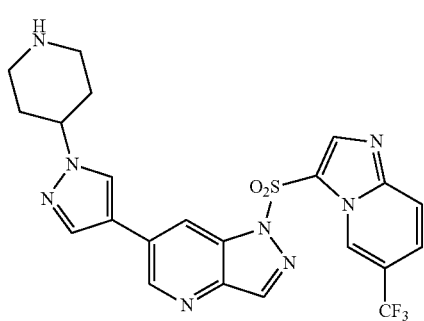
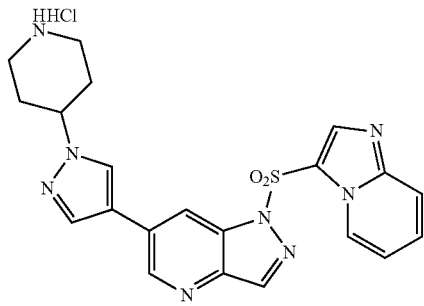
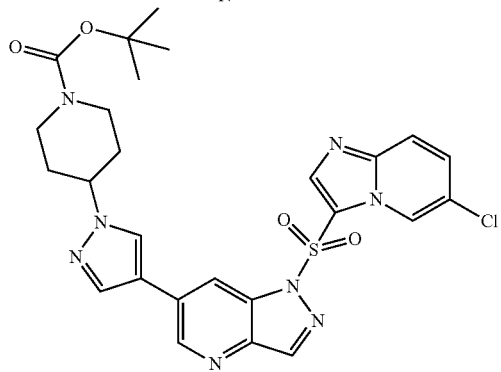
176
-continued
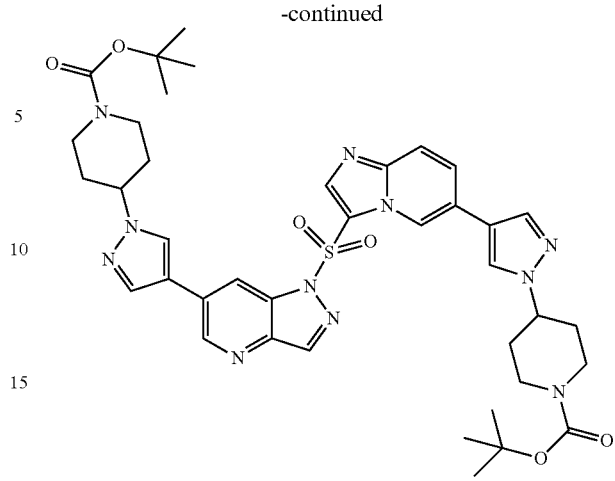
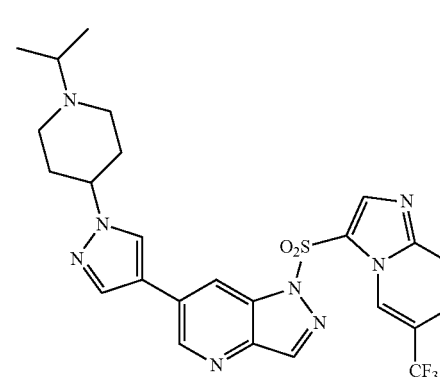
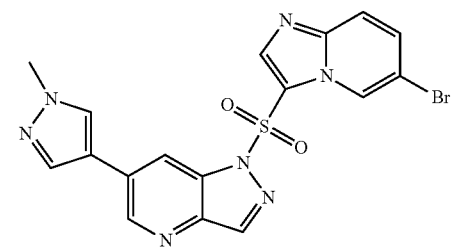
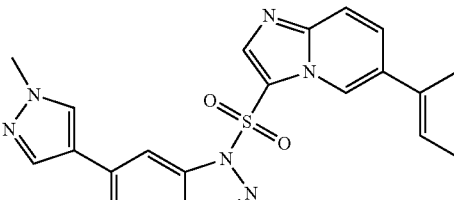
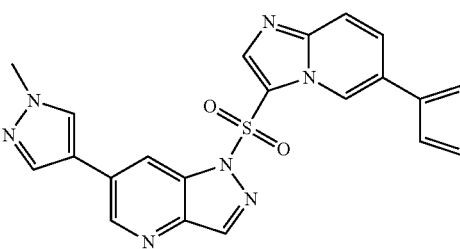

-continued
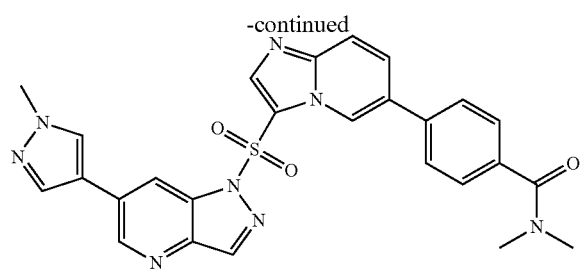
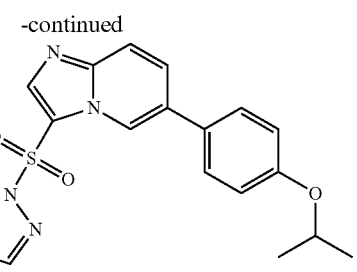
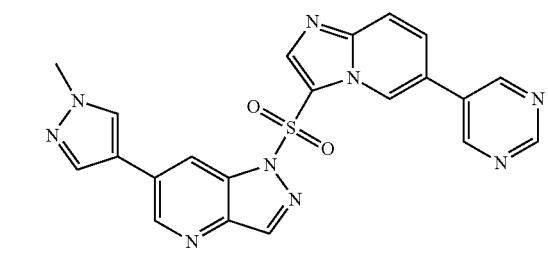
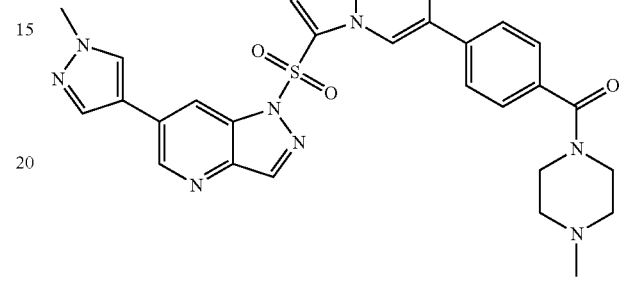
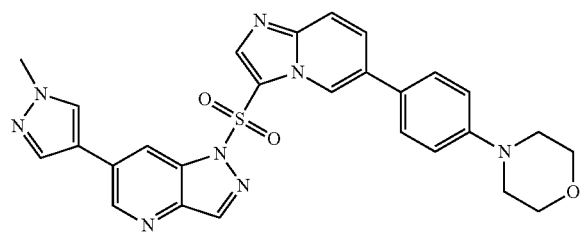
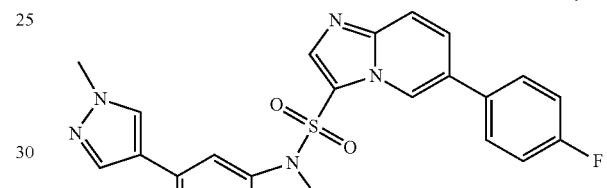
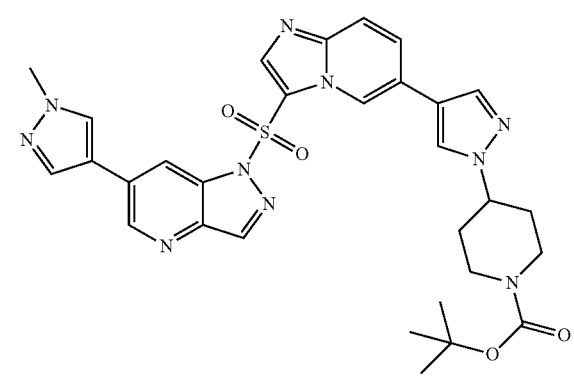
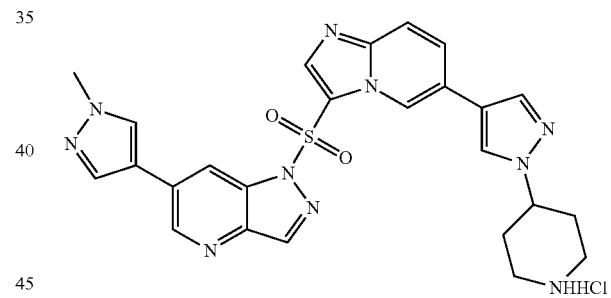
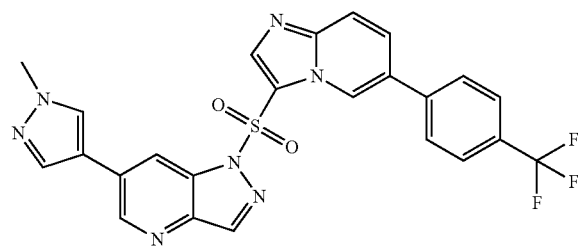
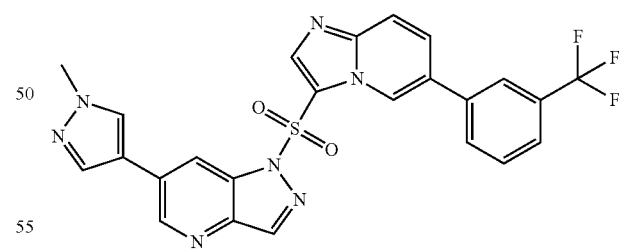
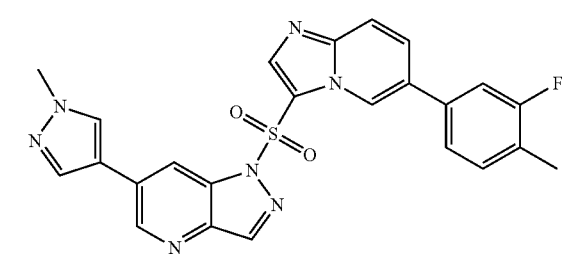
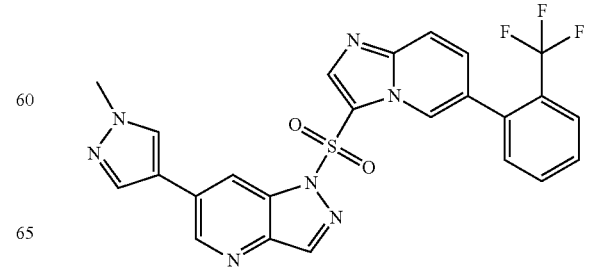

179
-continued
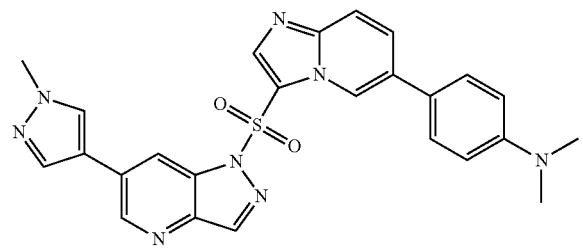
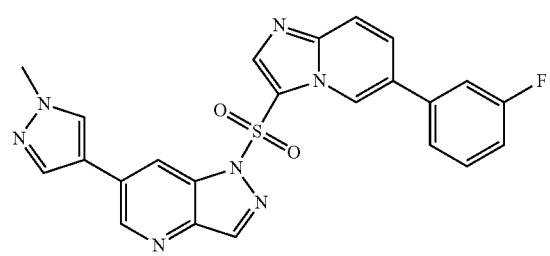
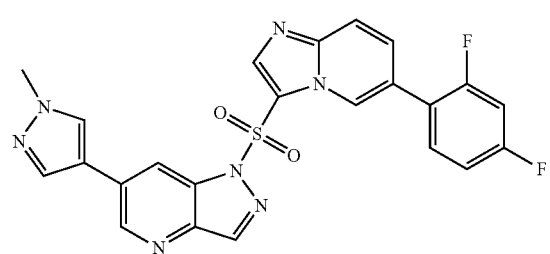
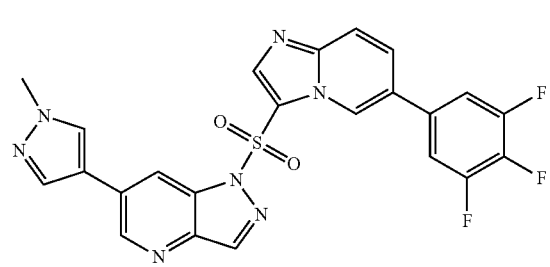
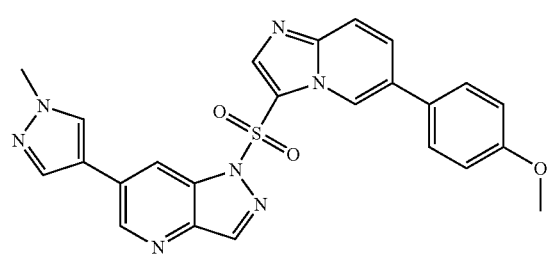
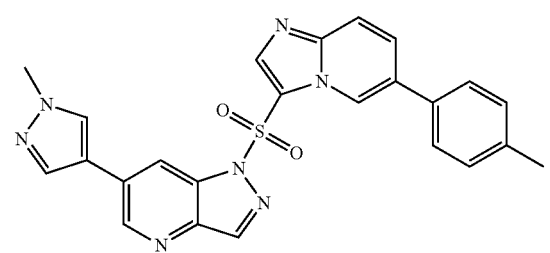
180
-continued
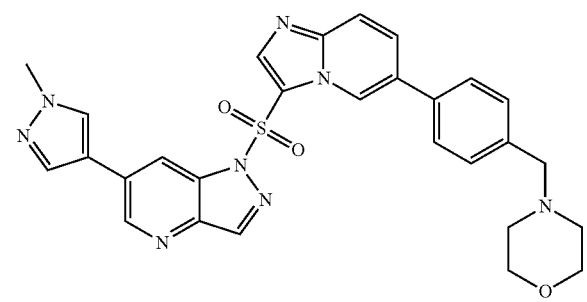
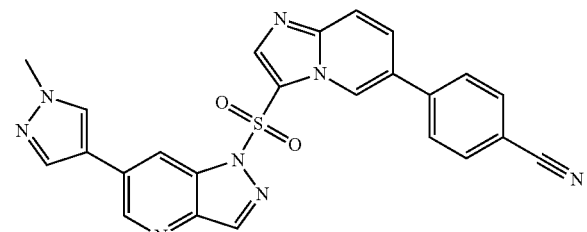
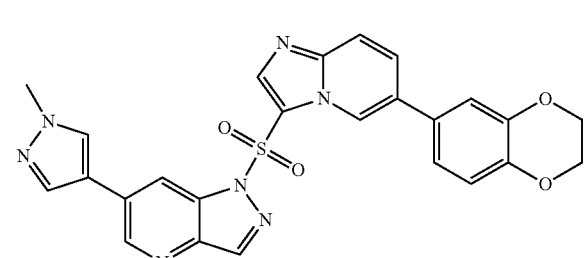
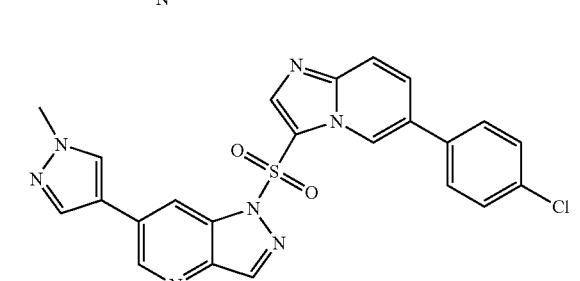
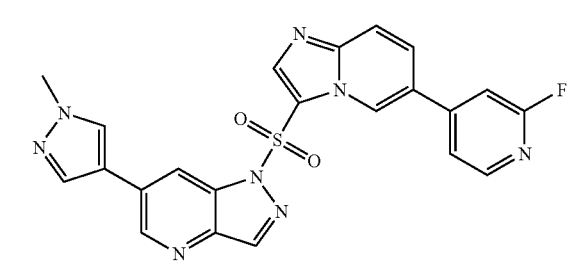
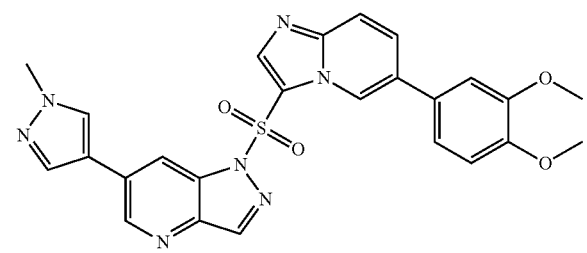

181
-continued
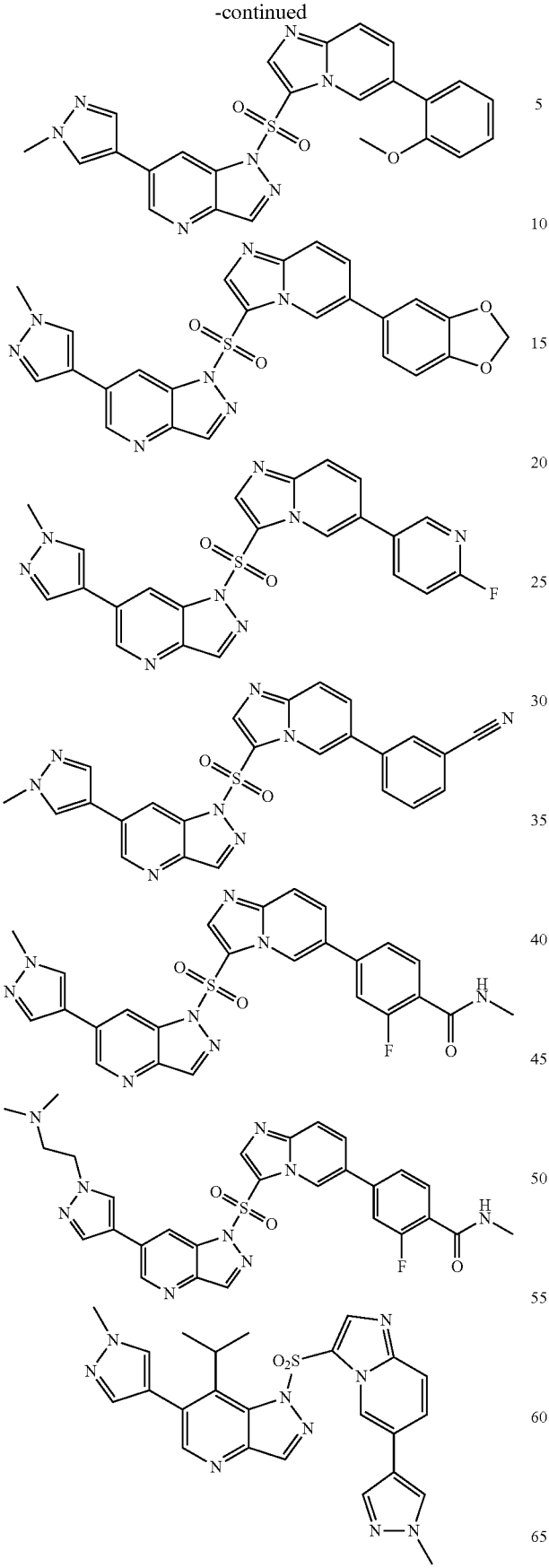
182
-continued
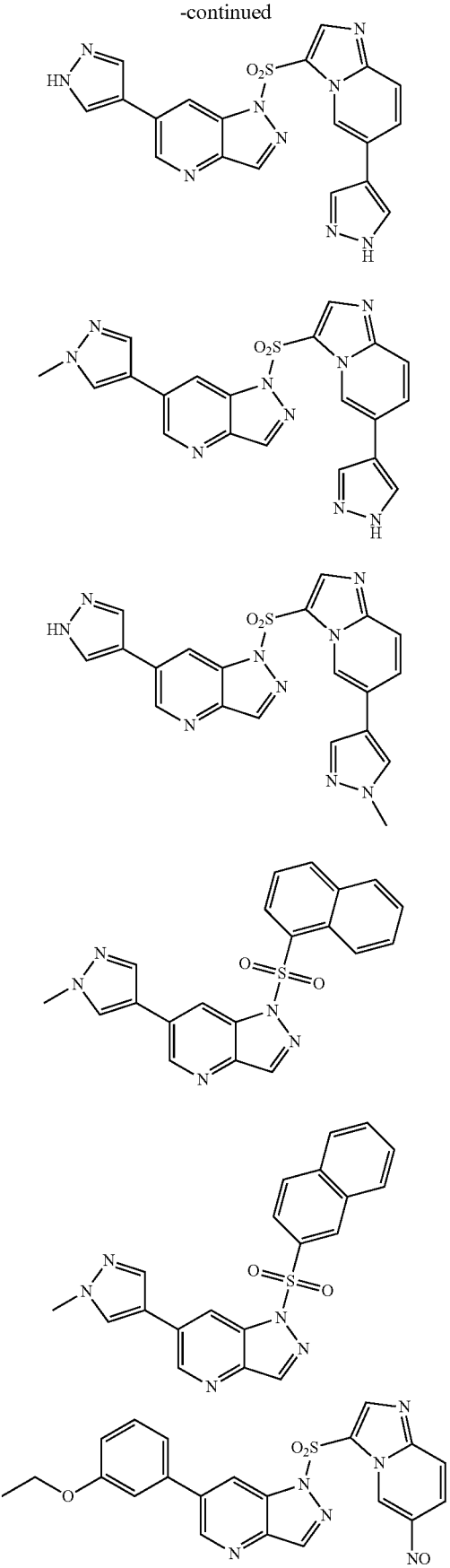

-continued
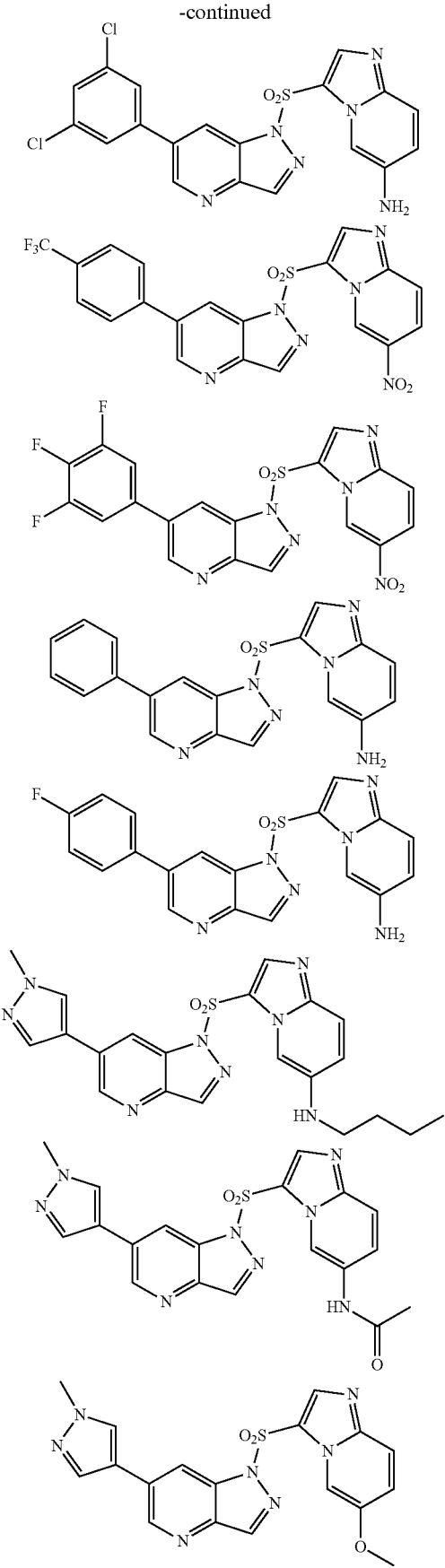
-continued
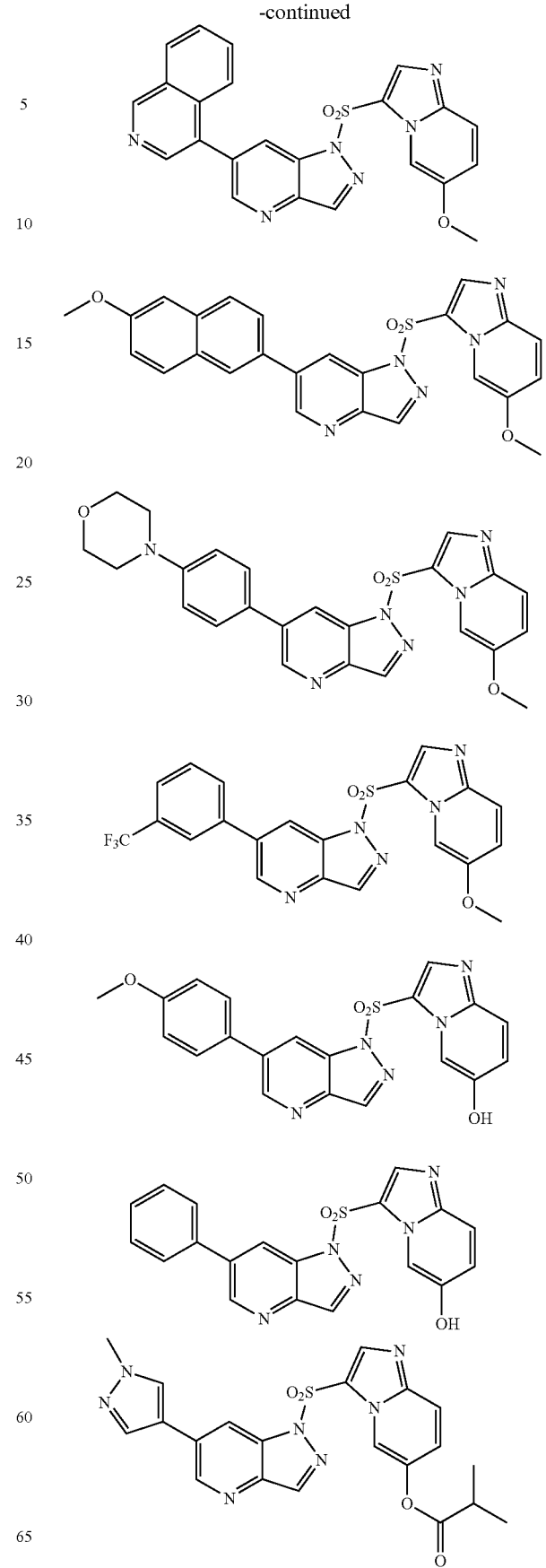

185
-continued
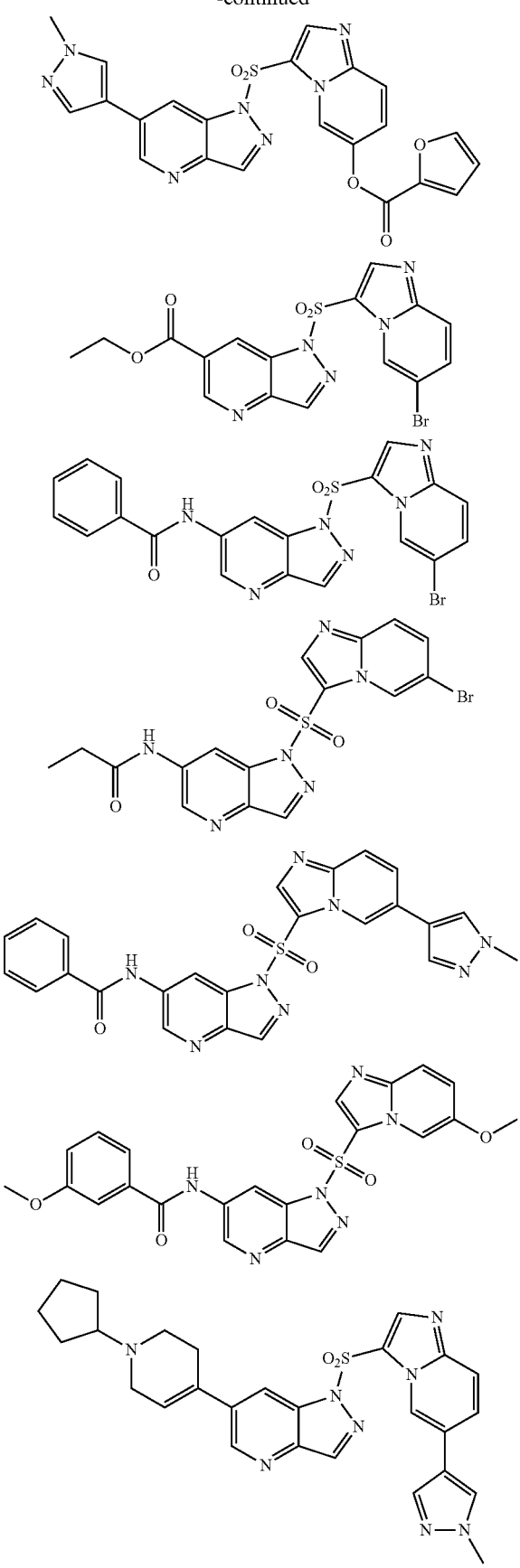
186
-continued
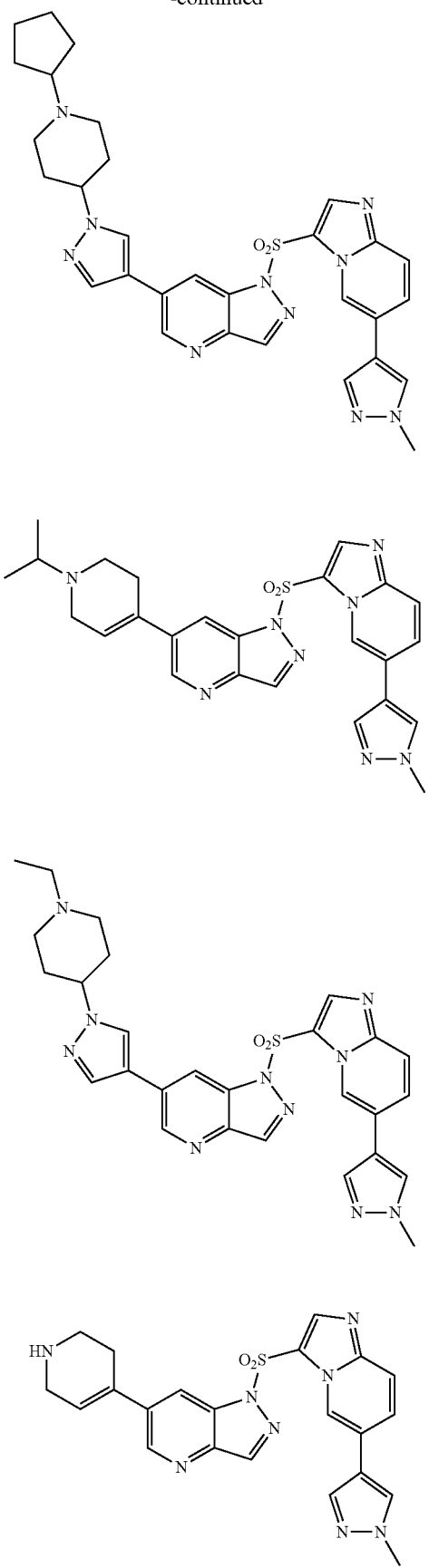

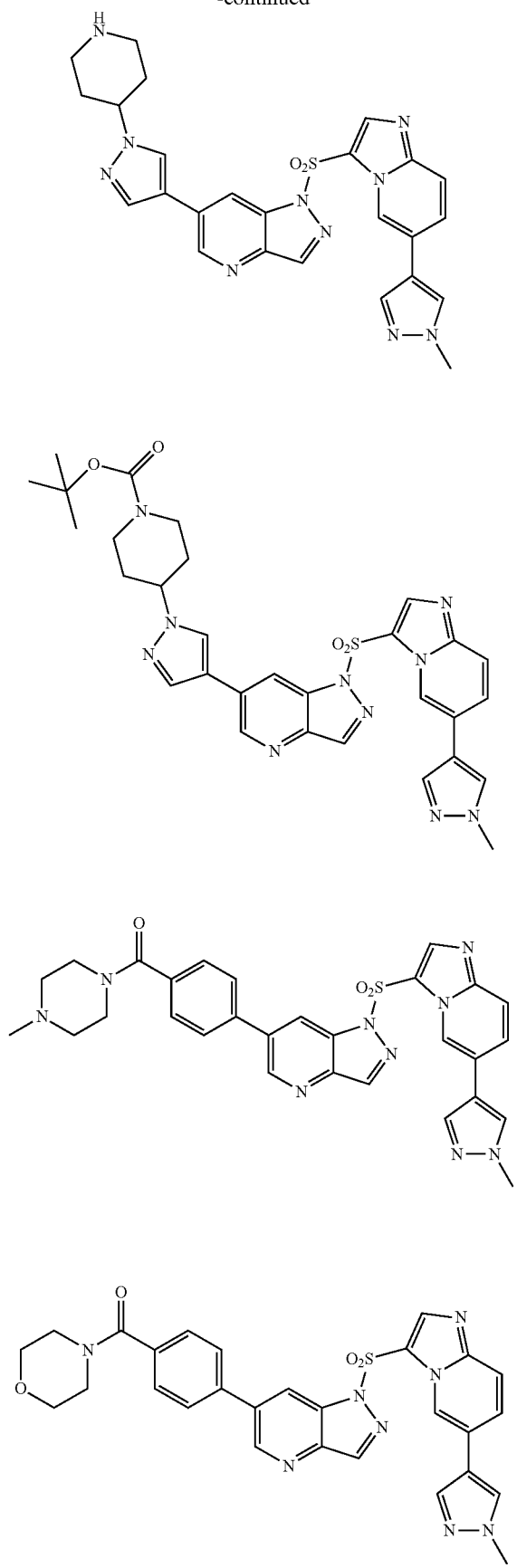

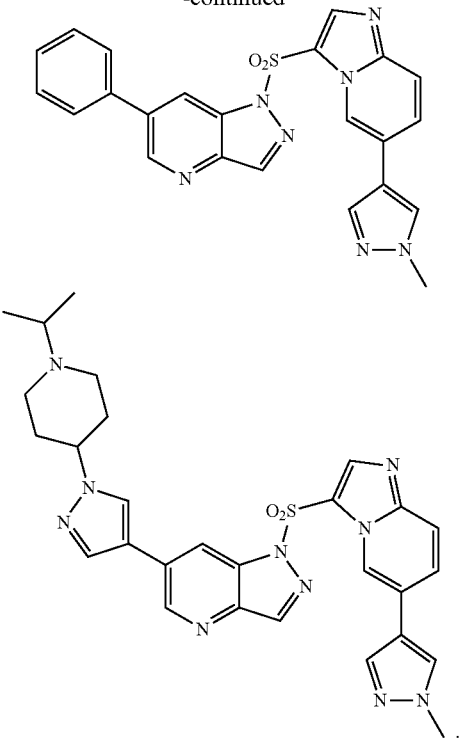

6. A pharmaceutical composition comprising a therapeutically effective amount of one or more 5-member-heterocycle-fused pyridine compound, pharmaceutically acceptable salts or pharmaceutically acceptable solvates thereof according to claim 1, and a pharmaceutically acceptable excipient.

7. The pharmaceutical composition of claim 6, wherein in the 5-member-heterocycle-fused pyridine compound, pharmaceutically acceptable salts or pharmaceutically acceptable solvates thereof, $R_1$ is selected from phenyl, naphthyl, isoxazolyl, imidazo[2,1-b]thiazolyl, imidazo[1,2-a]pyridinyl, benzo[1,2,5]oxadiazolyl, imidazo[1,2-b]pyridazinyl, pyrazolo[1,5-a]imidazolyl, imidazo[1,2-a]pyrimidinyl; wherein substituent in the substituted group is halogen; nitro; hydroxyl; cyano; unsubstituted or halogen- or morpholinyl-substituted $C_1$-$C_5$ alkyl; $C_1$-$C_5$ alkoxy; $C_1$-$C_5$ alkylcarbonyl; $C_1$-$C_5$ alkoxycarbonyl; —$NR_aR_b$; —$C(O)(NR_aR_b)$; unsubstituted phenyl or phenyl substituted by 1-3 of $R_3$; or unsubstituted 5-7 membered heteroaryl comprising 1-3 heteroatoms selected from N, O, and S or 5-7 membered heteroaryl comprising 1-3 heteroatoms selected from N, O, and S substituted by 1-3 of $R_4$, wherein said heteroaryl is selected from the group consisting of furanyl, thienyl, pyrrolyl, pyrazolyl, imidazolyl, oxazolyl, isoxazolyl, pyranyl, pyridinyl, morpholinyl, oxazinyl and pyrazinyl;

$R_2$ is substituted or unsubstituted $C_6$-$C_{10}$ aryl; substituted or unsubstituted 5-10 membered heteroaryl comprising 1-5 heteroatoms selected from N, O, and S; or substituted or unsubstituted 5-10 membered heterocyclyl comprising 1-5 heteroatoms selected from N, O, and S; wherein, substituent in the substituted group is halogen, nitro, cyano, $C_1$-$C_4$ alkylenedioxy; unsubstituted $C_1$-$C_5$ alkyl or $C_1$-$C_5$ alkyl substituted by halogen or —NR$_c$R$_d$; C$_1$-C$_5$ alkoxy; C$_1$-C$_5$ sulfamido; —NR$_a$R$_b$; —C(O)R'; morpholinyl; or unsubstituted or R"-substituted piperidinyl;

R$_3$ is halogen; nitro; cyano; C$_1$-C$_4$ alkylenedioxy; unsubstituted or halogen- or morpholinyl-substituted C$_1$-C$_5$ alkyl; C$_1$-C$_5$ alkoxy; —NR$_a$R$_b$; —C(O)R'; or morpholinyl;

R$_4$ is halogen, nitro, cyano, unsubstituted or halogen-substituted C$_1$-C$_5$ alkyl; C$_1$-C$_5$ alkoxy; —NR$_a$R$_b$; —C(O)R'; or unsubstituted or C$_1$-C$_5$ alkoxycarbonyl-substituted piperidinyl;

R' is C$_1$-C$_5$ alkyl; C$_1$-C$_5$ alkoxy; —NR$_a$R$_b$; or unsubstituted or halogen- or C$_1$-C$_5$ alkyl-substituted 5-6 membered heterocyclyl;

R" is C$_1$-C$_5$ alkyl; C$_3$-C$_6$ cycloalkyl; C$_1$-C$_5$ alkylcarbonyl; C$_1$-C$_5$ alkoxycarbonyl; C$_3$-C$_6$ cycloalkylcarbonyl; or unsubstituted benzoyl or benzoyl substituted by substituent(s) selected from halogen, C$_1$-C$_5$ alkyl, halogen-substituted C$_1$-C$_5$ alkyl;

R$_a$ and R$_b$ are independently H or C$_1$-C$_5$ alkyl; and

R$_c$ and R$_d$ are independently H or C$_1$-C$_5$ alkyl; or, R$_c$ and R$_d$, together with the N atom to which they are attached, form 3-7 membered heterocyclyl.

8. The pharmaceutical composition of claim 6, in the 5-member-heterocycle-fused pyridine compound, pharmaceutically acceptable salts or pharmaceutically acceptable solvates thereof,

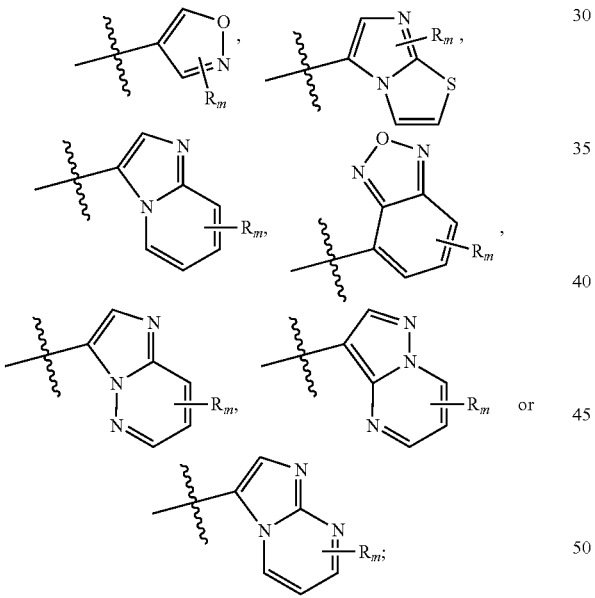

R$_m$ is H, halogen, nitro, cyano; unsubstituted or halogen- or morpholinyl-substituted C$_1$-C$_4$ alkyl; C$_1$-C$_4$ alkoxy; C$_1$-C$_4$ alkylcarbonyl; C$_1$-C$_4$ alkoxycarbonyl; —NR$_a$R$_b$; —C(O)(NR$_a$R$_b$); unsubstituted phenyl or phenyl substituted by 1-3 of R$_3$; or unsubstituted 5- to 7-membered heteroaryl containing 1-3 heteroatoms selected from the group consisting of N, O, and S, or 5- to 7-membered heteroaryl containing 1-3 heteroatoms selected from the group consisting of N, O, and S substituted by 1-3 of R$_4$, wherein said heteroaryl is selected from the group consisting of furanyl, thienyl, pyrrolyl, pyrazolyl, imidazolyl, oxazolyl, isoxazolyl, pyranyl, pyridinyl, morpholinyl, oxazinyl, and pyrazinyl;

R$_2$ is substituted or unsubstituted C$_6$-C$_{20}$ aryl; substituted or unsubstituted 5- to 10-membered heteroaryl containing 1-5 heteroatoms selected from the group consisting of N, O, and S; or substituted or unsubstituted 4- to 10-membered heterocyclyl containing 1-5 heteroatoms selected from the group consisting of N, O, and S; wherein, substituent in the substituted group is halogen, nitro, cyano, C$_1$-C$_4$ alkylenedioxy, unsubstituted or halogen- or —NR$_c$R$_d$-substituted C$_1$-C$_6$ alkyl, C$_1$-C$_6$ alkoxy, C$_1$-C$_6$ sulfamido, —NR$_a$R$_b$, —C(O)R', morpholinyl, or unsubstituted or R"-substituted piperidinyl;

R$_3$ is halogen, nitro, cyano, C$_1$-C$_2$ alkylenedioxy, unsubstituted or halogen- or morpholinyl- substituted C$_1$-C$_4$ alkyl, C$_1$-C$_4$ alkoxy, —NR$_a$R$_b$, —C(O)R', or 4-morpholinyl;

R$_4$ is halogen, nitro, cyano, unsubstituted or halogen-substituted C$_1$-C$_4$ alkyl, C$_1$-C$_4$ alkoxy, —NR$_a$R$_b$, —C(O)R', 4-piperidinyl, or 1-t-butoxycarbonyl-4-piperidinyl;

R' is C$_1$-C$_4$ alkyl, C$_1$-C$_4$ alkoxy, —NR$_a$R$_b$, or 4-methylpiperazinyl;

R" is C$_1$-C$_4$ alkyl, C$_3$-C$_6$ cycloalkyl, C$_1$-C$_4$ alkylcarbonyl, C$_1$-C$_4$ alkoxycarbonyl, C$_3$-C$_6$ cycloalkylcarbonyl, or p-trifluoromethylbenzoyl;

R$_a$ and R$_b$ are each independently H, C$_1$-C$_4$ alkyl or C$_1$-C$_4$ alkylcarbonyl; and R$_c$ and R$_d$ are each independently H or C$_1$-C$_6$ alkyl; or, R$_c$ and R$_d$, together with the N atom to which they are attached, form 3- to 7-membered heterocyclyl.

9. The pharmaceutical composition of claim 6, wherein in the 5-member-heterocycle-fused pyridine compound, pharmaceutically acceptable salts or pharmaceutically acceptable solvates thereof, R$_1$ is

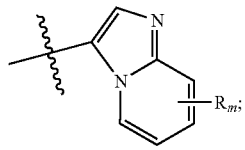

R$_2$ is

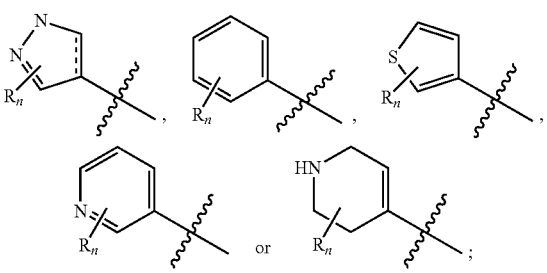

wherein, R$_m$ is H, halogen, nitro, hydroxyl, C$_1$-C$_4$ alkoxy, unsubstituted phenyl or phenyl substituted by 1-3 of R$_3$, or unsubstituted 5 to 7-membered heteroaryl containing 1-3 heteroatoms selected from the group consisting of N, O, and S, or 5 to 7-membered heteroaryl containing 1-3 heteroatoms selected from the group consisting of N, O, and S substituted by 1-3 of R$_4$, wherein said heteroaryl is selected from the group consisting of furanyl, thienyl, pyrrolyl, pyrazolyl, imidazolyl, oxazolyl, isoxazolyl, pyranyl, pyridinyl, morpholinyl, oxazinyl, and pyrazinyl;

$R_n$ is H, halogen; nitro; cyano; unsubstituted or halogen-, dimethylamino-, 4-morpholinyl-, 1-aziridinyl-, 1-azetidinyl-, 1-tetrahydropyrrolyl-, 1-piperidinyl- or 1-homopiperidinyl-substituted $C_1$-$C_4$ alkyl; $C_1$-$C_4$ alkoxy; $C_1$-$C_4$ sulfamido; —$NR_aR_b$; —C(O)R'; 4-morpholinyl; or unsubstituted or R"-substituted piperidinyl;

$R_3$ is halogen, nitro, cyano, $C_1$-$C_4$ alkylenedioxy, unsubstituted or halogen- or morpholinyl-substituted $C_1$-$C_6$ alkyl, $C_1$-$C_6$ alkoxy, —$NR_aR_b$ —C(O)R', or morpholinyl;

$R_4$ is halogen, nitro, cyano, unsubstituted or halogen-substituted $C_1$-$C_6$ alkyl, $C_1$-$C_6$ alkoxy, —$NR_aR_b$ —C(O)R', or unsubstituted or $C_1$-$C_6$ alkoxycarbonyl-substituted piperidinyl;

R' is $C_1$-$C_4$ alkyl, $C_1$-$C_4$ alkoxy, —$NR_aR_b$ or 4-methylpiperazinyl;

R" is $C_1$-$C_4$ alkyl, $C_3$-$C_6$ cycloalkyl, $C_1$-$C_4$ alkylcarbonyl, $C_1$-$C_4$ alkoxycarbonyl, $C_3$-$C_6$ cycloalkylcarbonyl, or p-trifluoromethylbenzoyl; and $R_a$ and $R_b$ are independently H, $C_1$-$C_4$ alkyl or $C_1$-$C_4$ alkylcarbonyl.

10. The pharmaceutical composition of claim 6, wherein the compound is selected from the group consisting of:

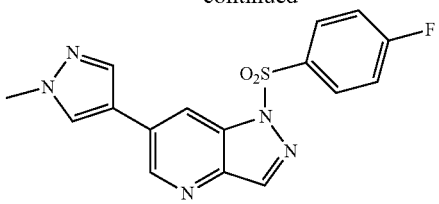

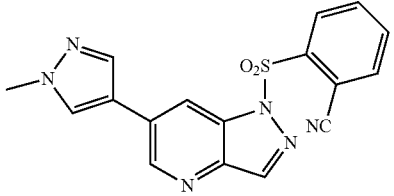

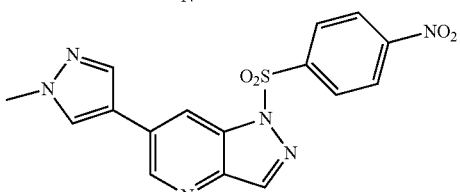

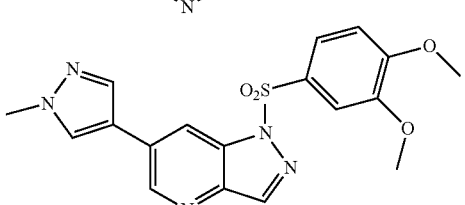

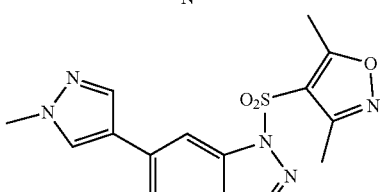

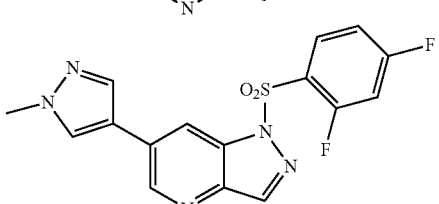

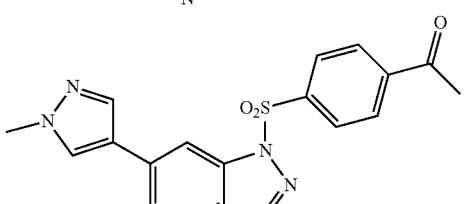

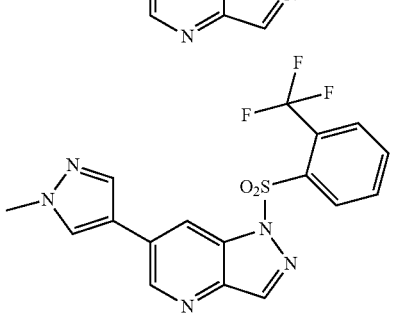

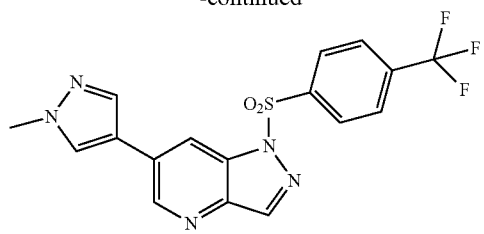
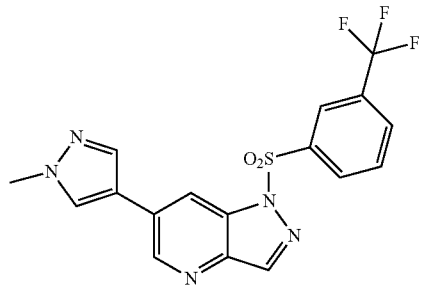
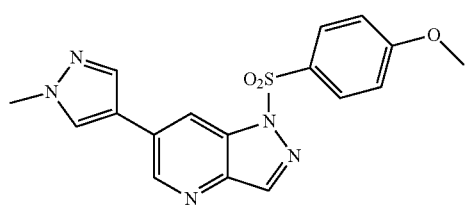
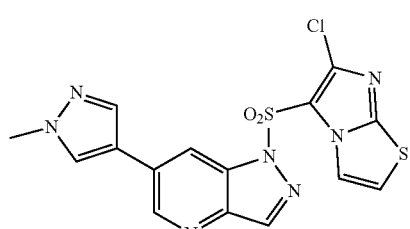
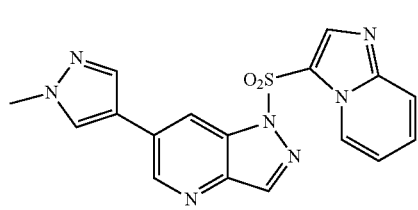
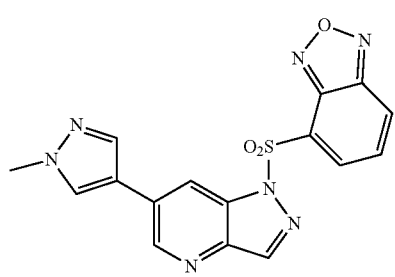
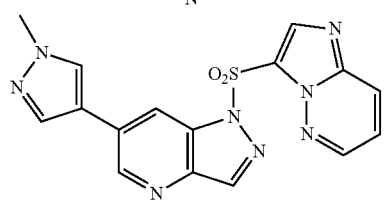
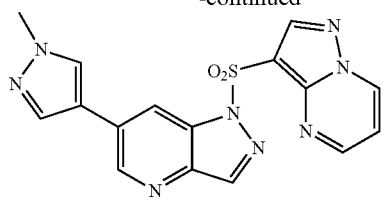
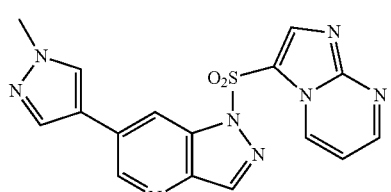
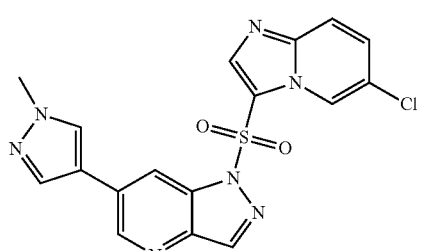
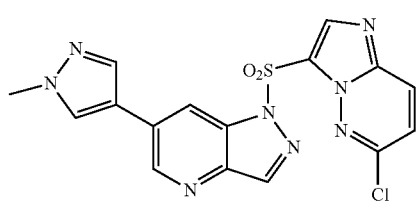
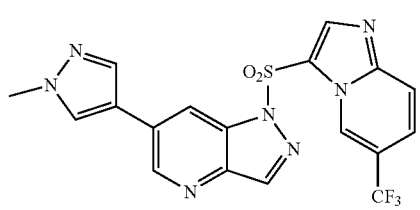
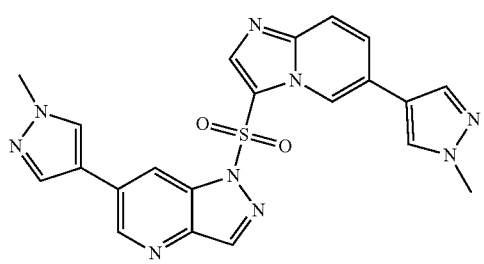
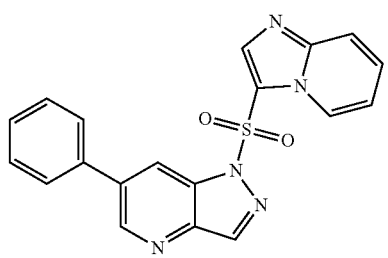

195
-continued
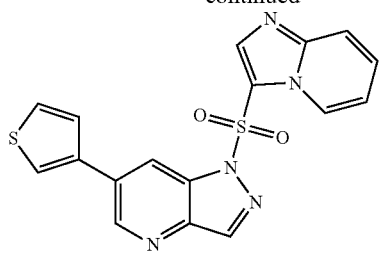
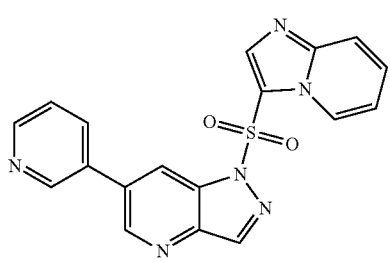
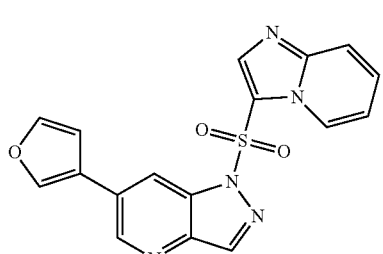
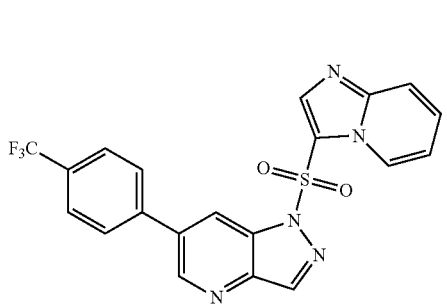
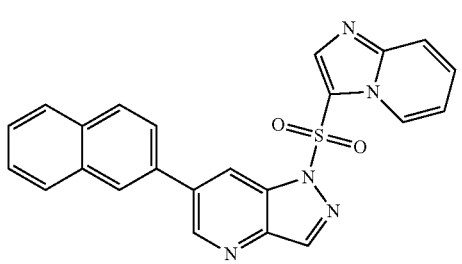
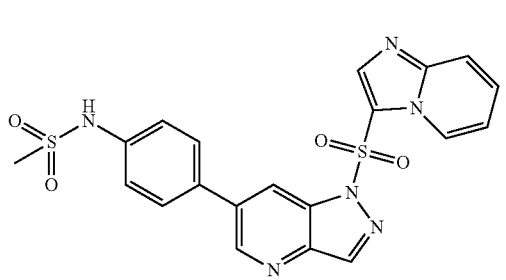
196
-continued
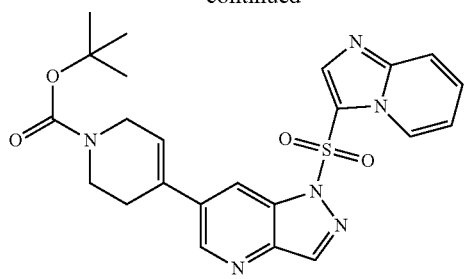
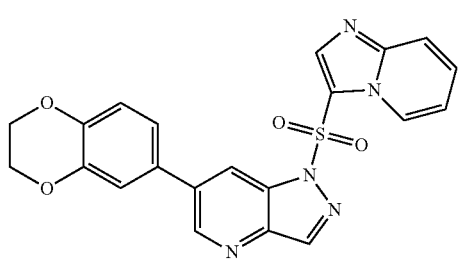
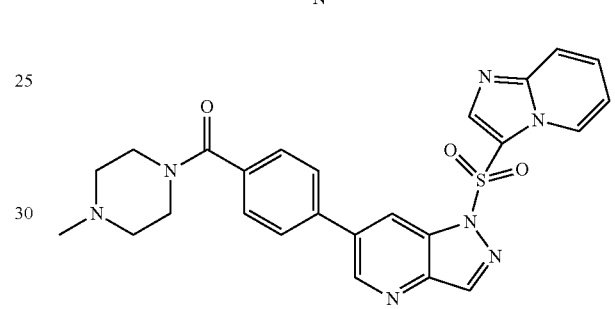
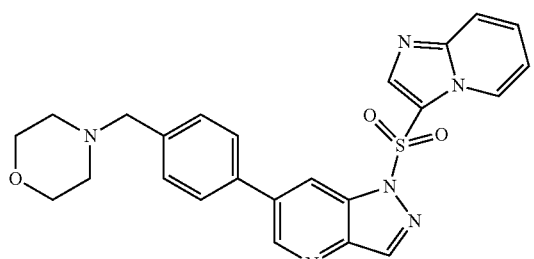
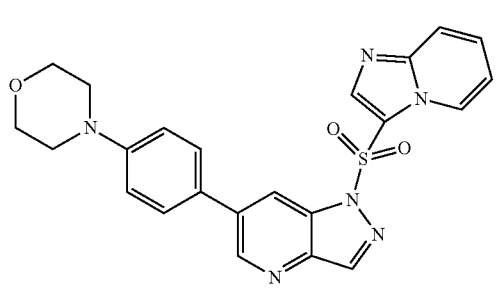
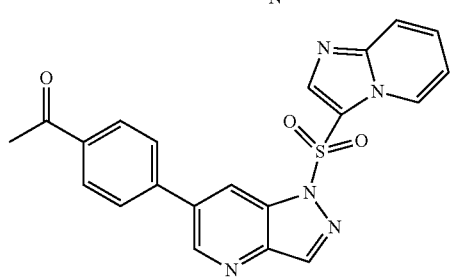

197
-continued
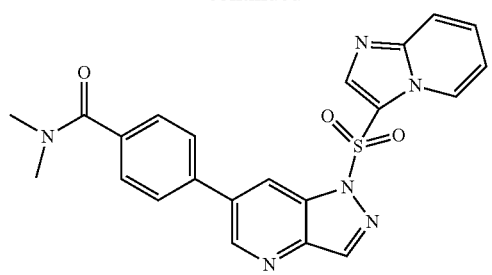
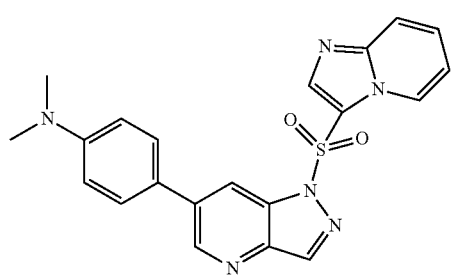
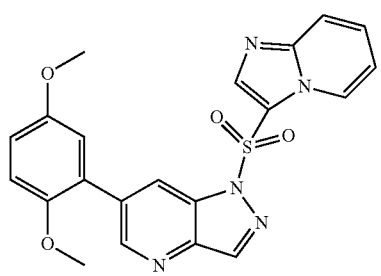
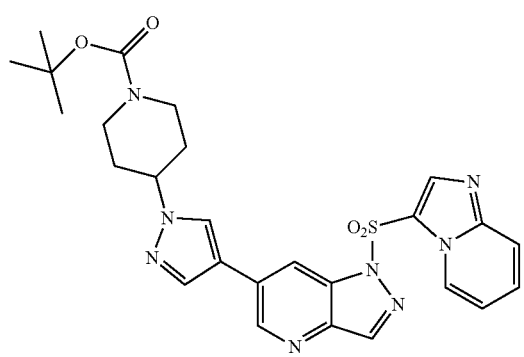
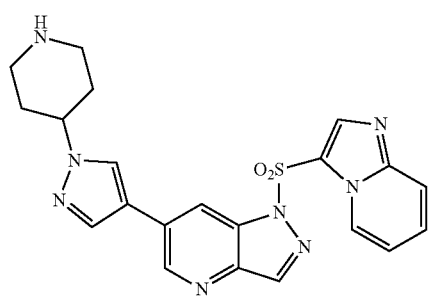
198
-continued
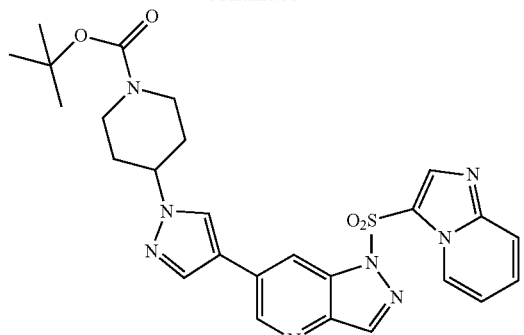
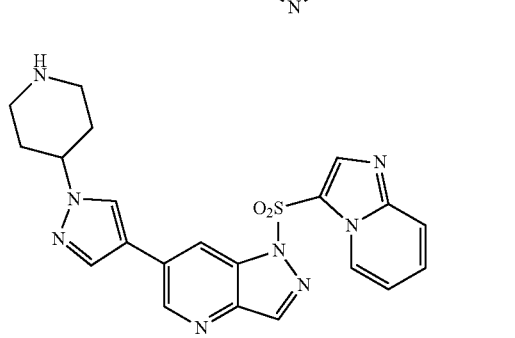
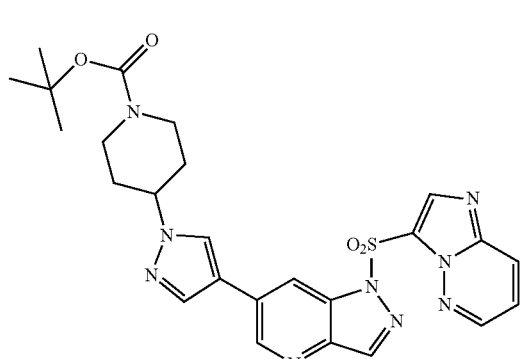
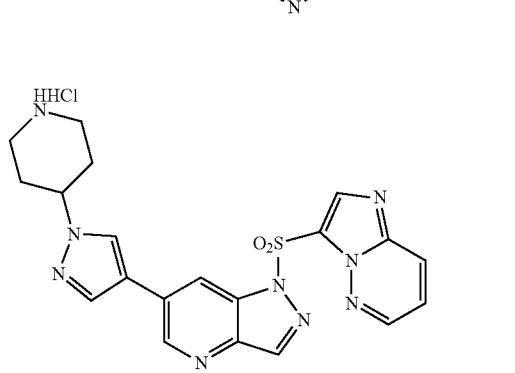
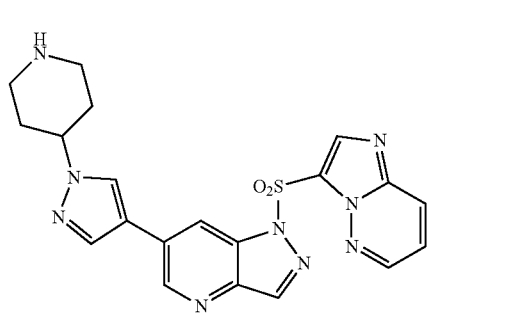

199
-continued
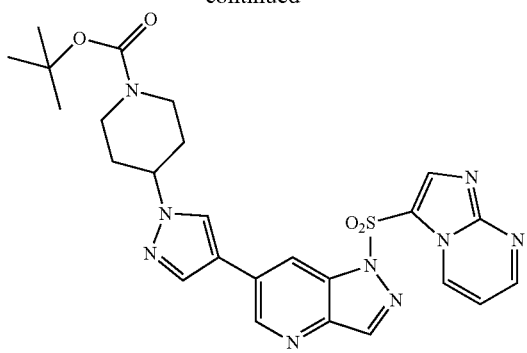
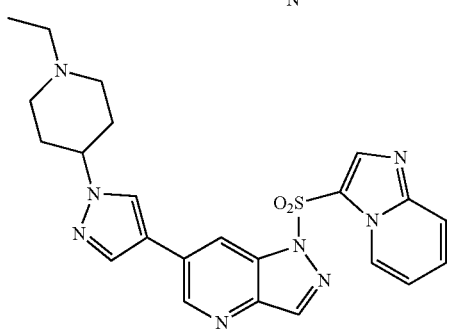
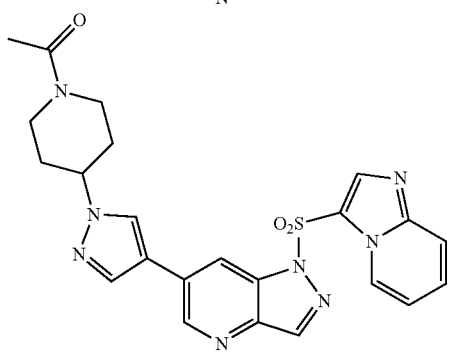
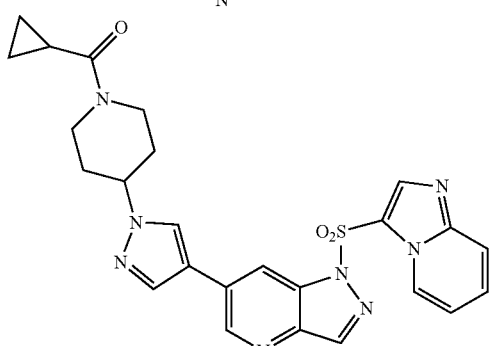
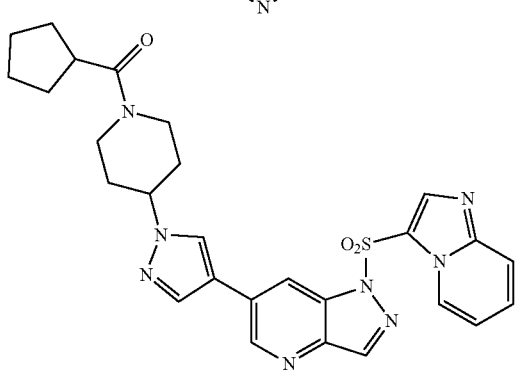
200
-continued
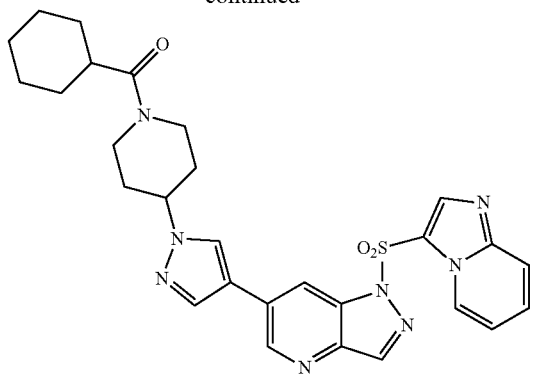
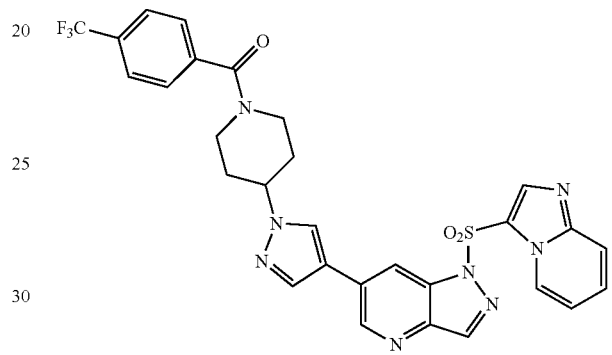
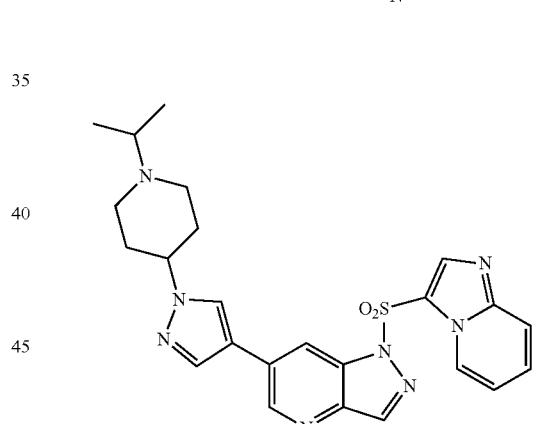
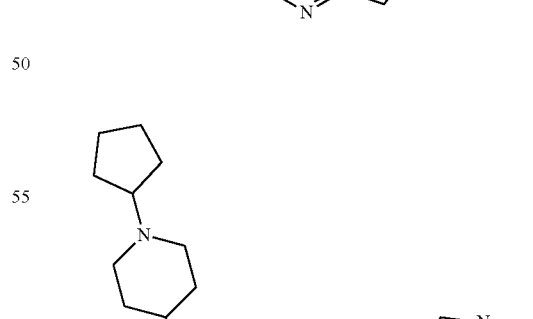
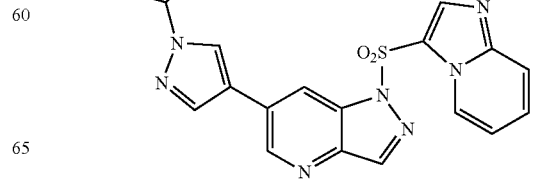

201
-continued
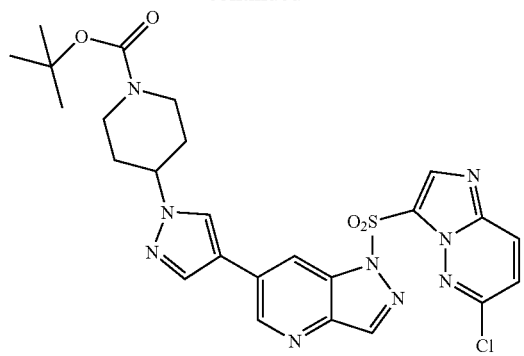
202
-continued
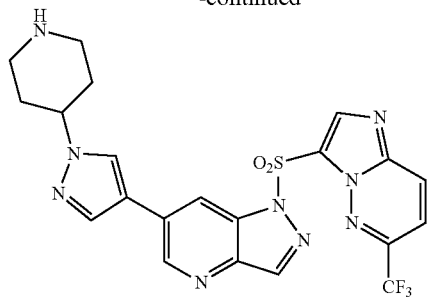
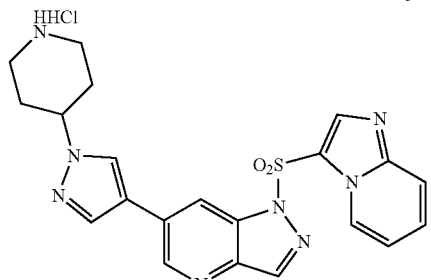
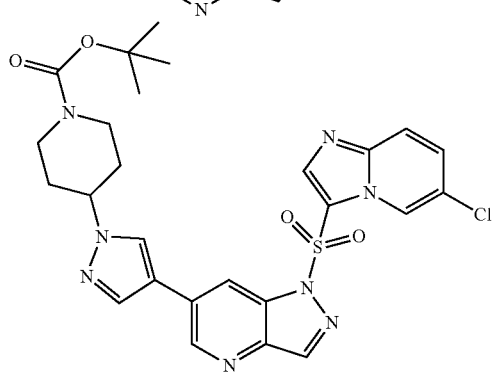
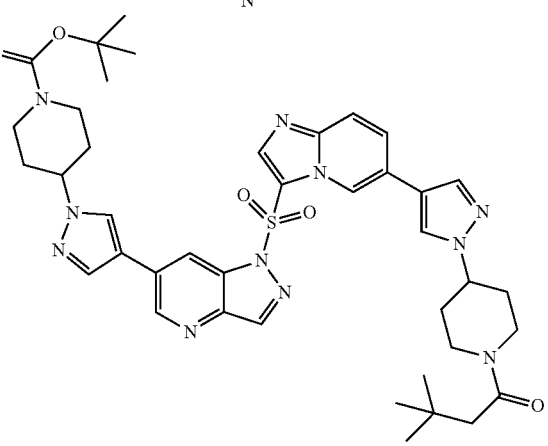
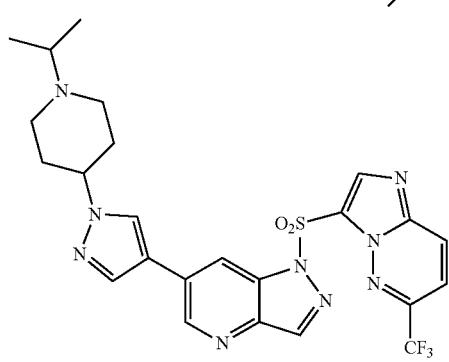

203
-continued
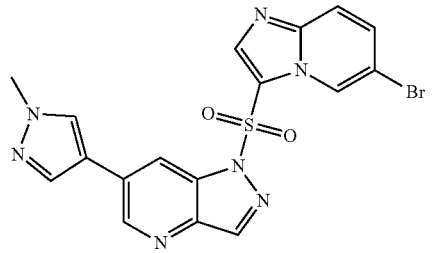
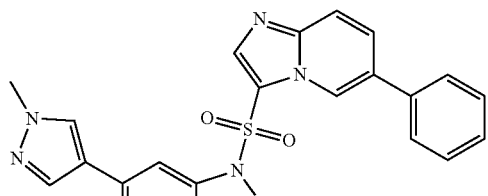
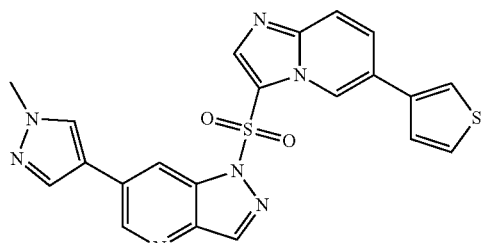
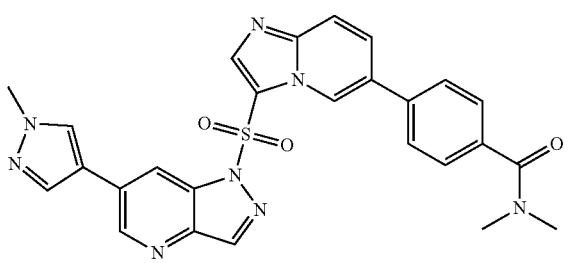
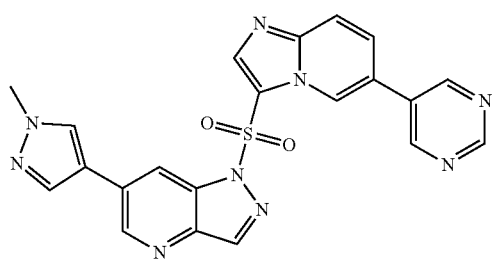
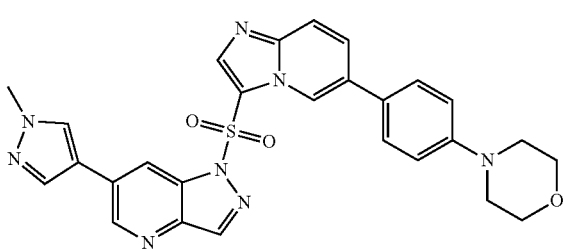
204
-continued
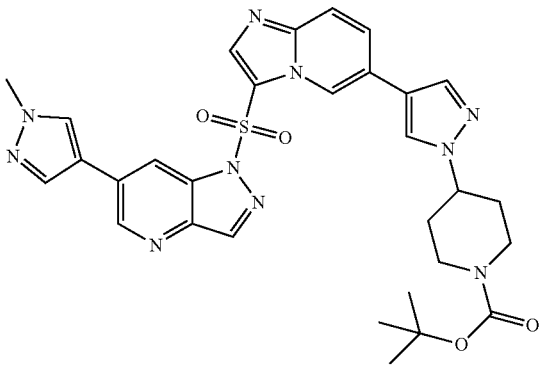
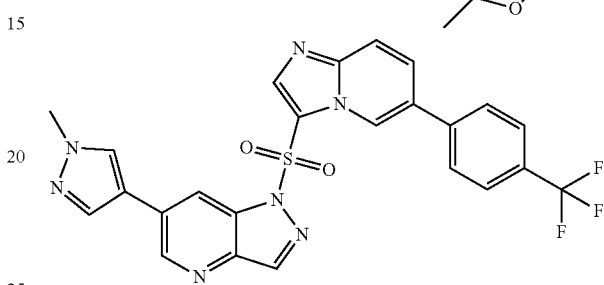
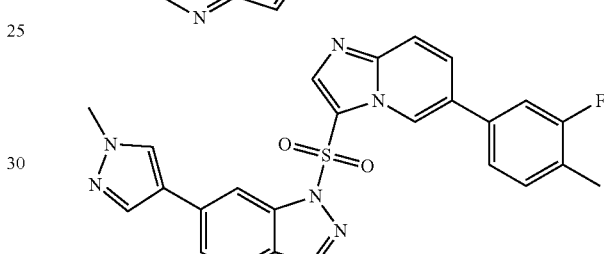
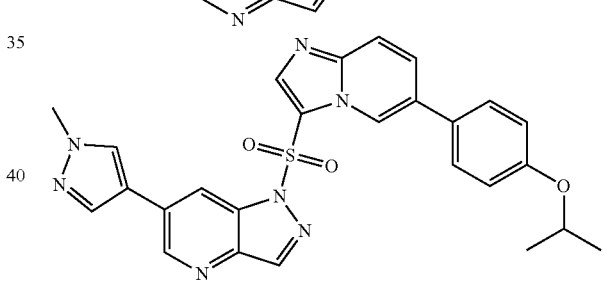
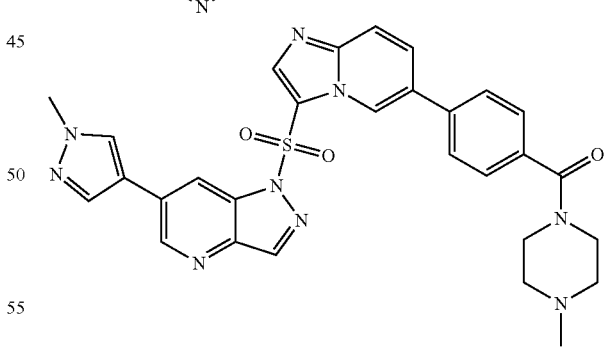
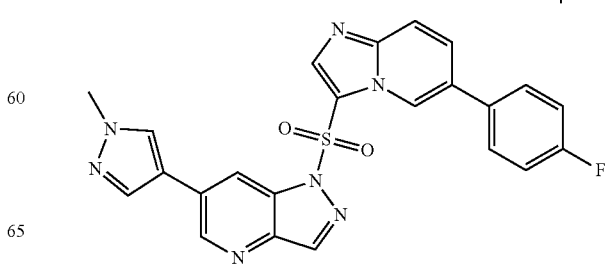

205
-continued
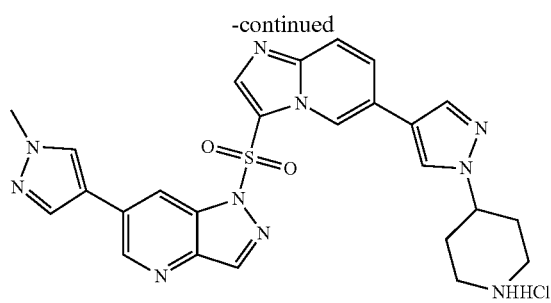
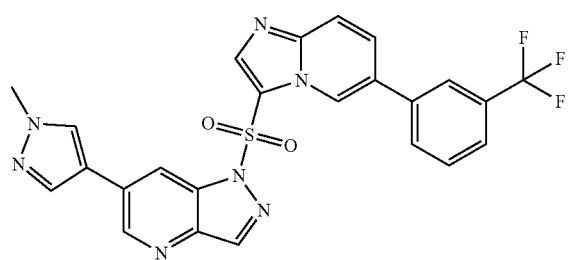
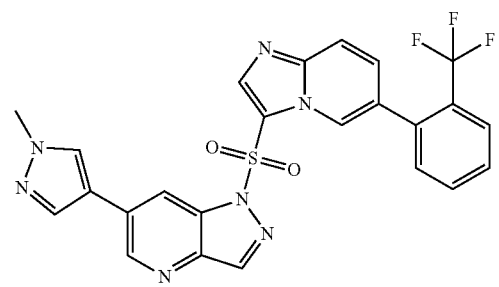
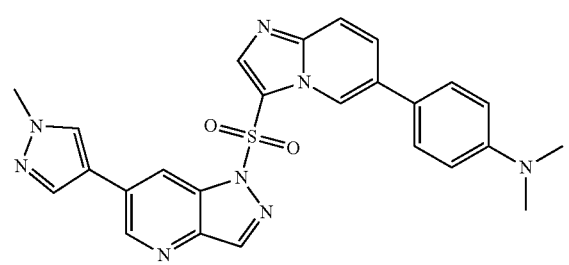
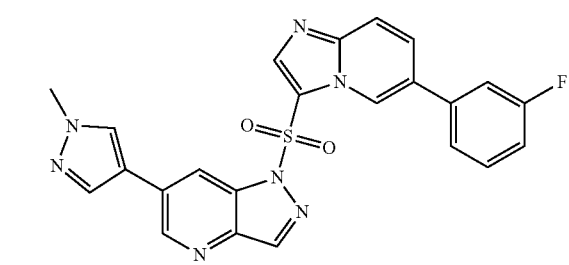
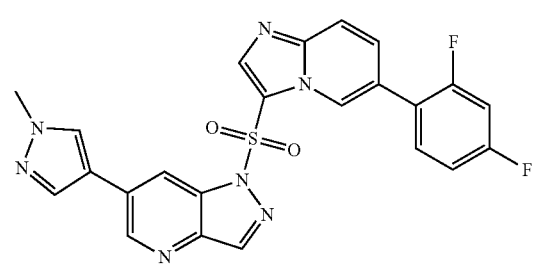
206
-continued
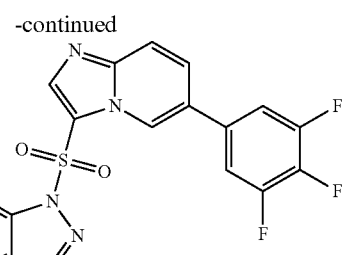
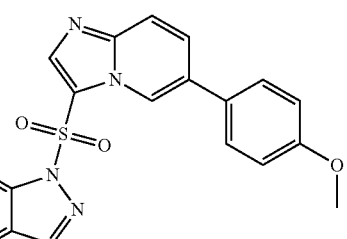
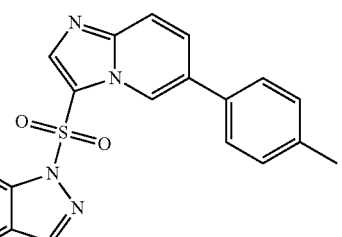
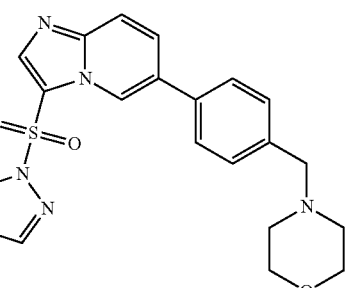
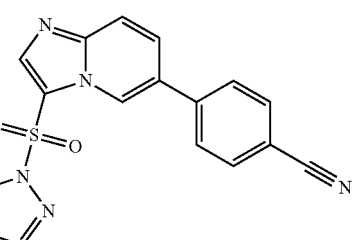
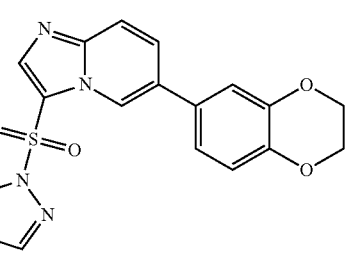

-continued
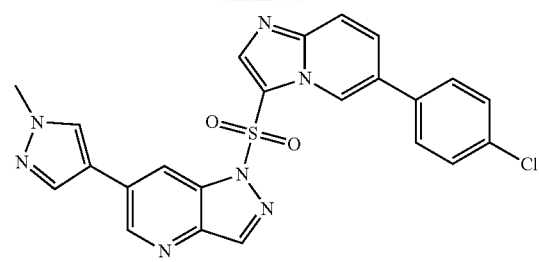
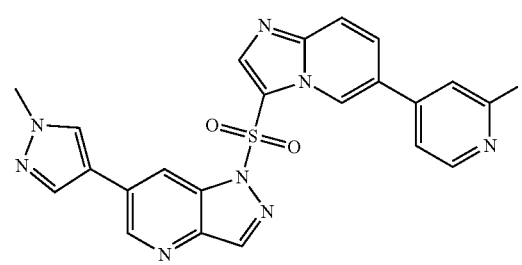
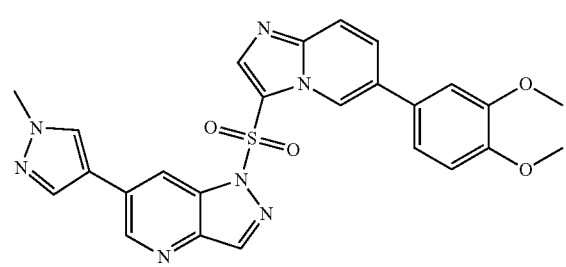
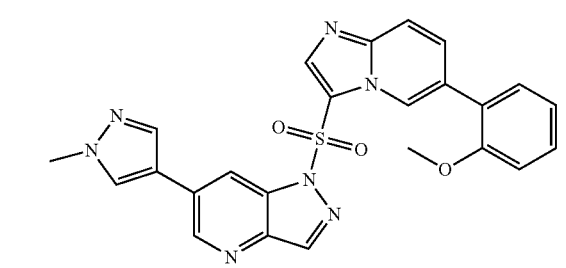
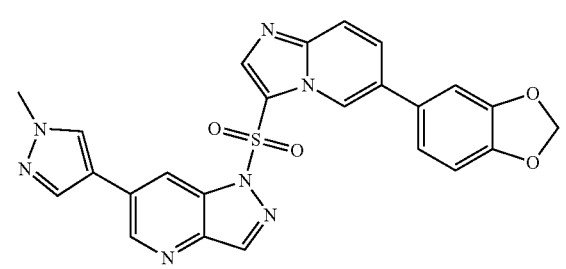
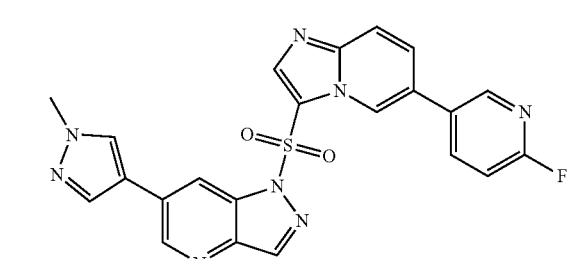
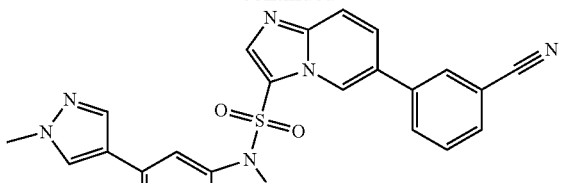
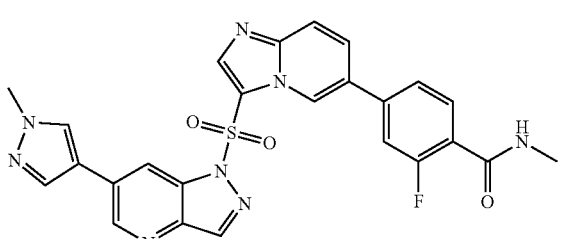
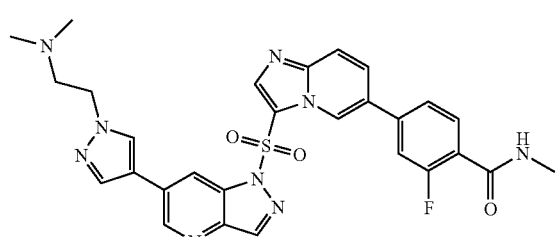
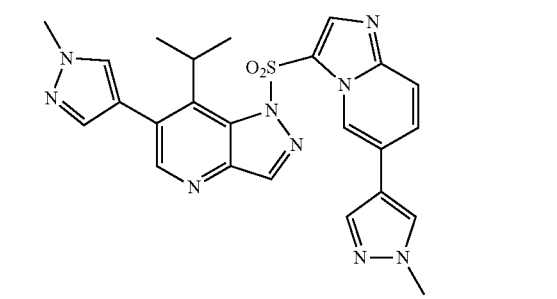
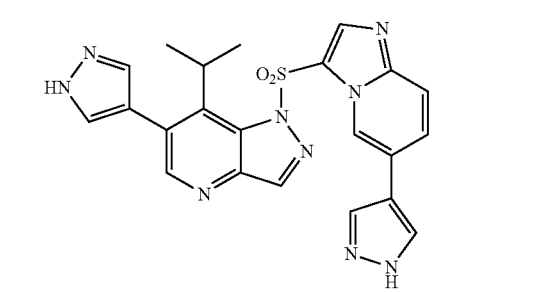
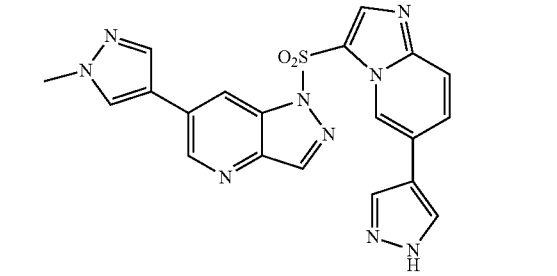

209
-continued
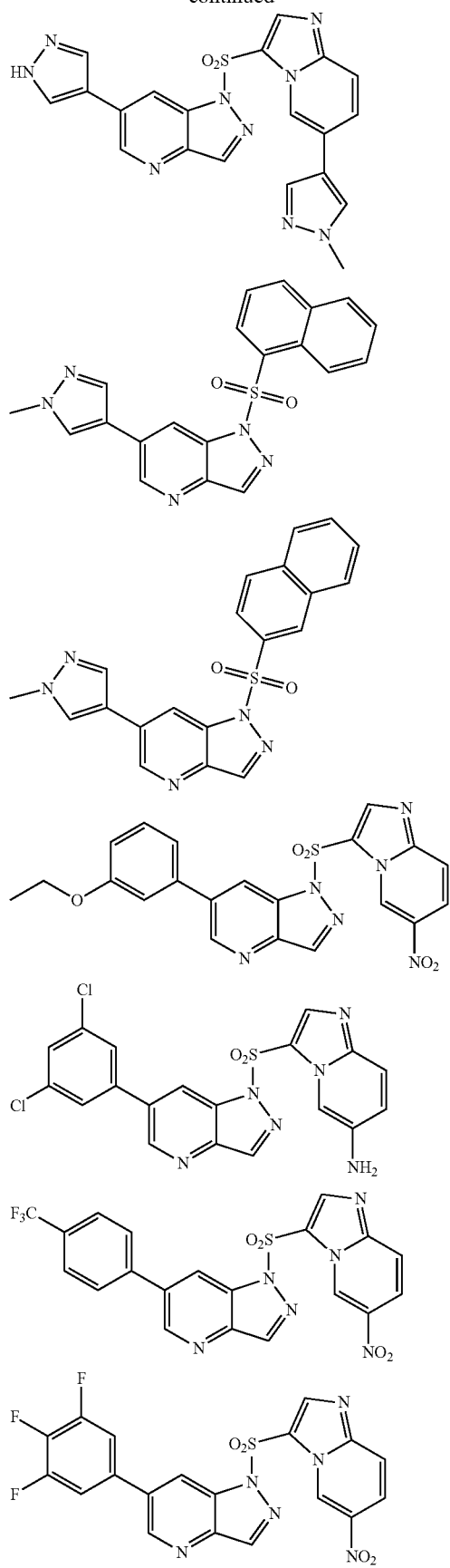
210
-continued
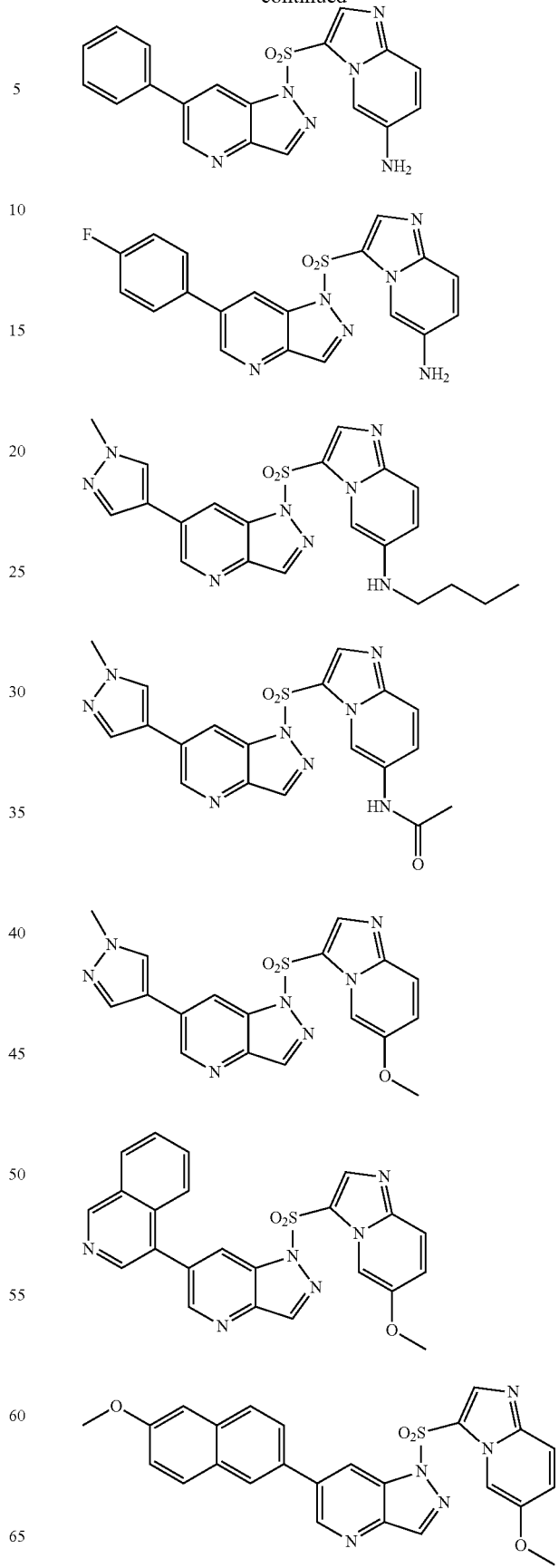

211
-continued
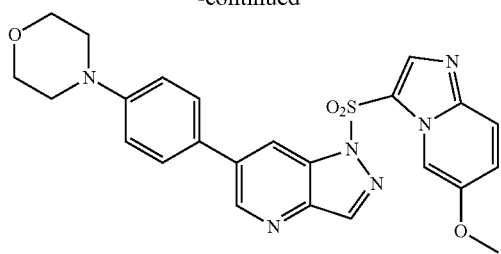
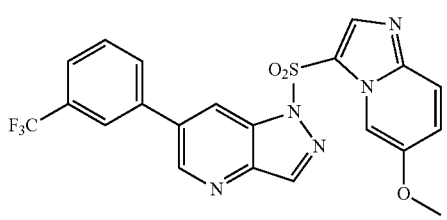
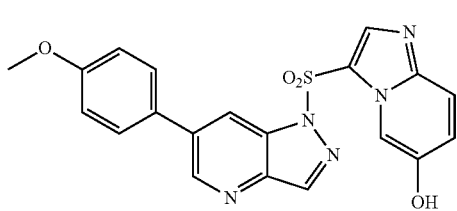
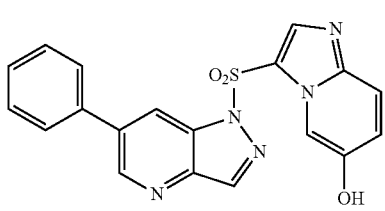
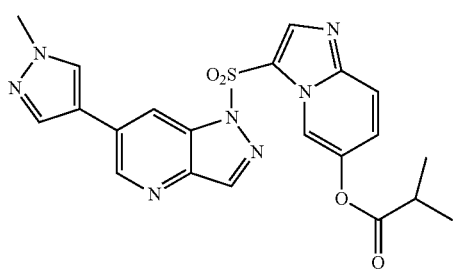
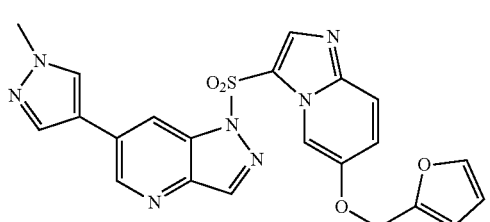
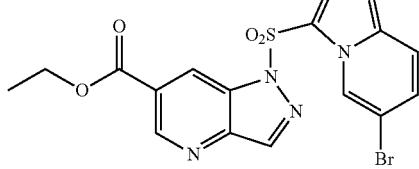
212
-continued
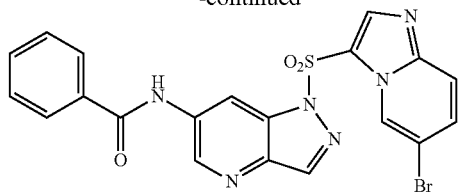
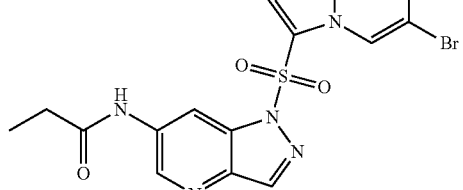
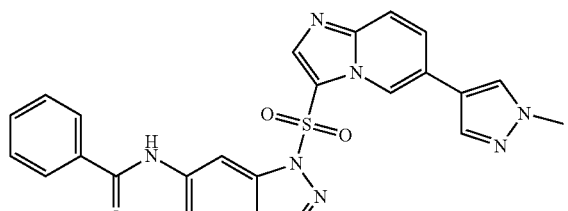
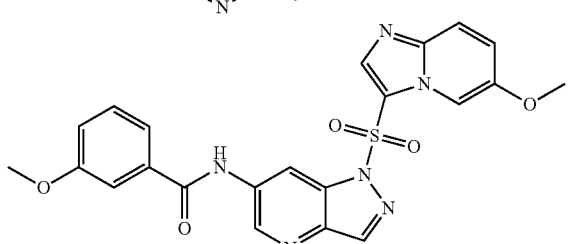
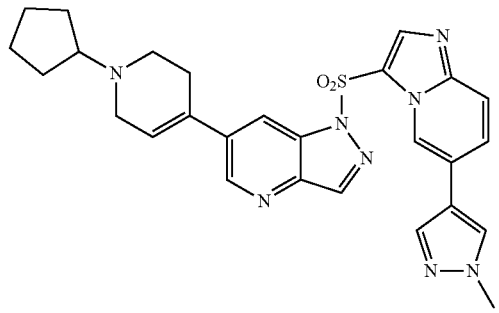
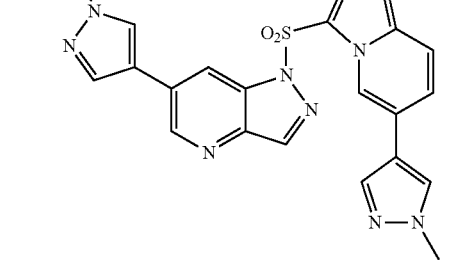

213
-continued
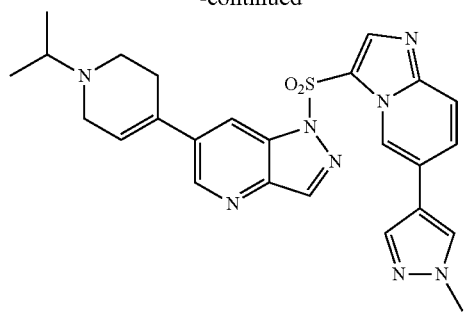
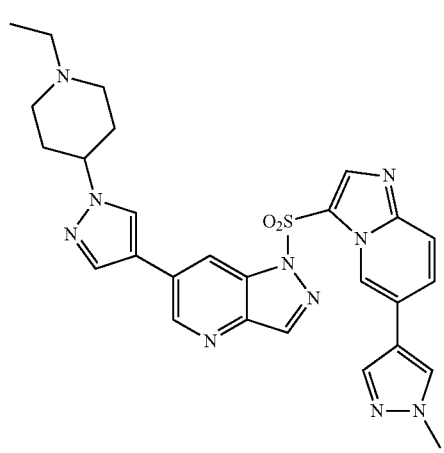
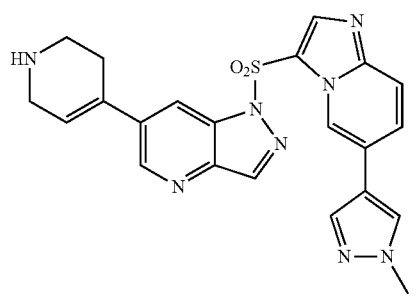
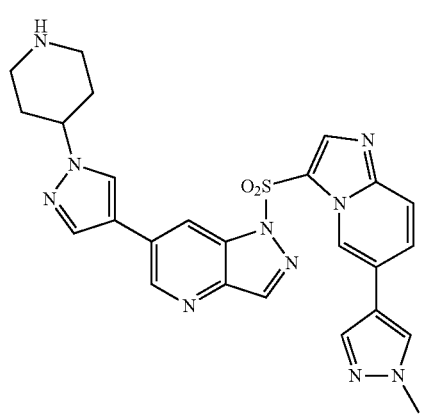
214
-continued
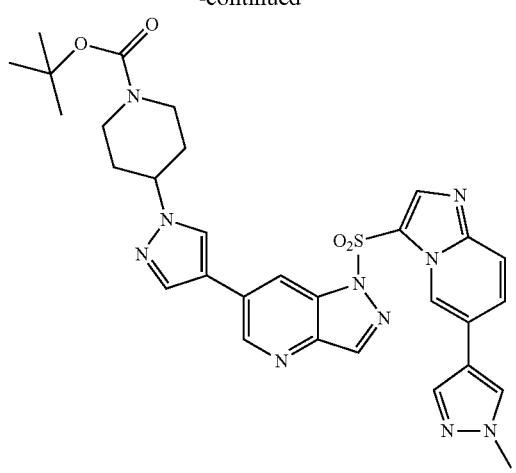
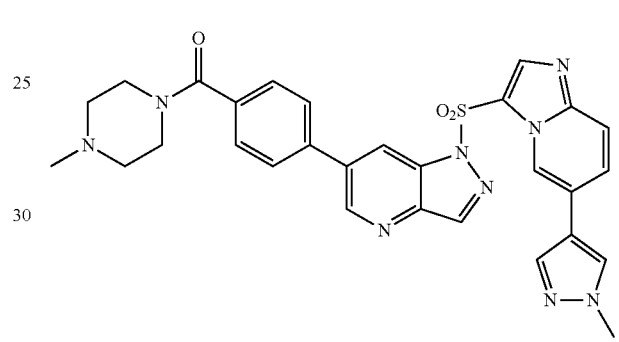
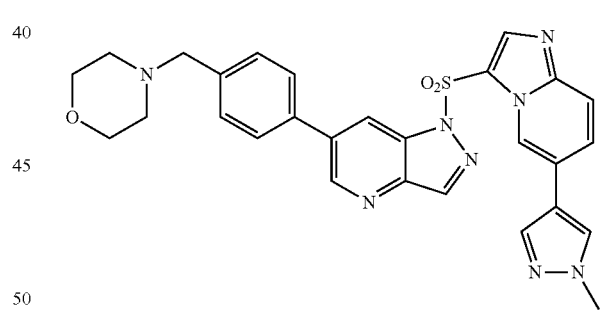
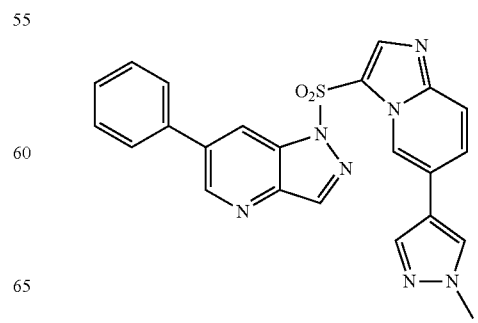

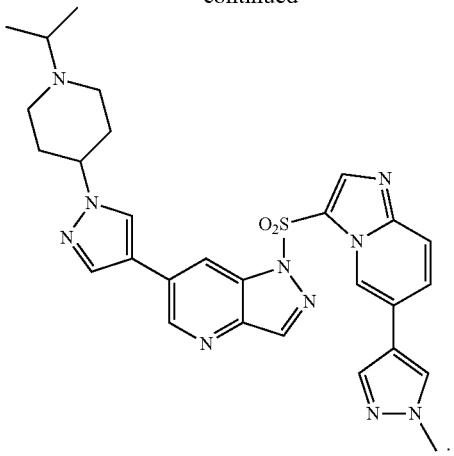

11. A method of treating, in a subject in need thereof, a disease associated with abnormal cell proliferation that is ameliorated by c-Met inhibition, comprising administering to the subject a therapeutically effective amount of the compound of claim 1, of a pharmaceutically acceptable salt thereof, of a pharmaceutically acceptable solvate thereof, or of a pharmaceutical composition comprising said compound, pharmaceutically acceptable salt, or pharmaceutically acceptable solvate.

12. The method according to claim 11, wherein in the 5-member-heterocycle-fused pyridine compound, pharmaceutically acceptable salts or pharmaceutically acceptable solvates thereof, $R_1$ is selected from phenyl, naphthyl, isoxazolyl, imidazo[2,1-b]thiazolyl, imidazo[1,2-a]pyridinyl, benzo[1,2,5]oxadiazolyl, imidazo[1,2-b]pyridazinyl, pyrazolo[1,5-a]imidazolyl, imidazo[1,2-a]pyrimidinyl; wherein substituent in the substituted group is halogen; nitro; hydroxyl; cyano; unsubstituted or halogen- or morpholinyl-substituted $C_1$-$C_5$ alkyl; $C_1$-$C_5$ alkoxy; $C_1$-$C_5$ alkylcarbonyl; $C_1$-$C_5$ alkoxycarbonyl; —$NR_aR_b$; —$C(O)(NR_aR_b)$; unsubstituted phenyl or phenyl substituted by 1-3 of $R_3$; or unsubstituted 5-7 membered heteroaryl comprising 1-3 heteroatoms selected from N, O, and S or 5-7 membered heteroaryl comprising 1-3 heteroatoms selected from N, O, and S substituted by 1-3 of $R_4$, wherein said heteroaryl is selected from the group consisting of furanyl, thienyl, pyrrolyl, pyrazolyl, imidazolyl, oxazolyl, isoxazolyl, pyranyl, pyridinyl, morpholinyl, oxazinyl and pyrazinyl;

$R_2$ is substituted or unsubstituted $C_6$-$C_{10}$ aryl; substituted or unsubstituted 5-10 membered heteroaryl comprising 1-5 heteroatoms selected from N, O, and S; or substituted or unsubstituted 5-10 membered heterocyclyl comprising 1-5 heteroatoms selected from N, O, and S; wherein, substituent in the substituted group is halogen, nitro, cyano, $C_1$-$C_4$ alkylenedioxy; unsubstituted $C_1$-$C_5$ alkyl or $C_1$-$C_5$ alkyl substituted by halogen or —$NR_cR_d$; $C_1$-$C_5$ alkoxy; $C_1$-$C_5$ sulfamido; —$NR_aR_b$; —C(O)R'; morpholinyl; or unsubstituted or R"-substituted piperidinyl;

$R_3$ is halogen; nitro; cyano; $C_1$-$C_4$ alkylenedioxy; unsubstituted or halogen- or morpholinyl-substituted $C_1$-$C_5$ alkyl; $C_1$-$C_5$ alkoxy; —$NR_aR_b$; —C(O)R'; or morpholinyl;

$R_4$ is halogen, nitro, cyano, unsubstituted or halogen-substituted $C_1$-$C_5$ alkyl; $C_1$-$C_5$ alkoxy; —$NR_aR_b$; —C(O)R'; or unsubstituted or $C_1$-$C_5$ alkoxycarbonyl-substituted piperidinyl;

R' is $C_1$-$C_5$ alkyl; $C_1$-$C_5$ alkoxy; —$NR_aR_b$; or unsubstituted or halogen- or $C_1$-$C_5$ alkyl-substituted 5-6 membered heterocyclyl;

R" is $C_1$-$C_5$ alkyl; $C_3$-$C_6$ cycloalkyl; $C_1$-$C_5$ alkylcarbonyl; $C_1$-$C_5$ alkoxycarbonyl; $C_3$-$C_6$ cycloalkylcarbonyl; or unsubstituted benzoyl or benzoyl substituted by substituent(s) selected from halogen, $C_1$-$C_5$ alkyl, halogen-substituted $C_1$-$C_5$ alkyl;

$R_a$ and $R_b$ are independently H or $C_1$-$C_5$ alkyl; and $R_c$ and $R_d$ are independently H or $C_1$-$C_5$ alkyl; or, $R_c$ and $R_d$, together with the N atom to which they are attached, form 3-7 membered heterocyclyl.

13. The method according to claim 11, wherein in the 5-member-heterocycle-fused pyridine compound, pharmaceutically acceptable salts or pharmaceutically acceptable solvates thereof, $R_1$ is

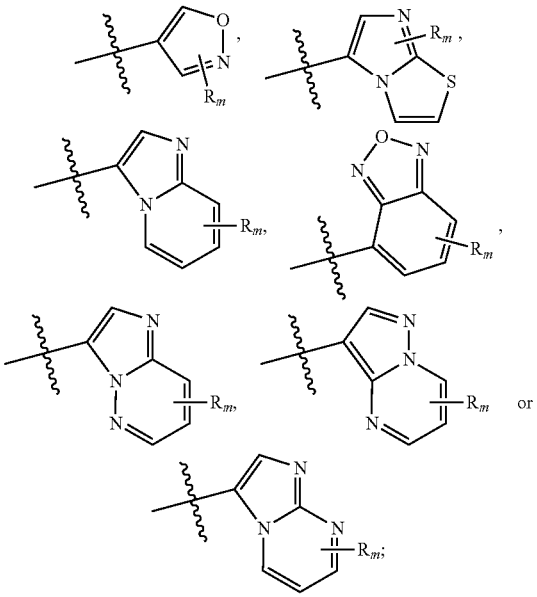

$R_m$ is H, halogen, nitro, cyano; unsubstituted or halogen- or morpholinyl-substituted $C_1$, $C_4$ alkyl; $C_1$-$C_4$ alkoxy; $C_1$-$C_4$ alkylcarbonyl; $C_1$-$C_4$ alkoxycarbonyl; —$NR_aR_b$; —C(O)(NR_aR_b)$; unsubstituted phenyl or phenyl substituted by 1-3 of $R_3$; or unsubstituted 5- to 7-membered heteroaryl containing 1-3 heteroatoms selected from the group consisting of N, O, and S, or 5- to 7-membered heteroaryl containing 1-3 heteroatoms selected from the group consisting of N, O, and S substituted by 1-3 of $R_4$, wherein said heteroaryl is selected from the group consisting of furanyl, thienyl, pyrrolyl, pyrazolyl, imidazolyl, oxazolyl, isoxazolyl, pyranyl, pyridinyl, morpholinyl, oxazinyl, and pyrazinyl;

$R_2$ is substituted or unsubstituted $C_6$-$C_{20}$ aryl; substituted or unsubstituted 5- to 10-membered heteroaryl containing 1-5 heteroatoms selected from the group consisting of N, O, and S; or substituted or unsubstituted 4- to 10-membered heterocyclyl containing 1-5 heteroatoms selected from the group consisting of N, O, and S; wherein, substituent in the substituted group is halogen, nitro, cyano, $C_1$-$C_4$ alkylenedioxy, unsubstituted or halogen- or —$NR_cR_d$-substituted $C_1$-$C_6$ alkyl or $C_3$-$C_6$ cycloalkyl, $C_1$-$C_6$ alkoxy, $C_1$-$C_6$ sulfamido, —$NR_aR_b$, —C(O)R', morpholinyl, morpholinylmethyl, or unsubstituted or R"-substituted piperidinyl;

R₃ is halogen, nitro, cyano, $C_1$-$C_2$ alkylenedioxy, unsubstituted or halogen- or morpholinyl-substituted $C_1$-$C_4$ alkyl, $C_1$-$C_4$ alkoxy, —$NR_aR_b$, —C(O)R', or 4-morpholinyl;

R₄ is halogen, nitro, cyano, unsubstituted or halogen-substituted $C_1$-$C_4$ alkyl, $C_1$-$C_4$ alkoxy, —$NR_aR_b$, —C(O)R', 4-piperidinyl, or 1-t-butoxycarbonyl-4-piperidinyl;

R' is $C_1$-$C_4$ alkyl, $C_1$-$C_4$ alkoxy, —$NR_aR_b$, or 4-methyl-piperazinyl;

R" is $C_1$-$C_4$ alkyl, $C_3$-$C_6$ cycloalkyl, $C_1$-$C_4$ alkylcarbonyl, $C_1$-$C_4$ alkoxycarbonyl, $C_3$-$C_6$ cycloalkylcarbonyl, or p-trifluoromethylbenzoyl;

$R_a$ and $R_b$ are each independently H, $C_1$-$C_4$ alkyl or $C_1$-$C_4$ alkylcarbonyl; and $R_c$ and $R_d$ are each independently H or $C_1$-$C_6$ alkyl; or, $R_c$ and $R_d$, together with the N atom to which they are attached, form 3- to 7-membered heterocyclyl.

14. The method of claim 11, wherein in the 5-member-heterocycle-fused pyridine compound, pharmaceutically acceptable salts or pharmaceutically acceptable solvates thereof, R₁ is

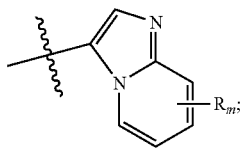

R₂ is

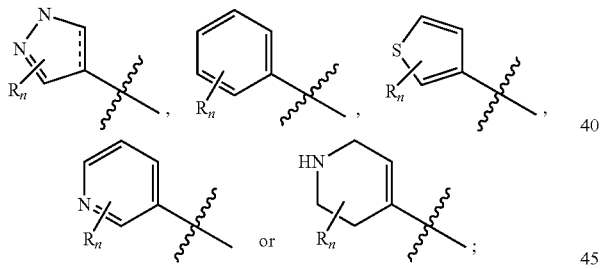

wherein, $R_m$ is H, halogen, nitro, hydroxyl, $C_1$-$C_4$ alkoxy, unsubstituted phenyl or phenyl substituted by 1-3 of R₃, or unsubstituted 5- to 7-membered heteroaryl containing 1-3 heteroatoms selected from the group consisting of N, O, and S, or 5- to 7-membered heteroaryl containing 1-3 heteroatoms selected from the group consisting of N, O, and S substituted by 1-3 of R₄, wherein said heteroaryl is selected from the group consisting of furanyl, thienyl, pyrrolyl, pyrazolyl, imidazolyl, oxazolyl, isoxazolyl, pyranyl, pyridinyl, morpholinyl, oxazinyl, and pyrazinyl;

$R_n$ is H, halogen; nitro; cyano; unsubstituted or halogen-, dimethylamino-, 4-morpholinyl-, 1-aziridinyl-, 1-azetidinyl-, 1-tetrahydropyrrolyl-, 1-piperidinyl- or 1-homopiperidinyl-substituted $C_1$-$C_4$ alkyl; $C_1$-$C_4$ alkoxy; $C_1$-$C_4$ sulfamido; —$NR_aR_b$; —C(O)R'; 4-morpholinyl; or unsubstituted or R"-substituted piperidinyl;

R₃ is halogen, nitro, cyano, $C_1$-$C_4$ alkylenedioxy, unsubstituted or halogen- or morpholinyl-substituted $C'$-$C_6$ alkyl, $C'$-$C_6$ alkoxy, —$NR_aR_b$, —C(O)R', or morpholinyl;

R₄ is halogen, nitro, cyano, unsubstituted or halogen-substituted $C'$-$C_6$ alkyl, $C'$-$C_6$ alkoxy, —$NR_aR_b$, —C(O)R', or unsubstituted or $C'$-$C_6$ alkoxycarbonyl-substituted piperidinyl;

R' is $C_1$-$C_4$ alkyl, $C_1$-$C_4$ alkoxy, —$NR_aR_b$, or 4-methyl-piperazinyl;

R" is $C_1$-$C_4$ alkyl, $C_3$-$C_6$ cycloalkyl, $C_1$-$C_4$ alkylcarbonyl, $C_1$-$C_4$ alkoxycarbonyl, $C_3$-$C_6$ cycloalkylcarbonyl, or p-trifluoromethylbenzoyl;

$R_a$ and $R_b$ are independently H, $C_1$-$C_4$ alkyl or $C_1$-$C_4$ alkylcarbonyl.

15. The method according to claim 11, wherein the compound is selected from the group consisting of:

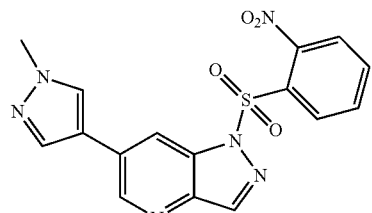

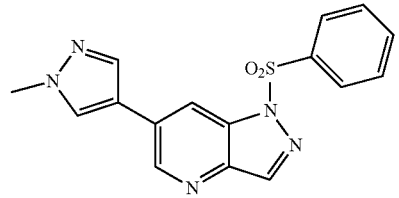

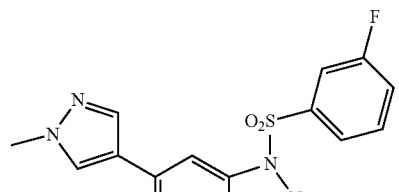

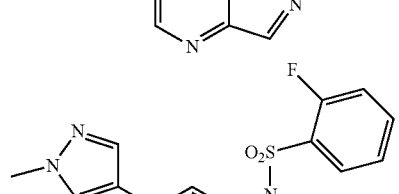

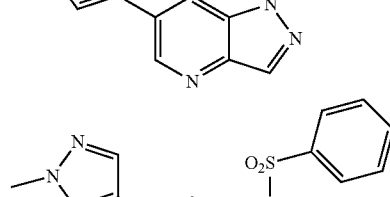

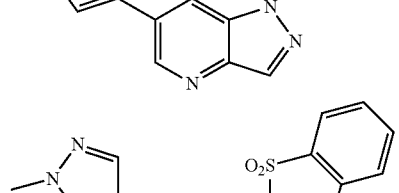

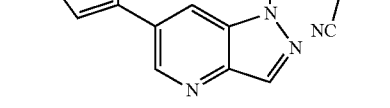

219
-continued
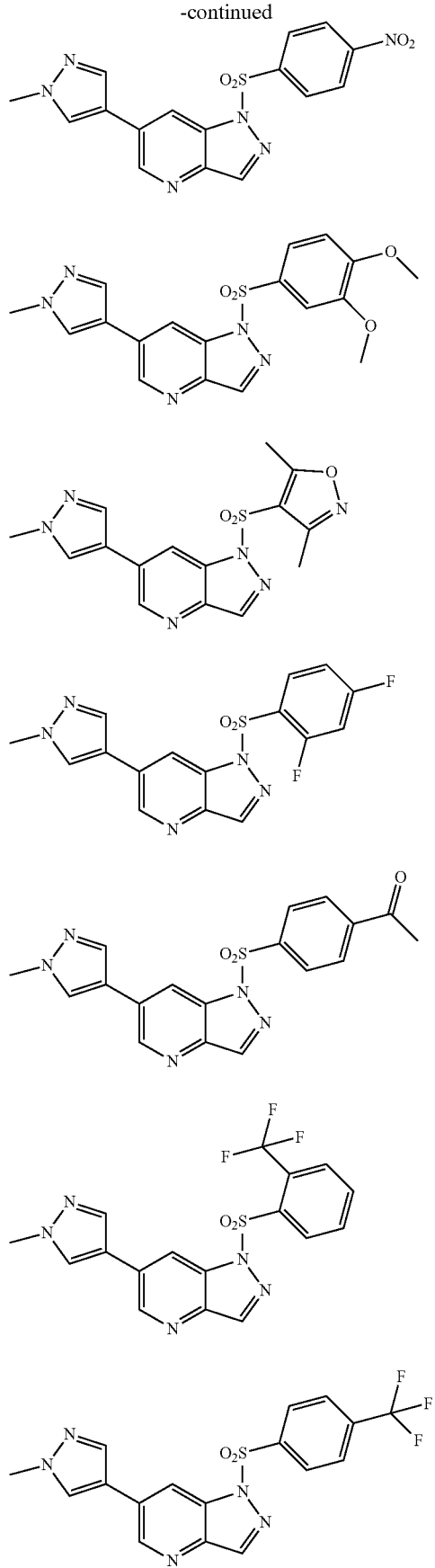
220
-continued
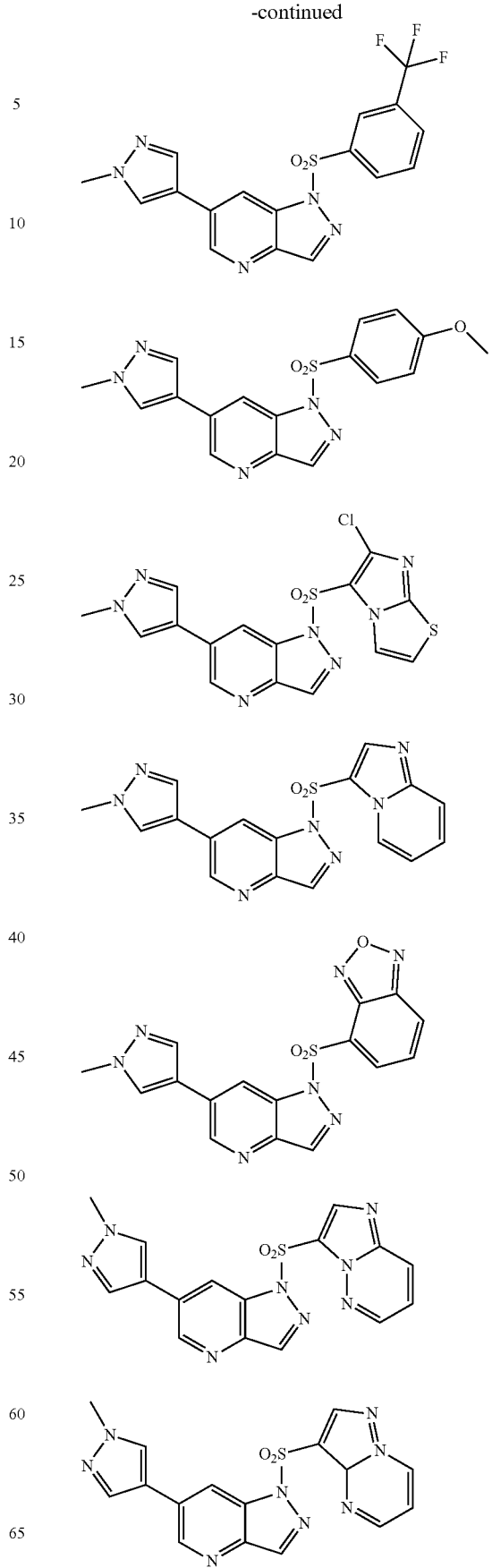

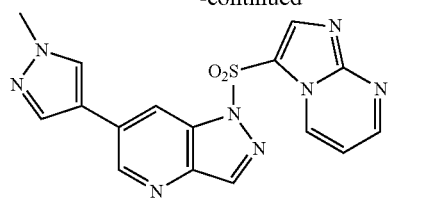
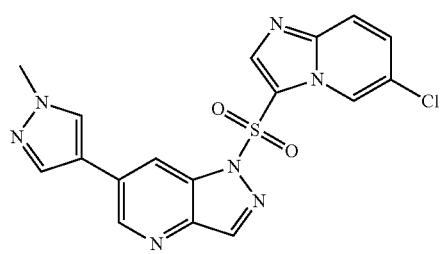
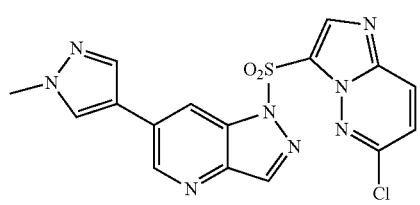
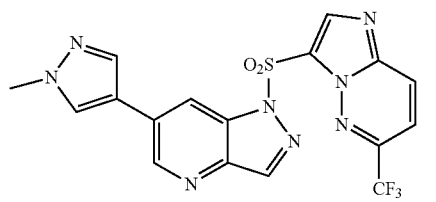
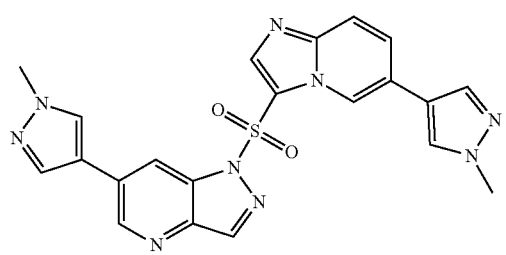
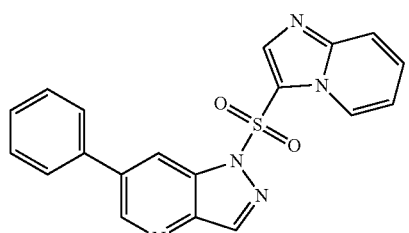
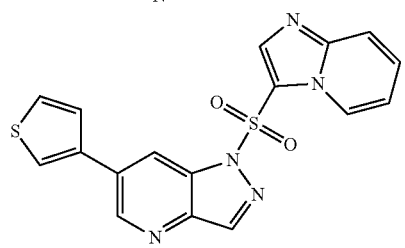
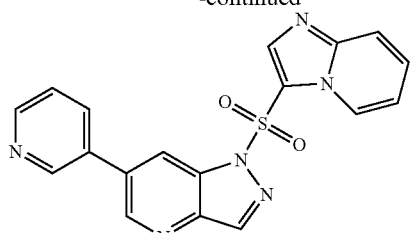
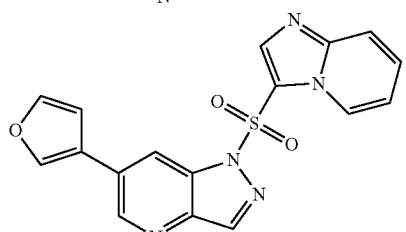
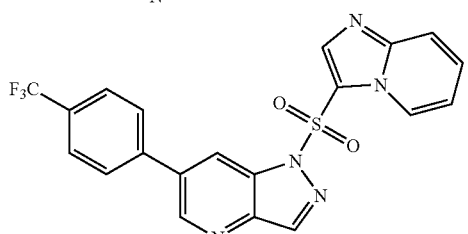
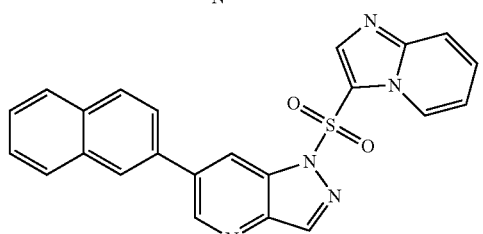
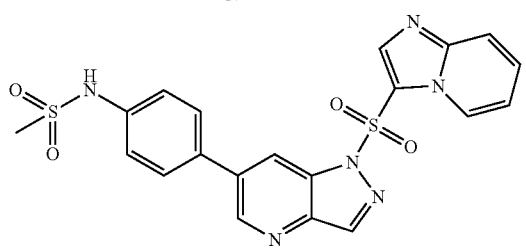
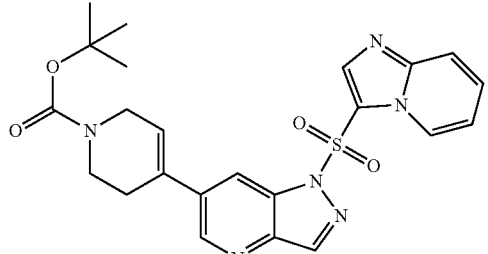
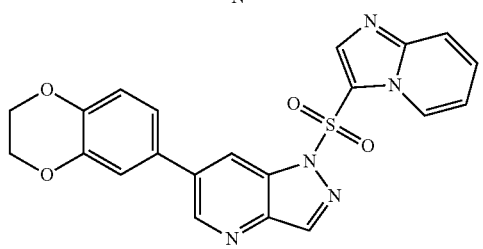

223
-continued
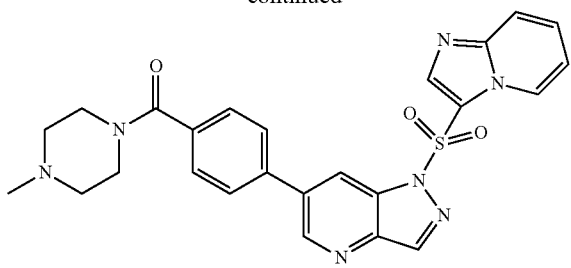
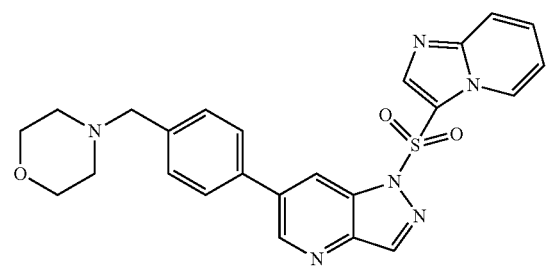
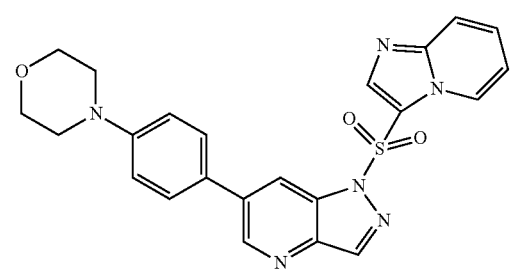
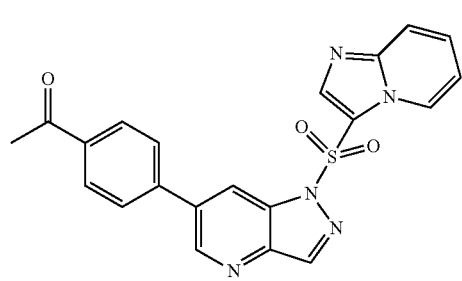
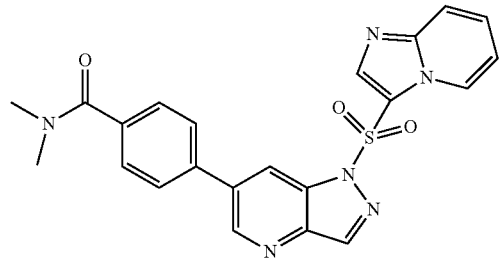
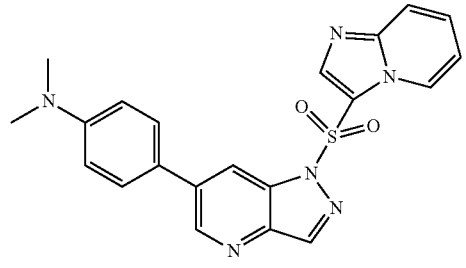
224
-continued
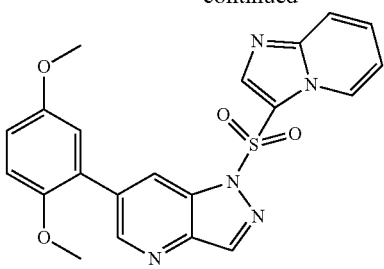
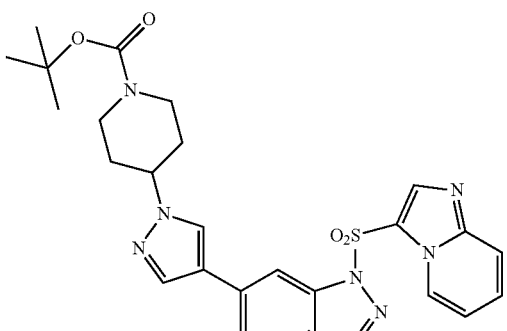
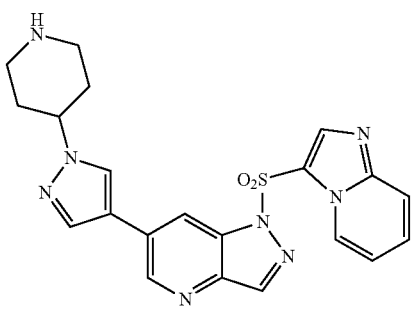
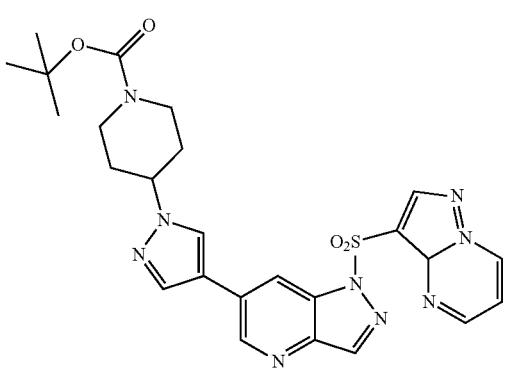
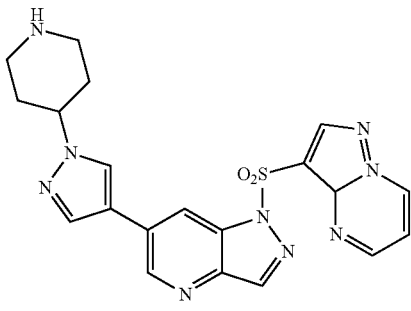

225
-continued
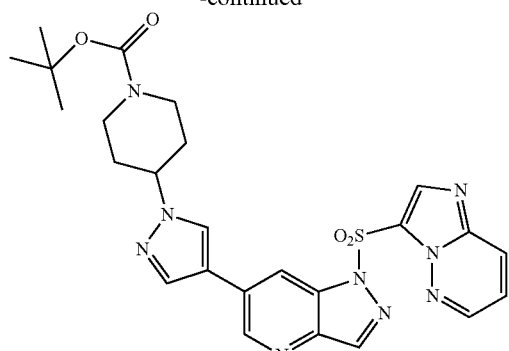
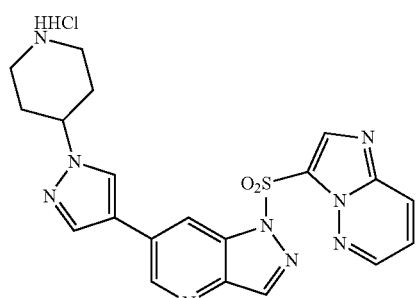
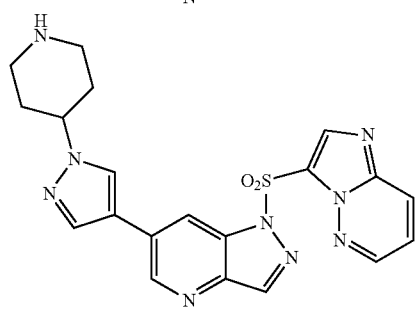
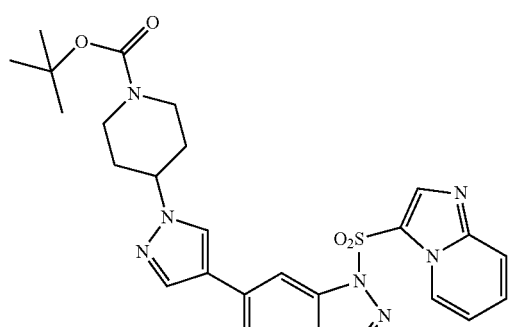
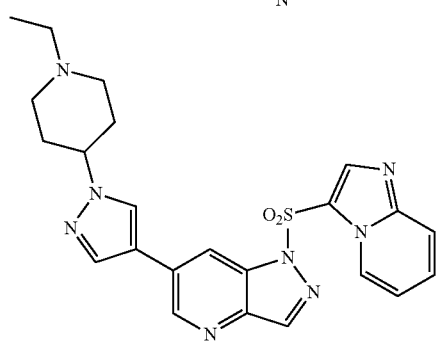
226
-continued
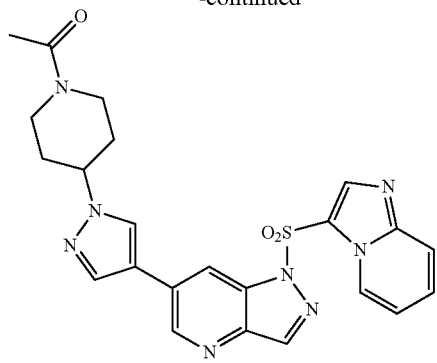
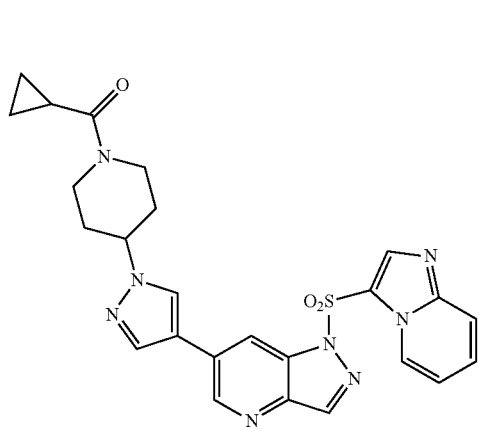
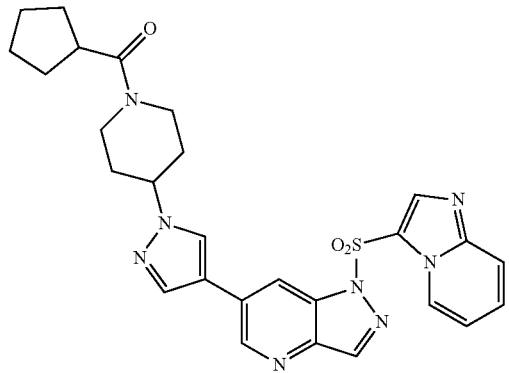
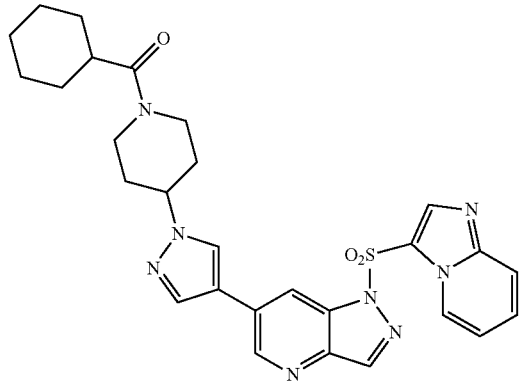

227
-continued
228
-continued
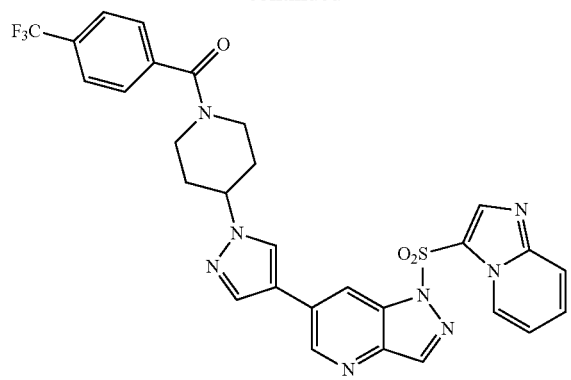
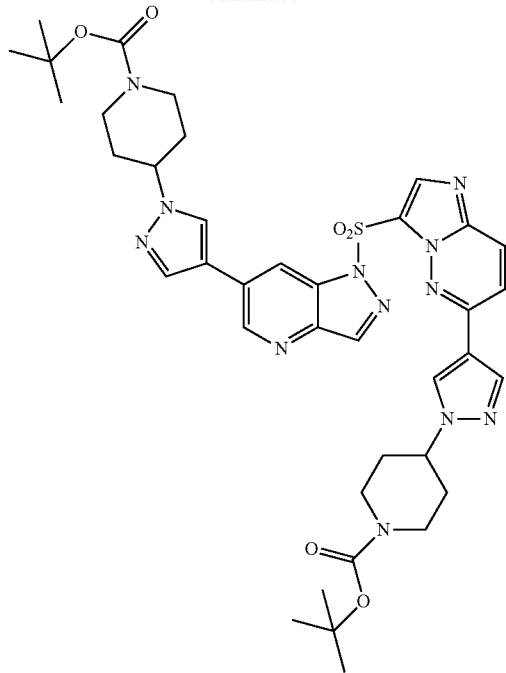
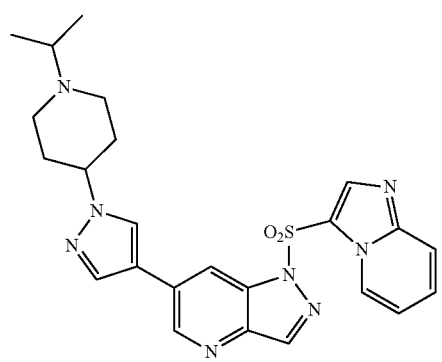
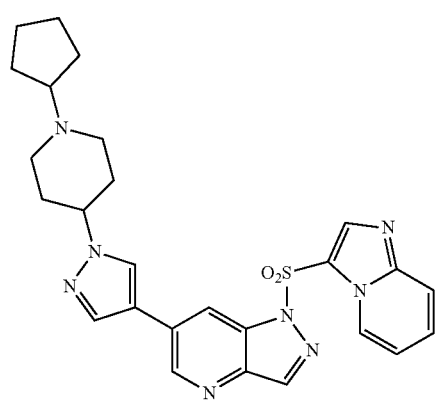
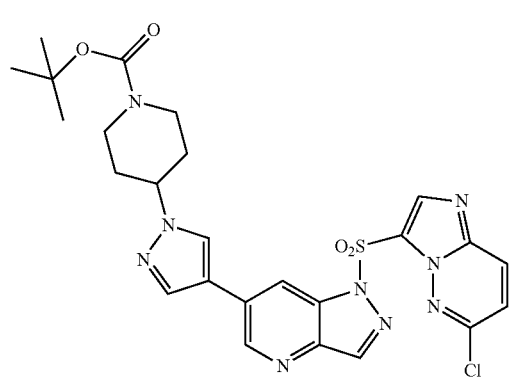
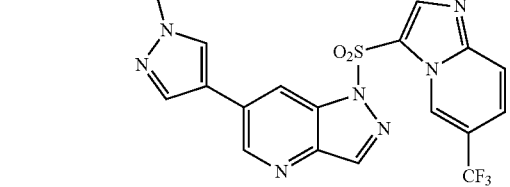
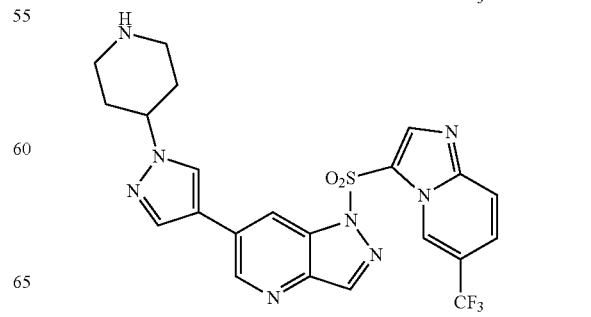

229
-continued
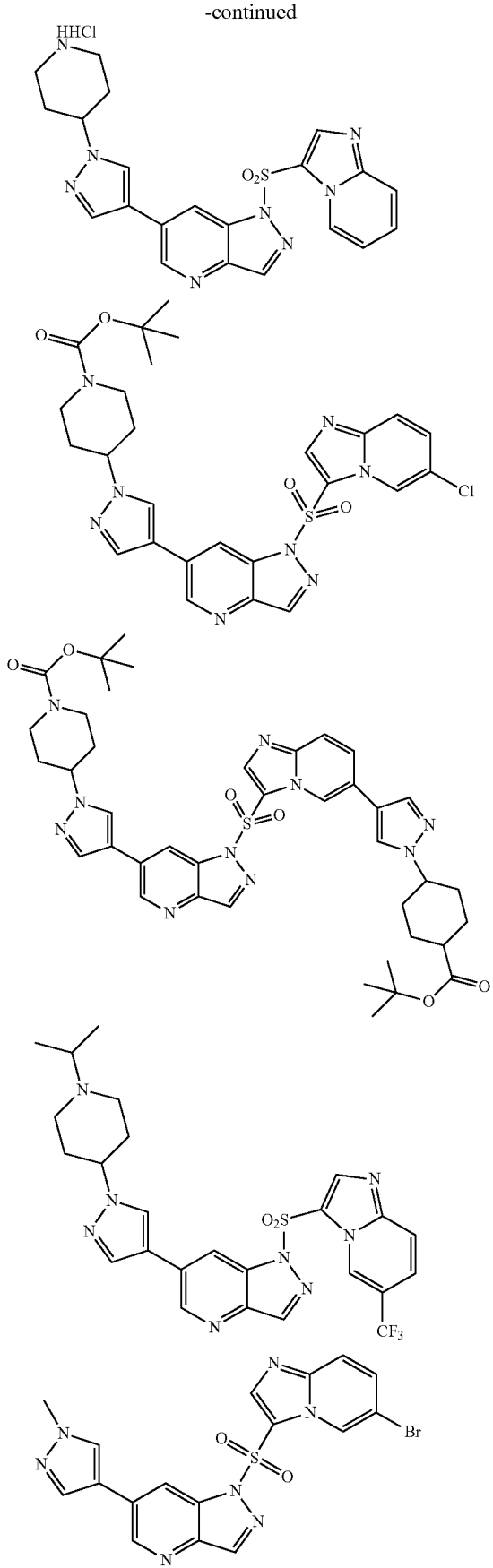
230
-continued
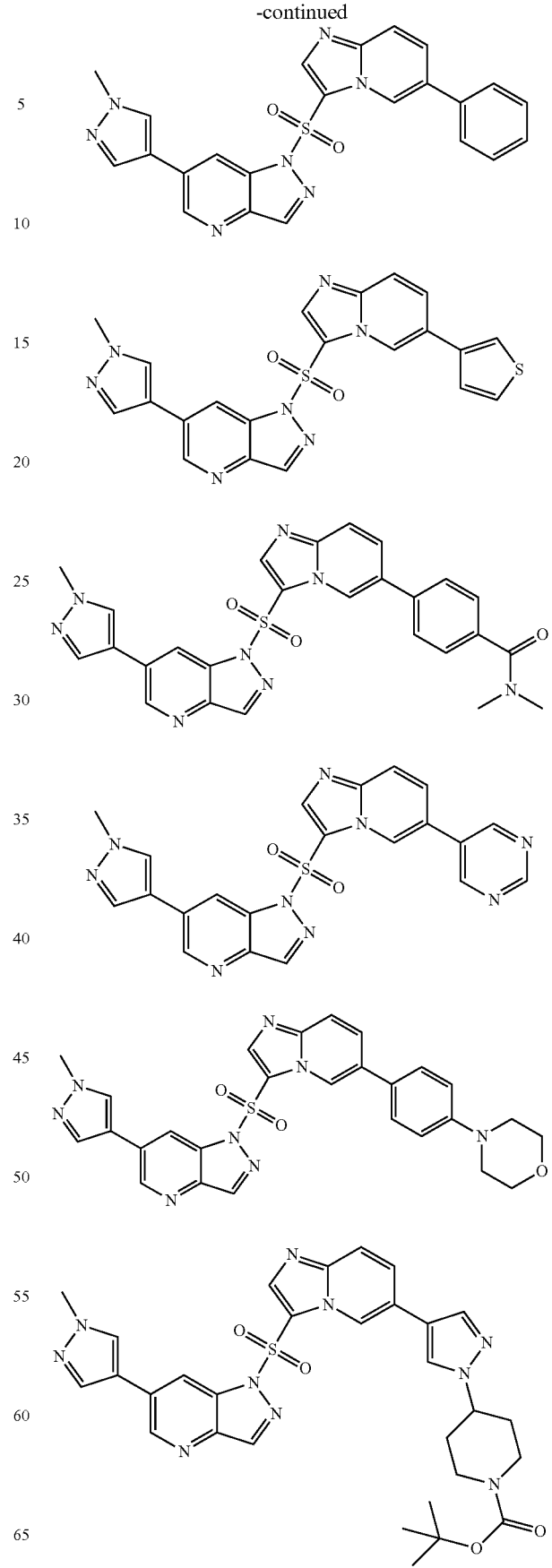

231
-continued
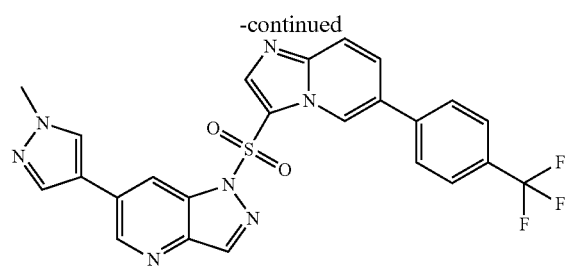
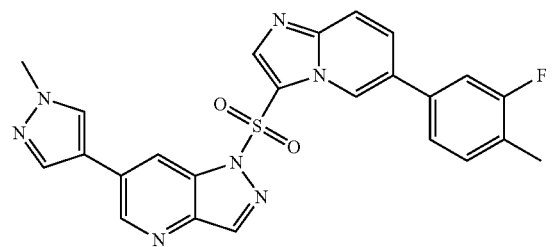
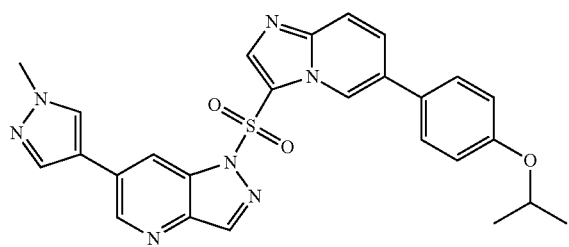
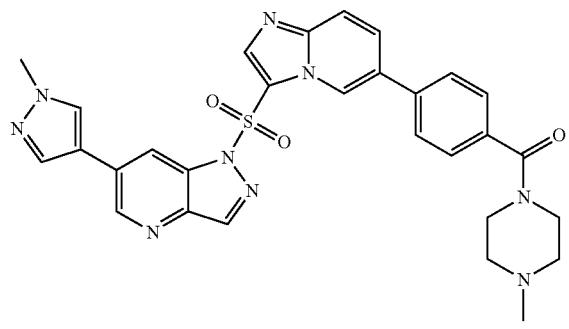
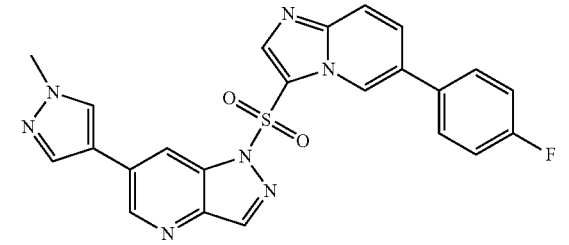
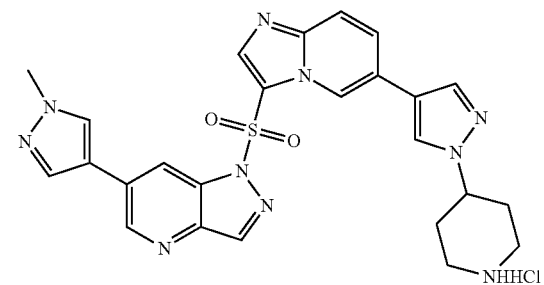
232
-continued
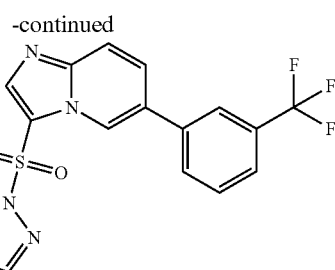
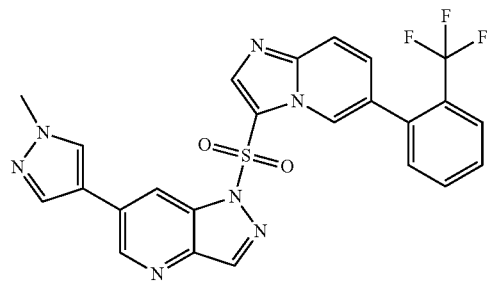
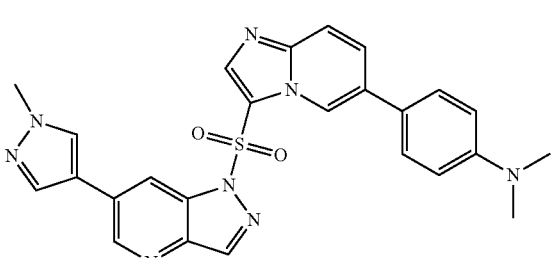
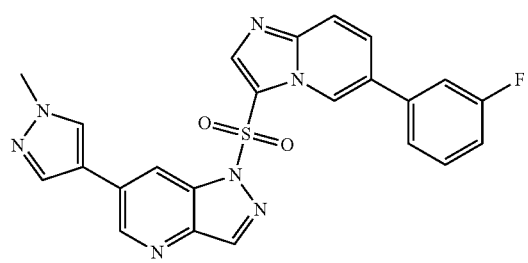
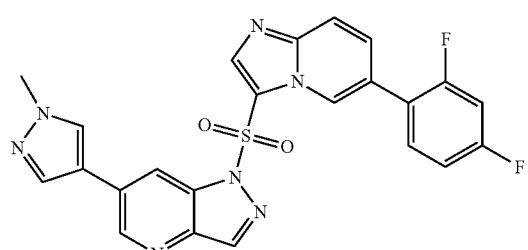
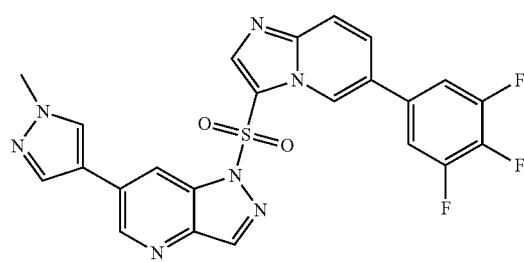

233
-continued
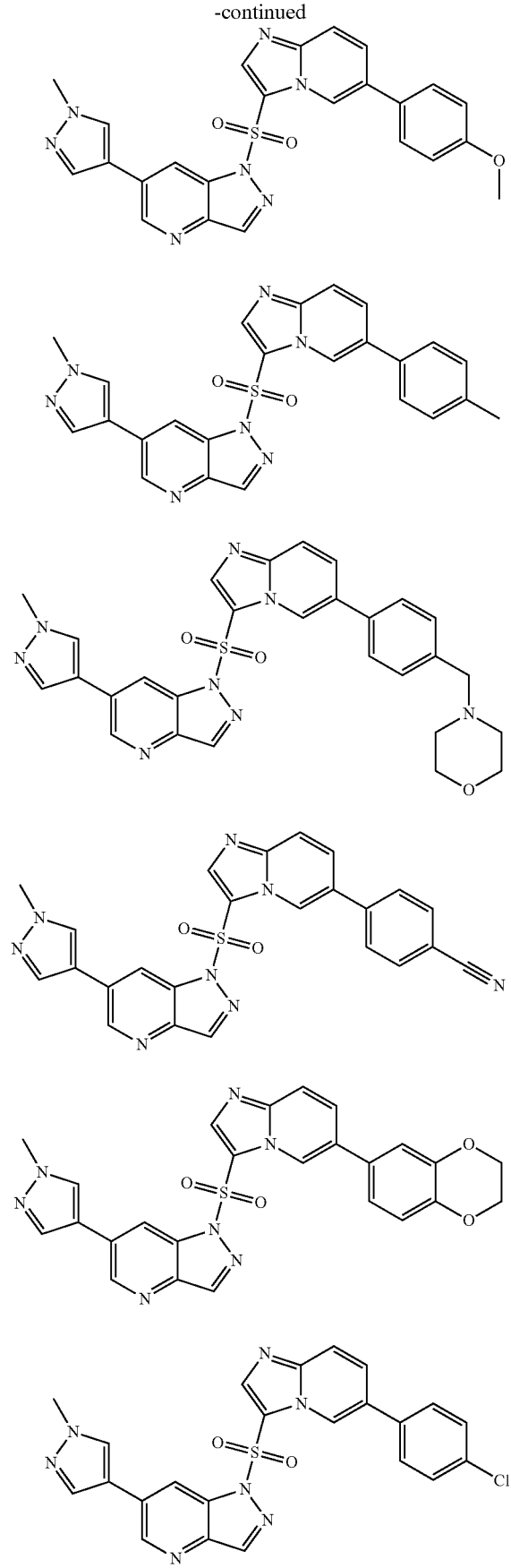
234
-continued
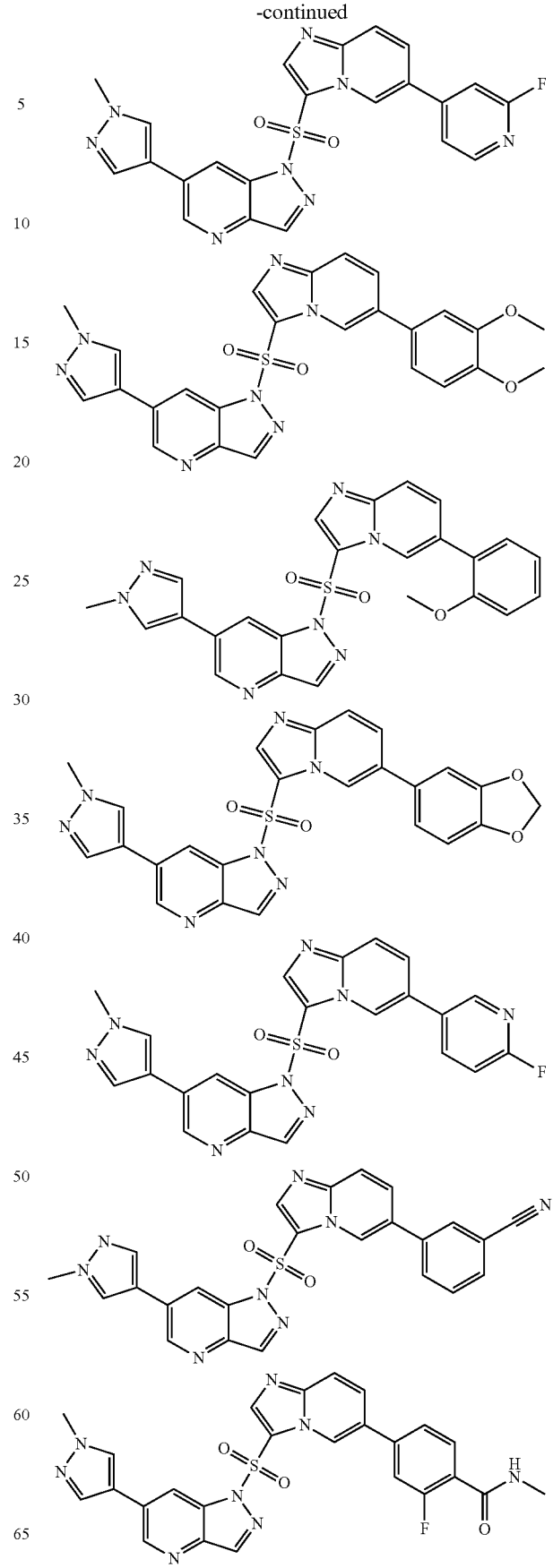

235
-continued
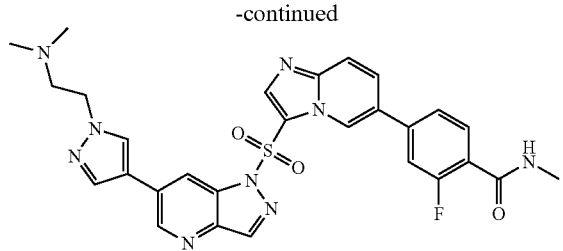
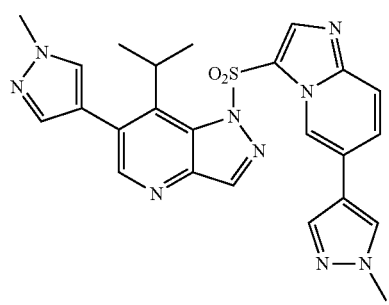
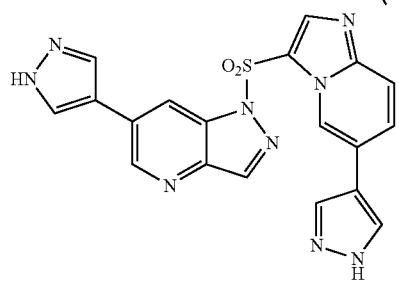
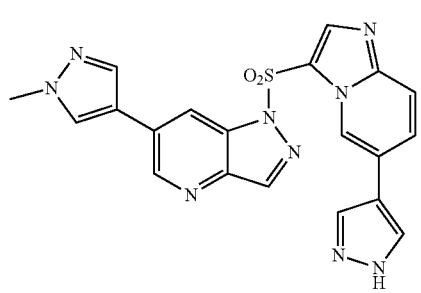
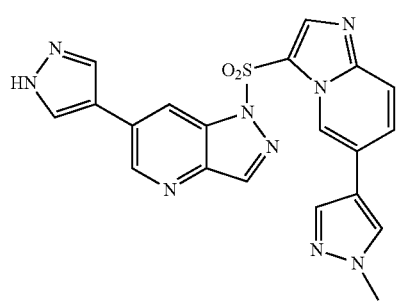
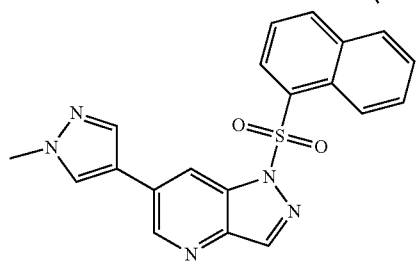
236
-continued
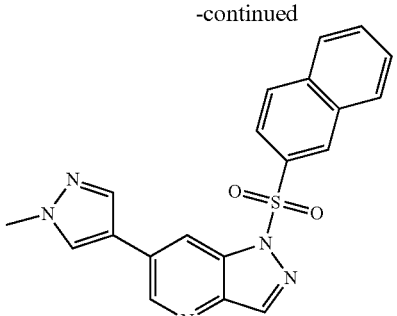
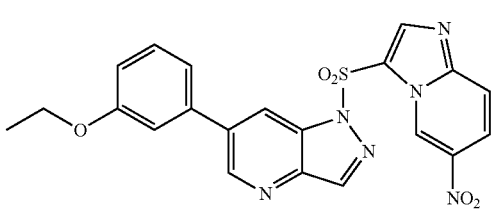
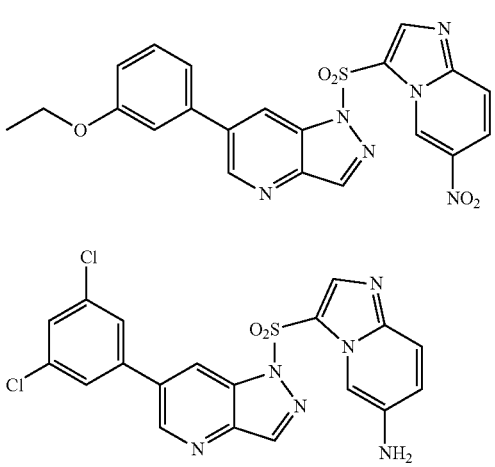
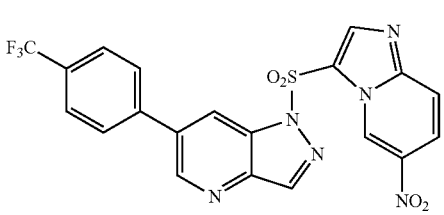
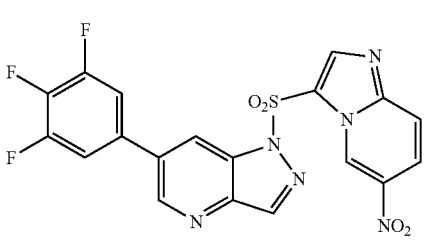
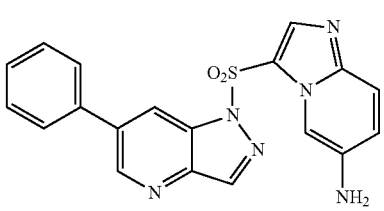
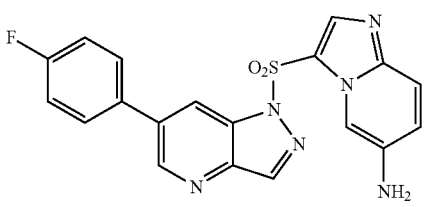

237
-continued
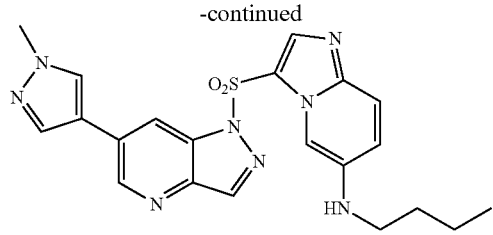
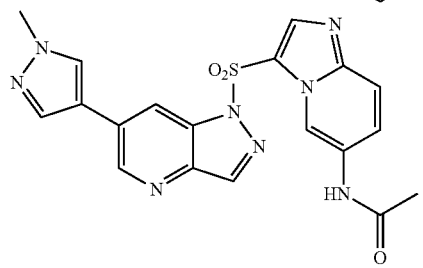
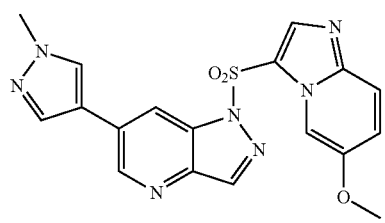
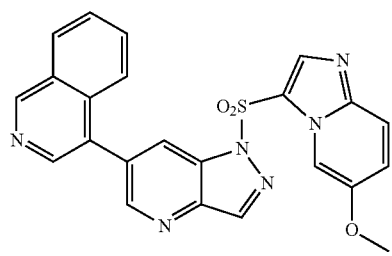
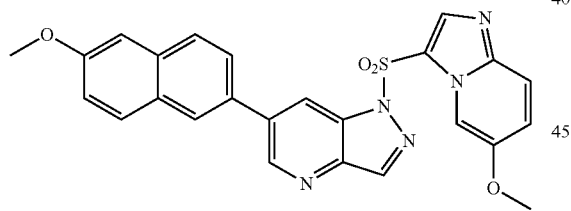
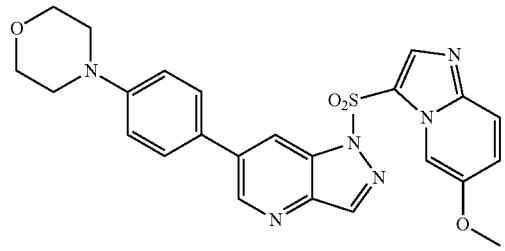
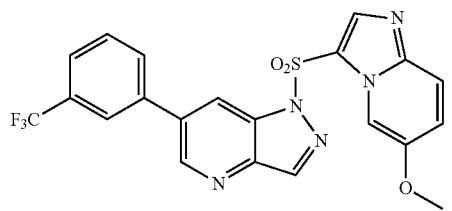
238
-continued
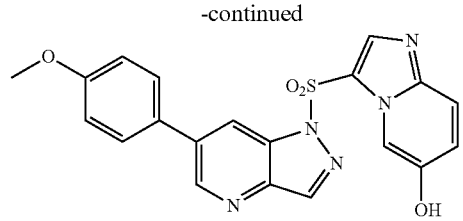
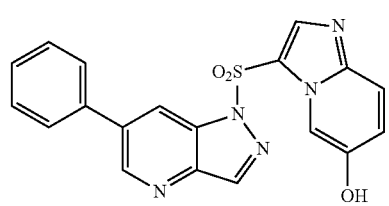
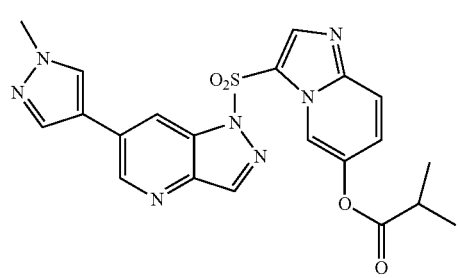
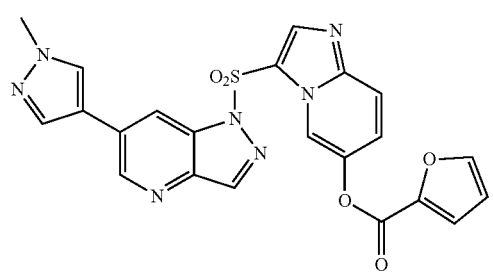
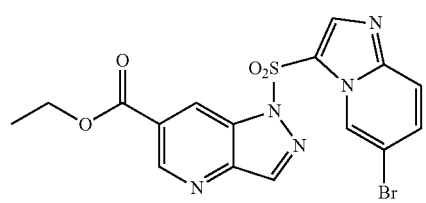
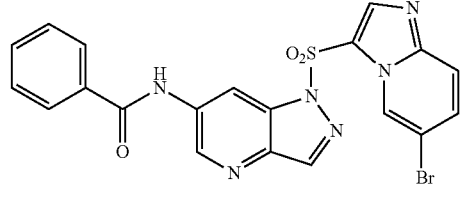
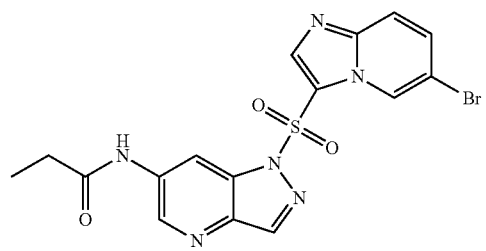

239
-continued
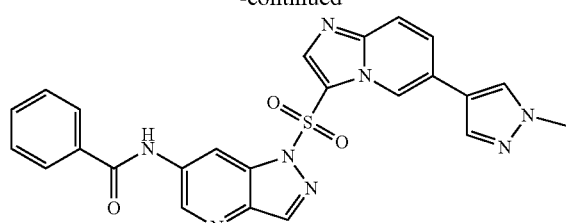
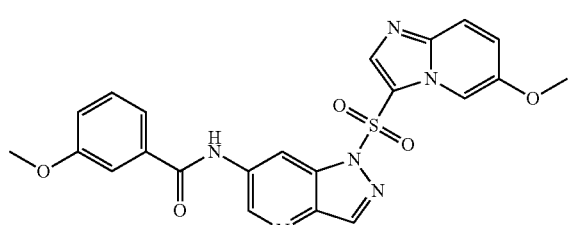
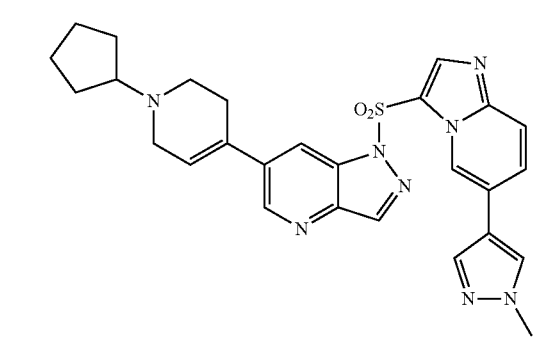
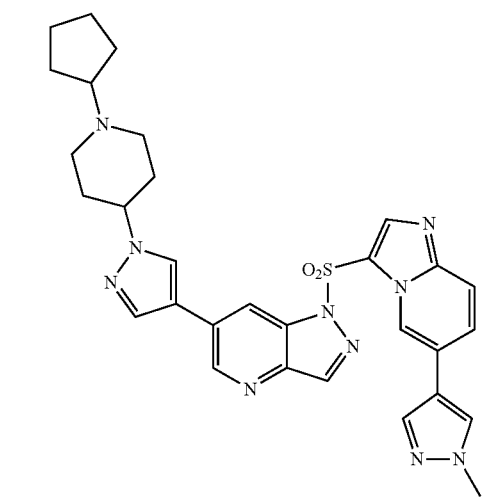
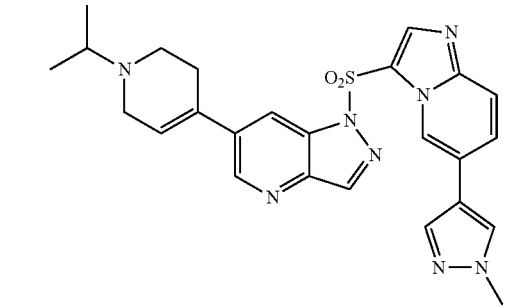
240
-continued
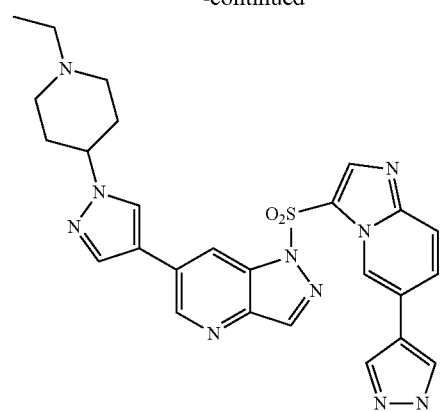
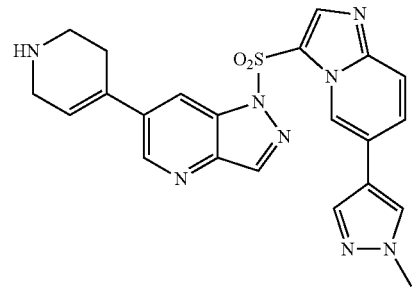
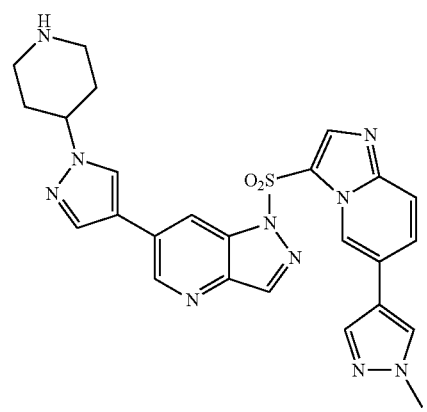
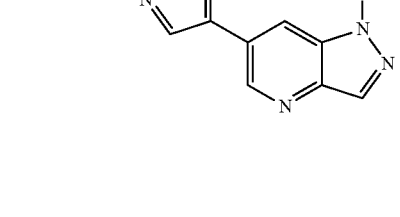

-continued

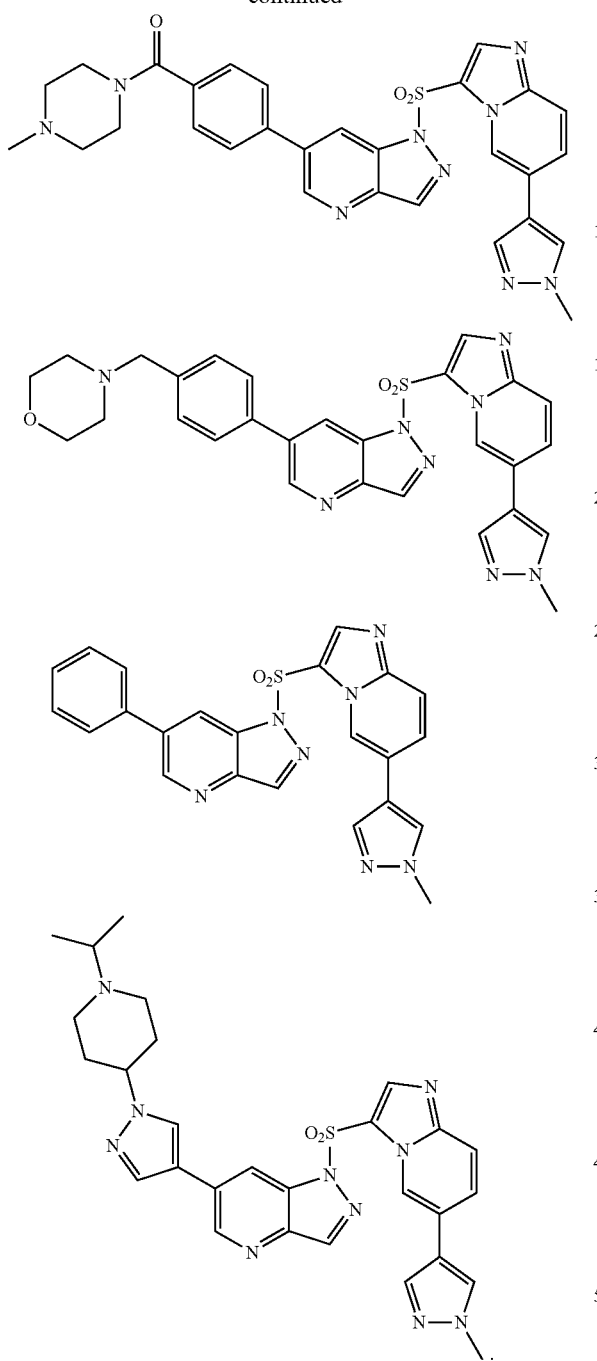

16. The method according to claim 11, wherein the disease associated with abnormal cell proliferation related to abnormal c-Met is a cancer associated with over-expression or over-activation of c-Met.

17. The method according to claim 16, wherein the caner associated with over-expression or over-activation of c-Met is selected from the group consisting of liver cancer, bile duct cancer, pancreatic cancer, lung cancer, thyroid cancer, pleural mesothelioma, lung cancer, stomach cancer, breast cancer, colon cancer, prostate cancer, pancreatic cancer, esophageal cancer, ovarian cancer, renal cancer, glioma and melanoma.

18. The 5-member-heterocycle-fused pyridine compound, pharmaceutically acceptable salts or pharmaceutically acceptable solvates thereof, according to claim 1, wherein $R_1$ is

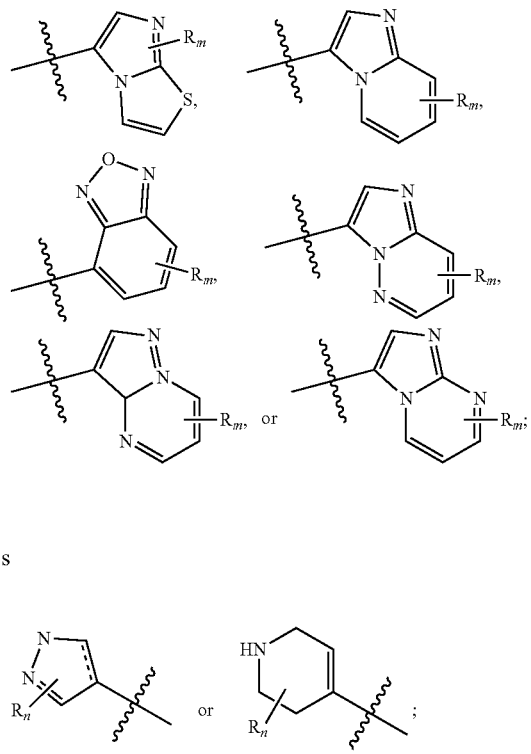

or
$R_2$ is

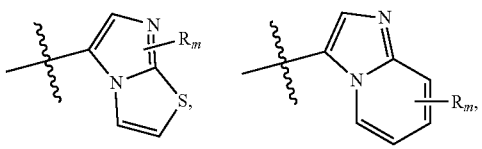

wherein, $R_m$ is H, halogen, nitro, cyano, $C_1$-$C_4$ alkyl, $C_1$-$C_4$ alkoxy, $C_1$-$C_4$ alkylcarbonyl, $C_1$-$C_4$ alkoxycarbonyl;

$R_n$ is H, halogen; nitro; cyano; $C_1$-$C_2$ alkylenedioxy; unsubstituted or halogen-, dimethylamino-, 4-morpholinyl-, 1-aziridinyl-, 1-azetidinyl-, 1-tetrahydropyrrolyl-, 1-piperidinyl- or 1-homopiperidinyl-substituted $C_1$-$C_4$ alkyl; $C_1$-$C_4$ alkoxy; $C_1$-$C_4$ sulfamido; —$NR_aR_b$; —C(O)R'; 4-morpholinyl; or unsubstituted or R"-substituted piperidinyl;

R' is $C_1$-$C_4$ alkyl; $C_1$-$C_4$ alkoxy; —$NR_aR_b$; or 4-methylpiperazinyl;

R" is $C_1$-$C_4$ alkyl; $C_3$-$C_6$ cycloalkyl; $C_1$-$C_4$ alkylcarbonyl; $C_1$-$C_4$ alkoxycarbonyl; $C_3$-$C_6$ cycloalkylcarbonyl; or p-trifluoromethylbenzoyl;

$R_a$ and $R_b$ are independently H, $C_1$-$C_4$ alkyl or $C_1$-$C_4$ alkylcarbonyl.

19. The 5-member-heterocycle-fused pyridine compound, pharmaceutically acceptable salts or pharmaceutically acceptable solvates thereof, according to claim 1, wherein $R_1$ is -continued

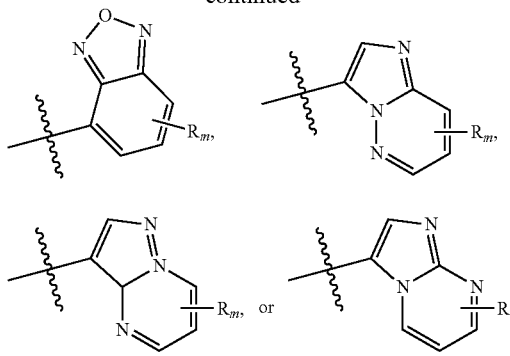

or
R₂ is

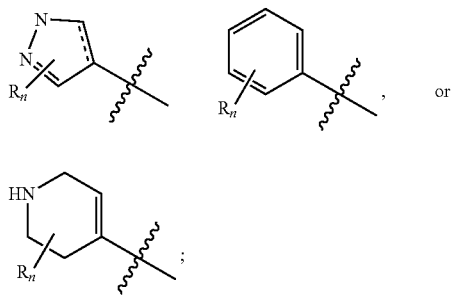

$R_m$ is H, halogen; nitro; cyano; unsubstituted or halogen- or morpholinyl-substituted $C_1$-$C_4$ alkyl; $C_1$-$C_4$ alkoxy; $C_1$-$C_4$ alkylcarbonyl; $C_1$-$C_4$ alkoxycarbonyl; —$NR_aR_b$; —$C(O)$ ($NR_aR_b$); unsubstituted phenyl or phenyl substituted by 1-3 of $R_3$; or unsubstituted 5-7 membered heteroaryl comprising 1-3 heteroatoms selected from N, O, and S or 5-7 membered heteroaryl comprising 1-3 heteroatoms selected from N, O, and S substituted by 1-3 of $R_4$, wherein said heteroaryl is selected from the group consisting of furanyl, thienyl, pyrrolyl, pyrazolyl, imidazolyl, oxazolyl, isoxazolyl, pyranyl, pyridinyl, morpholinyl, oxazinyl and pyrazinyl;

$R_n$ is H, halogen; unsubstituted or halogen-, dimethylamino-, 4-morpholinyl-, 1-aziridinyl-, 1-azetidinyl-, 1-tetrahydropyrrolyl-, 1-piperidinyl- or 1-homopiperidinyl-substituted $C_1$-$C_4$ alkyl;

$C_1$-$C_4$ alkoxy; $C_1$-$C_4$ sulfamido; -C(O)R'; 4-morpholinyl; or unsubstituted or R"-substituted piperidinyl;

$R_3$ is halogen, nitro, cyano, $C_1$-$C_2$ alkylenedioxy; unsubstituted or halogen- or morpholinyl-substituted $C_1$-$C_4$ alkyl; $C_1$-$C_4$ alkoxy; —$NR_aR_b$; —C(O)R'; or 4-morpholinyl;

$R_4$ is halogen, nitro, cyano, unsubstituted or halogen-substituted $C_1$-$C_4$ alkyl; $C_1$-$C_4$ alkoxy; —$NR_aR_b$; —C(O)R'; 4-piperidinyl; or 1-t-butoxycarbonyl-4-piperidinyl;

R' is $C_1$-$C_4$ alkyl; $C_1$-$C_4$ alkoxy; —$NR_aR_b$; or 4-methylpiperazinyl;

R" is $C_1$-$C_4$ alkyl; $C_3$-$C_6$ cycloalkyl; $C_1$-$C_4$ alkylcarbonyl; $C_1$-$C_4$ alkoxycarbonyl; $C_3$-$C_6$ cycloalkylcarbonyl; or p-trifluoromethylbenzoyl; and $R_a$ and $R_b$ are independently H, $C_1$-$C_4$ alkyl or $C_1$-$C_4$ alkylcarbonyl.

20. The pharmaceutical composition of claim 6, wherein in the 5-member-heterocycle-fused pyridine compound, pharmaceutically acceptable salts or pharmaceutically acceptable solvates thereof, $R_1$ is

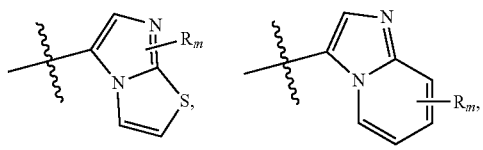

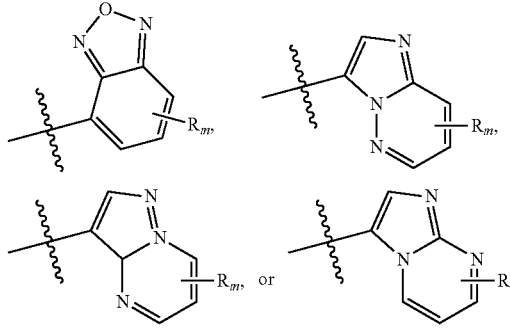

or
R₂ is

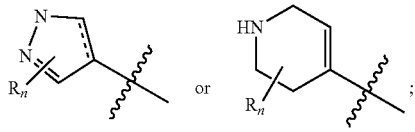

wherein, $R_m$ is H, halogen, nitro, cyano, $C_1$-$C_4$ alkyl, $C_1$-$C_4$ alkoxy, $C_1$-$C_4$ alkylcarbonyl, $C_1$-$C_4$ alkoxycarbonyl;

$R_n$ is H, halogen; nitro; cyano; $C_1$-$C_2$ alkylenedioxy; unsubstituted or halogen-, dimethylamino-, 4-morpholinyl-, 1-aziridinyl-, 1-azetidinyl-, 1-tetrahydropyrrolyl-, 1- piperidinyl- or 1-homopiperidinyl-substituted $C_1$-$C_4$ alkyl; $C_1$-$C_4$ alkoxy; $C_1$-$C_4$ sulfamido; —$NR_aR_b$; —C(O)R'; 4-morpholinyl; or unsubstituted or R"-substituted piperidinyl;

R' is $C_1$-$C_4$ alkyl; $C_1$-$C_4$ alkoxy; —$NR_aR_b$; or 4-methylpiperazinyl;

R" is $C_1$-$C_4$ alkyl; $C_3$-$C_6$ cycloalkyl; $C_1$-$C_4$ alkylcarbonyl; $C_1$-$C_4$ alkoxycarbonyl; $C_3$-$C_6$ cycloalkylcarbonyl; or p-trifluoromethylbenzoyl;

$R_a$ and $R_b$ are independently H, $C_1$-$C_4$ alkyl or $C_1$-$C_4$ alkylcarbonyl.

21. The pharmaceutical composition of claim 6, wherein in the 5-member-heterocycle-fused pyridine compound, pharmaceutically acceptable salts or pharmaceutically acceptable solvates thereof, $R_1$ is

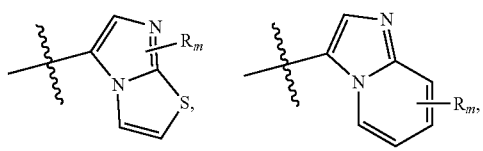

-continued

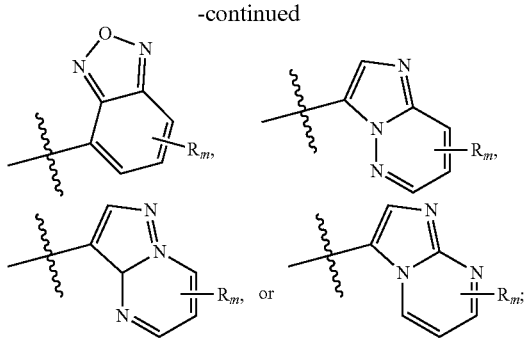

R₂ is

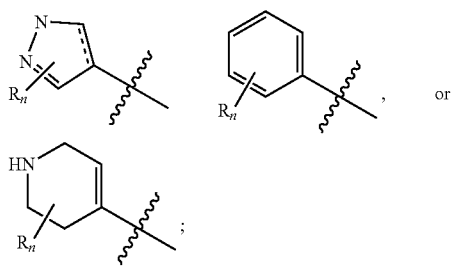

$R_m$ is H, halogen; nitro; cyano; unsubstituted or halogen- or morpholinyl-substituted $C_1$-$C_4$ alkyl; $C_1$-$C_4$ alkoxy; $C_1$-$C_4$ alkylcarbonyl; $C_1$-$C_4$ alkoxycarbonyl; —$NR_aR_b$; —C(O)($NR_aR_b$); unsubstituted phenyl or phenyl substituted by 1-3 of $R_3$; or unsubstituted 5-7 membered heteroaryl comprising 1-3 heteroatoms selected from N, O, and S or 5-7 membered heteroaryl comprising 1-3 heteroatoms selected from N, O, and S substituted by 1-3 of $R_4$, wherein said heteroaryl is selected from the group consisting of furanyl, thienyl, pyrrolyl, pyrazolyl, imidazolyl, oxazolyl, isoxazolyl, pyranyl, pyridinyl, morpholinyl, oxazinyl and pyrazinyl;

$R_n$ is H, halogen; unsubstituted or halogen-, dimethylamino-, 4-morpholinyl-, 1-aziridinyl-, 1-azetidinyl-, 1-tetrahydropyrrolyl-, 1-piperidinyl- or 1-homopiperidinyl-substituted $C_1$-$C_4$ alkyl; $C_1$-$C_4$ alkoxy; $C_1$-$C_4$ sulfamido; —C(O)R'; 4-morpholinyl; or unsubstituted or R''-substituted piperidinyl;

$R_3$ is halogen, nitro, cyano, $C_1$-$C_2$ alkylenedioxy; unsubstituted or halogen- or morpholinyl-substituted $C_1$-$C_4$ alkyl; $C_1$-$C_4$ alkoxy; —$NR_aR_b$; —C(O)R'; or 4-morpholinyl;

$R_4$ is halogen, nitro, cyano, unsubstituted or halogen-substituted $C_1$-$C_4$ alkyl; $C_1$-$C_4$ alkoxy; —$NR_aR_b$; —C(O)R'; 4-piperidinyl; or 1-t-butoxycarbonyl-4-piperidinyl;

R' is $C_1$-$C_4$ alkyl; $C_1$-$C_4$ alkoxy; —$NR_aR_b$; or 4-methylpiperazinyl;

R'' is $C_1$-$C_4$ alkyl; $C_3$-$C_6$ cycloalkyl; $C_1$-$C_4$ alkylcarbonyl; $C_1$-$C_4$ alkoxycarbonyl; $C_3$-$C_6$ cycloalkylcarbonyl; or p-trifluoromethylbenzoyl; and $R_a$ and $R_b$ are independently H, $C_1$-$C_4$ alkyl or $C_1$-$C_4$ alkylcarbonyl.

* * * * *

UNITED STATES PATENT AND TRADEMARK OFFICE
CERTIFICATE OF CORRECTION

PATENT NO. : 9,988,381 B2
APPLICATION NO. : 14/895832
DATED : June 5, 2018
INVENTOR(S) : Jingkang Shen et al.

It is certified that error appears in the above-identified patent and that said Letters Patent is hereby corrected as shown below:

On the Title Page

Item (72) Inventors: "Jing Al" should be -- Jing Ai --.

In the Specification

Column 35, Compound No. 50, "1-(imidazo[1,4-b]pyridazine-3-sulfonyl)-6-{[1-(4-piperidinyl)]-4-pyrazolyl}-4-pyrazolyl}-1-H-pyrazolo[4,3-b]pyridine chloride" should be -- 1-(imidazo[1,2-b]pyridazine-3-sulfonyl)-6-{[1-(4-piperidinyl)]-4-pyrazolyl}-1-H-pyrazolo[4,3-b]pyridine chloride --.

Column 35, Compound No. 51, "1-(imidazo[1,2-b]pyridazine-3-sulfonyl)-6-{[1-(4-piperidinyl)]-4-pyrazolyl}-4-pyrazolyl}-1-H-pyrazolo[4,3-b]pyridine" should be -- 1-(imidazo[1,2-b]pyridazine-3-sulfonyl)-6-{[1-(4-piperidinyl)]-4-pyrazolyl}-1-H-pyrazolo[4,3-b]pyridine --.

Column 39, Compound No. 58, "1-(imidazo[1,2-a]pyridine-3-sulfonyl)-6-{{1-[(1-p-trifluoroformyl)-4-piperidinyl]}-4-pyrazolyl}-1-H-pyrazolo[4,3-b]pyridine" should be -- 1-(imidazo[1,2-a]pyridine-3-sulfonyl)-6-{{1-[(1-p-trifluoromethyl)-4-piperidinyl]}-4-pyrazolyl}-1-H-pyrazolo[4,3-b]pyridine --.

Column 41, Compound No. 64, "1-[(6-trifluoromethyl-imidazo[1,2-a]pyridine)-3-sulfonyl)]-6-{[1-(4-piperidinyl)]-4-pyrazolyl}-4-pyrazolyl}-1-H-pyrazolo[4,3-b]pyridine chloride" should be -- 1-[(6-trifluoromethyl-imidazo[1,2-a]pyridine)-3-sulfonyl)]-6-{[1-(4-piperidinyl)]-4-pyrazolyl}-1-H-pyrazolo[4,3-b]pyridine chloride --.

Column 43, Compound No. 65, "1-[(6-trifluoromethyl-imidazo[1,2-a]pyridine)-3-sulfonyl)]-6-{[1-(4-piperidinyl)]-4-pyrazolyl}-4-pyrazolyl}-1-H-pyrazolo[4,3-b]pyridine" should be -- 1-[(6-trifluoromethyl-imidazo[1,2-a]pyridine)-3-sulfonyl)]-6-{[1-(4-piperidinyl)]-4-pyrazolyl}-1-H-pyrazolo[4,3-b]pyridine --.

Column 81, Line 28, "31H" should be -- 3H --.

Signed and Sealed this
Twenty-fourth Day of July, 2018

Andrei Iancu
*Director of the United States Patent and Trademark Office*

CERTIFICATE OF CORRECTION (continued)
U.S. Pat. No. 9,988,381 B2

Column 83, Line 4, "]-H" should be -- ]-1-H --.

Column 89, Lines 15-43,

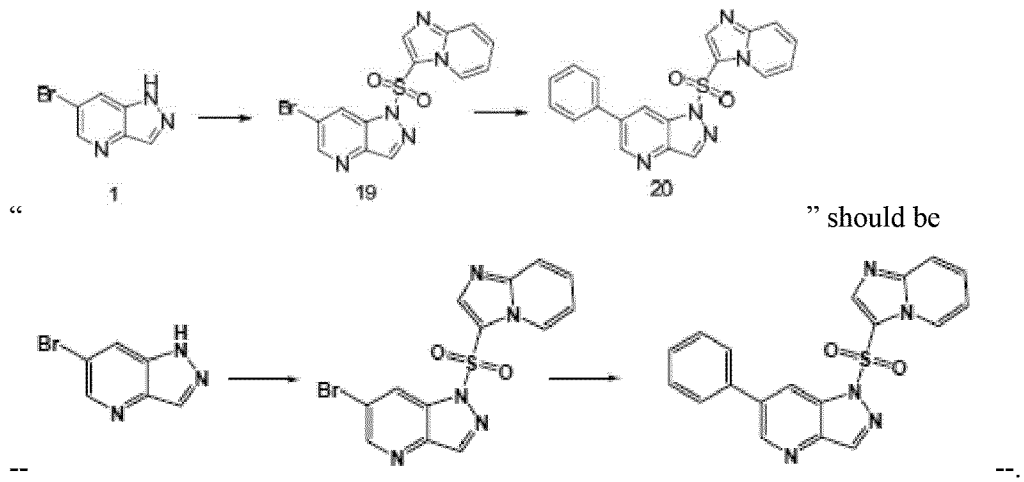

Column 89, Line 49, "compound 1" should be -- 6-bromo-1H-pyrazolo[4,3-b]pyridine --.

Column 89, Line 62, "compound 19" should be -- 1-(imidazo[1,2-a]pyridine-3-sulfonyl)-6-bromo-1-H-pyrazolo[4,3-b]pyridine --.

Column 91, Line 14, "sulfon" should be -- sulfonyl --.

Column 99, Line 11, "H-pyrazolo[4,3-b]pyridine" should be -- H-pyrrolo[4,3-b]pyridine --.

Column 99, Line 29, "pyrazolo[4,3-b]pyridine" should be -- pyrrolo[4,3-b]pyridine --.

Column 99, line 32, "eridinyl]}-4-pyrazolyl}-1-H-pyrazolo[4,3-b]pyridine" should be -- eridinyl]}-4-pyrazolyl}-1-H-pyrrolo[4,3-b]pyridine --.

Column 100, Line 31, "at 5 vacuum" should be -- at vacuum --.

Column 120, Line 5, "methyl-4" should be -- methyl)-4 --.

Column 132, Lines 44 and 45, "1-[(3-chlorophenyl)-1-H-pyrrolo[2,3-b]pyridine-3-sulfonyl]-1-H-pyrazolo[3,4-b]pyridine" should be -- 1-[(4-morpholinylphenyl)-1-H-pyrrolo[2,3-b]pyridine-3-sulfonyl]-1-H-pyrazolo[3,4-b]pyridine --.

Column 142, Line 53, "111" should be -- 1H --.

Column 142, Line 66, "211" should be -- 2H --.

Column 150, Line 11, "6-{(1" should be -- 6-{{1 --.

Column 158, Line 47, "do" should be -- $d_0$ --.